(12) United States Patent
Bhat et al.

(10) Patent No.: US 7,365,085 B2
(45) Date of Patent: Apr. 29, 2008

(54) COMPOUNDS AND METHODS

(75) Inventors: Ajita Bhat, Andover, MA (US); John Jeffrey McAtee, King of Prussia, PA (US); Scott K. Thompson, King of Prussia, PA (US); James S. Frazee, King of Prussia, PA (US); Lara S. Kallander, King of Prussia, PA (US); Chun Ma, Edgewater, NJ (US); Joseph Marino, King of Prussia, PA (US); Michael J. Neeb, King of Prussia, PA (US); Robert A. Stavenger, King of Prussia, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 317 days.

(21) Appl. No.: 10/508,894

(22) PCT Filed: Mar. 26, 2003

(86) PCT No.: PCT/US03/09450

§ 371 (c)(1),
(2), (4) Date: Sep. 22, 2004

(87) PCT Pub. No.: WO03/082205

PCT Pub. Date: Oct. 9, 2003

(65) Prior Publication Data

US 2005/0113580 A1     May 26, 2005

Related U.S. Application Data

(60) Provisional application No. 60/368,425, filed on Mar. 27, 2002.

(51) Int. Cl.
  *A01N 43/40*   (2006.01)
  *A01N 43/64*   (2006.01)
  *A01N 43/08*   (2006.01)
  *A61K 31/44*   (2006.01)
  *A61K 31/41*   (2006.01)

(52) U.S. Cl. ............ 514/357; 514/381; 514/383; 514/471; 514/538; 514/539; 514/568; 514/651; 546/300; 548/252; 560/27; 560/29; 562/431; 564/442; 564/443

(58) Field of Classification Search .......... None
See application file for complete search history.

(56) References Cited

U.S. PATENT DOCUMENTS

| | | | |
|---|---|---|---|
| 4,220,645 A * | 9/1980 | Chibret | 424/248.58 |
| 2003/0153541 A1 | 8/2003 | Dudley et al. | 514/171 |
| 2003/0162758 A1 | 8/2003 | Schwartz et al. | 514/172 |
| 2003/0229062 A1 | 12/2003 | Schwartz et al. | 514/177 |
| 2004/0072868 A1 | 4/2004 | Collins et al. | 514/318 |
| 2004/0266663 A1 | 12/2004 | Schwartz et al. | 514/2 |
| 2005/0036992 A1 | 2/2005 | Saez et al. | 424/93.21 |
| 2005/0107444 A1 | 5/2005 | Thompson et al. | 514/345 |
| 2005/0113580 A1 | 5/2005 | Thompson et al. | 546/268.1 |
| 2005/0131014 A1 | 6/2005 | Collini et al. | 514/311 |
| 2005/0171084 A1 | 8/2005 | Cairns et al. | 514/210.21 |
| 2005/0282750 A1 | 12/2005 | Schwartz et al. | 514/12 |
| 2005/0282908 A1 | 12/2005 | Collins et al. | 514/620 |

FOREIGN PATENT DOCUMENTS

| | | |
|---|---|---|
| EP | 0 394 440 | 10/1990 |
| EP | 0 485 890 A2 | 7/1991 |
| WO | WO 00/18723 * | 4/2000 |
| WO | WO 02/24632 | 3/2002 |
| WO | WO 03/082192 | 10/2003 |
| WO | WO 03/082802 | 10/2003 |
| WO | WO 04/043939 | 5/2004 |
| WO | WO 04/058819 A2 | 7/2004 |
| WO | WO 04/110368 A2 | 12/2004 |
| WO | WO 04/110375 A2 | 12/2004 |
| WO | WO 05/009383 A2 | 2/2005 |
| WO | WO 05/013946 A2 | 2/2005 |
| WO | WO 05/055998 A1 | 6/2005 |
| WO | WO 06/000576 A2 | 1/2006 |
| WO | WO 06/000577 A2 | 1/2006 |
| WO | WO 06/004030 A1 | 1/2006 |

OTHER PUBLICATIONS

Vippagunta et al, "Crystalline Solids" Advanced Drug Delivery Reviews, vol. 48, pp. 3-26 (2001).*

(Continued)

*Primary Examiner*—Zachary C Tucker
(74) *Attorney, Agent, or Firm*—Kathryn L. Sieburth; Kathryn E. McCarthy; Charles M. Kinzig

(57) ABSTRACT

Disclosed is a compound having the formula:

$$X-(CR^1R^2)_p-\underset{Z}{\underset{|}{\overset{(R^3)_k}{\bigcirc}}}-Y-(CR^4R^5)_n-N\underset{(CR^8R^9)_q}{\overset{(CR^6R^7)_m}{\diagup}}\underset{Q}{\diagdown}\Bigg)_t \quad \text{I}$$

pharmaceutically acceptable salts or solvates thereof and pharmaceutical compositions containing the same, wherein the structural variables are as defined herein. The compounds, salts and solvates of this invention are useful as LXR agonists.

36 Claims, No Drawings

OTHER PUBLICATIONS

Gavezzotti, "Are Crystal Structures Predictable?" Accounts of Chemical Research, vol. 27, pp. 309-314 (1994).*
U.S. Appl. 60/499,659, filed Sep. 3, 2003, Hoang et al.
U.S. Appl. 60/500,295, filed Sep. 4, 2003, Hoang et al.
U.S. Appl. 60/499,779, filed Sep. 3, 2003, Kallander et al.
U.S. Appl. 60/500,296, filed Sep. 4, 2003, Kallander et al.
U.S. Appl. 60/499,762, filed Sep. 3, 2004, Hoang et al.
Siegel et al., "Rapid Purification of Small Molecule Libraries by Ion Exchange Chromatography". *Tetrahedron Lett.*, 38(19): 3357-3360 (1997).
Collins et al., "Identification of a Nonsteroidal Liver X Receptor Agonist Through Parallel Array Synthesis of Tertiary Amines", *J. Med. Chem.*, 45: 1963-1966 (2002).
Grefhorst et al. *Am. J. Physiol. Endocrinol. Metab.*, 289: E829-E838 (2005).
Groot et al. *J. Lipid Res.*, 46: 2182-2191 (2005).
Jaye et al. *J. Med. Chem.*, 48: 5419-5422 (2005).
Ogawa et al. *Circ. Res.*, 96: e59-e67 (2005).
Quinet et al. *J. Lipid Res.*, 45: 1929-1942 (2004).
Miao et al. *J. Lipid Res.*, 45: 1410-1417 (2004).
Schmuth et al. *J. Invest. Dermatol.* 123: 41-48 (2004).
Farnegardh et al. *J. Biol. Chem.*, 278(40): 38821-38828 (2003).
Wang et al. *J. Molec. Graphics and Modelling*, 22: 173-181 (2003).
Fowler et al. *J. Invest. Dermatol.*, 120: 246-255 (2003).
Joseph et al. *PNAS USA*, 99(11): 7604-7609 (2002).
Fluhr et al. *J. Invest. Dermatol.*, 125: 1206-1214 (2005).
Naik et al. *Circulation*, 113: 90-97 (2006).
Kruit et al. *Gastroenterology*, 128: 147-156 (2005).
Laffitte et al. *PNAS USA*, 100(9): 5419-5424 (2003).
Castrillo et al. *J. Biol. Chem.*, 278(12): 10443-10449 (2003).
Laffitte et al. *Mol. & Cell. Biol.*, 23(6): 2182-2191 (2003).
Collins et al. *J. Med. Chem.*, 45: 1963-1966 (2002).
Terasaka et al. *FEBS Journal*, 272: 1546-1556 (2005).
Collins et al. *Abstracts of Papers, 230th ACS National Meeting*, Washington, DC. Aug. 28-Sep. 1, 2005. MEDI-237. Publisher: *American Chemical Society*, Washington, DC.
Rao et al. *Abstracts of Papers, 229th ACS National Meeting*, San Diego, CA. Mar. 13-17, 2005. COMP-258. Publisher: *American Chemical Society*, Washington, DC.
Jon L. Collins. *Abstracts of Papers, 225th ACS National Meeting*, New Orleans, LA. Mar. 23-27, 2003. MEDI-152. Publisher: *American Chemical Society*, Washington, DC.
Collins et al. *Abstracts of Papers, 223rd ACS National Meeting*, Orlando, FL. Apr. 7-11, 2002. MEDI-123. Publisher: *American Chemical Society*, Washington, DC.

* cited by examiner

SEQUENCE LISTING

<160> NUMBER OF SEQ ID NOS: 2

<210> SEQ ID NO 1
<211> LENGTH: 11
<212> TYPE: PRT
<213> ORGANISM: Artificial Sequence
<220> FEATURE:
<223> OTHER INFORMATION: Modified polyhistidine tag

```
                            -continued
<400> SEQUENCE: 1

Met Lys Lys Gly His His His His His Gly
1               5                   10

<210> SEQ ID NO 2
<211> LENGTH: 25
<212> TYPE: PRT
<213> ORGANISM: Artificial Sequence
<220> FEATURE:
<223> OTHER INFORMATION: Biotinylated peptide comprising amino acids
      675-699 or SRC-1

<400> SEQUENCE: 2

Cys Pro Ser Ser His Ser Ser Leu Thr Glu Arg His Lys Ile Leu His
1               5                   10                  15

Arg Leu Leu Gln Glu Gly Ser Pro Ser
            20                  25
```

COMPOUNDS AND METHODS

This application is a 371 of International Application No. PCT/US03/09450, filed 26 Mar. 2003, which claims the benefit of U.S. Provisional Application No. 60/368,425, filed 27 Mar. 2002.

FIELD OF THE INVENTION

The present invention relates to compounds useful as modulating agents for liver X receptors (LXR). Additionally, the present invention related to pharmaceutical formulations comprising such compounds, and the therapeutic use of the same.

BACKGROUND OF THE INVENTION

LXR is a transcription factor. The orphan nuclear receptors, LXRα and LXRβ (collectively LXR) play a role in the maintenance of cholesterol balance. Peet et al., *Curr. Opin. Genet. Dev.* 8:571-575 (1998). In addition, LXR binds to the ATP Binding Cassette Transporter-1 (ABCA1) gene and increases expression of the gene to result in increased ABCA1 protein. ABCA1 is a membrane bound transport protein that is involved in the regulation of cholesterol efflux from extrahepatic cells onto nascent HDL particles. Mutations in the ABCA1 gene are responsible for genetic diseases that result in the complete absence or low levels of HDL cholesterol and a concomitant highly increased risk of cardiovascular disease. See Brooks-Wilson et al., *Nat. Genet.* 22:336-345 (1999); Bodzioch et al., *Nat Genet.* 22:347-351 (1999); and Rust et al., *Nat. Genet.* 22:352-355 (1999). ABCA1 knockout mice homozygous for the mutation in the ABCA1 gene have virtually no plasma HDL, whereas the heterozygotes produce 50% of the HDL of wild type animals. See, Orso et al., *Nat. Genet.* 24:192-196 (2000) and McNeish et al., *Proc. Natl. Acad. Sci. USA* 97:4245-4250 (2000). ABCA1 knockout mice also show increased cholesterol absorption. See, McNeish et al., *Proc. Natl. Acad. Sci. USA* 97:4245-4250 (2000). Increased expression of ABCA1 results in increased HDL cholesterol, decreased absorption of cholesterol, and increased removal of excess cholesterol from extrahepatic tissues, including macrophages. LXR agonists also upregulate macrophage expression of apolipoprotein E and ABCG1, both of which contribute to the efflux of cellular cholesterol. By stimulating macrophage cholesterol efflux through upregulation of ABCA1, ABCG1, and apoE expression, as well as increasing the expression of other target genes including cholesteryl ester transfer protein and lipoprotein lipase, LXR agonists influence plasma lipoproteins.

Accordingly, compounds which function as LXR modulating agents, and particularly as LXR agonists, would be useful in methods of increasing ABCA1, ABCG1, and apolipoprotein E expression, increasing cholesterol efflux from peripheral cells, and treating LXR mediated diseases and conditions such as cardiovascular disease and Inflammation.

SUMMARY OF THE INVENTION

This invention is directed to a compound of Formula I:

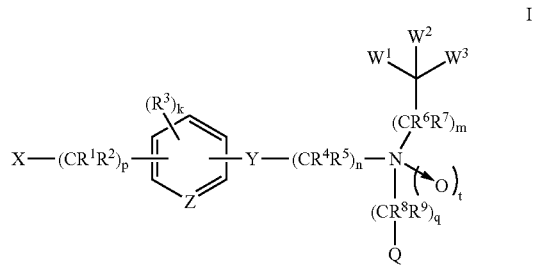

wherein:

X is selected from $C_1$-$C_8$ alkyl, halo, —$OR^{10}$, —$NR^{14}R^{15}$, nitro, cyano, —$COOR^{10}$, —$COR^{13}$, —$OCOR^{13}$, —$N(R^{17})COR^{13}$, —$N(R^{17})CONR^{14}R^{15}$, —$N(R^{17})COOR^{13}$, —$SO_3H$, —$SO_2NR^{14}R^{15}$, —$C(=NR^{17})NR^{14}R^{15}$, —$N(R^{17})SO_2R^{16}$, and a 5 or 6-membered heterocyclic group;

or X and an adjacent $R^3$, taken together with the atoms to which they are bonded, form an alkylenedioxy moiety;

Z is CH, $CR^3$ or N, wherein when Z is CH or $CR^3$, k is 0-4 and t is 0 or 1, and when Z is N, k is 0-3 and t is 0;

Y is selected from —O—, —S—, —$N(R^{10})$—, and —$C(R^4)(R^5)$—;

$W^1$ is selected from $C_1$-$C_6$ alkyl, $C_3$-$C_8$ cycloalkyl, aryl and Het, wherein said $C_1$-$C_8$ alkyl, $C_3$-$C_8$ cycloalkyl, Ar and Het are optionally unsubstituted or substituted with one or more groups independently selected from halo, cyano, nitro, $C_1$-$C_6$ alkyl, $C_3$-$C_6$ alkenyl, $C_3$-$C_6$ alkynyl, —$C_0$-$C_6$ alkyl-$CO_2R^{10}$, —$C_0$-$C_6$ alkyl-C(O)$SR^{10}$, —$C_0$-$C_6$ alkyl-$CONR^{11}R^{12}$, —$C_0$-$C_6$ alkyl-$COR^{13}$, —$C_0$-$C_6$ alkyl-$NR^{11}R^{12}$, —$C_0$-$C_6$ alkyl-$SR^{10}$, —$C_0$-$C_6$ alkyl-$OR^{10}$, —$C_0$-$C_6$ alkyl-$SO_3H$, —$C_0$-$C_6$ alkyl-$SO_2NR^{11}R^{12}$, —$C_0$-$C_6$ alkyl-$SO_2R^{10}$, —$C_0$-$C_6$ alkyl-$SOR^{13}$, —$C_0$-$C_6$ alkyl-$OCOR^{13}$, —$C_0$-$C_6$ alkyl-OC(O)$NR^{11}R^{12}$, —$C_0$-$C_6$ alkyl-OC(O)$OR^{13}$, —$C_0$-$C_6$ alkyl-$NR^{11}$C(O)$OR^{13}$, —$C_0$-$C_6$ alkyl-$NR^{11}$C(O)$NR^{11}R^{12}$, and —$C_0$-$C_6$ alkyl-$NR^{11}COR^{13}$, where said $C_1$-$C_6$ alkyl, is optionally unsubstituted or substituted by one or more halo substituents;

$W^2$ is selected from H, halo, $C_1$-$C_6$ alkyl, $C_2$-$C_6$ alkenyl, $C_2$-$C_6$ alkynyl, —$C_0$-$C_6$ alkyl-$NR^{11}R^{12}$, —$C_0$-$C_6$ alkyl-$SR^{10}$, —$C_0$-$C_6$ alkyl-$OR^{10}$, —$C_0$-$C_6$ alkyl-$CO_2R^{10}$, —$C_0$-$C_6$ alkyl-C(O)$SR^{10}$, —$C_0$-$C_6$ alkyl-$CONR^{11}R^{12}$, —$C_0$-$C_6$ alkyl-$COR^{13}$, —$C_0$-$C_6$ alkyl-$OCOR^{13}$, —$C_0$-$C_6$ alkyl-$OCONR^{11}R^{12}$, —$C_0$-$C_6$ alkyl-$NR^{11}CONR^{11}R^{12}$, —$C_0$-$C_6$ alkyl-$NR^{11}COR^{13}$, —$C_0$-$C_6$ alkyl-Het, —$C_0$-$C_6$ alkyl-Ar and —$C_0$-$C_6$ alkyl-$C_3$-$C_7$ cycloalkyl, wherein said $C_1$-$C_6$ alkyl is optionally unsubstituted or substituted by one or more halo substituents, and wherein the $C_3$-$C_7$ cycloalkyl, Ar and Het moieties of said —$C_0$-$C_6$ alkyl-Het, —$C_0$-$C_6$ alkyl-Ar and —$C_0$-$C_6$ alkyl-$C_3$-$C_7$ cycloalkyl are optionally unsubstituted or substituted with one or more groups independently selected from halo, cyano, nitro, $C_1$-$C_6$ alkyl, $C_3$-$C_6$ alkenyl, $C_3$-$C_6$ alkynyl, —$C_0$-$C_6$ alkyl-$CO_2R^{10}$, —$C_0$-$C_6$ alkyl-C(O)$SR^{10}$, —$C_0$-$C_6$ alkyl-$CONR^{11}R^{12}$, —$C_0$-$C_6$ alkyl-$COR^{13}$, —$C_0$-$C_6$ alkyl-$NR^{11}R^{12}$, —$C_0$-$C_6$ alkyl-$SR^{10}$, —$C_0$-$C_6$ alkyl-$OR^{10}$, —$C_0$-$C_6$ alkyl-$SO_3H$, —$C_0$-$C_6$ alkyl-$SO_2NR^{11}R^{12}$, —$C_0$-$C_6$ alkyl-$SO_2R^{10}$, —$C_0$-$C_6$ alkyl-$SOR^{13}$, —$C_0$-$C_6$ alkyl-$OCOR^{13}$, —$C_0$-$C_6$ alkyl-OC(O)$NR^{11}R^{12}$, —$C_0$-$C_6$ alkyl-OC(O)$OR^{13}$, —$C_0$-$C_6$ alkyl-$NR^{11}C(O)OR^{13}$, —$C_0$-$C_6$ alkyl-$NR^{11}C(O)NR^{11}R^{12}$, and —$C_0$-$C_6$ alkyl-$NR^{11}COR^{13}$, where said $C_1$-$C_6$ alkyl, is optionally unsubstituted or substituted by one or more halo substituents;

$W^3$ is selected from the group consisting of: H, halo, $C_1$-$C_6$ alkyl, —$C_0$-$C_6$ alkyl-$NR^{11}R^{12}$, —$C_0$-$C_6$ alkyl-$SR^{10}$, —$C_0$-$C_6$ alkyl-$OR^{10}$, —$C_0$-$C_6$ alkyl-$CO_2R^{10}$, —$C_0$-$C_6$ alkyl-$C(O)SR^{10}$, —$C_0$-$C_6$ alkyl-$CONR^{11}R^{12}$, —$C_0$-$C_6$ alkyl-$COR^{13}$, —$C_0$-$C_6$ alkyl-$OCOR^{13}$, —$C_0$-$C_6$ alkyl-$OCONR^{11}R^{12}$, —$C_0$-$C_6$ alkyl-$NR^{11}CONR^{11}R^{12}$, —$C_0$-$C_6$ alkyl-$NR^{11}COR^{13}$, —$C_0$-$C_6$ alkyl-Het, —$C_1$-$C_6$ alkyl-Ar and —$C_1$-$C_6$ alkyl-$C_3$-$C_7$ cycloalkyl, wherein said $C_1$-$C_6$ alkyl is optionally unsubstituted or substituted by one or more halo substituents;

Q is selected from $C_3$-$C_8$ cycloalkyl, Ar and Het; wherein said $C_3$-$C_8$ cycloalkyl, Ar and Het are optionally unsubstituted or substituted with one or more groups independently selected from halo, cyano, nitro, $C_1$-$C_6$ alkyl, $C_3$-$C_6$ alkenyl, $C_3$-$C_6$ alkynyl, —$C_0$-$C_6$ alkyl-$CO_2R^{10}$, —$C_0$-$C_6$ alkyl-$C(O)SR^{11}$, —$C_0$-$C_6$ alkyl-$CONR^{11}R^{12}$, —$C_0$-$C_6$ alkyl-$COR^{13}$, —$C_0$-$C_6$ alkyl-$NR^{11}R^{12}$, —$C_0$-$C_6$ alkyl-$SR^{10}$, —$C_0$-$C_6$ alkyl-$OR^{10}$, —$C_0$-$C_6$ alkyl-$SO_3H$, —$C_0$-$C_6$alkyl-$SO_2NR^{11}R^{12}$, —$C_0$-$C_6$ alkyl-$SO_2R^{10}$, —$C_0$-$C_6$ alkyl-$SOR^{13}$, —$C_0$-$C_6$ alkyl-$OCOR^{13}$, —$C_0$-$C_6$ alkyl-$OC(O)NR^{11}R^{12}$, —$C_0$-$C_6$ alkyl-$OC(O)OR^{13}$, —$C_0$-$C_6$ alkyl-$NR^{11}C(O)OR^{13}$, —$C_0$-$C_6$ alkyl-$NR^{11}C(O)NR^{11}R^{12}$, and —$C_0$-$C_6$ alkyl-$NR^{11}COR^{13}$, where said $C_1$-$C_6$ alkyl is optionally unsubstituted or substituted by one or more halo substituents;

p is 0-8;

n is 2-8;

m is 0 or 1;

q is 0 or 1;

t is 0 or 1;

each $R^1$ and $R^2$ are independently selected from H, halo, $C_1$-$C_6$ alkyl, $C_3$-$C_6$ alkenyl, $C_3$-$C_6$ alkynyl, —$C_0$-$C_6$ alkyl-$NR^{11}R^{12}$, —$C_0$-$C_6$ alkyl-$OR^{10}$, —$C_0$-$C_6$ alkyl-$SR^{10}$, —$C_0$-$C_6$ alkyl-Het, —$C_1$-$C_6$ alkyl-Ar and —$C_1$-$C_6$ alkyl-$C_3$-$C_7$ cycloalkyl, or $R^1$ and $R^2$ together with the carbon to which they are attached form a 3-5 membered carbocyclic or heterocyclic ring, wherein said heterocyclic ring contains one, or more heteroatoms selected from N, O, and S, where any of said $C_1$-$C_6$ alkyl is optionally unsubstituted or substituted by one or more halo substituents;

each $R^3$ is the same or different and is independently selected from halo, cyano, nitro, $C_1$-$C_6$ alkyl, $C_3$-$C_6$ alkenyl, $C_3$-$C_6$ alkynyl, —$C_0$-$C_6$ alkyl-Ar, —$C_0$-$C_6$ alkyl-Het, —$C_0$-$C_6$ alkyl-$C_3$-$C_7$ cycloalkyl, —$C_0$-$C_6$ alkyl-$CO_2R^{10}$, —$C_0$-$C_6$ alkyl-$C(O)SR^{10}$, —$C_0$-$C_6$ alkyl-$CONR^{11}R^{12}$, —$C_0$-$C_6$ alkyl-$COR^{13}$, —$C_0$-$C_6$ alkyl-$NR^{11}R^{12}$, —$C_0$-$C_6$ alkyl-$SR^{10}$, —$C_0$-$C_6$ alkyl-$OR^{10}$, —$C_0$-$C_6$ alkyl-$SO_3H$, —$C_0$-$C_6$ alkyl-$SO_2NR^{11}R^{12}$, —$C_0$-$C_6$ alkyl-$SO_2R^{10}$, —$C_0$-$C_6$ alkyl-$SOR^{13}$, —$C_0$-$C_6$ alkyl-$OCOR^{13}$, —$C_0$-$C_6$ alkyl-$OC(O)NR^{11}R^{12}$, —$C_0$-$C_6$ alkyl-$OC(O)OR^{13}$, —$C_0$-$C_6$ alkyl-$NR^{11}C(O)OR^{13}$, —$C_0$-$C_6$ and —$C_0$-$C_6$ alkyl-$NR^{11}COR^{13}$, wherein said $C_1$-$C_6$ alkyl is optionally unsubstituted or substituted by one or more halo substituents;

each $R^4$ and $R^5$ is independently selected from H, halo, $C_1$-$C_6$ alkyl, —$C_0$-$C_6$ alkyl-Het, —$C_0$-$C_6$ alkyl-Ar and —$C_0$-$C_6$ alkyl-$C_3$-$C_7$ cycloalkyl;

$R^6$ and $R^7$ are each independently selected from H, halo, $C_1$-$C_6$ alkyl, —$C_0$-$C_6$ alkyl-Het, —$C_0$-$C_6$ alkyl-Ar and —$C_0$-$C_6$ alkyl-$C_3$-$C_7$ cycloalkyl;

$R^8$ and $R^9$ are each independently selected from H, halo, $C_1$-$C_6$ alkyl, —$C_0$-$C_6$ alkyl-Het, —$C_0$-$C_6$ alkyl-Ar and —$C_0$-$C_6$ alkyl-$C_3$-$C_7$ cycloalkyl;

$R^{10}$ is selected from H, $C_1$-$C_6$ alkyl, $C_3$-$C_6$ alkenyl, $C_3$-$C_6$ alkynyl, —$C_0$-$C_6$ alkyl-Ar, —$C_0$-$C_6$ alkyl-Het and —$C_0$-$C_6$ alkyl-$C_3$-$C_7$ cycloalkyl;

each $R^{11}$ and each $R^{12}$ are independently selected from H, $C_1$-$C_6$ alkyl, $C_3$-$C_6$ alkenyl, $C_3$-$C_6$ alkynyl, —$C_0$-$C_6$ alkyl-Ar, —$C_0$-$C_6$ alkyl-Het and —$C_0$-$C_6$ alkyl-$C_3$-$C_7$ cycloalkyl, or $R^{11}$ and $R^{12}$ together with the nitrogen to which they are attached form a 4-7 membered heterocyclic ring which optionally contains one or more additional heteroatoms selected from N, O, and S;

$R^{13}$ is selected from $C_1$-$C_6$ alkyl, $C_3$-$C_6$ alkenyl, $C_3$-$C_6$ alkynyl, —$C_0$-$C_6$ alkyl-Ar, —$C_0$-$C_6$ alkyl-Het and —$C_0$-$C_6$ alkyl-$C_3$-$C_7$ cycloalkyl;

$R^{14}$ and $R^{15}$ are each independently selected from H, $C_1$-$C_6$ alkyl, $C_3$-$C_6$ alkenyl, $C_3$-$C_6$ alkynyl, —$C_0$-$C_6$ alkyl-Ar, —$C_0$-$C_6$ alkyl-Het, —$C_0$-$C_6$ alkyl-$C_3$-$C_7$ cycloalkyl, —$C_0$-$C_6$ alkyl-O—Ar, —$C_0$-$C_6$ alkyl-O-Het, —$C_0$-$C_6$ alkyl-O—$C_3$-$C_7$ cycloalkyl, —$C_0$-$C_6$ alkyl-$S(O)_x$—$C_1$-$C_6$ alkyl, —$C_0$-$C_6$ alkyl-$S(O)_x$—Ar, —$C_0$-$C_6$ alkyl-$S(O)_x$-Het, —$C_0$-$C_6$ alkyl-$S(O)_x$—$C_3$-$C_7$ cycloalkyl, —$C_0$-$C_6$ alkyl-NH-Het, —$C_0$-$C_6$ alkyl-NH—$C_3$-$C_7$ cycloalkyl, —$C_0$-$C_6$ alkyl-$N(C_1$-$C_4$ alkyl)-Ar, —$C_0$-$C_6$ alkyl-$N(C_1$-$C_4$ alkyl)-Het, —$C_0$-$C_6$ alkyl-$N(C_1$-$C_4$ alkyl)-$C_3$-$C_7$ cycloalkyl, —$C_0$-$C_6$ alkyl-Ar, —$C_0$-$C_6$ alkyl-Het and —$C_0$-$C_6$ alkyl-$C_3$-$C_7$ cycloalkyl, where x is 0, 1 or 2, or $R^{14}$ and $R^{15}$, together with the nitrogen to which they are attached, form a 4-7 membered heterocyclic ring which optionally contains one or more additional heteroatoms selected from N, O, and S, wherein said $C_1$-$C_6$ alkyl is optionally substituted by one or more of the substituents independently selected from the group halo, —OH, —SH, —$NH_2$, —NH(unsubstituted $C_1$-$C_6$ alkyl), —N(unsubstituted $C_1$-$C_6$ alkyl)(unsubstituted $C_1$-$C_6$ alkyl), unsubstituted —O$C_1$-$C_6$ alkyl, —$CO_2H$, —$CO_2$(unsubstituted $C_1$-$C_6$ alkyl), —$CONH_2$, —CONH(unsubstituted $C_1$-$C_6$ alkyl), —CON(unsubstituted $C_1$-$C_6$ alkyl)(unsubstituted $C_1$-$C_6$ alkyl), —$SO_3H$, —$SO_2NH_2$, —$SO_2NH$(unsubstituted $C_1$-$C_6$ alkyl) and —$SO_2N$(unsubstituted $C_1$-$C_6$ alkyl)(unsubstituted $C_1$-$C_6$ alkyl);

$R^{16}$ is $C_1$-$C_6$ alkyl, —$C_0$-$C_6$ alkyl-Ar or —$C_0$-$C_6$ alkyl-Het; and $R^{17}$ is H, $C_1$-$C_6$ alkyl, —$C_0$-$C_6$ alkyl-Ar or —$C_0$-$C_6$ alkyl-Het;

provided that X is not $COOR^{10}$ when Y is —O—, p is 0-8, n is 2-8, m is 1, q is 0 or 1, t is 0, each $R^1$ and $R^2$ is independently selected from H, $C_1$-$C_6$ alkyl, —OH, —O$C_1$-$C_6$ alkyl, —SH, and —S$C_1$-$C_6$ alkyl, each $R^4$, $R^5$, $R^6$, $R^7$, $R^5$ and $R^9$ are independently H or $C_1$-$C_4$ alkyl, k is 0 or 1, $W^3$ is H, $W^1$ and $W^2$ are each independently selected from $C_3$-$C_8$ cycloalkyl and aryl and $R^3$ and Q are as defined above; or provided that the compound is not 5-[3-[[(3,4-dichlorophenyl)methyl][2-(2-naphthalenyl)ethyl]amino]propoxy]-3-methoxy-1,2-benzenedicarboxylic acid 5-[3-[[(3,4-dichlorophenyl)methyl][2-(2-naphthalenyl)ethyl]amino]propoxy]-3-methoxy-1,2-benzenedicarboxylic acid, dimethyl ester 4-[[[2-(4-carboxyphenoxy)ethyl][2-[2-[(5-phenylpentyl)oxy]phenyl]ethyl]amino]methyl]benzoic acid 4-[[[2-[4-(ethoxycarbonyl)phenoxy]ethyl][2-[2-(octyloxy)phenyl]ethyl]amino]methyl]-benzoic acid methyl ester, 4-[[[2-(4-carboxyphenoxy)ethyl][2-[2-(octyloxy)phenyl]ethyl]amino]methyl], benzoic acid, α-[[[3-(4-fluorophenyl)-1,1-dimethylpropyl](phenylmethyl)amino]methyl]-3-(phenylmethoxy)-benzenemethanol hydrochloride, N-[2-(4-amino-3,5-dichlorophenyl)ethyl]-4-fluoro-N-(phenylmethyl)-benzenepropanamine monohydrochloride, N-[2-(4-amino-3,5-dichlorophenyl)ethyl]4-chloro-N-(phenylmethyl)-benzenepropanamine monohydrochloride, 4-amino-3,5-dichloro-α-[[[3-(4-fluorophenyl)propyl](phenylmethyl)amino]methyl]-benzenemethanol monohydrochloride, 4-amino-3,5-dichloro-α-[[[3-(4-chlorophenyl)propyl](phenylmethyl)amino]methyl]-benzenemethanol monohydrochloride, 2-chloro-5-[2-[[3-(4-fluorophenyl)-1-methylpropyl](phenylmethyl)amino]-1-hydroxyethyl]-benzamide monohydrochloride, 4-[2-[[2-hydroxy-2-[4-(phenylmethoxy)phenyl]ethyl](phenylmethyl)amino]ethoxy]-benzeneacetamide, 4-[2-[[2-[3,4-bis(phenylmethoxy)phenyl]ethyl](phenylmethyl)amino]ethoxy]-benzenesulfonamide monohydrochloride, (R)-3-(phenylmethoxy)-α-[[[3-[3-(phenylmethoxy)phenyl]propyl](phenylmethyl)amino]methyl]-benzenemethanol 2,2-dichloro-acetic acid (R){benzyl-[3-(3-benzyloxy-phenyl)-propyl]-amino}(3-benzyloxy-phenyl)-ethyl ester, 3-amino-α-[[[3-(3,4-dimethoxyphenyl)-1-methylpropyl](phenylmethyl)amino]methyl]-4-(phenylmethoxy)-benzenemethanol, α-[[[3-(3,4-dimethoxyphenyl)-1-methylpropyl](phenylmethyl)amino]methyl]-3-nitro-4-(phenylmethoxy)-benzenemethanol, α-[[[3-(3,4-dimethoxyphenyl)-1-methylpropyl](phenylmethyl)amino]methyl]-3-nitro-5-(phenylmethoxy)-benzenemethanol, 3-amino-α-[[[3-(3,4-dimethoxyphenyl)-1-methylpropyl](phenylmethyl)amino]methyl]-5(phenylmethoxy)-benzenemethanol, or 4-[2-[[2-(4-fluorophenoxy)ethyl](phenylmethyl)amino]ethyl]-1-piperazineacetic acid ethyl ester, or a pharmaceutically acceptable salt or solvate thereof.

This invention is also directed to methods for the prevention or treatment of an LXR mediated disease or condition comprising administering a therapeutically effective amount of a compound having Formula I-A:

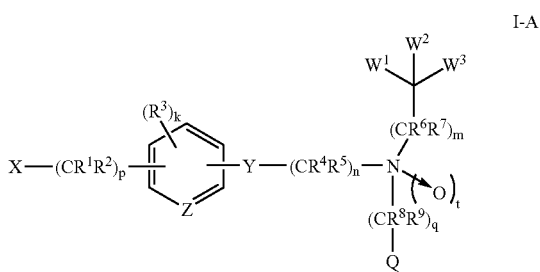

I-A wherein:

X is selected from $C_1$-$C_8$ alkyl, halo, —$OR^{10}$, —$NR^{14}R^{15}$, nitro, cyano, —$COOR^{10}$, —$COR^{13}$, —$OCOR^{13}$, —$N(R^{17})COR^{13}$, —$N(R^{17})CONR^{14}R^{15}$, —$N(R^{17})COOR^{13}$, —$SO_3H$, —$SO_2NR^{14}R^{15}$, —C(=$NR^{17}$)$NR^{14}R^{15}$, —$N(R^{17})SO_2R^{16}$, and a 5 or 6-membered heterocyclic group;

or X and an adjacent $R^3$, taken together with the atoms to which they are bonded, form an alkylenedioxy moiety;

Z is CH, $CR^3$ or N, wherein when Z is CH or $CR^3$, k is 0-4 and t is 0 or 1, and when Z is N, k is 0-3 and t is 0;

Y is selected from —O—, —S—, —N($R^{10}$)—, and —C($R^4$)($R^5$)—;

$W^1$ is selected from $C_1$-$C_6$ alkyl, $C_3$-$C_8$ cycloalkyl, aryl and Het, wherein said $C_1$-$C_8$ alkyl, $C_3$-$C_8$ cycloalkyl, Ar and Het are optionally unsubstituted or substituted with one or more groups independently selected from halo, cyano, nitro, $C_1$-$C_6$ alkyl, $C_3$-$C_6$ alkenyl, $C_3$-$C_6$ alkynyl, —$C_0$-$C_6$ alkyl-$CO_2R^{10}$, —$C_0$-$C_6$ alkyl-C(O)$SR^{10}$, —$C_0$-$C_6$ alkyl-$CONR^{11}R^{12}$, —$C_0$-$C_6$ alkyl-$COR^{13}$, —$C_0$-$C_6$ alkyl-$NR^{11}R^{12}$, —$C_0$-$C_6$ alkyl-$SR^{10}$, —$C_0$-$C_6$ alkyl-$OR^{10}$, —$C_0$-$C_6$ alkyl-$SO_3H$, —$C_0$-$C_6$ alkyl-$SO_2NR^{11}R^{12}$, —$C_0$-$C_6$ alkyl-$SO_2R^{10}$, —$C_0$-$C_6$ alkyl-$SOR^{13}$, —$C_0$-$C_6$ alkyl-$OCOR^{13}$, —$C_0$-$C_6$ alkyl-OC(O)$NR^{11}R^{12}$, —$C_0$-$C_6$ alkyl-OC(O)$OR^{13}$, —$C_0$-$C_6$ alkyl-$NR^{11}C(O)OR^{13}$, —$C_0$-$C_6$ alkyl-$NR^{11}C(O)NR^{11}R^{12}$, and —$C_0$-$C_6$ alkyl-$NR^{11}COR^{13}$, where said $C_1$-$C_6$ alkyl, is optionally unsubstituted or substituted by one or more halo substituents;

$W^2$ is selected from H, halo, $C_1$-$C_6$ alkyl, $C_2$-$C_6$ alkenyl, $C_2$-$C_6$ alkynyl, —$C_0$-$C_6$ alkyl-$NR^{11}R^{12}$, —$C_0$-$C_6$ alkyl-$SR^{10}$, —$C_1$-$C_6$ alkyl-$OR^{10}$, —$C_0$-$C_6$ alkyl-$CO_2R^{10}$, —$C_0$-$C_6$ alkyl-C(O)$SR^{10}$, —$C_0$-$C_6$ alkyl-$CONR^{11}R^{12}$, —$C_0$-$C_6$ alkyl-$COR^{13}$, —$C_0$-$C_6$ alkyl-$OCOR^{13}$, —$C_0$-$C_6$ alkyl-$OCONR^{11}R^2$, —$C_0$-$C_6$ alkyl-$NR^{11}CONR^{11}R^{12}$, —$C_0$-$C_6$ alkyl-$NR^{11}COR^{13}$, —$C_0$-$C_6$ alkyl-Het, —$C_0$-$C_6$ alkyl-Ar and —$C_0$-$C_6$ alkyl-$C_3$-$C_7$ cycloalkyl, wherein said $C_1$-$C_6$ alkyl is optionally unsubstituted or substituted by one or more halo substituents, and wherein the $C_3$-$C_7$ cycloalkyl, Ar and Het moieties of said —$C_0$-$C_6$ alkyl-Het, —$C_0$-$C_6$ alkyl-Ar and —$C_0$-$C_6$ alkyl-$C_3$-$C_7$ cycloalkyl are optionally unsubstituted or substituted with one or more groups independently selected from halo, cyano, nitro, $C_1$-$C_6$ alkyl, $C_3$-$C_6$ alkenyl, $C_3$-$C_6$ alkynyl, —$C_0$-$C_6$ alkyl-$CO_2R^{10}$, —$C_0$-$C_6$ alkyl-C(O)$SR^{10}$, —$C_0$-$C_6$ alkyl-$CONR^{11}R^{12}$, —$C_0$-$C_6$ alkyl-$COR^{13}$, —$C_0$-$C_6$ alkyl-$NR^{11}R^{12}$, —$C_0$-$C_6$ alkyl-$SR^{10}$, —$C_0$-$C_6$ alkyl-$OR^{10}$, —$C_0$-$C_6$ alkyl-$SO_3H$, —$C_0$-$C_6$ alkyl-$SO_2NR^{11}R^{12}$, —$C_0$-$C_6$ alkyl-$SO_2R^{10}$, —$C_0$-$C_6$ alkyl $OR^{13}$, —$C_0$-$C_6$ alkyl-$OCOR^{13}$, $C_0$-$C_6$ alkyl-OC(O)$NR^{11}R^{12}$, —$C_0$-$C_6$ alkyl-OC(O)$OR^{13}$, —$C_0$-$C_6$ alkyl-$NR^{11}C(O)OR^{13}$, —$C_0$-$C_6$ alkyl-$NR^{11}C(O)NR^{11}R^{12}$ and —$C_0$-$C_6$ alkyl-$NR^{11}COR^{13}$, where said $C_1$-$C_6$ alkyl, is optionally unsubstituted or substituted by one or more halo substituents;

$W^3$ is selected from the group consisting of: H, halo, $C_1$-$C_6$ alkyl, —$C_0$-$C_6$ alkyl-$NR^{11}R^{12}$, —$C_0$-$C_6$ alkyl-$SR^{11}$, —$C_0$-$C_6$ alkyl-$OR^{10}$, —$C_0$-$C_6$ alkyl-$CO_2R^{10}$, —$C_0$-$C_6$ alkyl-C(O)$SR^{10}$, —$C_0$-$C_6$ alkyl-$CONR^{11}R^{12}$, —$C_0$-$C_6$ alkyl-$COR^{13}$, —$C_0$-$C_6$ alkyl-$OCOR^{13}$, —$C_0$-$C_6$ alkyl-$OCONR^{11}R^{12}$, —$C_0$-$C_6$ alkyl-$NR^{11}CONR^{11}R^{12}$, —$C_0$-$C_6$ alkyl-$NRCOR^{13}$, —$C_0$-$C_6$ alkyl-Het, —$C_1$-$C_6$ alkyl-Ar and —$C_1$-$C_6$ alkyl-$C_3$-$C_7$ cycloalkyl, wherein said $C_1$-$C_6$ alkyl is optionally unsubstituted or substituted by one or more halo substituents;

Q is selected from $C_3$-$C_8$ cycloalkyl, Ar and Het; wherein said $C_3$-$C_8$ cycloalkyl, Ar and Het are optionally unsubstituted or substituted with one or more groups independently selected from halo, cyano, nitro, $C_1$-$C_6$ alkyl, $C_3$-$C_6$ alkenyl, $C_3$-$C_6$ alkynyl, —$C_0$-$C_6$ alkyl-$CO_2R'''$, —$C_0$-$C_6$ alkyl-C(O)$SR^{10}$, —$C_0$-$C_6$ alkyl-$CONR^{11}R^{12}$, —$C_0$-$C_6$ alkyl-$COR^{13}$, —$C_0$-$C_6$ alkyl-$NR^{11}R^{12}$, —$C_0$-$C_6$ alkyl-$SR^{10}$, —$C_0$-$C_6$ alkyl-$OR^{10}$, —$C_0$-$C_6$ alkyl-$SO_3H$, —$C_0$-$C_6$ alkyl-$NR^{11}R^{12}$, —$C_0$-$C_6$ alkyl-$SO_2R^{10}$, —$C_0$-$C_6$ alkyl-$SOR^{13}$, —$C_0$-$C_6$ alkyl-$OCOR^{13}$, —$C_0$-$C_6$ alkyl-OC(O)$NR^{11}R^{12}$, —$C_0$-$C_6$ alkyl-OC(O)$OR^{13}$, —$C_0$-$C_6$ alkyl-$NR^{11}C(O)OR^{13}$, —$C_0$-$C_6$ alkyl-$NR^{11}C(O)NR^{11}R^{12}$, and —$C_0$-$C_6$ alkyl-$NR^{11}COR^{13}$, where said $C_1$-$C_6$ alkyl is optionally unsubstituted or substituted by one or more halo substituents;

p is 0-8;

n is 2-8;

m is 0 or 1;

q is 0 or 1;

t is 0 or 1;

each $R^1$ and $R^2$ are independently selected from H, halo, $C_1$-$C_6$ alkyl, $C_3$-$C_6$ alkenyl, $C_3$-$C_6$ alkynyl, —$C_0$-$C_6$ alkyl-$NR^{11}R^{12}$, —$C_0$-$C_6$ alkyl-$OR^{10}$, —$C_0$-$C_6$ alkyl-$SR^{10}$, —$C_0$-$C_6$ alkyl-Het, —$C_1$-$C_6$ alkyl-Ar and —$C_1$-$C_6$ alkyl-$C_3$-$C_7$ cycloalkyl, or $R^1$ and $R^2$ together with the carbon to which they are attached form a 3-5 membered carbocyclic or heterocyclic ring, wherein said heterocyclic ring contains one, or more heteroatoms selected from N, O, and S, where any of said $C_1$-$C_6$ alkyl is optionally unsubstituted or substituted by one or more halo substituents;

each $R^3$ is the same or different and is independently selected from halo, cyano, nitro, $C_1$-$C_6$ alkyl, $C_3$-$C_6$ alkenyl, $C_3$-$C_6$ alkynyl, —$C_0$-$C_6$ alkyl-Ar, —$C_0$-$C_6$ alkyl-Het, —$C_0$-$C_6$ alkyl-$C_3$-$C_7$ cycloalkyl, —$C_0$-$C_6$ alkyl-$CO_2R^{10}$, —$C_0$-$C_6$ alkyl-$C(O)SR^{10}$, —$C_0$-$C_6$ alkyl-$CONR^{11}R^{12}$, —$C_0$-$C_6$ alkyl-$COR^{13}$, —$C_0$-$C_6$ alkyl-$NR^{11}R^{12}$, —$C_0$-$C_6$ alkyl-$SR^{10}$, —$C_0$-$C_6$ alkyl-$OR^{10}$, —$C_0$-$C_6$ alkyl-$SO_3H$, —$C_0$-$C_6$ alkyl-$SO_2NR^{11}R^{12}$, —$C_0$-$C_6$ alkyl-$SO_2R^{10}$, —$C_0$-$C_6$ alkyl-$SOR^{13}$, —$C_0$-$C_6$ alkyl-$OCOR^{13}$, —$C_0$-$C_6$ alkyl-$OC(O)NR^{11}R^{13}$, —$C_0$-$C_6$ alkyl-$OC(O)OR^{13}$, —$C_0$-$C_6$ alkyl-$NR^{11}C(O)OR^{13}$, —$C_0$-$C_6$ alkyl-$NR^{11}C(O)NR^{11}R^{12}$, and —$C_0$-$C_6$ alkyl-$NR^{11}COR^{13}$, wherein said $C_1$-$C_6$ alkyl is optionally unsubstituted or substituted by one or more halo substituents;

each $R^4$ and $R^5$ is independently selected from H, halo, $C_1$-$C_6$ alkyl, —$C_0$-$C_6$ alkyl-Het, —$C_0$-$C_6$ alkyl-Ar and —$C_0$-$C_6$ alkyl-$C_3$-$C_7$ cycloalkyl;

$R^6$ and $R^7$ are each independently selected from H, halo, $C_1$-$C_6$ alkyl, —$C_0$-$C_6$ alkyl-Het, —$C_0$-$C_6$ alkyl-Ar and —$C_0$-$C_6$ alkyl-$C_3$-$C_7$ cycloalkyl;

$R^8$ and $R^9$ are each independently selected from H, halo, $C_1$-$C_6$ alkyl, —$C_0$-$C_6$ alkyl-Het, —$C_0$-$C_6$ alkyl-Ar and —$C_0$-$C_6$ alkyl-$C_3$-$C_7$ cycloalkyl;

$R^{10}$ is selected from H, $C_1$-$C_6$ alkyl, $C_3$-$C_6$ alkenyl, $C_3$-$C_6$ alkynyl, —$C_0$-$C_6$ alkyl-Ar, —$C_0$-$C_6$ alkyl-Het and —$C_0$-$C_6$ alkyl-$C_3$-$C_7$ cycloalkyl;

each $R^{11}$ and each $R^{12}$ are independently selected from H, $C_1$-$C_6$ alkyl, $C_3$-$C_6$ alkenyl, $C_3$-$C_6$ alkynyl, —$C_0$-$C_6$ alkyl-Ar, —$C_0$-$C_6$ alkyl-Het and —$C_0$-$C_6$ alkyl-$C_3$-$C_7$ cycloalkyl, or $R^{11}$ and $R^{12}$ together with the nitrogen to which they are attached form a 4-7 membered heterocyclic ring which optionally contains one or more additional heteroatoms selected from N, O, and S;

$R^{13}$ is selected from $C_1$-$C_6$ alkyl, $C_3$-$C_6$ alkenyl, $C_3$-$C_6$ alkynyl, —$C_0$-$C_6$ alkyl-Ar, —$C_0$-$C_6$ alkyl-Het and —$C_0$-$C_6$ alkyl-$C_3$-$C_7$ cycloalkyl;

$R^{14}$ and $R^{15}$ are each independently selected from H, $C_1$-$C_6$ alkyl, $C_3$-$C_6$ alkenyl, $C_3$-$C_6$ alkynyl, —$C_0$-$C_6$ alkyl-Ar, —$C_0$-$C_6$ alkyl-Het, —$C_0$-$C_6$ alkyl-$C_3$-$C_7$ cycloalkyl, —$C_0$-$C_6$ alkyl-O—Ar, —$C_0$-$C_6$ alkyl-O-Het, —$C_0$-$C_6$ alkyl-O—$C_3$-$C_7$ cycloalkyl, —$C_0$-$C_6$ alkyl-$S(O)_x$—$C_1$-$C_6$ alkyl, —$C_0$-$C_6$ alkyl-$S(O)_x$—Ar, —$C_0$-$C_6$ alkyl-$S(O)_x$-Het, —$C_0$-$C_6$ alkyl-$S(O)_x$—$C_3$-$C_7$ cycloalkyl, —$C_0$-$C_6$ alkyl-NH-Het, —$C_0$-$C_6$ alkyl-NH—$C_3$-$C_7$ cycloalkyl, —$C_0$-$C_6$ alkyl-$N(C_1$-$C_4$ alkyl)-Ar, —$C_0$-$C_6$ alkyl-$N(C_1$-$C_4$ alkyl)-Het, —$C_0$-$C_6$ alkyl-$N(C_1$-$C_4$ alkyl)-$C_3$-$C_7$ cycloalkyl, —$C_0$-$C_6$ alkyl-Ar, —$C_0$-$C_6$ alkyl-Het and —$C_0$-$C_6$ alkyl-$C_3$-$C_7$ cycloalkyl, where x is 0, 1 or 2, or $R^{14}$ and $R^{15}$, together with the nitrogen to which they are attached, form a 4-7 membered heterocyclic ring which optionally contains one or more additional heteroatoms selected from N, O, and S, wherein said $C_1$-$C_6$ alkyl is optionally substituted by one or more of the substituents independently selected from the group halo, —OH, —SH, —$NH_2$, —NH(unsubstituted $C_1$-$C_6$ alkyl), —N(unsubstituted $C_1$-$C_6$ alkyl)(unsubstituted $C_1$-$C_6$ alkyl), unsubstituted —$OC_1$-$C_6$ alkyl, —$CO_2H$, —$CO_2$(unsubstituted $C_1$-$C_6$ alkyl), —$CONH_2$, —CONH(unsubstituted $C_1$-$C_6$ alkyl), —CON(unsubstituted $C_1$-$C_6$ alkyl)(unsubstituted $C_1$-$C_6$ alkyl), —$SO_3H$, —$SO_2NH_2$, —$SO_2NH$(unsubstituted $C_1$-$C_6$ alkyl) and —$SO_2N$(unsubstituted $C_1$-$C_8$ alkyl)(unsubstituted $C_1$-$C_6$ alkyl);

$R^{16}$ is $C_1$-$C_6$ alkyl, —$C_0$-$C_6$ alkyl-Ar or —$C_0$-$C_6$ alkyl-Het; and $R^{17}$ is H, $C_1$-$C_6$ alkyl, —$C_0$-$C_6$ alkyl-Ar or —$C_0$-$C_6$ alkyl-Het;

provided that X is not $COOR^{10}$ when Y is —O—, p is 0-8, n is 2-8, m is 1, q is 0 or 1, t is 0, each $R^1$ and $R^2$ is independently selected from H, $C_1$-$C_6$ alkyl, —OH, —O—$C_1$-$C_6$ alkyl, —SH, and —S—$C_1$-$C_6$ alkyl, each $R^4$, $R^5$, $R^6$, $R^7$, $R^8$ and $R^9$ are independently H or $C_1$-$C_4$ alkyl, k is 0 or 1, $W^3$ is H, $W^1$ and $W^2$ are each independently selected from $C_3$-$C_8$ cycloalkyl and aryl and $R^3$ and Q are as defined above;

or a pharmaceutically acceptable salt or solvate thereof.

Also included within the scope of this invention are methods for preparing compounds of this invention, or pharmaceutically acceptable salts or solvates thereof.

Unless otherwise provided, each alkyl, alkoxy, alkenyl, alkynyl, cycloalkyl, aryl or Het (including any 3-5-membered, 4-7-membered, 56-membered or 5-7-membered carbocyclic or heterocyclic rings or ring moieties) herein is independently unsubstituted or substituted with one ore more substituents defined hereinbelow.

LXR mediated diseases or conditions include inflammation, cardiovascular disease and atherosclerosis. Accordingly, the methods of this invention further comprise methods for increasing reverse cholesterol transport, inhibiting cholesterol absorption, and decreasing inflammation. The present invention also provides pharmaceutical compositions comprising a compound of this invention.

DETAILED DESCRIPTION OF THE INVENTION

As used herein, the term "alkyl" represents a straight-or branched-chain saturated hydrocarbon, containing 1 to 10 carbon atoms, unless otherwise provided, which may be unsubstituted or substituted by one or more of the substituents described below. Exemplary alkyls include, but are not limited to methyl (Me), ethyl (Et), n-propyl, isopropyl, n-butyl, isobutyl, t-butyl, n-pentyl, neopentyl and hexyl and structural isomers thereof. Any "alkyl" herein may be optionally substituted by one or more of the substituents independently selected from the group halo, —OH, —SH, —$NH_2$, —NH(unsubstituted $C_1$-$C_6$ alkyl), —N(unsubstituted $C_1$-$C_6$ alkyl)(unsubstituted $C_1$-$C_6$ alkyl), unsubstituted —$OC_1$-$C_6$ alkyl, —$CO_2H$, and —$CO_2$(unsubstituted $C_1$-$C_6$ alkyl).

When combined with another substituent term (e.g., aryl or cycloalkyl as in -alkyl-Ar or -alkyl-cycloalkyl), the "alkyl" term therein refers to an alkylene moiety, that is, an unsubstituted divalent straight-or branched-chain saturated hydrocarbon moiety, containing 1 to 10 carbon atoms, unless otherwise provided. For example, the term "—$C_0$-$C_6$ alkyl-Ar", where C is 1-6 is intended to mean the radical -alkyl-aryl (e.g., —$CH_2$-aryl or —$CH(CH_3)$-aryl) and is represented by the bonding arrangement present in a benzyl group. The term "$C_0$ alkyl" in a moiety, such as —$C_0$-$C_6$ alkyl-Ar or —O—($C_0$-$C_6$ alkyl)-Ar, provides for no alkyl/alkylene group being present in the moiety. Thus, when C is zero, —$C_0$-$C_6$ alkyl-Ar is equivalent to —Ar and —O-($C_0$-$C_6$ alkyl)-Ar is equivalent to —O—Ar.

As used herein, the term "alkenyl" represents a straight-or branched-chain hydrocarbon, containing 2 to 10 carbon atoms, unless otherwise provided, and one or more carbon-carbon double bonds. Alkenyl groups may be unsubstituted or substituted by one or more of the substituents described below. Exemplary alkenyls include, but are not limited ethenyl, 1-propenyl, 2-propenyl, 1-butenyl, 2-butenyl, isobutenyl, butadienyl, pentenyl and hexenyl and structural isomers thereof. Both cis (Z) and trans (E) isomers of each double bond that may be present in the compounds of this invention are included within the scope of this invention. Any "alkenyl" herein may be optionally substituted by one or more of the substituents independently selected from the group halo, —OH, —SH, —NH$_2$, —NH(unsubstituted C$_1$-C$_6$ alkyl), —N(unsubstituted C$_1$-C$_6$ alkyl)(unsubstituted C$_1$-C$_6$ alkyl), unsubstituted —OC$_1$-C$_6$ alkyl, —CO$_2$H, and —CO$_2$(unsubstituted C$_1$-C$_6$ alkyl).

As used herein, the term "alkynyl" represents a straight-or branched-chain hydrocarbon, containing 2 to 10 carbon atoms, unless otherwise provided, and one or more carbon-carbon triple bonds and, optionally, one or more carbon-carbon double bonds. Both cis (Z) and trans (E) isomers of each double bond that may be present in the compounds of this invention are included within the scope of this invention. Exemplary alkynyls include, but are not limited ethynyl, propynyl (propargyl, isopropynyl), 1-butynyl, 2-butynyl, 3-butynyl, pentynyl and hexynyl and structural isomers thereof. Any "alkynyl" herein may be optionally substituted by one or more of the substituents independently selected from the group halo, —OH, —SH, —NH$_2$, —NH(unsubstituted C$_1$-C$_6$ alkyl), —N(unsubstituted C$_1$-C$_6$ alkyl)(unsubstituted C$_1$-C$_6$ alkyl), unsubstituted —OC$_1$-C$_6$ alkyl, —CO$_2$H, and —CO$_2$(unsubstituted C$_1$-C$_6$ alkyl).

For the purposes of this invention, when an alkenyl or alkynyl group is a substituent on an oxygen, nitrogen or sulfur atom (e.g., as in oxy (—OR), thio (—SR), ester (—CO$_2$R or —C(O)SR), amino (—NRR) or amido (—CONRR) moieties and the like), it is understood that a double or triple bond of the alkenyl or alkynyl group is not located on carbons that are α,β to the oxygen, nitrogen or sulfur atom. Compounds containing ene-amino or enol-type moieties (—NR—CR═CR— or —O—CR═CR—) are not intended to be included within the scope of this invention.

"Cycloalkyl" represents a non-aromatic monocyclic, bicyclic, or tricyclic hydrocarbon containing from 3 to 10 carbon atoms which may be unsubstituted or substituted by one or more of the substituents described below and may be saturated or partially unsaturated. Exemplary cycloalkyls include monocyclic rings having from 3-7, preferably 36, carbon atoms, such as cyclopropyl, cyclobutyl, cyclopentyl, cyclopentenyl, cyclopentadienyl, cyclohexyl, cyclohexenyl and cycloheptyl. Any "cycloalkyl" herein may be optionally substituted by one or more of the substituents independently selected from the group halo, cyano, C$_1$-C$_6$ alkyl (which specifically includes C$_1$-C$_6$ haloalkyl, —C$_0$-C$_6$ alkyl-OH, —C$_0$-C$_6$ alkyl-SH and —C$_0$-C$_6$ alkyl-NR'R"), C$_3$-C$_6$ alkenyl, oxo, —OC$_1$-C$_6$alkyl, —OC$_1$-C$_6$ alkenyl, —C$_0$-C$_6$ alkyl-COR', —C$_0$-C$_6$ alkyl-CO$_2$R', —C$_0$-C$_6$ alkyl-CONR'R", —OC$_0$-C$_6$ alkyl-CO$_2$H, —OC$_2$-C$_6$ alkyl-NR'R", and —C$_0$-C$_6$ alkyl-SO$_2$NR'R", wherein each R' and R" are independently selected from H and unsubstituted C$_1$-C$_6$ alkyl.

The terms "Ar" or "aryl" as used herein interchangeably at all occurrences mean a substituted or unsubstituted carbocyclic aromatic group, which may be optionally fused to another carbocyclic aromatic group moiety or to a cycloalkyl group moiety, which may be optionally substituted or unsubstituted. Examples of suitable Ar or aryl groups include phenyl, naphthyl indenyl, 1-oxo-1H-indenyl and tetrahydronaphthyl. Any "Ar", "aryl" or "phenyl" herein may be optionally unsubstituted or substituted by one or more of the substituents independently selected from the group halo, cyano, C$_1$-C$_6$ alkyl (which specifically includes C$_1$-C$_6$ haloalkyl, —C$_0$-C$_6$ alkyl-OH, —C$_0$-C$_6$ alkyl-SH and —C$_0$-C$_6$ alkyl-NR'R"), C$_3$-C$_6$ alkenyl, —OC$_1$-C$_6$alkyl, —OC$_1$-C$_6$ alkenyl, —C$_0$-C$_6$ alkyl-COR', —C$_0$-C$_6$ alkyl-CO$_2$R', —C$_0$-C$_6$ alkyl-CONR'R", —OC$_0$-C$_6$ alkyl-CO$_2$H, —OC$_2$-C$_6$ alkyl-NR'R", —C$_0$-C$_6$ alkyl-C(═NR')NR'R", and —C$_0$-C$_6$ alkyl-SO$_2$NR'R", wherein each R' and R" are independently selected from H and unsubstituted C$_1$-C$_6$ alkyl.

The term "Het" as used herein means a stable 5- to 7-membered monocyclic, a stable 7- to 10-membered bicyclic, or a stable 11- to 18-membered tricyclic heterocyclic ring group, all of which are saturated, unsaturated or aromatic, and consist of carbon atoms and from one to three heteroatoms selected from N, O and S, and which includes bicyclic and tricyclic rings containing one or more fused cycloalkyl, aryl (e.g., phenyl) or heteroaryl (aromatic Het) ring moieties. As used herein the term "Het is also intended to encompass heterocyclic groups containing nitrogen and/or sulfur where the nitrogen or sulfur heteroatoms are optionally oxidized or the nitrogen heteroatom is optionally quaternized. The heterocyclic group may be attached at any heteroatom or carbon atom that results in the creation of a stable structure. Any "Het" herein may be optionally unsubstituted or substituted by one or more of the substituents independently selected from the group halo, cyano, C$_1$-C$_6$ alkyl (which specifically includes C$_0$-C$_6$ haloalkyl, —C$_0$-C$_6$ alkyl-OH, —C$_0$-C$_6$ alkyl-SH and —C$_0$-C$_6$ alkyl-NR'R"), C$_3$-C$_6$ alkenyl, oxo, —OC$_1$-C$_6$alkyl, —OC$_1$-C$_6$ alkenyl, —C$_0$-C$_6$ alkyl-COR', —C$_0$-C$_6$ alkyl-CO$_2$R', —C$_0$-C$_6$ alkyl-CONR'R", —OC$_0$-C$_6$ alkyl-CO$_2$H, —OC$_2$-C$_6$ alkyl-NR'R", —C$_0$-C$_6$ alkyl-C(═NR')NR'R" and —C$_0$-C$_6$ alkyl-SO$_2$NR'R", wherein each R' and R" are independently selected from H and unsubstituted C$_1$-C$_6$ alkyl.

Examples of such heterocyclic groups include, but are not limited to piperidinyl, piperazinyl, 2-oxopiperazinyl, 2-oxopiperidinyl, 2-oxopyrrolodinyl, 2-oxoazepinyl, azepanyl, pyrrolyl, 4-piperidonyl, pyrrolidinyl, pyrazolyl, pyrazolidinyl, imidazolyl, pyridinyl, pyrazinyl, oxazolidinyl, oxazolinyl, oxazolyl, isoxazolyl, morpholinyl, thiazolidinyl, thiazolinyl, thiazolyl, 1,3-benzodioxolyl (e.g., methylenedioxy-substituted phenyl), 1,4-benzodioxolyl, quinuclidinyl, indolyl, quinolinyl, isoquinolinyl, benzimidazolyl, benzopyranyl, benzoxazolyl, furyl, pyranyl, tetrahydrofuryl, tetrahydropyranyl, thienyl, benzoxazolyl, benzofuranyl, benzothienyl, dihydrobenzofuranyl, dihydrobenzothienyl, dihydroindolyl, tetrazolyl, thiamorpholinyl sulfoxide, thiamorpholinyl sulfone, and oxadiazolyl, as well as triazolyl, thiadiazolyl, oxadiazolyl, isoxazolyl, isothiazolyl, imidazolyl, pyridazinyl, pyrimidinyl and triazinyl which are available by routine chemical synthesis and are stable.

Examples of the 4-7 membered heterocyclic rings useful in the compounds of this invention, include, but are not limited to azetidinyl, piperidinyl, piperazinyl, 2-oxopiperazinyl, 2-oxopiperidinyl, 2-oxopyrrolodinyl, azepanyl, pyrrolyl, 4-piperidonyl, pyrrolidinyl, pyrazolyl, pyrazolidinyl, imidazolyl, pyridinyl, pyrazinyl, oxazolidinyl, oxazolinyl, oxazolyl, isoxazolyl, morpholinyl, thiazolidinyl, thiazolinyl, thiazolyl, furyl, pyranyl, tetrahydrofuryl, tetrahydropyranyl, thienyl, tetrazolyl, thiamorpholinyl sulfoxide, thiamorpholinyl sulfone, and oxadiazolyl, as well as triazolyl, thiadiazolyl, oxadiazolyl, isoxazolyl, isothiazolyl, imidazolyl, pyridazinyl, pyrimidinyl and triazinyl which are available by routine chemical synthesis and are stable. The 4-7 membered heterocyclic group may be optionally unsubstituted or substituted by one or more of the substituents independently selected from the group halo, cyano, $C_1$-$C_6$ alkyl (which specifically includes $C_0$-$C_6$ haloalkyl, —$C_0$-$C_6$ alkyl-OH, —$C_0$-$C_6$ alkyl-SH and —$C_0$-$C_6$ alkyl-NR'R"), $C_3$-$C_6$ alkenyl, oxo, —$OC_1$-$C_6$alkyl, —$OC_1$-$C_5$ alkenyl, —$C_0$-$C_6$ alkyl-COR', —$C_0$-$C_6$ alkyl-$CO_2$R', —$C_0$-$C_6$ alkyl-CONR'R", —$OC_0$-$C_6$ alkyl-$CO_2$H, —$OC_2$-$C_6$ alkyl-NR'R", —$C_0$-$C_6$ alkyl-C(=NR')NR'R" and —$C_0$-$C_6$ alkyl-$SO_2$NR'R", wherein each R' and R" are independently selected from H and unsubstituted $C_1$-$C_6$ alkyl.

Examples of 5 or 6 membered heterocyclic groups include, but are not limited to piperidinyl, piperazinyl, 2-oxopiperazinyl, 2-oxopiperidinyl, 2-oxopyrrolodinyl, pyrrolyl, 4-piperidonyl, pyrrolidinyl, pyrazolyl, pyrazolidinyl, imidazolyl, pyridinyl, pyrazinyl, oxazolidinyl, oxazolinyl, oxazolyl, isoxazolyl, morpholinyl, thiazolidinyl, thiazolinyl, thiazolyl, furyl, pyranyl, tetrahydrofuryl, tetrahydropyranyl, thienyl, tetrazolyl, thiamorpholinyl sulfoxide, thiamorpholinyl sulfone, and oxadiazolyl, as well as triazolyl, thiadiazolyl, oxadiazolyl, isoxazolyl, isothiazolyl, imidazolyl, pyridinyl, pyrimidinyl and triazinyl which are available by routine chemical synthesis and are stable. The 5-6 membered heterocyclic group may be attached at any heteroatom or carbon atom that results in the creation of a stable structure. The 5-6 membered heterocyclic group may be optionally unsubstituted or substituted by one or more of the substituents independently selected from the group halo, cyano, $C_1$-$C_6$ alkyl (which specifically includes $C_1$-$C_6$ haloalkyl, —$C_0$-$C_6$ alkyl-OH, —$C_0$-$C_6$ alkyl-SH and —$C_0$-$C_6$ alkyl-NR'R"), $C_3$-$C_6$ alkenyl, oxo, —$OC_1$-$C_6$ alkyl, —$OC_3$-$C_6$ alkenyl, —$C_0$-$C_6$ alkyl-COR', —$C_0$-$C_6$ alkyl-$CO_2$R', —$C_0$-$C_6$ alkyl-CONR'R", —$OC_0$-$C_6$ alkyl-$CO_2$H, —$OC_2$-$C_6$ alkyl-NR'R", —$C_0$-$C_6$ alkyl-C(=NR')NR'R" and —$C_0$-$C_6$ alkyl-$SO_2$NR'R", wherein each R' and R" are independently selected from H and unsubstituted $C_1$-$C_6$ alkyl.

The terms "halogen" and "halo" represent chloro, fluoro, bromo or iodo substituents. "Alkoxy" is intended to mean the radical —$OR_a$, where $R_a$ is an alkyl group, wherein alkyl is as defined above, provided that —O—$C_1$ alkyl may be optionally substituted by one or more of the substituents independently selected from the group halo and —$CO_2$H. Exemplary alkoxy groups include methoxy, ethoxy, propoxy, and the like. "Phenoxy" is intended to mean the radical —$OR_{ar}$, where $R_{ar}$ is a phenyl group. "Acetoxy" is intended to mean the radical —O—C(=O)-methyl. "Benzoyloxy" is intended to mean the radical —O—C(=O)-phenyl. "Alkylenedioxy" is intended to mean the divalent radical —$OR_a$O— which is bonded to adjacent atoms (e.g., adjacent atoms on a phenyl or naphthyl ring), wherein $R_a$ is a lower alkyl group. "Oxo" is intended to mean the keto diradical =O, such as present on a pyrrolidin-2-one ring.

If a substituent described herein is not compatible with the synthetic methods of this invention, the substituent may be protected with a suitable protecting group that is stable to the reaction conditions used in these methods. The protecting group may be removed at a suitable point in the reaction sequence of the method to provide a desired intermediate or target compound. Suitable protecting groups and the methods for protecting and de-protecting different substituents using such suitable protecting groups are well known to those skilled in the art; examples of which may be found in T. Greene and P. Wuts, *Protecting Groups in Chemical Synthesis* (3rd ed.), John Wiley & Sons, NY (1999), which is incorporated herein by reference in its entirety. In some instances, a substituent may be specifically selected to be reactive under the reaction conditions used in the methods of this invention. Under these circumstances, the reaction conditions convert the selected substituent into another substituent that is either useful as an intermediate compound in the methods of this invention or is a desired substituent in a target compound.

The term "pharmaceutically acceptable salt" is intended to describe a salt that retains the biological effectiveness of the free acid or base of a specified compound and is not biologically or otherwise undesirable.

If an inventive compound is a base, a desired salt may be prepared by any suitable method known in the art, including treatment of the free base with an inorganic acid, such as hydrochloric acid, hydrobromic acid, sulfuric acid, sulfamic acid, nitric acid, phosphoric acid, metaphosphoric acid and the like, or with an organic acid, such as acetic acid, trifluoroacetic acid, formic acid, maleic acid, lactic acid, succinic acid, mandelic acid, fumaric acid, malonic acid, malic acid, pyruvic acid, oxalic acid, glycolic acid, citric acid, tartaric acid, gluconic acid, glutaric acid, lactobionic, orotic, cholic, a pyranosidyl acid, such as glucuronic acid or galacturonic acid, an amino acid, such as aspartic acid or glutamic acid, an aromatic acid, such as benzoic acid, salicylic acid, cinnamic acid, pamoic acid or 1-hydroxy-2-naphthoic acid, a sulfonic acid, such as benzenesulfonic acid, p-toluenesulfonic acid, naphthalenesulfonic acid, methanesulfonic acid, ethanesulfonic acid or the like. Additional examples of pharmaceutically acceptable salts include sulfates, pyrosulfates, bisulfates, sulfites, bisulfites, phosphates, chlorides, bromides, iodides, acetates, propionates, decanoates, caprylates, acrylates, formates, isobutyrates, caproates, heptanoates, propiolates, oxalates, malonates succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, phenylacetates, phenylpropionates, phenylbutrates, citrates, lactates, γ-hydroxybutyrates, glycollates, tartrates mandelates, and sulfonates, such as xylenesulfonates, methanesulfonates, propanesulfonates, naphthalene-1-sulfonates and naphthalene-2-sulfonates. Embodiments of a pharmaceutically acceptable salts (e.g., hydrochloride salts, dihydrochloride salts, methanesulfonate salts, dimethanesulfonate salts and trifluoroacetic acid salts) of the compounds of this invention are provided in the Examples.

If an inventive compound is an acid, a desired salt may be prepared by any suitable method known to the art, including treatment of the free acid with an excess of an inorganic or organic alkaline reagent. Illustrative examples of suitable salts include salts derived from ammonia; primary, secondary, tertiary amines (including secondary and tertiary cyclic amines), such as ethylene diamine, dicyclohexylamine, ethanolamine, piperidine, morpholine, and piperazine; salts derived from amino acids such as glycine and arginine; as well as salts derived from an alkali metal, alkaline earth metal, or ammonium hydroxide, carbonate, alkoxide or sulfate, such as sodium hydroxide, sodium carbonate, sodium bicarbonate, sodium sulfate, etc., and corresponding alkaline salts containing, for example, $Li^+$, $K^+$, $Ca^{++}$, $Mg^{++}$ and $NH_4^+$ cations.

The term "solvate" is intended to mean a pharmaceutically acceptable solvate form of a specified compound of this invention, or a salt thereof, that retains the biological effectiveness of such compound. Examples of solvates include compounds of the invention in combination with water, isopropanol, ethanol, methanol, DMSO, ethyl acetate, acetic acid, or ethanolamine. In the case of compounds, salts, or solvates that are solids, it is understood by those skilled in the art that the Inventive compounds, salts, or solvates may exist in different crystal forms, all of which are intended to be within the scope of the present invention and specified formulas.

Because the compounds of this invention may contain both acid and base moieties, pharmaceutically acceptable salts may be prepared by treating these compounds with an alkaline reagent or an acid reagent, respectively. Accordingly, this invention also provides for the conversion of one pharmaceutically acceptable salt of a compound of this invention, e.g., a hydrochloride salt, into another pharmaceutically acceptable salt of a compound of this invention, e.g., a mesylate salt or a sodium salt.

Also included within the scope of this invention are prodrugs of the compounds of this invention. The ester compounds of this invention, wherein X is other than —OH, may be considered prodrugs. Such ester compounds may be converted to compounds that are active as LXR modulators and may be, themselves, active as LXR modulators. The term "prodrug" is intended to mean a compound that is converted under physiological conditions, e.g., by solvolysis or metabolically, to a compound according to this invention that is pharmaceutically active. A prodrug may be a derivative of one of the compounds of this invention that contains a carboxylic or phosphoric acid ester or amide moiety that may be cleaved under physiological conditions. A prodrug containing such a moiety may be prepared according to conventional procedures, for example, by treatment of a compound of this invention containing an amino, amido or hydroxyl moiety with a suitable derivatizing agent, for example, a carboxylic or phosphoric acid halide or acid anhydride, or by converting a carboxyl moiety of a compound of this invention to an ester or amide. Prodrugs of the compounds of this invention may be determined using techniques known in the art, for example, through metabolic studies. See, e.g., "Design of Prodrugs," (H. Bundgaard, Ed.) 1985, Elsevier Publishers B. V., Amsterdam, The Netherlands.

It will be appreciated by those skilled in the art that the compounds of this invention may exist in different tautomeric forms. All tautomeric forms of the compounds described herein are intended to be encompassed within the scope of the present invention.

The compounds of this invention may contain at least one chiral center and may exist as single stereoisomers (e.g., single enantiomers), mixtures of stereoisomers (e.g., any mixture of enantiomers or diastereomers) or racemic mixtures thereof. All such single stereoisomers, mixtures and racemates are intended to be encompassed within the broad scope of the present invention. Compounds identified herein as single stereoisomers are meant to describe compounds that are present in a form that are at least 90% enantiomerically pure. Where the stereochemistry of the chiral carbons present in the chemical structures illustrated herein is not specified, the chemical structure is intended to encompass compounds containing either stereoisomer of each chiral center present in the compound. Such compounds may be obtained synthetically, according to the procedures described herein using optically pure (enantiomerically pure) or substantially optically pure materials. Alternatively, these compounds may be obtained by resolution/separation of a mixture of stereoisomers, including racemic mixtures, using conventional procedures. Exemplary methods that may be useful for the resolution/separation of mixtures of stereoisomers include chromatography and crystallization/re-crystallization. Other useful methods may be found in "*Enantiomers, Racemates, and Resolutions*," J. Jacques et al., 1981, John Wiley and Sons, New York, N.Y., the disclosure of which is incorporated herein by reference.

In one embodiment of this invention, the group X—$(CR^1R^2)_p$— is located on the

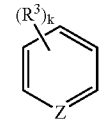

moiety in a position that is meta or para to the —Y—$(CR^4R^5)_n$— moiety. Preferably, the group X—$(CR^1R^2)_p$— is located in a position that is meta to the —Y—$(CR^4R^5)_n$— moiety.

In another embodiment, this invention is directed to a compound of Formula II:

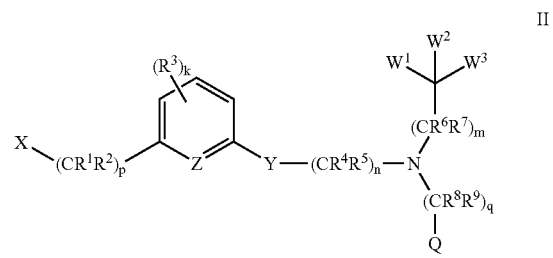

II wherein:

X is selected from $C_1$-$C_8$ alkyl, halo, —$OR^{10}$, —$NR^{14}R^{15}$, cyano, —$COR^{13}$, $COOR^{10}$, —$OCOR^{13}$, —$N(R^{17})COR^{13}$, —$N(R^{17})CONR^{14}R^{15}$, —$N(R^{17})COOR^{13}$, —$SO_2NR^{14}R^{15}$, —$C(=NR^{17})NR^{14}R^{15}$, —$N(R^{17})SO_2R^{16}$, and a 5 or 6-membered heterocyclic group;

or X and an adjacent $R^3$, taken together with the atoms to which they are bonded, form an alkylenedioxy moiety;

Z is CH or N, wherein k is 0, 1 or 2;

Y is —O— or —$C(R^4)(R^5)$—;

$W^1$ is $C_3$-$C_8$ cycloalkyl, aryl or Het, wherein said $C_3$-$C_8$ cycloalkyl, Ar and Het are optionally unsubstituted or substituted with one or more groups independently selected from halo, cyano, nitro, $C_1$-$C_6$ alkyl, $C_3$-$C_6$ alkenyl, $C_3$-$C_6$ alkynyl, —$C_0$-$C_4$ alkyl-$CO_2R^{10}$, —$C_0$-$C_4$ alkyl-C(O)SR, —$C_0$-$C_4$ alkyl-CONR$^{11}$R$^{12}$, —$C_0$-$C_4$ alkyl-COR$^{13}$, —$C_0$-$C_4$ alkyl-NR$^{11}$R$^{12}$, —$C_0$-$C_4$ alkyl-SR$^{10}$, —$C_0$-$C_4$ alkyl-OR$^{10}$, —$C_0$-$C_4$ alkyl-SO$_3$H, —$C_0$-$C_4$ alkyl-SO$_2$NR$^{11}$R$^{12}$, —$C_0$-$C_4$ alkyl-SO$_2$R$^{10}$, —$C_0$-$C_4$ alkyl-SOR$^{13}$, —$C_0$-$C_4$ alkyl-OCOR$^{13}$, —$C_0$-$C_4$ alkyl-OC(O)NR$^{11}$R$^{12}$, —$C_0$-$C_4$ alkyl-OC(O)OR$^{13}$, —$C_1$-$C_4$ alkyl-NR$^{11}$C(O)OR$^{13}$, —$C_0$-$C_4$ alkyl-NR$^{11}$C(O)NR$^{11}$R$^{12}$, and —$C_0$-$C_4$ alkyl-NR$^{11}$COR$^{13}$, where said $C_0$-$C_6$ alkyl is optionally unsubstituted or substituted by one or more halo substituents;

$W^2$ is selected from H, halo, $C_1$-$C_6$ alkyl, $C_2$-$C_6$ alkenyl, $C_2$-$C_6$ alkynyl, —$C_0$-$C_4$ alkyl-NR$^{11}$R$^{12}$, —$C_0$-$C_4$ alkyl-SR$^{10}$, —$C_0$-$C_4$ alkyl-OR$^{10}$, —$C_0$-$C_4$ alkyl-CO$_2$R$^{10}$, —$C_0$-$C_4$ alkyl-C(O)SR$^{10}$, —$C_0$-$C_4$ alkyl-CONR$^{11}$R$^{12}$, —$C_0$-$C_4$ alkyl-COR$^{13}$, —$C_0$-$C_4$ alkyl-OCOR$^{13}$, —$C_0$-$C_4$ alkyl-OCONR$^{11}$R$^{12}$, —$C_0$-$C_4$ alkyl-NR$^{11}$CONR$^{11}$R$^{12}$, —$C_0$-$C_4$ alkyl-NR$^{11}$CORR$^{13}$, —$C_0$-$C_4$ alkyl-Het, —$C_0$-$C_4$ alkyl-Ar and —$C_0$-$C_4$ alkyl-$C_3$-$C_7$ cycloalkyl, wherein said $C_1$-$C_6$ alkyl is optionally unsubstituted or substituted by one or more halo substituents, and wherein the $C_3$-$C_7$ cycloalkyl, Ar and Het moieties of said —$C_0$-$C_4$ alkyl-Het, —$C_0$-$C_4$ alkyl-Ar and —$C_0$-$C_4$ alkyl-$C_3$-$C_7$ cycloalkyl are optionally unsubstituted or substituted with one or more groups independently selected from halo, cyano, nitro, $C_1$-$C_6$ alkyl, $C_3$-$C_6$ alkenyl, $C_3$-$C_6$ alkynyl, —$C_0$-$C_4$ alkyl-$CO_2R^{10}$, —$C_0$-$C_4$ alkyl-C(O)$SR^{10}$, —$C_0$-$C_4$ alkyl-$CONR^{11}R^{12}$, —$C_0$-$C_4$ alkyl-$COR^{13}$, —$C_0$-$C_4$ alkyl-$NR^{11}R^{12}$, —$C_0$-$C_4$ alkyl-$SR^{10}$, —$C_0$-$C_4$ alkyl-$OR^{10}$, —$C_0$-$C_4$ alkyl-$SO_3H$, —$C_0$-$C_4$ alkyl-$SO_2NR^{11}R^{12}$, —$C_0$-$C_4$ alkyl-$SO_2R^{10}$, —$C_0$-$C_4$ alkyl-$SOR^{13}$, —$C_0$-$C_4$ alkyl-$OCOR^{13}$, —$C_0$-$C_4$ alkyl-OC(O)$NR^{11}R^{12}$, —$C_0$-$C_4$ alkyl-OC(O)$OR^{13}$, —$C_0$-$C_4$ alkyl-$NR^{11}C(O)OR^{13}$, —$C_0$-$C_4$ alkyl-$NR^{11}C(O)NR^{11}R^{12}$, and —$C_0$-$C_4$ alkyl-$NR^{11}COR^{13}$, where said $C_1$-$C_6$ alkyl is optionally unsubstituted or substituted by one or more halo substituents;

$W^3$ is selected from the group consisting of: H, halo, $C_1$-$C_6$ alkyl, —$C_0$-$C_4$ alkyl-$NR^{11}R^{12}$, —$C_0$-$C_4$ alkyl-$SR^{10}$, —$C_0$-$C_4$ alkyl-$OR^{10}$, —$C_0$-$C_4$ alkyl-$CO_2R^{10}$, —$C_0$-$C_4$ alkyl-C(O)$SR^{10}$, —$C_1$-$C_4$ alkyl-$CONR^{11}R^{12}$, —$C_0$-$C_4$ alkyl-$COR^{13}$, —$C_0$-$C_4$ alkyl-$OCOR^{13}$, —$C_0$-$C_4$ alkyl-$OCONR^{11}R^{12}$, —$C_0$-$C_4$ alkyl-$NR^{11}CONR^{11}R^{12}$, —$C_0$-$C_4$ alkyl-$NR^{11}COR^{13}$, —$C_0$-$C_4$ alkyl-Het, —$C_1$-$C_4$ alkyl-Ar and —$C_1$-$C_4$ alkyl-$C_3$-$C_7$ cycloalkyl, wherein said $C_1$-$C_6$ alkyl is optionally unsubstituted or substituted by one or more halo substituents;

Q is Ar or Het; wherein said Ar and Het are optionally unsubstituted or substituted with one or more groups independently selected from halo, cyano, nitro, $C_1$-$C_6$ alkyl, $C_3$-$C_6$ alkenyl, $C_3$-$C_6$ alkynyl, —$C_0$-$C_4$ alkyl-$CO_2R^{10}$, —$C_0$-$C_4$ alkyl-C(O)$SR^{10}$, —$C_0$-$C_4$ alkyl-$CONR^{11}R^{12}$, —$C_0$-$C_4$ alkyl-$COR^{13}$, —$C_0$-$C_4$alkyl-$NR^{11}R^{12}$, —$C_0$-$C_4$ alkyl-$SR^{10}$, —$C_0$-$C_4$ alkyl-$OR^{10}$, —$C_0$-$C_4$ alkyl-$SO_3H$, —$C_0$-$C_4$ alkyl-$SO_2NR^{11}R^{12}$, —$C_0$-$C_4$ alkyl-$SO_2R^{10}$, —$C_0$-$C_4$ alkyl-$SOR^{13}$, —$C_0$-$C_4$ alkyl-$OCOR^{13}$, —$C_0$-$C_4$alkyl-OC(O)$NR^{11}R^{12}$, —$C_0$-$C_4$ alkyl-OC(O)$OR^{13}$, —$C_0$-$C_4$ alkyl-$NR^{11}C(O)OR^{13}$, —$C_0$-$C_4$ alkyl-$NR^{11}C(O)NR^{11}R^{12}$, and —$C_0$-$C_4$ alkyl-$NR^{11}COR^{13}$, where said $C_1$-$C_6$ alkyl is optionally unsubstituted or substituted by one or more halo substituents, p is 0-4;
n is 3;
m is 0 or 1;
q is 0 or 1;
t is 0;

each $R^1$ and $R^2$ are independently selected from H, fluoro, $C_1$-$C_6$ alkyl, —$C_0$-$C_4$ alkyl-$OR^{10}$, —$C_0$-$C_4$ alkyl-$SR^{10}$, —$C_1$-$C_4$ alkyl-Het, —$C_1$-$C_4$ alkyl-Ar and —$C_1$-$C_4$ alkyl-$C_3$-$C_7$ cycloalkyl, where said $C_1$-$C_6$ alkyl or any of said $C_1$-$C_4$ alkyl is optionally unsubstituted or substituted by one or more halo substituents;

or $R^1$ and $R^2$ together with the carbon to which they are attached form a 3-5 membered carbocyclic or heterocyclic ring, wherein said heterocyclic ring contains one, or more heteroatoms selected from N, O and S, where any of said $C_1$-$C_6$ alkyl is optionally unsubstituted or substituted by one or more halo substituents;

each $R^3$ is the same or different and is independently selected from halo, cyano, $C_1$-$C_6$ alkyl, —$C_0$-$C_4$ alkyl-$NR^{11}R^{12}$, —$C_0$-$C_4$ alkyl-$OR^{10}$, —$C_0$-$C_4$ alkyl-$SO_2NR^{11}R^{12}$, and —$C_0$-$C_4$ alkyl-$CO_2H$, wherein said $C_1$-$C_6$ alkyl is optionally unsubstituted or substituted by one or more halo substituents;

each $R^4$ and $R^5$ is independently selected from H, fluoro and $C_1$-$C_6$ alkyl;

$R^6$ and $R^7$ are each independently selected from H, fluoro and $C_1$-$C_6$ alkyl;

$R^8$ and $R^9$ are each independently selected from H, fluoro and $C_1$-$C_6$ alkyl;

$R^{10}$ is selected from H, $C_1$-$C_6$ alkyl, —$C_0$-$C_4$ alkyl-Ar, —$C_0$-$C_4$ alkyl-Het and —$C_0$-$C_4$ alkyl-$C_3$-$C_7$ cycloalkyl;

each $R^{11}$ and each $R^{12}$ are independently selected from H, $C_1$-$C_6$ alkyl, —$C_0$-$C_4$ alkyl-Ar, —$C_0$-$C_4$ alkyl-Het and —$C_0$-$C_4$ alkyl-$C_3$-$C_7$ cycloalkyl, or $R^{11}$ and $R^{12}$ together with the nitrogen to which they are attached form a 4-7 membered heterocyclic ring which optionally contains one or more additional heteroatoms selected from N, O, and S;

$R^{13}$ is selected from $C_1$-$C_6$ alkyl, —$C_0$-$C_4$ alkyl-Ar, —$C_0$-$C_4$ alkyl-Het and —$C_0$-$C_4$ alkyl-$C_3$-$C_7$ cycloalkyl;

$R^{14}$ and $R^{15}$ are each independently selected from H, $C_1$-$C_6$ alkyl, $C_3$-$C_6$ alkenyl, $C_3$-$C_6$ alkynyl, —$C_0$-$C_4$ alkyl-Ar, —$C_0$-$C_4$ alkyl-Het, —$C_0$-$C_4$ alkyl-$C_3$-$C_7$ cycloalkyl, —$C_0$-$C_4$ alkyl-O—Ar, —$C_0$-$C_4$ alkyl-O-Het, —$C_0$-$C_4$ alkyl-O—$C_3$-$C_7$ cycloalkyl, —$C_0$-$C_4$ alkyl-S(O)$_x$—$C_1$-$C_4$ alkyl, —$C_0$-$C_4$ alkyl-S(O)$_x$—Ar, —$C_0$-$C_4$ alkyl-S(O)$_x$-Het, —$C_0$-$C_4$ alkyl-S(O)$_x$—$C_3$-$C_7$ cycloalkyl, —$C_0$-$C_4$ alkyl-NH—Ar, —$C_0$-$C_4$ alkyl-NH-Het, —$C_0$-$C_4$ alkyl-NH—$C_3$-$C_7$ cycloalkyl, —$C_0$-$C_4$ alkyl-N($C_1$-$C_4$ alkyl)-Ar, —$C_0$-$C_4$ alkyl-N($C_1$-$C_4$ alkyl)-Het, —$C_0$-$C_4$ alkyl-N($C_1$-$C_4$ alkyl)$C_3$-$C_7$ cycloalkyl, —$C_0$-$C_4$ alkyl-Ar, —$C_0$-$C_4$ alkyl-Het and —$C_0$-$C_4$ alkyl-$C_3$-$C_7$ cycloalkyl, where x is 0, 1 or 2, or $R^{14}$ and $R_{16}$, together with the nitrogen to which they are attached, form a 4-7 membered heterocyclic ring which optionally contains one or more additional heteroatoms selected from N, O, and S, wherein said $C_1$-$C_6$ alkyl, $C_3$-$C_6$ alkenyl, $C_3$-$C_6$ alkynyl are optionally substituted by one or more of the substituents independently selected from the group halo, —OH, —SH, —$NH_2$, —NH(unsubstituted $C_1$-$C_4$ alkyl), —N(unsubstituted $C_1$-$C_4$ alkyl)(unsubstituted $C_1$-$C_4$ alkyl), unsubstituted —$OC_1$-$C_4$ alkyl, —$CO_2H$, —$CO_2$(unsubstituted $C_1$-$C_4$ alkyl), —$CONH_2$, —CONH (unsubstituted $C_1$-$C_4$ alkyl), —CON(unsubstituted $C_1$-$C_4$ alkyl)(unsubstituted $C_1$-$C_4$ alkyl), —$SO_3H$, —$SO_2NH_2$, —$SO_2NH$(unsubstituted $C_1$-$C_4$ alkyl) and —$SO_2N$(unsubstituted $C_1$-$C_4$ alkyl)(unsubstituted $C_1$-$C_4$ alkyl);

$R^{16}$ is $C_1$-$C_6$ alkyl, —$C_0$-$C_4$ alkyl-Ar or —$C_0$-$C_4$ alkyl-Het; and $R^{17}$ is H, $C_1$-$C_6$ alkyl, —$C_0$-$C_4$ alkyl-Ar or —$C_0$-$C_4$ alkyl-Het;

provided that X is not $COOR^{10}$ when Y is —O—, p is 0-4, n is 3, m is 1, q is 0 or 1, t is 0, each $R^1$ and $R^2$ is independently selected from H, $C_1$-$C_6$ alkyl, —OH, —O—$C_1$-$C_6$ alkyl, —SH, and —S—$C_1$-$C_6$ alkyl, each $R^4$, $R^5$, $R^6$, $R^7$, $R^8$ and $R^9$ are independently H or $C_1$-$C_4$ alkyl, k is 0 or 1, $W^3$ is H, $W^1$ and $w^2$ are each independently selected from $C_3$-$C_8$ cycloalkyl and aryl and $R^3$ and Q are as defined above; or provided that the compound is not:

5-[3-[[(3,4-dichlorophenyl)methyl][2-(2-naphthalenyl) ethyl]amino]propoxy]-3-methoxy-1,2-benzenedicarboxylic acid, or 5-[3-[[(3,4-dichlorophenyl)methyl][2-(2-naphthalenyl) ethyl]amino]propoxy]-3-methoxy-1,2-benzenedicarboxylic acid, dimethyl ester;

or a pharmaceutically acceptable salt or solvate thereof.

In another embodiment, this invention is directed to methods for the prevention or treatment of an LXR mediated disease or condition comprising administering a therapeutically effective amount of a compound having Formula II-A:

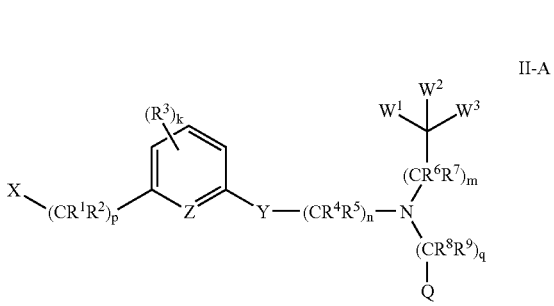

II-A wherein:

X is selected from $C_1$-$C_8$ alkyl, halo, —$OR^{10}$, —$NR^{14}R^{15}$, cyano, —$COR^{13}$, $COOR^{10}$, —$OCOR^{13}$, —$N(R^{17})COR^{13}$, —$N(R^{17})CONR^{14}R^{15}$, —$N(R^{17})COOR^{13}$, —$SO_2NR^{14}R^{15}$, —$C(=NR^{17})NR^{14}R^{15}$, —$N(R^{17})SO_2R^{16}$, and a 5 or 6-membered heterocyclic group;

or X and an adjacent $R^3$, taken together with the atoms to which they are bonded, form an alkylenedioxy moiety;

Z is CH or N, wherein k is 0, 1 or 2;

Y is —O— or —$C(R^4)(R^5)$—;

$W^1$ is $C_3$-$C_8$ cycloalkyl, aryl or Het, wherein said $C_3$-$C_8$ cycloalkyl, Ar and Het are optionally unsubstituted or substituted with one or more groups independently selected from halo, cyano, nitro, $C_1$-$C_6$ alkyl, $C_3$-$C_6$ alkenyl, $C_3$-$C_6$ alkynyl, —$C_0$-$C_4$ alkyl-$CO_2R^{10}$, —$C_0$-$C_4$ alkyl-$C(O)SR^{10}$, —$C_0$-$C_4$ alkyl-$CONR^{11}R^{12}$, —$C_0$-$C_4$ alkyl-$COR^{13}$, —$C_0$-$C_4$ alkyl-$NR^{11}R^{12}$, —$C_0$-$C_4$ alkyl-$SR^{10}$, —$C_0$-$C_4$ alkyl-$OR^{10}$, —$C_0$-$C_4$ alkyl-$SO_3H$, —$C_0$-$C_4$ alkyl-$SO_2NR^{11}R^{12}$, —$C_0$-$C_4$ alkyl-$SO_2R^{10}$, —$C_0$-$C_4$ alkyl-$SOR^{13}$, —$C_0$-$C_4$ alkyl-$OCOR^{13}$, —$C_0$-$C_4$ alkyl-$OC(O)NR^{11}R^{12}$, —$C_0$-$C_4$ alkyl-$OC(O)OR^{13}$, —$C_0$-$C_4$ alkyl-$NR^{11}C(O)OR^{13}$, —$C_0$-$C_4$ alkyl-$NR^{11}C(O)NR^{11}R^{12}$, and —$C_0$-$C_4$ alkyl-$NR^{11}CR^{13}$, where said $C_1$-$C_6$ alkyl is optionally unsubstituted or substituted by one or more halo substituents;

$W^2$ is selected from H, halo, $C_1$-$C_6$ alkyl, $C_2$-$C_6$ alkenyl, $C_2$-$C_6$ alkynyl, —$C_0$-$C_4$ alkyl-$NR^{11}R^{12}$, —$C_0$-$C_4$ alkyl-$SR^{10}$, —$C_0$-$C_4$ alkyl-$OR^{10}$, —$C_0$-$C_4$ alkyl-$CO_2R^{10}$, —$C_0$-$C_4$ alkyl-$C(O)SR^{10}$, —$C_0$-$C_4$ alkyl-$CONR^{11}R^{12}$, —$C_0$-$C_4$ alkyl-$COR^{13}$, —$C_0$-$C_4$ alkyl-$OCOR^{13}$, —$C_0$-$C_4$ alkyl-$OCONR^{11}R^{12}$, —$C_0$-$C_4$ alkyl-$NR^{11}CONR^{11}R^{12}$, —$C_0$-$C_4$ alkyl-$NR^{11}COR^{13}$, —$C_0$-$C_4$ alkyl-Het, —$C_0$-$C_4$ alkyl-Ar and —$C_0$-$C_4$ alkyl-$C_3$-$C_7$ cycloalkyl, wherein said $C_1$-$C_6$ alkyl is optionally unsubstituted or substituted by one or more halo substituents, and wherein the $C_3$-$C_7$ cycloalkyl, Ar and Het moieties of said —$C_0$-$C_4$ alkyl-Het, —$C_0$-$C_4$ alkyl-Ar and —$C_0$-$C_4$ alkyl-$C_3$-$C_7$ cycloalkyl are optionally unsubstituted or substituted with one or more groups independently selected from halo, cyano, nitro, $C_1$-$C_6$ alkyl, $C_3$-$C_6$ alkenyl, $C_3$-$C_6$ alkynyl, —$C_0$-$C_4$ alkyl-$CO_2R^{10}$, —$C_0$-$C_4$ alkyl-$C(O)SR^{10}$, —$C_0$-$C_4$ alkyl-$CONR^{11}R^{12}$, —$C_0$-$C_4$ alkyl-$COR^{13}$, —$C_0$-$C_4$ alkyl-$NR^{11}R^{12}$, —$C_0$-$C_4$ alkyl-$SR^{10}$, —$C_0$-$C_4$ alkyl-$OR^{10}$, —$C_0$-$C_4$ alkyl-$SO_3H$, —$C_0$-$C_4$ alkyl-$SO_2NR^{11}R^{12}$, —$C_0$-$C_4$ alkyl-$SO_2R^{10}$, —$C_0$-$C_4$ alkyl-$SOR^{13}$, —$C_0$-$C_4$ alkyl-$OCOR^{13}$, —$C_0$-$C_4$ alkyl-$OC(O)NR^{11}R^{12}$, —$C_0$-$C_4$ alkyl-$OC(O)OR^{13}$, —$C_0$-$C_4$ alkyl-$NR^{11}C(O)OR^{13}$, —$C_0$-$C_4$ alkyl-$NR^{11}C(O)NR^{11}R^{12}$, and —$C_0$-$C_4$ alkyl-$NR^{11}COR^{13}$, where said $C_1$-$C_6$ alkyl is optionally unsubstituted or substituted by one or more halo substituents;

$W^3$ is selected from the group consisting of H, halo, $C_1$-$C_6$ alkyl, —$C_0$-$C_4$ alkyl-$NR^{11}R^{12}$, —$C_0$-$C_4$ alkyl-$SR^{10}$, —$C_0$-$C_4$ alkyl-$OR^{10}$, —$C_0$-$C_4$ alkyl-$CO_2R^{10}$, —$C_0$-$C_4$ alkyl-$C(O)SR^{10}$, —$C_0$-$C_4$ alkyl-$CONR^{11}R^{12}$, —$C_0$-$C_4$ alkyl-$COR^{13}$, —$C_0$-$C_4$ alkyl-$OCOR^{13}$, —$C_0$-$C_4$ alkyl-$OCONR^{11}R^{12}$, —$C_0$-$C_4$ alkyl-$NR^{11}CONR^{11}R^{12}$, —$C_0$-$C_4$ alkyl-$NR^{11}COR^{13}$, —$C_0$-$C_4$ alkyl-Het, —$C_1$-$C_4$ alkyl-Ar and —$C_1$-$C_4$ alkyl-$C_3$-$C_7$ cycloalkyl, wherein said $C_1$-$C_6$ alkyl is optionally unsubstituted or substituted by one or more halo substituents;

Q is Ar or Het; wherein said Ar and Het are optionally unsubstituted or substituted with one or more groups independently selected from halo, cyano, nitro, $C_1$-$C_6$ alkyl, $C_3$-$C_6$ alkenyl, $C_3$-$C_6$ alkynyl, —$C_0$-$C_4$ alkyl-$CO_2R^{10}$, —$C_0$-$C_4$ alkyl-$C(O)SR^{10}$, —$C_0$-$C_4$ alkyl-$CONR^{11}R^{12}$, —$C_0$-$C_4$ alkyl-$COR^{13}$, —$C_0$-$C_4$alkyl-$NR^{11}R^{12}$, —$C_0$-$C_4$ alkyl-$SR^{10}$, —$C_0$-$C_4$ alkyl-$OR^{10}$, —$C_0$-$C_4$ alkyl-$SO_3H$, —$C_0$-$C_4$ alkyl-$SO_2NR^{11}R^{12}$, —$C_0$-$C_4$alkyl-$SO_2R^{10}$, —$C_0$-$C_4$ alkyl-$SOR^{13}$, —$C_0$-$C_4$ alkyl-$OCOR^{13}$, —$C_0$-$C_4$ alkyl-$OC(O)NR^{11}R^{12}$, —$C_0$-$C_4$ alkyl-$OC(O)OR^{13}$, —$C_0$-$C_4$ alkyl-$NR^{11}C(O)OR^{13}$, —$C_0$-$C_4$ alkyl-$NR^{11}C(O)NR^{11}R^{12}$, and —$C_0$-$C_4$ alkyl-$NR^{11}COR^{13}$, where said $C_1$-$C_6$ alkyl is optionally unsubstituted or substituted by one or more halo substituents, p is 0-4;

n is 3;

m is 0 or 1;

q is 0 or 1;

t is 0;

each $R^1$ and $R^2$ are independently selected from H, fluoro, $C_1$-$C_6$ alkyl, —$C_0$-$C_4$ alkyl-$OR^{10}$, —$C_0$-$C_4$ alkyl-$SR^{10}$, —$C_1$-$C_4$ alkyl-Het, —$C_1$-$C_4$ alkyl-Ar and —$C_1$-$C_4$ alkyl-$C_3$-$C_7$ cycloalkyl, where said $C_1$-$C_6$ alkyl or any of said $C_1$-$C_4$ alkyl is optionally unsubstituted or substituted by one or more halo substituents;

or $R^1$ and $R^2$ together with the carbon to which they are attached form a 3-5 membered carbocyclic or heterocyclic ring, wherein said heterocyclic ring contains one, or more heteroatoms selected from N, O, and S, where any of said $C_1$-$C_6$ alkyl is optionally unsubstituted or substituted by one or more halo substituents;

each $R^3$ is the same or different and is independently selected from halo, cyano, $C_1$-$C_6$alkyl, —$C_0$-$C_4$ alkyl-$NR^{11}R^{12}$, —$C_0$-$C_4$ alkyl-$OR^{10}$, —$C_0$-$C_4$ alkyl-$SO_2NR^{11}R^{12}$, and —$C_0$-$C_4$ alkyl-$CO_2H$, wherein said $C_1$-$C_6$ alkyl is optionally unsubstituted or substituted by one or more halo substituents;

each $R^4$ and $R^5$ is independently selected from H, fluoro and $C_1$-$C_6$ alkyl;

$R^6$ and $R^7$ are each independently selected from H, fluoro and $C_1$-$C_6$ alkyl;

$R^8$ and $R^9$ are each independently selected from H, fluoro and $C_1$-$C_6$ alkyl;

$R^{10}$ is selected from H, $C_1$-$C_6$ alkyl, —$C_0$-$C_4$ alkyl-Ar, —$C_0$-$C_4$ alkyl-Het and —$C_0$-$C_4$ alkyl-$C_3$-$C_7$ cycloalkyl;

each $R^{11}$ and each $R^{12}$ are independently selected from H, $C_1$-$C_6$ alkyl, —$C_0$-$C_4$ alkyl-Ar, —$C_0$-$C_4$ alkyl-Het and —$C_0$-$C_4$ alkyl-$C_3$-$C_7$ cycloalkyl, or $R^{11}$ and $R^{12}$ together with the nitrogen to which they are attached form a 4-7 membered heterocyclic ring which optionally contains one or more additional heteroatoms selected from N, O, and S;

$R^{13}$ is selected from $C_1$-$C_6$ alkyl, —$C_0$-$C_4$ alkyl-Ar, —$C_0$-$C_4$ alkyl-Het and —$C_0$-$C_4$ alkyl-$C_3$-$C_7$ cycloalkyl;

$R^{14}$ and $R^{15}$ are each independently selected from H, $C_1$-$C_6$ alkyl, $C_3$-$C_6$ alkenyl, $C_3$-$C_6$ alkynyl, —$C_0$-$C_4$ alkyl-Ar, —$C_0$-$C_4$ alkyl-Het, —$C_0$-$C_4$ alkyl-$C_3$-$C_7$ cycloalkyl, —$C_0$-$C_4$ alkyl-O—, —$C_0$-$C_4$ alkyl-O—Ar, —$C_0$-$C_4$ alkyl-O-Het, —$C_0$-$C_4$ alkyl-O—$C_3$-$C_7$ cycloalkyl, —$C_0$-$C_4$ alkyl-S(O)$_x$—$C_1$-$C_4$ alkyl, —$C_0$-$C_4$ alkyl-S(O)$_x$, Ar, —$C_0$-$C_4$ alkyl-S(O)$_x$, Het, —$C_0$-$C_4$ alkyl-S(O)$_x$—$C_3$-$C_7$ cycloalkyl, —$C_0$-$C_4$ alkyl-NH—Ar, —$C_0$-$C_4$ alkyl-NH-Het, —$C_0$-$C_4$ alkyl-NH—$C_3$-$C_7$ cycloalkyl, —$C_0$-$C_4$ alkyl-N($C_1$-$C_4$ alkyl)-Ar, —$C_0$-$C_4$ alkyl-N($C_1$-$C_4$ alkyl)-Het, —$C_0$-$C_4$ alkyl-N($C_1$-$C_4$ alkyl)-$C_3$-$C_7$ cycloalkyl, —$C_0$-$C_4$ alkyl-Ar, —$C_0$-$C_4$ alkyl-Het and —$C_0$-$C_4$ alkyl-$C_3$-$C_7$ cycloalkyl, where x is 0, 1 or 2, or $R^{14}$ and $R^{15}$, together with the nitrogen to which they are attached, form a 4-7 membered heterocyclic ring which optionally contains one or more additional heteroatoms selected from N, O, and S, wherein said $C_1$-$C_6$ alkyl, $C_3$-$C_6$ alkenyl, $C_3$-$C_6$ alkynyl are optionally substituted by one or more of the substituents independently selected from the group halo, —OH, —SH, —NH$_2$, —NH(unsubstituted $C_1$-$C_4$ alkyl), —N(unsubstituted $C_1$-$C_4$ alkyl)(unsubstituted $C_1$-$C_4$ alkyl), unsubstituted —O$C_1$-$C_4$ alkyl, —CO$_2$H, —CO$_2$(unsubstituted $C_1$-$C_4$ alkyl), —CONH$_2$, —CONH (unsubstituted $C_1$-$C_4$ alkyl), —CON(unsubstituted $C_1$-$C_4$ alkyl)(unsubstituted $C_1$-$C_4$ alkyl), —SO$_3$H, —SO$_2$NH$_2$, —SO$_2$NH(unsubstituted $C_1$-$C_4$ alkyl) and —SO$_2$N(unsubstituted $C_1$-$C_4$ alkyl)(unsubstituted $C_1$-$C_4$ alkyl);

$R^{16}$ is $C_1$-$C_6$ alkyl, —$C_0$-$C_4$ alkyl-Ar or —$C_0$-$C_4$ alkyl-Het; and $R^{17}$ is H, $C_1$-$C_6$ alkyl, —$C_0$-$C_4$ alkyl-Ar or —$C_0$-$C_4$ alkyl-Het;

provided that X is not COOR$^{10}$ when Y is —O—, p is 0-4, n is 3, m is 1, q is 0 or 1, t is 0, each $R^1$ and $R^2$ is independently selected from H, $C_1$-$C_6$ alkyl, —OH, —O—$C_1$-$C_6$ alkyl, —SH, and —S—$C_1$-$C_6$ alkyl, each $R^4$, $R^5$, $R^6$, $R^7$, $R^8$ and $R^9$ are independently H or $C_1$-$C_4$ alkyl, k is 0 or 1, $W^3$ is H, $W^1$ and $W^2$ are each independently selected from $C_3$-$C_8$ cycloalkyl and aryl and $R^3$ and Q are as defined above;

or a pharmaceutically acceptable salt or solvate thereof.

Unless otherwise provided, each alkyl, alkoxy, alkenyl, alkynyl, cycloalkyl, aryl or Het herein is independently unsubstituted or substituted with one ore more substituents defined hereinabove.

The LXR modulating agents of this invention may contain the variety of X groups defined above. In more specific embodiments of this invention, X is selected from $C_1$-$C_6$ alkyl, halo, —OR$^{10}$, —NR$^{14}$R$^{15}$, cyano, —COR$^{13}$, —COOR$^{10}$, OCOR$^{13}$, —N(R$^{17}$)CONR$^{14}$R$^{15}$, —N(R$^{17}$) COR$^{13}$, —SO$_2$NR$^{14}$R$^{15}$, —N(R$^{17}$)SO$_2$R$^{16}$, and a 5 or 6-membered heterocyclic group or X and an adjacent $R^3$, taken together with the atoms to which they are bonded, form an alkylenedioxy moiety, where $R^{10}$ is H, $C_1$-$C_4$ alkyl or phenyl; $R^{13}$ is H, $C_1$-$C_4$ alkyl, —$C_0$-$C_4$ alkyl-$C_3$-$C_7$ cycloalkyl, or —$C_0$-$C_4$ alkyl-phenyl; $R^{14}$ and $R^{15}$ are each independently selected from H, $C_1$-$C_6$ alkyl, —$C_0$-$C_4$ alkyl-Ar, —$C_0$-$C_4$ alkyl-Het, —$C_0$-$C_4$ alkyl-$C_3$-$C_7$ cycloalkyl, —$C_0$-$C_4$ alkyl-O—Ar, —$C_0$-$C_4$ alkyl-O-Het, —$C_0$-$C_4$ alkyl-O—$C_3$-$C_7$ cycloalkyl, —$C_0$-$C_4$ alkyl-S(O)$_2$-$C_1$-$C_4$ alkyl, —$C_0$-$C_4$ alkyl-S(O)$_2$—Ar, —$C_0$-$C_4$ alkyl-S(O)$_2$-Het, —$C_0$-$C_4$ alkyl-S(O)$_2$-$C_3$-$C_7$ cycloalkyl, —$C_0$-$C_4$ alkyl-NH—Ar, —$C_0$-$C_4$ alkyl-NH-Het, —$C_0$-$C_4$ alkyl-NH—$C_3$-$C_7$ cycloalkyl, —$C_0$-$C_4$ alkyl-N($C_1$-$C_4$ alkyl)-Ar, —$C_0$-$C_4$ alkyl-N($C_1$-$C_4$ alkyl)-Het, —$C_0$-$C_4$ alkyl-N($C_1$-$C_4$ alkyl)-$C_3$-$C_7$ cycloalkyl, —$C_0$-$C_4$ alkyl-Ar, —$C_0$-$C_4$ alkyl-Het and —$C_0$-$C_4$ alkyl-$C_3$-$C_7$ cycloalkyl, or $R^{14}$ and $R^{15}$, together with the nitrogen to which they are attached, form a 4-7 membered heterocyclic ring which optionally contains one or more additional heteroatoms selected from N, O, and S, wherein said $C_1$-$C_6$ alkyl is optionally substituted by one or more of the substituents independently selected from the group halo, —OH, —SH, —NH$_2$, —NH(unsubstituted $C_1$-$C_4$ alkyl), —N(unsubstituted $C_1$-$C_4$ alkyl)(unsubstituted $C_1$-$C_4$ alkyl), unsubstituted —O$C_1$-$C_4$ alkyl, —CO$_2$H, —CO$_2$(unsubstituted $C_1$-$C_4$ alkyl), —CONH$_2$, —CONH (unsubstituted $C_1$-$C_4$ alkyl), —CON(unsubstituted $C_1$-$C_4$ alkyl)(unsubstituted $C_1$-$C_4$ alkyl), —SO$_3$H, —SO$_2$NH$_2$, —SO$_2$NH(unsubstituted $C_1$-$C_4$ alkyl) and —SO$_2$N(unsubstituted $C_1$-$C_4$ alkyl)(unsubstituted $C_1$-$C_4$ alkyl); $R^{16}$ is $C_1$-$C_4$ alkyl or phenyl; and $R^{17}$ is H or $C_1$-$C_4$ alkyl.

More specifically, X and an adjacent $R^3$, taken together with the phenyl ring to which they are bound form a benzo [1,3]dioxyl group. In other specific embodiments, X is chloro, bromo, cyano, carboxy-, methylcarboxy-, hydroxy, methoxy, methyl, trifluoromethyl, 1,3-dihydroxy-prop-2-yl (—CH(CH$_2$OH)$_2$, isopropyl, n-butyl, isobutyl, 2,2-dimethylpropyl, phenylcarbonyl, triazolyl, tetrazolyl, —NH$_2$, —NHCH$_3$, —NHCH$_2$CH$_3$, —NHCH$_2$CH$_2$CH$_3$, —NHCH$_2$CH$_2$CH$_2$CH$_3$, —NHCH$_2$CH$_2$CH$_2$CH$_2$CH$_3$, —NHCH$_2$C(CH$_3$)$_3$, —NHCH$_2$CH(CH$_3$)$_2$, —NHCH$_2$CH$_2$CH(CH$_3$)$_2$, —NH-cyclopentyl, —NH-phenyl, —NHCH$_2$-cyclopropyl, —NHCH(CH$_3$)$_2$, —NHCH$_2$CF$_3$, —N(CH$_3$)$_2$, —N(CH$_2$CH$_3$)$_2$, —NHCH (CH$_2$CH$_3$)$_2$, —NHCH$_2$CH(CH$_2$CH$_3$)$_2$, —NHCH$_2$CH$_2$OH, —NHCH$_2$CO$_2$H, —N(CH$_3$)CH$_2$CO$_2$H, —NHC(CH$_3$)$_2$CO$_2$H, —NHCH(CH$_3$)CO$_2$H, —(R)—NHCH(CH$_3$)CO$_2$H, —(S)—NHCH(CH$_3$)CO$_2$H, —NHCH$_2$-1H-imidazol-2-yl, —NHCH$_2$-(1-CH$_3$-imidazol-2-yl, —NH-(pyrimidin-2-yl), -morpholin-4-yl, -thiomorpholin-4-yl, -piperidin-1-yl, -piperidin-1-yl-(4-carboxylic acid), -piperidin-1-yl-(4-acetic acid), -piperidin-4-yl-(1-acetic acid), -2,5-dimethyl-pyrrol-1-yl, -pyrrolidin-1-yl, —((R)-2-CO$_2$H-pyrrolidin-1-yl), —((S)-2-CO$_2$H-pyrrolidin-1-yl), -piperazin-1-yl, -(4-methyl-piperazin-1-yl), -piperazin-1-yl-(4-acetic acid), —NHCH$_2$-(5-bromo-thien-2-yl), —NHCH$_2$-1H-imidazol-2-yl, —NHCH$_2$-(1-methyl-imidazol-2-yl), —NHCOCH$_3$, —N(CH$_3$)COCH$_3$, —NHCO$_2$C(CH$_3$)$_3$, —NHCOCH$_2$CH$_3$, —NHCOC(CH$_3$)$_2$, —NHCO-furan-2-yl, —N(CH$_3$)CO-furan-2-yl, —NHCO-thien-2-yl, —NHCO-cyclopropyl, —NHCO-(5-bromo-thien-2-yl, —NHCO-(2,5-dimethyl-pyrrol-3-yl), —NHSO$_2$CH$_3$, —N(CH$_3$)SO$_2$CH$_3$, —NHSO$_2$CF$_3$, —NHSO$_2$phenyl, —N(CH$_3$)SO$_2$phenyl, —NHSO$_2$CH$_2$CH$_3$, —NHSO$_2$CH$_2$CF$_3$, —NHSO$_2$CH$_2$CH$_2$CH$_3$, —NHSO$_2$CH(CH$_3$)$_2$, —NHCONH (2-chlorophenyl), —N(CH$_3$)CONH(3,5-dimethoxyphenyl), —N(CH$_3$)CONH(2-chlorophenyl), —N(CH$_3$)CO-(benzo[1,3]diox-5-yl), —SO$_2$NHCH$_3$, and —SO$_2$N(CH$_3$)$_2$.

It will be understood by those skilled in the art, that the triazolyl or tetrazolyl groups present in the compounds of this invention will exist in different tautomeric forms, as follows (where R is H or a substituent, such as a protecting group):

Triazolyl:

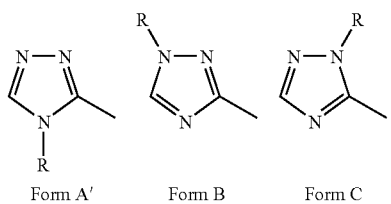

Form A'  Form B  Form C

Tetrazolyl:

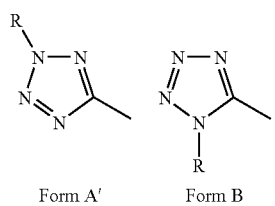

Form A'  Form B

As a convention, compounds exemplified herein have been depicted and have been assigned names based on the structure of Tautomeric Form A (above) for each of the triazolyl and tetrazolyl groups. It is to be understood that any reference to such tautomeric compounds is intended to encompass all tautomers and any mixtures of tautomers thereof, and should not be interpreted to limit the scope of the compounds of this invention or of the intermediates used in the preparation thereof.

In specific embodiments, the compounds of this invention of this invention are defined wherein p is 0-3. In specific embodiments, p is 0, 1 or 2.

In other embodiments, each $R^1$ and $R^2$ are independently H or $C_1$-$C_4$ alkyl or $R^1$ and $R^2$ together with the carbon to which they are attached form a 3-5 membered carbocyclic ring. By virtue of the definitions given above for the term "alkyl", this definition of $R^1$ and $R^2$ also encompasses alkyl and cycloalkyl groups that are optionally substituted with the substituents specified in the definitions above. In specific embodiments of the compounds of this invention, $R^1$ and $R^2$ are independently selected from H and $C_1$-$C_4$ alkyl, specifically methyl and hydroxymethyl-, or $R^1$ and $R^2$ together with the carbon to which they are attached form a spirocyclopropyl, cyclobutyl or cyclopentyl ring.

The group

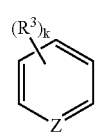

describes a 6-membered aromatic ring, specifically, a phenyl or pyridyl ring, which may be unsubstituted (k=0) or substituted by one or more substituents $R^3$. In the specific embodiments of this invention, Z is CH (which includes $C(R^3)$) or N. The total number of $R^3$ substituents that may be present in a compound of this invention is represented by "k". When Z is $CR^3$, k is 0-4, meaning that there can be up to four $R^3$ substituents on the 6-membered aromatic ring. When Z is CH or N, k is 0-3, meaning that there can be up to three $R^3$ substituents on the 6-membered aromatic ring. In this embodiment, $R^3$ is not attached to the Z moiety (N or C atom) of the ring. In the embodiments of this invention, k is 0 or 1.

In the embodiments wherein k is 1 or more, each $R^3$ may be the same or different and may be independently selected from halo, $C_1$-$C_4$ alkyl and $C_1$-$C_4$ alkoxy. By virtue of the definitions given above for the term "alkyl", this definition of $R^3$ also encompasses alkyl groups that are optionally substituted with the substituents specified in the definitions above. In the specific embodiments of this invention, $R^3$ is methyl, trifluoromethyl, chloro or methoxy.

In another embodiment of the compounds this invention, $R^4$ and $R^5$ are independently selected from H and $C_1$-$C_3$ alkyl. By virtue of the definition given above for the term "alkyl", $R^4$ and $R^5$ also encompasses the alkyls optionally substituted with the substituents specified in the definition above. In specific embodiments of this invention, each $R^4$ and $R^5$ are H or one $R^4$ or $R^5$ is methyl.

When the moiety —Y(CR$^4$R$^5$)$_n$— is substituted and $R^4$ and $R^5$ are different on at least one (CR$^4$R$^5$) moiety (e.g., when one of $R^4$ or $R^5$ is methyl and the other of $R^4$ and $R^5$ is hydrogen) a chiral compound is obtained. Such chiral compounds preferably possess at least one $R^4$ or $R^5$ substituent having the following stereochemistry (illustrated where Y is —O—):

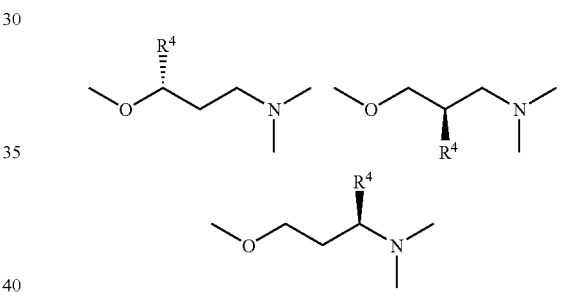

where the substituent $R^4$ is used merely to illustrate the stereochemical orientation of a non-hydrogen substituent (e.g., methyl).

In another embodiment, the compounds of this invention are defined wherein n is 2-4. In specific embodiments, n is 3.

In the compounds of this invention, t may be 0 or 1. When Z is CH or $CR^3$ and t is 1, the compound of this invention is the N-oxide of the tertiary amine, having the formula:

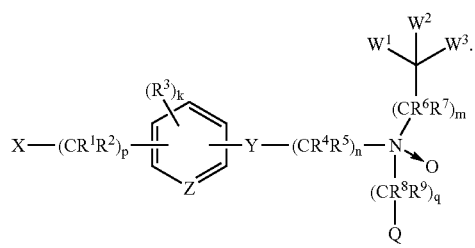

When Z is CH, $CR^3$ or N and t is 0, the compound of this invention is the tertiary amine having the formula:

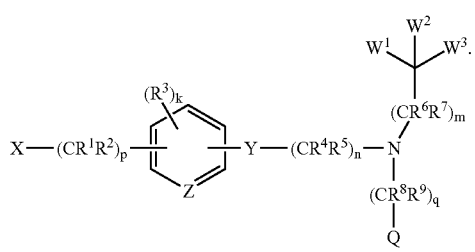

In specific embodiments' of the compounds this invention, q is 1 and Re and $R^9$ are both H.

Group Q is selected from $C_3$-$C_7$ cycloalkyl, aryl and Het. By virtue of the definitions given above for the terms "cycloalkyl", "aryl" and "Het", this definition of Q also encompasses cycloalkyl, aryl and Het groups that are optionally substituted from 1 to 4 times, more preferably, from 1 to 3 times with the substituents specified in the definitions above. In one embodiment, Q is an aryl or Het group. In specific non-limiting embodiments, Q is a substituted or unsubstituted phenyl or furanyl group or a benzo[1,3]dioxyl or benzo[1,4]dioxyl group containing one, two or three substituents selected from halo, $C_1$-$C_4$ alkyl; including $C_1$-$C_4$ haloalkyl, $C_1$-$C_4$ alkylthio; or —$NR^{Q1}R^{Q2}$ where $R^{Q1}$ and $R^{Q2}$ taken together with the nitrogen to which they are attached form a 4-7 membered heterocyclic ring, which may optionally contain one or more additional heteroatoms selected form N, O and S. Specific substituents include fluoro, chloro, trifluoromethyl, tert-butyl, isopropyl, methylthio and piperidin-1-yl. More specifically, Q is 2-chloro-3-(trifluoromethyl)phenyl, 3-methyl-4-fluoro-phenyl, 4-tert-butyl-phenyl, 4-(methylthio)phenyl, 2,4,5-trifluoro-phenyl, 4-isopropyl-phenyl, 5-(piperidin-1-yl)-furan-2-yl, benzo[1,3]diox-5-yl, or 2,3-dihydrobenzo[1,4]dioxin-6-yl. In particular embodiments, Q is a 2-chloro-3-(trifluoromethyl) phenyl group.

In one embodiment of the compounds of this invention, m is 0 or 1 and $R^6$ and $R^7$ are independently selected from H and $C_1$-$C_4$ alkyl, specifically methyl.

In yet another embodiment, $W^1$ is $C_1$-$C_4$ alkyl, aryl or Het; $W^2$ is selected from $C_1$-$C_4$ alkyl, $C_2$-$C_4$ alkynyl, —$CO_2R^{10}$, —$OR^{10}$, —$NR^{11}R^{12}$, —$CONR^{11}R^{12}$, —$OCOR^{13}$, —$OCONR^{11}R^{12}$, $C_1$-$C_4$ alkyl, —$C_0$-$C_4$ alkyl-$OR^{10}$, —$C_0$-$C_4$ alkyl-Het, —$C_0$-$C_4$ alkyl-Ar and —$C_0$-$C_4$ alkyl-$C_3$-$C_6$ cycloalkyl, and $W^3$ is H or $C_1$-$C_4$ alkyl. By virtue of the definitions given above, for the terms "alkyl", "cycloalkyl", "aryl" and "Het", $W^1$, $W^2$, and $W^3$ also encompasses the foregoing groups optionally substituted with the substituents specified in the definitions above. In one embodiment, $W^1$ and/or $W^2$ may be phenyl, naphthyl, thienyl, pyridyl, furanyl, pyrrolyl, cyclohexyl, cyclopentyl, morpholinyl, or pyrrolidinyl, where each phenyl, naphthyl, thienyl, pyridyl, furanyl, pyrrolyl, cyclohexyl, cyclopentyl, morpholinyl, or pyrrolidinyl may be optionally substituted from 1 to 3 times, more preferably from 1 to 2 times with one or more of the substituents defined hereinabove. For example, $W^1$ and/or $W^2$ may be independently substituted by one or more substituents independently selected from $C_1$-$C_4$ alkyl, —OH, halo, —O—$C_1$-$C_4$ alkyl, and —$C_1$-$C_4$ haloalkyl. In more specific embodiments, $W^1$ is selected from methyl, unsubstituted or substituted phenyl, naphthyl, pyridyl, thienyl or pyrrolyl. More specifically, $W^1$ is methyl, unsubstituted phenyl, naphthyl, pyridyl, thienyl or pyrrolyl or substituted phenyl or pyridyl containing one or two substituents independently selected from halo, alkyl and alkoxy, specifically, chloro, methyl and methoxy. In specific embodiments, $W^1$ is methyl, phenyl, naphth-1-yl, pyrid-2-yl, 4-methyl-pyrid-2-yl, thien-2-yl, thien-3-yl, pyrrol-2-yl, 2-chlorophenyl, 3-chlorophenyl, 4-chlorophenyl, 2-methoxyphenyl, or 4-methoxyphenyl. In other specific embodiments, $W^2$ is $C_1$-$C_4$ alkyl, $C_2$-$C_4$ alkynyl, $C_3$-$C_6$ cycloalkyl, aryl, Het hydroxy, aryloxy-, $C_1$-$C_4$ alkoxy-, —$OCOC_1$-$C_4$ alkyl, —OCOaryl, or —$NR^{W1}R^{W2}$, where $R^{W1}$ and $R^{W2}$ are independently H or $C_1$-$C_4$ alkyl or taken together with the nitrogen to which they are attached form a 4-7 membered heterocyclic ring, which may optionally contain one or more additional heteroatoms selected form N, O and S. In more specific embodiments, $W^2$ is methyl, ethyl, ethynyl, isopropyl, n-butyl, 2-methylpropyl, trifluorormethyl, cyclohexyl, unsubstituted phenyl, hydroxy, methoxy, phenoxy, dimethylamino, morpholin-4-yl, phenylcarbonyloxy, or methylcarbonyloxy. In another embodiment, $W^3$ is H or $C_1$-$C_4$ alkyl, specifically, methyl.

In other embodiments of this invention, the —$C_0$-$C_6$ alkyl- and —$C_0$-$C_4$ alkyl- moieties of the substituents defined herein are unsubstituted —$C_0$-$C_6$ alkyl- and unsubstituted —$C_0$-$C_4$ alkyl- moieties, respectively.

It is to be understood that the present invention covers all combinations of particular and preferred groups described hereinabove.

Specific embodiments of this invention comprise compounds wherein X is selected from $C_1$-$C_6$ alkyl, halo, —$OR^{10}$, —$NR^{14}R^{15}$, cyano, —$COR^{13}$, —$COOR^{10}$, —$OCOR^{13}$, —$N(R^{17})CONR^{14}R^{15}$, —$N(R^{17})COR^{13}$, —$SO_2NR^{14}R^{15}$, —$N(R^{17})SO_2R^{16}$, and a 5 or 6-membered heterocyclic group or X and an adjacent $R^3$, taken together with the atoms to which they are bonded, form an alkylenedioxy moiety, where $R^{10}$ is H, $C_1$-$C_4$ alkyl or phenyl, $R^{13}$ is H, $C_1$-$C_4$ alkyl, —$C_0$-$C_4$ alkyl-$C_3$-$C_7$ cycloalkyl, or —$C_0$-$C_4$ alkyl-phenyl, $R^{14}$ and $R^{15}$ are each independently selected from H, $C_1$-$C_6$ alkyl, —$C_0$-$C_4$ alkyl-Ar, —$C_0$-$C_4$ alkyl-Het, —$C_0$-$C_4$ alkyl-$C_3$-$C_7$ cycloalkyl, —$C_0$-$C_4$ alkyl-O—Ar, —$C_0$-$C_4$ alkyl-O-Het, —$C_0$-$C_4$ alkyl-O—$C_3$-$C_7$ cycloalkyl, —$C_0$-$C_4$ alkyl-S(O)$_2$-$C_1$-$C_4$ alkyl, —$C_0$-$C_4$ alkyl-S(O)$_2$—Ar, —$C_0$-$C_4$ alkyl-S(O)$_2$-Het, —$C_0$-$C_4$ alkyl-S(O)$_2$-$C_3$-$C_7$ cycloalkyl, —$C_0$-$C_4$ alkyl-NH—Ar, —$C_0$-$C_4$ alkyl-NH-Het, —$C_0$-$C_4$ alkyl-NH—$C_3$-$C_7$ cycloalkyl, —$C_0$-$C_4$ alkyl-N($C_1$-$C_4$ alkyl)-Ar, —$C_0$-$C_4$ alkyl-N($C_1$-$C_4$ alkyl)-Het, —$C_0$-$C_4$ alkyl-N($C_1$-$C_4$ alkyl)-$C_3$-$C_7$ cycloalkyl, —$C_0$-$C_4$ alkyl-Ar, —$C_0$-$C_4$ alkyl-Het and —$C_0$-$C_4$ alkyl-$C_3$-$C_7$ cycloalkyl, or $R^{14}$ and $R^{15}$, together with the nitrogen to which they are attached, form a 4-7 membered heterocyclic ring which optionally contains one or more additional heteroatoms selected from N, O, and S, wherein said $C_1$-$C_6$ alkyl is optionally substituted by one or more of the substituents independently selected from the group halo, —OH, —SH, —$NH_2$, —NH(unsubstituted $C_1$-$C_4$ alkyl), —N(unsubstituted $C_1$-$C_4$ alkyl)(unsubstituted $C_1$-$C_4$ alkyl), unsubstituted —$OC_1$-$C_4$ alkyl, —$CO_2H$, —$CO_2$(unsubstituted $C_1$-$C_4$ alkyl), —$CONH_2$, —CONH(unsubstituted $C_1$-$C_4$ alkyl), —CON(unsubstituted $C_1$-$C_4$ alkyl)(unsubstituted $C_1$-$C_4$ alkyl), —$SO_3H$, —$SO_2NH_2$, —$SO_2NH$(unsubstituted $C_1$-$C_4$ alkyl) and —$SO_2N$(unsubstituted $C_1$-$C_4$ alkyl)(unsubstituted $C_1$-$C_4$ alkyl), $R^{16}$ is $C_1$-$C_4$ alkyl or phenyl, and $R^{17}$ is H or $C_1$-$C_4$ alkyl; p is 0, 1 or 2; $R^1$ and $R^2$ are independently H or $C_1$-$C_4$ alkyl or $R^1$ and $R^2$ together with the carbon to which they are attached form a 3-5 membered carbocyclic ring; k is 0 or k is 1 and $R^3$ is halo, $C_1$-$C_4$ alkyl or $C_1$-$C_4$ alkoxy; n is 3 and each $R^4$ and $R^5$ are independently from H and $C_1$-$C_3$ alkyl; Z is CH or N; Y is —O— or —C($R^4$)($R^5$)—; q is 1; $R^8$ and $R^9$ are each H; Q is a substituted or unsubstituted phenyl or furanyl group or a benzo[1,3]dioxyl or benzo[1,4]dioxyl group, where the substituted phenyl or furanyl group contains one, two or three substituents selected from halo, $C_1$-$C_4$ alkyl; $C_1$-$C_4$ alkylthio; or —NR$^{Q1}$R$^{Q2}$, where R$^{Q1}$ and R$^{Q2}$ taken together with the nitrogen to which they are attached form a 4-7 membered heterocyclic ring, which may optionally contain one or more additional heteroatoms selected form N, O and S; t is 0 or 1; m is 0 or 1; $R^6$ and $R^7$ are independently selected from H and $C_1$-$C_4$ alkyl; $W^1$ is methyl, unsubstituted phenyl, naphthyl, pyridyl, thienyl or pyrrolyl or substituted phenyl or pyridyl containing one or two substituents independently selected from halo, alkyl and alkoxy, specifically, chloro, methyl and methoxy; $W^2$ is $C_1$-$C_4$ alkyl, $C_2$-$C_4$ alkynyl, $C_3$-$C_6$ cycloalkyl, aryl, Het hydroxy, aryloxy-, $C_1$-$C_4$ alkoxy-, —OCOC$_1$-$C_4$ alkyl, —OCOaryl, or —NR$^{W1}$R$^{W2}$, where R$^{W1}$ and R$^{W2}$ are independently H or $C_1$-$C_4$ alkyl or taken together with the nitrogen to which they are attached form a 4-7 membered heterocyclic ring, which may optionally contain one or more additional heteroatoms selected form N, O and S; $W^3$ is H or $C_1$-$C_4$ alkyl; or a pharmaceutically acceptable salt or solvate thereof.

More specific embodiments of this invention comprise compounds wherein X is chloro, bromo, cyano, carboxy-, methylcarboxy-, hydroxy, methoxy, methyl, trifluoromethyl, 1,3-dihydroxy-prop-2-yl (—CH(CH$_2$OH)$_2$, isopropyl, n-butyl, isobutyl, 2,2-dimethylpropyl, phenylcarbonyl, triazolyl, tetrazolyl, —NH$_2$, —NHCH$_3$, —NHCH$_2$CH$_3$, —NHCH$_2$CH$_2$CH$_3$, —NHCH$_2$CH$_2$CH$_2$CH$_3$, —NHCH$_2$CH$_2$CH$_2$CH$_2$CH$_2$CH$_3$, —NHCH$_2$C(CH$_3$)$_3$, —NHCH$_2$CH(CH$_3$)$_2$, —NHCH$_2$CH$_2$CH(CH$_3$)$_2$, —NH-cyclopentyl, —NH-phenyl, —NHCH$_2$-cyclopropyl, —NHCH(CH$_3$)$_2$, —NHCH$_2$CF$_3$, —N(CH$_3$)$_2$, —N(CH$_2$CH$_3$)$_2$, —NHCH(CH$_2$CH$_3$)$_2$, —NHCH$_2$CH(CH$_2$CH$_3$)$_2$, —NHCH$_2$CH$_2$OH, —NHCH$_2$CO$_2$H, —N(CH$_3$)CH$_2$CO$_2$H, —NHC(CH$_3$)$_2$CO$_2$H, —NHCH(CH$_3$)CO$_2$H, —(R)—NHCH(CH$_3$)CO$_2$H, —(S)—NHCH(CH$_3$)CO$_2$H, —NHCH$_2$-1H-imidazol-2-yl, —NHCH$_2$-(1-CH$_3$-imidazol-2-yl, —NH-(pyrimidin-2-yl), -morpholin-4-yl, -thiomorpholin-4-yl, -piperidin-1-yl, -piperidin-1-yl-(4-carboxylic acid), -piperidin-1-yl-(4-acetic acid), -piperidin-4-yl-(1-acetic acid), -2,5-dimethyl-pyrrol-1-yl, -pyrrolidin-1-yl, —((R)-2-CO$_2$H-pyrrolidin-1-yl), —((S)-2-CO$_2$H-pyrrolidin-1-yl), -piperazin-1-yl, -(4-methyl-piperazin-1-yl), -piperazin-1-yl-(4-acetic acid), —NHCH$_2$-(5-bromo-thien-2-yl), —NHCH$_2$-1H-imidazol-2-yl, —NHCH2-(1-methyl-imidazol-2-yl, —NHCOCH$_3$, —N(CH$_3$)COCH$_3$, —NHCO$_2$C(CH$_3$)$_3$, —NHCOCH$_2$CH$_3$, —NHCOC(CH$_3$)$_2$, —NHCO-furan-2-yl, —N(CH$_3$)CO-furan-2-yl, —NHCO-thien-2-yl, —NHCO-cyclopropyl, —NHCO-(5-bromo-thien-2-yl, —NHCO-(2,5-dimethyl-pyrrol-3-yl), —NHSO$_2$CH$_3$, —N(CH$_3$)SO$_2$CH$_3$, —NHSO$_2$CF$_3$, —NHSO$_2$phenyl, —N(CH$_3$)SO$_2$phenyl, —NHSO$_2$CH$_2$CH$_3$, —NHSO$_2$CH$_2$CF$_3$, —NHSO$_2$CH$_2$CH$_2$CH$_3$, —NHSO$_2$CH(CH$_3$)$_2$, —NHCONH(2-chlorophenyl), —N(CH$_3$)CONH(3,5-dimethoxyphenyl), —N(CH$_3$)CONH(2-chlorophenyl), —N(CH$_3$)CO-(benzo[1,3]diox-5-yl), —SO$_2$NHCH$_3$, and —SO$_2$N(CH$_3$)$_2$; p is 0, 1 or 2; $R^1$ and $R^2$ are H $C_1$-$C_4$ alkyl or $R^1$ and $R^2$ together with the carbon to which they are attached form a 3, 4 or 5 membered carbocyclic ring; Z is CH of N; k is 0 or k is 1 and $R^3$ is methyl, trifluoromethyl, chloro or methoxy; n is 3 and $R^4$ and $R^5$ are independently selected from H and methyl; Y is —O— or —C(R$^4$)(R$^5$)—; q is 1; $R^8$ and $R^9$ are each H; Q is 2-chloro-3-(trifluoromethyl)phenyl, 3-methyl-4-fluoro-phenyl, 4-tert-butyl-phenyl, 4-(methylthio)phenyl, 2,4,5-trifluoro-phenyl, 4-isopropyl-phenyl, 5-(piperidin-1-yl)-furan-2-yl, benzo[1,3]diox-5-yl, or 2,3-dihydrobenzo[1,4]dioxin-6-yl; t is 0 or 1; m is 0 or 1; $R^6$ and $R^7$ are independently selected from H and methyl; $W^1$ is methyl, phenyl, naphth-1-yl, pyrid-2-yl, 4-methyl-pyrid-2-yl, thien-2-yl, thien-3-yl, pyrrol-2-yl, 2-chlorophenyl, 3-chlorophenyl, 4-chlorophenyl, 2-methoxyphenyl, or 4-methoxyphenyl; $W^2$ is methyl, ethyl, ethynyl, isopropyl, n-butyl, 2-methylpropyl, trifluororrmethyl, cyclohexyl, unsubstituted phenyl, hydroxy, methoxy, phenoxy, dimethylamino, morpholin-4-yl, phenylcarbonyloxy, or methylcarbonyloxy; $W^3$ is H or methyl; or a pharmaceutically acceptable salt or solvate thereof.

Particular embodiments of this invention are directed to a compound of Formula I, II, I-A or II-A, as defined above, wherein X is selected from $C_1$-$C_8$ alkyl, halo, —OR$^{10}$, —NR$^{14}$R$^{15}$, nitro, cyano, —COR$^{13}$, —OCOR$^{13}$, —N(R$^{17}$)COR$^{13}$, —N(R$^{17}$)CONR$^{14}$R$^{15}$, —N(R$^{17}$)COOR$^{13}$, —SO$_3$H, —SO$_2$NR$^{14}$R$^{15}$, —C(=NR$^{17}$)NR$^{14}$R$^{15}$, —N(R$^{17}$)SO$_2$R$^{16}$, and a 5 or 6-membered heterocyclic group; or X and an adjacent $R^3$, taken together with the atoms to which they are bonded, form an alkylenedioxy moiety; Z is CH, CR$^3$ or N, wherein when Z is CH or CR$^3$, k is 0-4 and t is 0 or 1, and when Z is N, k is 0-3 and t is 0; Y is selected from —O—, —S—, —N(R$^{10}$)—, and —C(R$^4$)(R$^5$)—; $W^1$ is selected from $C_1$-$C_6$ alkyl, $C_3$-$C_8$ cycloalkyl, aryl and Het, wherein said $C_1$-$C_8$ alkyl, $C_3$-$C_8$ cycloalkyl, Ar and Het are optionally unsubstituted or substituted with one or more groups independently selected from halo, cyano, nitro, $C_1$-$C_6$ alkyl, $C_3$-$C_6$ alkenyl, $C_3$-$C_6$ alkynyl, —C$_0$-C$_6$ alkyl-CO$_2$R$^{10}$, —C$_0$-C$_6$ alkyl-C(O)SR$^{10}$, —C$_0$-C$_6$ alkyl-CONR$^{11}$R$^{12}$, —C$_0$-C$_6$ alkyl-COR$^{13}$, —C$_0$-C$_6$ alkyl-NR$^{11}$R$^{12}$, —C$_0$-C$_6$ alkyl-SR$^{10}$, —C$_0$-C$_6$ alkyl-OR$^{10}$, —C$_0$-C$_6$ alkyl-SO$_3$H, —C$_0$-C$_6$ alkyl-SO$_2$NR$^{11}$R$^{12}$, —C$_0$-C$_6$ alkyl-SO$_2$R$^{10}$, —C$_0$-C$_6$ alkyl-SOR$^{13}$, —C$_0$-C$_6$ alkyl-OCOR$^{13}$, —C$_0$-C$_6$ alkyl-OC(O)NR$^{11}$R$^{12}$, —C$_0$-C$_6$ alkyl-OC(O)OR$^{13}$, —C$_0$-C$_6$ alkyl-NR$^{11}$C(O)OR$^{13}$, —C$_0$-C$_6$ alkyl-NR$^{11}$C(O)NR$^{11}$R$^{12}$, and —C$_0$-C$_6$ alkyl-NR$^{11}$COR$^{13}$, where said $C_1$-$C_6$ alkyl, is optionally unsubstituted or substituted by one or more halo substituents; $W^2$ is selected from H, halo, $C_1$-$C_6$ alkyl, $C_2$-$C_6$ alkenyl, $C_2$-$C_6$ alkynyl, —C$_0$-C$_6$ alkyl-NR$^{11}$R$^{12}$, —C$_0$-C$_6$ alkyl-SR$^{10}$, —C$_0$-C$_6$ alkyl-OR$^{10}$, —C$_0$-C$_6$ alkyl-CO$_2$R$^{10}$, —C$_0$-C$_6$ alkyl-C(O)SR$^{10}$, —C$_0$-C$_6$ alkyl-CONR$^{11}$R$^{12}$, —C$_0$-C$_6$ alkyl-COR$^{13}$, —C$_0$-C$_6$ alkyl-COR$^{13}$, —C$_0$-C$_6$ alkyl-OCONR$^{11}$R$^{12}$, —C$_0$-C$_6$ alkyl-NR$^{11}$CONR$^{11}$R$^{12}$, —C$_0$-C$_6$ alkyl-NR$^{11}$COR$^{13}$, —C$_0$-C$_6$ alkyl-Het, —C$_0$-C$_6$ alkyl-Ar and —C$_0$-C$_6$ alkyl-C$_3$-C$_7$ cycloalkyl, wherein said $C_1$-$C_6$ alkyl is optionally unsubstituted or substituted by one or more halo substituents, and wherein the $C_3$-$C_7$ cycloalkyl, Ar and Het moieties of said —C$_0$-C$_6$ alkyl-Het, —C$_0$-C$_6$ alkyl-Ar and —C$_0$-C$_6$ alkyl-C$_3$-C$_7$ cycloalkyl are optionally unsubstituted or substituted with one or more groups independently selected from halo, cyano, nitro, $C_1$-$C_6$ alkyl, $C_3$-$C_6$ alkenyl, $C_3$-$C_6$ alkynyl, —C$_0$-C$_6$ alkyl-CO$_2$R$^{10}$, —C$_0$-C$_6$ alkyl-C(O)SR$^{10}$, —C$_0$-C$_6$ alkyl-CONR$^{11}$R$^{12}$, —C$_0$-C$_6$ alkyl-COR$^{13}$, —C$_0$-C$_6$ alkyl-NR$^{11}$R$^{12}$, —C$_0$-C$_6$ alkyl-SR$^{10}$, —C$_0$-C$_6$ alkyl-OR$^{10}$, —C$_0$-C$_6$ alkyl-SO$_3$H, —C$_0$-C$_6$ alkyl-SO$_{12}$NR$^{11}$R$^2$, —C$_0$-C$_6$ alkyl-SO$_2$R$^{10}$, —C$_0$-C$_6$ alkyl-SOR$^{13}$, —C$_0$-C$_6$ alkyl-OCOR$^{13}$, —C$_0$-C$_6$ alkyl-OC(O)NR$^{11}$R$^{12}$, —C$_0$-C$_6$ alkyl-OC(O)OR$^{13}$, —C$_0$-C$_6$ alkyl-NR$^{11}$C(O)OR$^{13}$, —C$_0$-C$_6$ alkyl-NR$^{11}$C(O)NR$^{11}$R$^{12}$, and —C$_0$-C$_6$ alkyl-NR$^{11}$COR$^{13}$, where said $C_1$-$C_6$ alkyl, is optionally unsubstituted or substituted by one or more halo substituents; $W^3$ is selected from the group consisting of: H, halo, $C_1$-$C_6$ alkyl, —C$_0$-C$_6$ alkyl-NR$^{11}$R$^{12}$, —C$_0$-C$_6$ alkyl-SR$^{10}$, —C$_0$-C$_6$ alkyl-OR$^{10}$, —C$_0$-C$_6$ alkyl-CO$_2$R$^{10}$, —C$_0$-C$_6$ alkyl-C(O)SR$^{10}$, —C$_0$-C$_6$ alkyl-CONR$^{11}$R$^{12}$, —C$_0$-C$_6$ alkyl-COR$^{13}$, —C$_0$-C$_6$ alkyl-OCOR$^{13}$, —C$_0$-C$_6$ alkyl- OCONR$^{11}$R$^{12}$, —C$_0$-C$_6$ alkyl-NR$^{11}$CONR$^{11}$R$^{12}$, —C$_0$-C$_6$ alkyl-NR$^{11}$COR$^{13}$, —C$_0$-C$_6$ alkyl-Het, —C$_1$-C$_6$ alkyl-Ar and —C$_1$-C$_6$ alkyl-C$_3$-C$_7$ cycloalkyl, wherein said C$_1$-C$_6$ alkyl is optionally unsubstituted or substituted by one or more halo substituents; Q is selected from C$_3$-C$_8$ cycloalkyl, Ar and Het; wherein said C$_3$-C$_8$ cycloalkyl, Ar and Het are optionally unsubstituted or substituted with one or more groups independently selected from halo, cyano, nitro, C$_1$-C$_6$ alkyl, C$_3$-C$_6$ alkenyl, C$_3$-C$_6$ alkynyl, —C$_0$-C$_6$ alkyl-CO$_2$R$^{10}$, —C$_0$-C$_6$ alkyl-C(O)SR$^{10}$, —C$_0$-C$_6$ alkyl-CONR$^{11}$R$^{12}$, —C$_0$-C$_6$ alkyl-COR$^{13}$, —C$_0$-C$_6$ alkyl-NR$^{11}$R$^{12}$, —C$_0$-C$_6$ alkyl-SR$^{10}$, —C$_0$-C$_6$ alkyl-OR$^{10}$, —C$_0$-C$_6$ alkyl-SO$_3$H, —C$_0$-C$_6$ alkyl-SO$_2$NR$^{11}$R$^{12}$, —C$_0$-C$_6$ alkyl-SO$_2$R$^{10}$, —C$_0$-C$_6$ alkyl-SOR$^{13}$, —C$_0$-C$_6$ alkyl-OCOR$^{13}$, 'C$_0$-C$_6$ alkyl-OC(O)NR$^{11}$R$^{12}$, —C$_0$-C$_6$ alkyl-OC(O)OR$^{13}$, —C$_0$-C$_6$ alkyl-NR$^{11}$C(O)OR$^{13}$, —C$_0$-C$_6$ alkyl-NR$^{11}$C(O)NR$^{11}$ R$^{12}$, and —C$_0$-C$_6$ alkyl-NR$^{11}$COR$^{13}$, where said C$_1$-C$_6$ alkyl is optionally unsubstituted or substituted by one or more halo substituents; p is 0-8; n is 2-8; m is 0 or 1; q is 0 or 1; t is 0 or 1; each R$^1$ and R$^2$ are independently selected from H, halo, C$_1$-C$_6$ alkyl, C$_3$-C$_6$ alkenyl, C$_3$-C$_6$ alkynyl, —C$_0$-C$_6$ alkyl-NR$^{11}$R$^{12}$, —C$_0$-C$_6$ alkyl-OR$^{10}$, —C$_0$-C$_6$ alkyl-SR$^{10}$, —C$_1$-C$_6$ alkyl-Het, —C$_1$-C$_6$ alkyl-Ar and —C$_1$-C$_6$ alkyl-C$_3$-C$_7$ cycloalkyl, or R$^1$ and R$^2$ together with the carbon to which they are attached form a 3-5 membered carbocyclic or heterocyclic ring, wherein said heterocyclic ring contains one, or more heteroatoms selected from N, O, and 8, where any of said C$_1$-C$_6$ alkyl is optionally unsubstituted or substituted by one or more halo substituents; each R$^3$ is the same or different and is independently selected from halo, cyano, nitro, C$_1$-C$_6$ alkyl, C$_3$-C$_6$ alkenyl, C$_3$-C$_6$ alkynyl, —C$_0$-C$_6$ alkyl-Ar, —C$_0$-C$_6$ alkyl-Het, —C$_0$-C$_6$ alkyl-C$_3$-C$_7$ cycloalkyl, —C$_0$-C$_6$ alkyl-CO$_2$R$^{10}$, —C$_0$-C$_6$ alkyl-C(O)SR$^{10}$, —C$_0$-C$_6$ alkyl-CONR$^{11}$R$^{12}$, —C$_0$-C$_6$ alkyl-COR$^{13}$, —C$_0$-C$_6$ alkyl-NR$^{11}$R$^{12}$, —C$_0$-C$_6$ alkyl-SR$^{10}$, —C$_0$-C$_6$ alkyl-OR$^{10}$, —C$_0$-C$_6$ alkyl-SO$_3$H, —C$_0$-C$_6$ alkyl-SO$_2$NR$^{11}$R$^{12}$, —C$_0$-C$_6$ alkyl-SO$_2$R$^{10}$, —C$_0$-C$_6$ alkyl-SOR$^{13}$, —C$_0$-C$_6$ alkyl-OCOR$^{13}$, —C$_0$-C$_6$ alkyl-OC(O)NR$^{11}$R$^{12}$, —C$_0$-C$_6$ alkyl-OC(O)OR$^{13}$, —C$_0$-C$_6$ alkyl-NR$^{11}$C(O)OR$^{13}$, —C$_0$-C$_6$ alkyl-NR$^{11}$C(O)NR$^{11}$R$^{12}$, and —C$_0$-C$_6$ alkyl-NR$^{11}$COR$^{13}$, wherein said C$_1$-C$_6$ alkyl is optionally unsubstituted or substituted by one or more halo substituents; each R$^4$ and R$^5$ is independently selected from H, halo, C$_1$-C$_6$ alkyl, —C$_0$-C$_6$ alkyl-Het, —C$_0$-C$_6$ alkyl-Ar and —C$_0$-C$_6$ alkyl-C$_3$-C$_7$ cycloalkyl; R$^6$ and R$^7$ are each independently selected from H, halo, C$_1$-C$_6$ alkyl, —C$_0$-C$_6$ alkyl-Het, —C$_0$-C$_6$ alkyl-Ar and —C$_0$-C$_6$ alkyl-C$_3$-C$_7$ cycloalkyl; R$^8$ and R$^9$ are each independently selected from H, halo, C$_1$-C$_6$ alkyl, —C$_0$-C$_6$ alkyl-Het, —C$_0$-C$_6$ alkyl-Ar and —C$_0$-C$_6$ alkyl-C$_3$-C$_7$ cycloalkyl; R$^{10}$ is selected from H, C$_1$-C$_6$ alkyl, C$_3$-C$_6$ alkenyl, C$_3$-C$_6$ alkynyl, —C$_0$-C$_6$ alkyl-Ar, —C$_0$-C$_6$ alkyl-Het and —C$_0$-C$_6$ alkyl-C$_3$-C$_7$ cycloalkyl; each R$^{11}$ and each R$^{12}$ are independently selected from H, C$_1$-C$_6$ alkyl, C$_3$-C$_6$ alkenyl, C$_3$-C$_6$ alkynyl, —C$_0$-C$_6$ alkyl-Ar, —C$_0$-C$_6$ alkyl-Het and —C$_0$-C$_6$ alkyl-C$_3$-C$_7$ cycloalkyl, or R$^{11}$ and R$^{12}$ together with the nitrogen to which they are attached form a 4-7 membered heterocyclic ring which optionally contains one or more additional heteroatoms selected from N, O, and S; R$^{13}$ is selected from C$_1$-C$_6$ alkyl, C$_3$-C$_6$ alkenyl, C$_3$-C$_6$ alkynyl, —C$_0$-C$_6$ alkyl-Ar, —C$_0$-C$_6$ alkyl-Het and —C$_0$-C$_6$ alkyl-C$_3$-C$_7$ cycloalkyl; R$^{14}$ and R$^{15}$ are each independently selected from H, C$_1$-C$_6$ alkyl, C$_3$-C$_6$ alkenyl, C$_3$-C$_6$ alkynyl, —C$_0$-C$_6$ alkyl-Ar, —C$_0$-C$_6$ alkyl-Het, —C$_0$-C$_6$ alkyl-C$_3$-C$_7$ cycloalkyl, —C$_0$-C$_6$ alkyl-O—Ar, —C$_0$-C$_6$ alkyl-O-Het, —C$_0$-C$_6$ alkyl-O—C$_3$-C$_7$ cycloalkyl, —C$_0$-C$_6$ alkyl-S(O)$_x$—C$_1$-C$_6$ alkyl, —C$_0$-C$_6$ alkyl-S(O)$_x$—Ar, —C$_0$-C$_6$ alkyl-S(O)$_x$-Het, —C$_0$-C$_6$ alkyl-S(O)$_x$—C$_3$-C$_7$ cycloalkyl, —C$_0$-C$_6$ alkyl-NH-Het, —C$_0$-C$_6$ alkyl-NH—C$_3$-C$_7$ cycloalkyl, —C$_0$-C$_6$ alkyl-N(C$_1$-C$_4$ alkyl)-Ar, —C$_0$-C$_6$ alkyl-N(C$_1$-C$_4$ alkyl)-Het, —C$_0$-C$_6$ alkyl-N(C$_1$-C$_4$ alkyl)-C$_3$-C$_7$ cycloalkyl, —C$_0$-C$_6$ alkyl-Ar, —C$_0$-C$_6$ alkyl-Het and —C$_0$-C$_6$ alkyl-C$_3$-C$_7$ cycloalkyl, where x is 0, 1 or 2, or R$^{14}$ and R$^{15}$, together with the nitrogen to which they are attached, form a 4-7 membered heterocyclic ring which optionally contains one or more additional heteroatoms selected from N, O, and S, wherein said C$_1$-C$_6$ alkyl is optionally substituted by one or more of the substituents independently selected from the group halo, —OH, —SH, —NH$_2$, —NH(unsubstituted C$_1$-C$_6$ alkyl), —N(unsubstituted C$_1$-C$_6$ alkyl)(unsubstituted C$_1$-C$_6$ alkyl), unsubstituted —OC$_1$-C$_6$ alkyl, —CO$_2$H, —CO$_2$(unsubstituted C$_1$-C$_6$ alkyl), —CONH$_2$, —CONH(unsubstituted C$_1$-C$_6$ alkyl), —CON(unsubstituted C$_1$-C$_6$ alkyl)(unsubstituted C$_1$-C$_6$ alkyl), —SO$_3$H, —SO$_2$NH$_2$, —SO$_2$NH(unsubstituted C$_1$-C$_6$ alkyl) and —SO$_2$N(unsubstituted C$_1$-C$_6$ alkyl)(unsubstituted C$_1$-C$_6$ alkyl); R$^{16}$ is C$_1$-C$_6$ alkyl, —C$_0$-C$_6$ alkyl-Ar or —C$_0$-C$_6$ alkyl-Het; and R$^{17}$ is H, C$_1$-C$_6$ alkyl, —C$_0$-C$_6$ alkyl-Ar or —C$_0$-C$_6$ alkyl-Het; and a pharmaceutically acceptable salt or solvate thereof.

Another particular embodiment of this invention is directed to a compound of Formula I, II, I-A or II-A, as defined above, wherein X is —COOR$^{10}$ and at least one of Y, W$^1$, W$^2$, W$^3$, m, t, R$^1$, R$^2$, R$^3$, R$^4$, R5, R$^6$, R$^7$, R$^8$ or R$^9$ is defined as follows: wherein Y is —S—, —N(R$^{10}$)—, or —C(R$^4$)(R$^5$)—; or W$^1$ is C$_1$-C$_6$ alkyl or Het, wherein said C$_1$-C$_8$ alkyl or and Het is optionally unsubstituted or substituted with one or more groups independently selected from halo, cyano, nitro, C$_1$-C$_6$ alkyl, C$_3$-C$_6$ alkenyl, C$_3$-C$_6$ alkynyl, —C$_0$-C$_6$ alkyl-CO$_2$R$^{10}$, —C$_0$-C$_6$ alkyl-C(O)SR$^{10}$, —C$_0$-C$_6$ alkyl-CONR$^{11}$R$^{12}$, —C$_0$-C$_6$ alkyl-COR$^{13}$, —C$_0$-C$_6$ alkyl-NR$^{11}$R$^{12}$, —C$_0$-C$_6$ alkyl-SR$^{10}$, —C$_0$-C$_6$ alkyl-OR$^{10}$, —C$_0$-C$_6$ alkyl-SO$_3$H, —C$_0$-C$_6$ alkyl-SO$_2$NR$^{11}$R$^{12}$, —C$_0$-C$_6$ alkyl-SO$_2$R$^{10}$, —C$_0$-C$_6$ alkyl-SOR$^{13}$, —C$_0$-C$_6$ alkyl-OCOR$^{13}$, —C$_0$-C$_6$ alkyl-OC(O)NR$^{11}$R$^{12}$, —C$_0$-C$_6$ alkyl-OC(O)OR$^{13}$, —C$_0$-C$_6$ alkyl-NR$^{11}$C(O)OR$^{13}$, —C$_0$-C$_6$ alkyl-NR$^{11}$C(O)NR$^{11}$R$^{12}$, and —C$_0$-C$_6$ alkyl-NR$^{11}$COR$^{13}$, where said C$_1$-C$_6$ alkyl, is optionally unsubstituted or substituted by one or more halo substituents; or W$^2$ is H, halo, C$_1$-C$_6$ alkyl, C$_2$-C$_6$ alkenyl, C$_2$-C$_6$ alkynyl, —C$_0$-C$_6$ alkyl-NR$^{11}$R$^{12}$, —C$_0$-C$_6$ alkyl-SR$^{10}$, —C$_0$-C$_6$ alkyl-OR$^{10}$, —C$_0$-C$_6$ alkyl-CO$_2$R$^{10}$, —C$_0$-C$_6$ alkyl-C(O)SR$^{10}$, C$_0$-C$_6$ alkyl-CONR$^{11}$R$^{12}$, —C$_0$-C$_6$ alkyl-COR$^{13}$, —C$_0$-C$_6$ alkyl-OCOR$^{13}$, —C$_0$-C$_6$ alkyl-OCONR R$^{12}$, —C$_0$-C$_6$ alkyl-NR$^{11}$CONR$^{11}$R$^{12}$, —C$_0$-C$_6$ alkyl-NR$^{11}$COR$^{13}$, —C$_0$-C$_6$ alkyl-Het, —C$_1$-C$_6$ alkyl-Ar or —C$_1$-C$_6$ alkyl-C$_3$-C$_7$ cycloalkyl, wherein said C$_1$-C$_6$ alkyl is optionally unsubstituted or substituted by one or more halo substituents, and wherein the C$_3$-C$_7$ cycloalkyl, Ar and Het moieties of said —C$_0$-C$_6$ alkyl-Het, —C$_1$-C$_6$ alkyl-Ar and —C$_1$-C$_6$ alkyl-C$_3$-C$_7$ cycloalkyl are optionally unsubstituted or substituted with one or more groups independently selected from halo, cyano, nitro, C$_1$-C$_6$ alkyl, C$_3$-C$_6$ alkenyl, C$_3$-C$_6$ alkynyl, —C$_0$-C$_6$ alkyl-CO$_2$R$^{10}$, —C$_0$-C$_6$ alkyl-C(O)SR$^{10}$, —C$_0$-C$_6$ alkyl-CONR$^{11}$R$^{12}$, —C$_0$-C$_6$ alkyl-COR$^{13}$, —C$_0$-C$_6$ alkyl-NR$^{11}$R$^{12}$, —C$_0$-C$_6$ alkyl-SR$^{10}$, —C$_0$-C$_6$ alkyl-OR$^{10}$, —C$_0$-C$_6$ alkyl-SO$_3$H, —C$_0$-C$_6$ alkyl-SO$_2$NR$^{11}$R$^{12}$, —C$_0$-C$_6$ alkyl-SO$_2$R$^{10}$, —C$_0$-C$_6$ alkyl-SOR$^{13}$, —C$_0$-C$_6$ alkyl-OCOR$^{13}$, —C$_0$-C$_6$ alkyl-OC(O)NR$^{11}$R$^{12}$, —C$_0$-C$_6$ alkyl-OC(O)OR$^{13}$, —C$_0$-C$_6$ alkyl-NR$^{11}$C(O)OR$^{13}$, —C$_0$-C$_6$ alkyl-NR$^{11}$C(O)NR$^{11}$R$^{12}$, and —C$_0$-C$_6$ alkyl-NR$^{11}$COR$^{13}$, where said C$_1$-C$_6$ alkyl, is optionally unsubstituted or substituted by one or more halo substituents; or W$^3$ is H, halo, C$_1$-C$_6$ alkyl, —C$_0$-C$_6$ alkyl-NR$^{11}$R$^{12}$, —C$_0$-C$_6$ alkyl-SR$^{10}$, —C$_0$-C$_6$ alkyl-OR$^{10}$, —C$_0$-C$_6$ alkyl-CO$_2$R$^{10}$, —C$_0$-C$_6$ alkyl-C(O)

SR$^{10}$, —C$_0$-C$_6$ alkyl-CONR$^{11}$R$^{12}$, —C$_0$-C$_6$ alkyl-COR$^{13}$, —C$_0$-C$_6$ alkyl-OCOR$^{13}$, —C$_0$-C$_6$ alkyl-OCONR$^{11}$R$^{12}$, —C$_0$-C$_6$ alkyl-NR$^{11}$CONR$^{11}$R$^{12}$, —C$_0$-C$_6$ alkyl-NR$^{11}$COR$^{13}$, —C$_0$-C$_6$ alkyl-Ar-Het, —C$_1$-C$_6$ alkyl-Ar or —C$_1$-C$_6$ alkyl-C$_3$-C$_7$ cycloalkyl, wherein said C$_1$-C$_6$ alkyl is optionally unsubstituted or substituted by one or more halo substituents; or m is 0; or t is 1; or at least one of R$^1$ or R$^2$ is halo, C$_3$-C$_6$ alkenyl, C$_3$-C$_6$ alkynyl, —C$_0$-C$_6$ alkyl-NR$^{11}$R$^{12}$, —C$_0$-C$_6$ alkyl-OR$^{10'}$, —C$_0$-C$_6$ alkyl-SR$^{10'}$, —C$_1$-C$_6$ alkyl-Het, —C$_1$-C$_6$ alkyl-Ar and —C$_1$-C$_6$ alkyl-C$_3$-C$_7$ cycloalkyl, or R$^1$ and R$^2$ together with the carbon to which they are attached form a 3-5 membered carbocyclic or heterocyclic ring, wherein said heterocyclic ring contains one, or more heteroatoms selected from N, O, and S, where any of said C$_1$-C$_6$ alkyl is optionally unsubstituted or substituted by one or more halo substituents, where R$^{10'}$, is selected from H, C$_3$-C$_6$ alkenyl, C$_3$-C$_6$ alkynyl, —C$_0$-C$_6$ alkyl-Ar, —C$_0$-C$_6$ alkyl-Het and —C$_0$-C$_6$ alkyl-C$_3$-C$_7$ cycloalkyl; or at least one R$^3$ is C$_3$-C$_6$ alkynyl, —C$_0$-C$_6$ alkyl-Ar, —C$_0$-C$_6$ alkyl-Het, —C$_0$-C$_6$ alkyl-C$_3$-C$_7$ cycloalkyl, —C$_0$-C$_6$ alkyl-C(O)SR$^{10}$, —C$_1$-C$_6$ alkyl-CONR$^{11}$R$^{12}$, —C$_1$-C$_6$ alkyl-COR$^{13}$, —C$_1$-C$_6$ alkyl-SR$^{10}$, —C$_1$-C$_6$ alkyl-OR$^{10}$, —C$_0$-C$_6$ alkyl-SO$_3$H, —C$_0$-C$_6$ alkyl-SO$_2$NR$^{11}$R$^{12}$, —C$_1$-C$_6$ alkyl-SO$_2$R$^{10}$, —C$_1$-C$_6$ alkyl-SOR$^{13}$, —C$_1$-C$_6$ alkyl-OCOR$^{13}$, —C$_0$-C$_6$ alkyl-OC(O)NR$^{11}$R$^{12}$, —C$_0$-C$_6$ alkyl-OC(O)OR$^{13}$, —C$_0$-C$_6$ alkyl-NR$^{11}$C(O)OR$^{13}$, —C$_0$-C$_6$ alkyl-NR$^{11}$C(O)NR$^{11}$R$^{12}$, or —C$_0$-C$_6$ alkyl-NR$^{11}$COR$^{13}$, wherein said C$_1$-C$_6$ alkyl is optionally unsubstituted or substituted by one or more halo substituents; or at least one of R$^4$ or R$^5$ is halo, C$_1$-C$_6$ alkyl, —C$_0$-C$_6$ alkyl-Het, —C$_0$-C$_6$ alkyl-Ar or —C$_0$-C$_6$ alkyl-C$_3$-C$_7$ cycloalkyl; or at least one of R$^6$ or R$^7$ is halo, C$_1$-C$_6$ alkyl, —C$_0$-C$_6$ alkyl-Het, —C$_0$-C$_6$ alkyl-Ar or —C$_0$-C$_6$ alkyl-C$_3$-C$_7$ cycloalkyl; or R$^9$ is halo, —C$_0$-C$_6$ alkyl-Het, —C$_0$-C$_6$ alkyl-Ar or —C$_0$-C$_6$ alkyl-C$_3$-C$_7$ cycloalkyl; or both R$^8$ and R$^9$ are each independently selected from halo, C$_1$-C$_6$ alkyl, —C$_0$-C$_6$ alkyl-Het, —C$_0$-C$_6$ alkyl-Ar and —C$_0$-C$_6$ alkyl-C$_3$-C$_7$ cycloalkyl; or and R$^{10}$, R$^{11}$, R$^{12}$, R$^{13}$, R$^{14}$, R$^{15}$, R$^{16}$ and R$^{17}$ are as defined herein.

Yet another particular embodiment of this invention is directed to a compound of Formula I, I-A, II or II-A, as defined above, wherein W$^1$ and W$^2$ are not each independently C$_3$-C$_8$ cycloalkyl or aryl or W$^3$ is not H (that is, W$^1$ and W$^2$ are other than C$_3$-C$_8$ cycloalkyl or aryl or W$^3$ is other than H) or any one of R$^6$ or R$^7$ is not H or R$^8$ and R$^9$ are each C$_1$-C$_4$ alkyl when: X is COOR$^{10}$; Z is CH or CR$^3$ and k is 0-4 or Z is N and k is 0-3; p is 0-8; n is 2-8; q is 0 or 1; Q is selected from optionally unsubstituted or substituted C$_3$-C$_8$ cycloalkyl, phenyl and monocyclic Het; each R$^1$ and R$^2$ is independently selected from H, C$_1$-C$_6$ alkyl, —OH, —O—C$_1$-C$_6$ alkyl, —SH, and —S—C$_1$-C$_6$ alkyl; each R$^3$ is the same or different and is independently selected from halo, cyano, nitro, —CONR$^{12}$R$^{13}$, —COR$^{14}$, —SR$^{11}$, —SO$_2$R$^{11}$, —SOR$^{14}$—OCOR$^{14}$ and optionally unsubstituted or substituted C$_1$-C$_6$ alkyl, C$_3$-C$_6$ alkenyl, -5-6 membered-Het, —C$_0$-C$_6$ alkyl-CO$_2$R$^{11}$, or —C$_0$-C$_6$ alkyl-NR$^{12}$R$^{13}$, where the optionally unsubstituted or substituted C$_3$-C$_8$ cycloalkyl, phenyl and monocyclic Het; optionally unsubstituted or substituted C$_1$-C$_6$ alkyl, C$_3$-C$_6$ alkenyl, 5-6 membered-Het, —C$_0$-C$_6$ alkyl-CO$_2$R$^{11}$, or —C$_0$-C$_6$ alkyl-NR$^{12}$R$^{13}$, R$^{11}$, R$^{12}$ and R$^{13}$ and R$^{14}$ are as defined herein.

Another particular embodiment of this invention is directed to a compound of Formula I, I-A, II or II-A, as defined above, wherein W$^1$ and W$^2$ are not each independently C$_3$-C$_8$ cycloalkyl or aryl or W$^3$ is not H (that is, W$^1$ and W$^2$ are other than C$_3$-C$_8$ cycloalkyl or aryl or W$^3$ is other than H) when: X is COOR$^{10}$; Z is CH, CR$^3$ or N; wherein when Z is CH or CR$^3$, k is 0-4 and when Z is N, k is 0-3; p is 0-8; n is 2-8; q is 0 or 1; Q is selected from C$_3$-C$_8$ cycloalkyl, phenyl, and monocyclic Het; wherein said C$_3$-C$_8$ cycloalkyl, phenyl and monocyclic Het are optionally unsubstituted or substituted with one or more groups independently selected from halo, cyano, nitro, C$_1$-C$_6$ alkyl, C$_3$-C$_6$ alkenyl, C$_3$-C$_6$ alkynyl, —C$_0$-C$_6$ alkyl-CO$_2$R$^{11}$, —C$_0$-C$_6$ alkyl-C(O)SR$^{11}$, —C$_0$-C$_6$ alkyl-CONR$^{12}$R$^{13}$, —C$_0$-C$_6$ alkyl-COR$^{14}$, —C$_0$-C$_6$ alkyl-NR$^{12}$R$^{13}$, —C$_0$-C$_6$ alkyl-SR$^{11}$, —C$_0$-C$_6$ alkyl-OR$^{11}$, —C$_0$-C$_6$ alkyl-SO$_3$H, —C$_0$-C$_6$ alkyl-SO$_2$NR$^{12}$R$^{13}$, —C$_0$-C$_6$ alkyl-SO$_2$R$^{11}$, —C$_0$-C$_6$ alkyl-SOR$^{14}$, —C$_0$-C$_6$ alkyl-OCOR$^{14}$, —C$_0$-C$_6$ alkyl-OC(O)NR$^{12}$R$^{13}$, —C$_0$-C$_6$ alkyl-OC(O)OR$^{14}$, —C$_0$-C$_6$ alkyl-NR$^{12}$C(O)OR$^{14}$, —C$_0$-C$_6$ alkyl-NR$^{12}$C(O)NR$^{12}$R$^{13}$, and —C$_0$-C$_6$ alkyl-NR$^{12}$COR$^{14}$, where said C$_1$-C$_6$ alkyl is optionally unsubstituted or substituted by one or more halo substituents; each R$^1$ and R$^2$ is independently selected from H, C$_1$-C$_6$ alkyl, —OH, —O—C$_1$-C$_6$ alkyl, —SH, and —S—C$_1$-C$_6$ alkyl; each R$^3$ is the same or different and is independently selected from halo, cyano, nitro, C$_1$-C$_6$ alkyl, C$_3$-C$_6$ alkenyl, C$_3$-C$_6$ alkynyl, —C$_0$-C$_6$ alkyl-Ar, —C$_0$-C$_6$ alkyl-Het, —C$_0$-C$_6$ alkyl-C$_3$-C$_7$ cycloalkyl, —C$_0$-C$_6$ alkyl-CO$_2$R$^{11}$, —C$_0$-C$_6$ alkyl-C(O)SR$^{11}$, —C$_0$-C$_6$ alkyl-CONR$^{12}$R$^{13}$; —C$_0$-C$_6$ alkyl-COR$^{14}$, —C$_0$-C$_6$ alkyl-NR$^{12}$R$^{13}$, —C$_1$-C$_6$ alkyl-SR$^{11}$, —C$_0$-C$_6$ alkyl-OR$^{11}$, —C$_0$-C$_6$ alkyl-SO$_3$H, —C$_0$-C$_6$ alkyl-SO$_2$NR$^{12}$R$^{13}$, —C$_0$-C$_6$ alkyl-SO$_2$R$^{11}$, —C$_0$-C$_6$ alkyl-SOR$^{14}$, —C$_0$-C$_6$ alkyl-OCOR$^{14}$, —C$_0$-C$_6$ alkyl-OC(O)NR$^{12}$R$^{13}$, —C$_0$-C$_6$ alkyl-OC(O)OR$^{14}$, —C$_0$-C$_6$ alkyl-NR$^{12}$C(O)OR$^{14}$, —C$_0$-C$_6$ alkyl-NR$^{12}$C(O)NR$^{12}$R$^{13}$, and —C$_0$-C$_6$ alkyl-NR$^{12}$COR$^{14}$, wherein said C$_1$-C$_6$ alkyl is optionally unsubstituted or substituted by one or more halo substituents; each R$^4$ and R$^5$ is independently H or C$_1$-C$_4$ alkyl; R$^6$ and R$^7$ are each independently H or C$_1$-C$_4$ alkyl; R$^8$ and R$^9$ are each independently H or C$_1$-C$_4$ alkyl; R$^{10}$ is selected from H, C$_1$-C$_8$ alkyl, C$_3$-C$_8$ alkenyl, C$_3$-C$_6$ alkynyl, —C$_0$-C$_6$ alkyl-Ar, —C$_0$-C$_6$ alkyl-Het and —C$_0$-C$_6$ alkyl-C$_3$-C$_7$ cycloalkyl; R$^{11}$ is selected from H, C$_1$-C$_6$ alkyl, C$_3$-C$_6$ alkenyl, C$_3$-C$_6$ alkynyl, —C$_0$-C$_6$ alkyl-Ar, —C$_0$-C$_6$ alkyl-Het and —C$_0$-C$_6$ alkyl-C$_3$-C$_7$ cycloalkyl; each R$^{12}$ and each R$^{13}$ are independently selected from H, C$_1$-C$_6$ alkyl, C$_3$-C$_6$ alkenyl, C$_3$-C$_6$ alkynyl, —C$_0$-C$_6$ alkyl-Ar, —C$_0$-C$_6$ alkyl-Het and —C$_0$-C$_6$ alkyl-C$_3$-C$_7$ cycloalkyl, or R$^{13}$ and R$^{14}$ together with the nitrogen to which they are attached form a 4-7 membered heterocyclic ring which optionally contains one or more additional heteroatoms selected from N, O, and S; and R$^{14}$ is selected from C$_1$-C$_6$ alkyl, C$_3$-C$_6$ alkenyl, C$_3$-C$_6$ alkynyl, —C$_0$-C$_6$ alkyl-Ar, —C$_0$-C$_6$ alkyl-Het and —C$_0$-C$_6$ alkyl-C$_3$-C$_7$ cycloalkyl; or a pharmaceutically acceptable salt or solvate thereof.

Compounds according to this invention include: 2-(3-{3-[[2-Chloro-3-(trifluoromethyl)benzyl](2,2-dephenylethyl)amino]propoxy}phenyl)-ethanol 2-(3-{3-[[2-Chloro-3-(trifluoromethyl)benzyl](2,2-diphenylethyl)amino]propoxy}-phenyl)acetic acid, N-oxide; (3-{3-[[2-Chloro-3-(trifluoromethyl)benzyl](2,2-diphenylethyl)amino] propoxy)bromobenzene; (4-{3-[[2-Chloro-3-(trifluoromethyl)benzyl](2,2-diphenylethyl)amino] propoxy}-bromobenzene; (2-Chloro-3-trifluoromethyl-benzyl)-(2,2-diphenylethyl)-{3-[3-(1,2,4-triazol-3-ylmethyl)-phenoxy]-propyl}-amine; (2-Chloro-3-trifluoromethyl-benzyl)-(2,2-diphenyl-ethyl)-{3-[3-(1,2,3,4-tetrazol-5-ylmethyl)-phenoxy]-propyl}amine; (2-Chloro-3-trifluoromethyl-benzyl)-(2-cyclohexyl-2-phenyl-ethyl)-{3-[3-(1,2,3,4-tetrazol-5-ylmethyl)-phenoxy]-propyl}-amine; (S)-(2-Chloro-3-trifluoromethyl-benzyl)-(2-phenyl-propyl)-{3-[3-(1,2,3,4-tetrazol-3-ylmethyl)-phenoxy]-propyl}-amine; (R)-(2-Chloro-3-trifluoromethyl-benzyl)-

(2-phenyl-propyl)-{3-[3-(1,2,3,4-tetrazol-3-ylmethyl)-phenoxy]-propyl}amine; (S)-2-(3-{3-[[2-Chloro-3-(trifluoromethyl)benzyl](2-phenyl-propyl)amino]propoxy}-phenyl)acetic acid; (R)-2-(3-{3-[[2-Chloro-3-(trifluoromethyl)benzyl](2-phenyl-propyl)amino]propoxy}-phenyl)acetic acid; 2-(3-{3-[[2-Chloro-3-(trifluoromethyl)benzyl]naphthalen-1-ylmethyl-amino]propoxy}-phenyl) acetic acid; 2-(3-{3-[[2-Chloro-3-(trifluoromethyl)benzyl]-benzylamino]propoxy}-phenyl)acetic acid; 2-(3-{3-[[2-Chloro-3-(trifluoromethyl)-benzyl]phenethylamino] propoxy}-phenyl)acetic acid; 2-(3-{3-[[2-Chloro-3-(trifluoromethyl)benzyl](2-hydroxy-2-phenyl-ethyl)amino] propoxy}-phenyl)acetic acid; 2-(3-{3-[[2-Chloro-3-(trifluoromethyl)benzyl](2-acetoxy-2-phenyl-ethyl)amino] propoxy}-phenyl)acetic acid; 2-(3-{3-[[2-chloro-3-(trifluoromethyl)benzyl](2-phenoxy-2-phenyl-ethyl)amino] propoxy}-phenyl)acetic acid; Benzoic acid 2-[3-(3-carboxymethyl-phenoxy){2-chloro-3-(trifluoromethyl) benzyl}propylamino]-1-phenyl ethyl ester; (3-{3-[(2-Acetoxy-2-phenyl-ethyl)-(2-chloro-3-trifluoromethyl-benzyl)-amino]-propoxy}-phenyl)-acetc acid methyl ester; Benzoic acid 2-[3-(3-methoxycarbonylmethyl-phenoxy){2-chloro-3-(trifluoromethyl)benzyl}propylamino]-1-phenyl ethyl ester; (3-{4-[(2-Chloro-3-(trifluoromethyl)benzyl)-(2, 2-diphenylethyl)-amino]butyl}phenyl)-acetic acid; Preparation of (3-{3-[(4-Fluoro-3-methyl-benzyl)-((R)-2-phenyl-propyl)-amino]-propoxy}-phenyl)-acetic acid; (3-{3-[Benzo[1,3]dioxol-5-ylmethyl-((R)-2-phenyl-propyl)-amino]-propoxy}phenyl)-acetic acid; (3-{3-[(4-tert-Butyl-benzyl)-((R)-2-phenyl-propyl)-amino]-propoxy}-phenyl)-acetic acid; (3-{3-[(2,3-Dihydro-benzo[1,4]dioxin-6-ylmethyl)-((R)-2-phenyl-propyl)-amino]-propoxy}-phenyl)-acetic acid; (3-{3-[(4-Methylsulfanyl-benzyl)-((R)-2-phenyl-propyl)-amino]-propoxy}-phenyl)-acetic acid; (3-{3-[((R)-2-Phenyl-propyl)-(2,4,5-trifluoro-benzyl)-amino]-propoxy}-phenyl)-acetic acid; (3-{3-[((R)-2-Phenyl-propyl)-(5-piperidin-1-yl-furan-2-ylmethyl)-amino]-propoxy}-phenyl)-acetic acid; (3-{3-[(4-Isopropyl-benzyl)-((R)-2-phenyl-propyl)-amino]-propoxy}phenyl)-acetic acid; 2-(3-{3-[(2-Chloro-3-trifluoromethyl-benzyl)-diphenyl-ethyl-amino]-propoxy}phenyl)-propane-1,3-diol; N-(3-{3-[(2-Chloro-3-trifluoromethyl-benzyl)-2,2-diphenylethyl-amino]-propoxy}-phenyl)-carbamic acid tert-butyl ester; 3-{3-[(2-Chloro-3-trifluoromethyl-benzyl)-2,2-diphenyl-ethylamino]-propoxy}-phenylamine; N-(3-{3-[(2-Chloro-3-trifluoromethyl-benzyl)-2,2-diphenylethyl-amino]-propoxy}phenyl)-acetamide; Furan-2-carboxylic acid N-(3-{3-[(2-Chloro-3-trifluoromethyl-benzyl)-2,2-diphenylethyl-amino]-propoxy}-phenyl)-amide; N-(3-{3-[(2-Chloro-3-trifluoromethyl-benzyl)-2,2-diphenylethyl-amino]-propoxy}-phenyl)-methanesulfonamide; N-(3-{3-[(2-Chloro-3-trifluoromethyl-benzyl)-2,2-diphenylethyl-amino]-propoxy}-phenyl)-benzenesulfonamide; 1-(2-Chloro-phenyl)-3-(3-{3-[(2-chloro-3-trifluoromethyl-benzyl)-2,2-diphenylethyl-amino]-propoxy}-phenyl)-urea; N-(3-{3-[(2-Chloro-3-trifluoromethyl-benzyl)-2,2-diphenylethyl-amino]-propoxy}-phenyl)-N-methyl-amine; N-(3-{3-[(2-Chloro-3-trifluoromethyl-benzyl)-2,2-diphenylethyl-amino]-propoxy}-phenyl)-N-methyl-acetamide; Furan-2-carboxylic acid N-(3-(3-[(2-Chloro-3-trifluoromethyl-benzyl)-2,2-diphenylethyl-amino]-propoxy}-phenyl)-N-methyl-amide; N-(3-{3-[(2-Chloro-3-trifluoromethyl-benzyl)-2,2-diphenylethyl-amino]-propoxy}-phenyl)-N-methyl-methanesulfonamide; (3-{3-[(2-Chloro-3-trifluoromethyl-benzyl)-2,2-diphenylethyl-amino]-propoxy}-phenyl)-N-methyl-benzenesulfonamide; 3-(2-Chloro-phenyl)-1-(3-{3-[(2-chloro-3-trifluoromethyl-benzyl)-2,2-diphenylethyl-amino]-propoxy}-phenyl)-1-methyl-urea; Benzo[1,3]dioxole-5-carboxylic acid N-(3-{3-[(2-Chloro-3-trifluoromethyl-benzyl)-2,2-diphenylethyl-amino]-propoxy}-phenyl)-N-methyl-amide; 1-(3-{3-[(2-Chloro-3-trifluoromethyl-benzyl)-2,2-diphenylethyl-amino]-propoxy}-phenyl)-3-(3,5-dimethoxy-phenyl)-1-methyl-urea; Propane-1-sulfonic acid (5-{3-[(2-chloro-3-trifluoromethyl-benzyl)-diphenylethyl-amino]-propoxy}-2-methyl-phenyl)-amide; 3-{3-[(2-Chloro-3-trifluoromethyl-benzyl)-diphenylethyl-amino]-propoxy}-2-methyl-phenylamine; 2-Chloro-5-{3-[(2-chloro-3-trifluoromethyl-benzyl)-diphenylethyl-amino]-propoxy}-phenylamine; 3-{3-[(2-Chloro-3-trifluoromethyl-benzyl)-(2,2-diphenyl-ethyl)-amino]-propoxy}-phenyl)-cyclopentyl-amine, (3-{3-[(2-Chloro-3-trifluoromethyl-benzyl)-(2,2-diphenyl-ethyl)-amino]-propoxy}-phenyl)-isopropyl-amine, Chloro-3-trifluoromethyl-benzyl)-(2,2-diphenyl-ethyl)-amino]-propoxy}-phenyl)-ethyl-amine, (3-{3-[(2-Chloro-3-trifluoromethyl-benzyl)-(2,2-diphenyl-ethyl)-amino]-propoxy}-phenyl)-(3-methyl-butyl)-amine, (3-{3-[(2-Chloro-3-trifluoromethyl-benzyl)-diphenylethyl-amino]-propoxy}-phenyl)-isobutyl-amine, (3-{3-[(2-Chloro-3-trifluoromethyl-benzyl)-(2,2-diphenyl-ethyl)-amino]-propoxy}-phenyl)-(2,2,2-trifluoroethyl)-amine, (3-{3-[(2-Chloro-3-trifluoromethyl-benzyl)-(2,2-diphenyl-ethyl)-amino]-propoxy}-phenyl)-cyclopropylmethy-l-amine, (3-{3-[(2-Chloro-3-trifluoromethyl-benzyl)-(2,2-diphenyl-ethyl)-amino]-propoxy}-phenyl)-(2-ethyl-butyl)-amine, (3-{3-[(2-Chloro-3-trifluoromethyl-benzyl)-(2,2-diphenyl-ethyl)-amino]-propoxy}-phenyl)-(2,2-dimethyl-propyl)-amine, (3-{3-[(2-Chloro-3-trifluoromethyl-benzyl)-(2,2-diphenyl-ethyl)-amino]-propoxy}-phenyl)-hexyl-amine, Butyl-(3-{3[(2-chloro-3-trifluoromethyl-benzyl)-(2,2-diphenyl-ethyl)-amino]-propoxy}-phenyl)-amine, [1-(3-{3-[(2-Chloro-3-(trifluoromethyl)-benzyl)-(2,2-diphenylethyl)-amino]-propoxy}-phenyl-piperidine-4-carboxylic acid, [1-(3-{3-[(2-Chloro-3-(trifluoromethyl)-benzyl)-(2,2-diphenylethyl)-amino]-propoxy}-phenyl-piperidine-4-yl-acetic acid; [4-(3-{3-[(2-Chloro-3-(trifluoromethyl)-benzyl)-(2,2-diphenylethyl-amino]-propoxy}-phenyl)-piperidin-1-yl]-acetic acid, rac-±-(3-{3-[(2-Chloro-3-trifluoromethyl-benzyl)-(trifluoro-phenyl-propyl)-amino]-propoxy}-phenyl)-acetic acid; rac-±-(3-{3-[(2-Chloro-3-trifluoromethyl-benzyl)-(2-dimethylamino-2-phenyl-ethyl)-amino]-propoxy}-phenyl)-acetic acid; rac-±-(3-{3-[(2-Chloro-3-trifluoromethyl-benzyl)-(2-morpholin-4-yl-2-phenyl-ethyl)-amino]-propoxy}-phenyl)-acetic acid; (2-Chloro-3-trifluoromethyl-benzyl)-(2,2-diphenyl-ethyl)-[3-(6-morpholin-4-yl-pyridin-2-yloxy)-propyl]-amine; [3-(6-Chloro-pyridin-2-yloxy)-propyl](2-Chloro-3-trifluoromethyl-benzyl)-(2,2-diphenyl-ethyl)-amine; (2-Chloro-3-trifluoromethyl-benzyl)-(2,2-diphenyl-ethyl)-{3-[6-(4-methyl-piperazin-1-yl)-pyridin-2-yloxy]-propyl}-amine; (2-Chloro-3-trifluoromethyl-benzyl)-(2,2-diphenyl-ethyl)-[3-(6-piperazin-1-yl-pyridin-2-yloxy)-propyl]-amine; [4-(6-{3-[(2-Chloro-3-trifluoromethyl-benzyl)-(2,2-diphenyl-ethyl)-amino]-propoxy}-pyridin-2-yl)-piperazin-1-yl]-acetic acid; 2-(3-{3-[[2-Chloro-3-(trifluoromethyl)benzyl]((S)-2-phenyl-propyl)amino]-(R)-1-methyl-propoxy}-phenyl)acetic acid; 2-(3-{3-[[2-Chloro-3-(trifluoromethyl)benzyl]((S)-2-phenyl-propyl)amino]-(R)-1-methyl-propoxy}-phenyl)ethanol; 2-(3-{3-[[2-Chloro-3-(trifluoromethyl)benzyl]((S)-2-phenyl-propyl)amino]-(R)-2-methyl-propoxy}-phenyl)acetic acid; 2-(3-{3-[[2-Chloro-3-(trifluoromethyl)benzyl]((S)-2-phenyl-propyl)amino]-(R)-2-methyl-propoxy}-phenyl)ethanol; 2-(3-{[2-Chloro-3-(trifluoromethyl)benzyl]((R)-2-phenyl-propyl)

amino]-(R)-2-methyl-propoxy}-phenyl)acetic acid; 2-(3-{3-[[2-Chloro-3-(trifluoromethyl)benzyl]((R)-2-phenyl-propyl)amino]-(R)-2-methyl-propoxy}-phenyl)ethanol; (R)-2-(3-{3-[[2-Chloro-3-(trifluoromethyl)benzyl](2,2-diphenylethyl)amino]-2-methyl-propoxy}-phenyl)ethanol; 3-{3-[(3-Chloro-2-trifluoromethyl-benzyl)-diphenylethyl-amino]-propoxy-N,N-dimethyl-benzenesulfonamide, Cyclopropanecarboxylic acid 3-{3-[(2-chloro-3-trifluoromethyl-benzyl)-diphenylethyl-amino]-propoxy}-benzylamide; N-(3-{3-[(2-Chloro-3-trifluoromethyl-benzyl)-diphenylethyl-amino]-propoxy}-benzyl)-isobutyramide; Acetic acid (3-{3-[(2-chloro-3-trifluoromethyl-benzyl)-diphenylethyl-amino]-propoxy}-benzylcarbamoyl)-methyl ester; N--(3-{3-[(2-Chloro-3-trifluoromethyl-benzyl)-diphenylethyl-amino]-propoxy}-benzyl)-propionamide; 2,5-Dimethyl-2-H-pyrazole-3-carboxylic acid 3-{3-[(2-chloro-3-trifluoromethyl-benzyl)-diphenylethyl-amino]-propoxy}-benzylamide; (2-Chloro-3-trifluoromethyl-benzyl)-(2,2-diphenyl-ethyl)-(3-o-tolyloxy-propyl)-amine; 2-{3-[(2-Chloro-3-trifluoromethyl-benzyl)-diphenylethyl-amino]-propoxy}-benzonitrile; [3-{3-[(2-Chloro-3-trifluoromethyl-benzyl)-diphenylethyl-amino]-propoxy}benzonitrile; [3-(3-Chloro-phenoxy)-propyl]-(2-chloro-3-trifluoromethyl-benzyl)-(2,2-diphenyl-ethyl)-amine; (2-Chloro-3-trifluoromethyl-benzyl)-(2,2-diphenyl-ethyl)-[3-(2-methoxy-phenoxy)-propyl]-amine; [3-(2-Chloro-phenoxy)-propyl]-(2-chloro-3-trifluoromethyl-benzyl)-(2,2-diphenyl-ethyl)-amine; (2-Chloro-3-trifluoromethyl-benzyl)-(2,2-diphenyl-ethyl)-(3-phenoxy-propyl)-amine; (2-Chloro-3-trifluoromethyl-benzyl)-(2,2-diphenyl-ethyl)-[3-(3-isopropyl-phenoxy)-propyl]-amine; (2-Chloro-3-trifluoromethyl-benzyl)-(2,2-diphenyl-ethyl)-[3-(4-methoxy-phenoxy)-propyl]-amine; 3-{3-[(Chloro-trifluoromethyl-benzyl)-diphenylethyl-amino]-propoxy}-phenol; 2-{3-[(Chloro-trifluoromethyl-benzyl)-diphenylethyl-amino]-propoxy}-phenol; 3-{3-[(Chloro-trifluoromethyl-benzyl)-diphenylethyl-amino]-propoxy}-phenylamine; (2-Chloro-3-trifluoromethyl-benzyl)-(2,2-diphenyl-ethyl)-[3-(3-trifluoromethyl-phenoxy)-propyl]-amine; 1-(3-{3-[(Chloro-trifluoromethyl-benzyl)-diphenylethyl-amino]-propoxy}-phenyl)-ethanone; (3-{3-[(2-Chloro-3-trifluoromethyl-benzyl)-diphenylethyl-amino]-propoxy}-phenyl)-phenyl-amine; [3-(Benzo[1,3]dioxol-5-yloxy)-propyl]-(2-chloro-3-trifluoromethyl-benzyl)-(2,2-diphenyl-ethyl)-amine; (2-Chloro-3-trifluoromethyl-benzyl)-(2,2-diphenyl-ethyl)-(3-m-tolyloxy-propyl)-amine; (2-Chloro-3-trifluoromethyl-benzyl)-(2,2-diphenyl-ethyl)-[3-(3-methoxy-phenoxy)-propyl]-amine; (2-Chloro-3-trifluoromethyl-benzyl)-(2,2-diphenyl-ethyl)-[3-(3-isobutyl-phenoxy)-propyl]-amine; [3-(3-Butyl-phenoxy)-propyl]-(2-chloro-3-trifluoromethyl-benzyl)-(2,2-diphenyl-ethyl)-amine; (2-Chloro-3-trifluoromethyl-benzyl)-{3-[3-(2,2-dimethyl-propyl)-phenoxy]-propyl}-(2,2-diphenyl-ethyl)-amine; (4-{3-[(2-Chloro-3-trifluoromethyl-benzyl)-diphenylethyl-amino]-propoxy}-benzyl)-methyl-amine; (2-Chloro-3-trifluoromethyl-benzyl)-[3-(4-dimethylaminomethyl-phenoxy)-propyl]-(2,2-diphenyl-ethyl)-amine; (2-Chloro-3-trifluoromethyl-benzyl)-(2,2-diphenyl-ethyl)-[3-(4-morpholin-4-ylmethyl-phenoxy)-propyl]-amine; (2-Chloro-3-trifluoromethyl-benzyl)-(2,2-diphenyl-ethyl)-{3-[4-(4-methyl-piperazin-1-ylmethyl)-phenoxy]-propyl}-amine; (3-{3-[(Chloro-trifluoromethyl-benzyl)-diphenylethyl-amino]-propoxy}-benzyl)-methyl-amine; (2-Chloro-3-trifluoromethyl-benzyl)-[3-(3-dimethylaminomethyl-phenoxy)-propyl]-(2,2-diphenyl-ethyl)-amine; (2-Chloro-3-trifluoromethyl-benzyl)-(2,2-diphenyl-ethyl)-[3-(3-morpholin-4-ylmethyl-phenoxy)-propyl]-amine; (2-Chloro-3-trifluoromethyl-benzyl)-(2,2-diphenyl-ethyl)-{3-[3-(4-methyl-piperazin-1-ylmethyl)-phenoxy]-propyl}-amine; (3-{3-[(2-Chloro-3-trifluoromethyl-benzyl)-diphenylethyl-amino]-propoxy}-benzyl)-isopropyl-amine; {3-[(2-Chloro-3-trifluoromethyl-benzyl)-(2,2-diphenyl-ethyl-amino)]-propoxy}-4-trifluoromethyl-phenylamine; {3-[(2-Chloro-3-trifluoromethyl-benzyl)-(2,2-diphenyl-ethyl-amino)]-propoxy}-4-methyl-phenylamine; Ethanesulfonic acid (3-{3-[(2-chloro-3-trifluoromethyl-benzyl)-(2,2-diphenyl-ethyl-amino)]-propoxy}-4-methyl-phenyl)-amide; Propane-2-sulfonic acid (3-{3-[(2-chloro-3-trifluoromethyl-benzyl)-(2,2-diphenyl-ethyl-amino)]-propoxy}-4-methyl-phenyl)-amide; Methanesulfonic acid (3-{3-[(2-Chloro-3-trifluoromethyl-benzyl)-(2,2-diphenyl-ethyl-amino)]-propoxy}-4-methyl-phenyl)-amide; 2,2,2-Trifluoro-ethanesulfonic acid (3-{3-[(2-Chloro-3-trifluoromethyl-benzyl)-(2,2-diphenyl-ethyl-amino)]-propoxy}-4-methyl-phenyl)-amide; Ethanesulfonic acid (3-{3-[(2-Chloro-3-trifluoromethyl-benzyl)-(2,2-diphenyl-ethyl-amino)]-propoxy}-phenyl)-amide; 2,2,2-Trifluoro-ethanesulfonic acid (3-{3-[(2-Chloro-3-trifluoromethyl-benzyl)-(2,2-diphenyl-ethyl-amino)]-propoxy}-phenyl)-amide; N-(3-{3-[(2-Chloro-3-trifluoromethyl-benzyl)-(2,2-diphenyl-ethyl-amino)]-propoxy}-phenyl)-1,1,1-trifluoro-methanesulfonamide; Propane-2-sulfonic acid (3-{3-[(2-Chloro-3-trifluoromethyl-benzyl)-(2,2-diphenyl-ethyl-amino)]-propoxy}-phenyl)-amide; {3-[(2-Chloro-3-trifluoromethyl-benzyl)-(2,2-diphenyl-ethyl-amino)]-propoxy}-4-methoxy-phenylamine; Ethanesulfonic acid (3-{3-[(2-chloro-3-trifluoromethyl-benzyl)-(2,2-diphenyl-ethyl-amino)]-propoxy}-4-methoxy-phenyl)-amide; (2-Chloro-3-trifluoromethyl-benzyl)-{3-[3-(2-morpholin-4-yl-ethyl)-phenoxy]-propyl}-((S)-2-phenyl-propyl amine; (2-Chloro-3-trifluoromethyl-benzyl)-{3-[3-(2-ethylamino-ethyl)-phenoxy]-propyl}((S)-2-phenyl-propyl)-amine; (3-{-(R)-3-[(2-Chloro-3-trifluoromethyl-benzyl)-((S)-2-phenyl-propyl)-amino]-butoxy}-phenyl)-acetic acid; (3{(S)-3-[(2-Chloro-3-trifluoromethyl-benzyl)-((S)-2-phenyl-propyl)-amino]-butoxy}-phenyl)-acetic acid; 2-(3-{3-[(2-Chloro-3-trifluoromethyl-benzyl)-((S)-2-phenyl-propyl)-amino]-propoxy}-phenyl)-ethanol; 2-(3-{3-[(2-Chloro-3-trifluoromethyl-benzyl)-((S)-2-phenyl-propyl)-amino]-propoxy}-phenyl)-2-methyl-propionic acid; 2-(3-{3-[(2-Chloro-3-trifluoromethyl-benzyl)-((R)-2-phenyl-propyl)-amino]-propoxy}-phenyl)-2-methyl-propionic acid; (3-{3-[(2-Chloro-3-trifluoromethyl-benzyl)-(2-thiophen-3-yl-propyl)-amino]-propoxy}-phenyl)-acetic acid; 2-(3-{3-[(2-Chloro-3-trifluoromethyl-benzyl)-(2-thiophen-3-yl-propyl)-amino]-propoxy}-phenyl)-ethanol; (3-{3-[(2-Chloro-3-trifluoromethyl-benzyl)-(2-thiophen-2-yl-propyl)-amino]-propoxy}-phenyl)-acetic acid; (3-{3-[(2-Chloro-3-trifluoromethyl-benzyl)-(2-pyridin-2-yl-propyl)-amino]-propoxy}-phenyl)-acetic acid; [3-(3-{(2-Chloro-3-trifluoromethyl-benzyl)-[2-(4-methyl-pyridin-2-yl)-propyl]-amino}-propoxy)-phenyl]-acetic acid; [3-(3{(2-Chloro-3-trifluoromethyl-benzyl)-[3,3,3-trifluoro-2-(1H-pyrrol-2-yl)-propyl]-amino}-propoxy)-phenyl]-acetic acid; (2-Chloro-3-trifluoromethyl-benzyl)-(2,2-diphenyl-ethyl)-(3-{3-[2-(4-methyl-piperazin-1-yl)-ethyl]-phenoxy}-propyl)-amine; (2-Chloro-3-trifluoromethyl-benzyl)-(2,2-diphenyl-ethyl)-{3-[3-(2-methylamino-ethyl)-phenoxy]-propyl}-amine; (2-Chloro-3-trifluoromethyl-benzyl)-(2,2-diphenyl-ethyl)-[3-(3-{2-[(1H-imidazol-2-ylmethyl)-amino]-ethyl}-phenoxy)-propyl]-amine; (2-Chloro-3-trifluoromethyl-benzyl)-(2,2-diphenyl-ethyl)-{3-[3-(2-ethylamino-ethyl)-phenoxy]-propyl}-amine; [3-(3-{2-[(5-Bromo-thiophen-2-ylmethyl)- amino]-ethyl}-phenoxy)-propyl]-(2-chloro-3-trifluoromethyl-benzyl)-(2,2-diphenyl-ethyl)-amine; (2-Chloro-3-trifluoromethyl-benzyl)-(2,2-diphenyl-ethyl)-[3-(3-{2-[(thiophen-2-ylmethyl)-amino]-ethyl}-phenoxy)-propyl]-amine; (2-Chloro-3-trifluoromethyl-benzyl)-{3-[3-(2-dimethylamino-ethyl)-phenoxy]-propyl}-(2,2-diphenyl-ethyl)-amine; (2-Chloro-3-trifluoromethyl-benzyl)-(2,2-diphenyl-ethyl)-{3-[3-(2-pyrrolidin-1-yl-ethyl)-phenoxy]-propyl}-amine; (2-Chloro-3-trifluoromethyl-benzyl)-(2,2-diphenyl-ethyl){3-[3-(2-morpholin-4-yl-ethyl)-phenoxy]-propyl}-amine; (2-Chloro-3-trifluoromethyl-benzyl)-(2,2-diphenyl-ethyl){(R)-1-methyl-3-[3-(2-morpholin-4-yl-ethyl)-{phenoxy]-propyl}-amine; (2-Chloro-3-trifluoromethyl-benzyl)-(2,2-diphenyl-ethyl)-{(R)-2-methyl-3-[3-(2-morpholin-4-yl-ethyl)-phenoxy]-propyl}-amine; {3-[3-(2-Amino-ethyl)-phenoxy]-propyl}-(2-chloro-3-trifluoromethyl-benzyl)-(2,2-diphenyl-ethyl)-amine; [2-(3-{3-[(2-chloro-3-trifluoromethyl-benzyl)-diphenylethyl-amino]-propoxy}-phenyl)-ethyl]-isopropyl-amine; [2-(3-{3-[(2-chloro-3-trifluoromethyl-benzyl)-diphenylethyl-amino]-propoxy}-phenyl)-ethyl]-propyl-amine; 2-[2-(3-{3-[(2-chloro-3-trifluoromethyl-benzyl)-diphenylethyl-amino]-propoxy}-phenyl)-ethylamino]-ethanol; (2-Chloro-3-trifluoromethyl-benzyl)-(2,2-diphenyl-ethyl)-[3-(3-{2-[(1-methyl-1H-imidazol-2-ylmethyl)-amino]-ethyl}-phenoxy)-propyl]-amine; (2-Chloro-3-trifluoromethyl-benzyl)-(2,2-diphenyl-ethyl)-{3-[3-(2-thiomorpholin 4-yl-ethyl)-phenoxy]-propyl}-amine; [2-(3-{3-[(2-chloro-3-trifluoromethyl-benzyl)-diphenylethyl-amino]-propoxy}-phenyl)-ethylamino]-acetic acid; [2-(3-{(R)-3-[(2-chloro-3-trifluoromethyl-benzyl)-diphenylethyl-amino]-butoxy}-phenyl)-ethylamino]-acetic acid; {[2-(3-{3-[(2-chloro-3-trifluoromethyl-benzyl)-diphenylethyl-amino]-propoxy}-phenyl)-ethyl]-methyl-amino}-acetic acid; 2-[2-(3-{3-[(2-chloro-3-trifluoromethyl-benzyl)-diphenylethyl-amino]-propoxy}-phenyl)-ethylamino]-2-methyl-propionic acid; (S)-2-[2-(3-{3-[(2-chloro-3-trifluoromethyl-benzyl)-diphenylethyl-amino]-propoxy}-phenyl)-ethylamino]-propionic acid; (R)-1-[2-(3-{3-[(2-chloro-3-trifluoromethyl-benzyl)-diphenylethyl-amino]-propoxy}-phenyl)-ethyl]-pyrrolidine-2-carboxylic acid; (S)-1-[2-(3-{3-[(2-chloro-3-trifluoromethyl-benzyl)-diphenylethyl-amino]-propoxy}-phenyl)-ethyl]-pyrrolidine-2-carboxylic acid; [2-(3-{3-[(2-chloro-3-trifluoromethyl-benzyl)-diphenylethyl-amino]-propoxy}-phenyl)-ethyl]-pyrimidin-2-yl-amine; (2-Chloro-3-trifluoromethyl-benzyl)-(2,2-diphenyl-ethyl)-[3-(3-morpholin-4-yl-phenoxy)-propyl]-amine; (2-Chloro-3-trifluoromethyl-benzyl)-(2,2-diphenyl-ethyl)-[3-(3-piperidin-1-yl-phenoxy)-propyl]-amine; (3-{3-[(2-chloro-3-trifluoromethyl-benzyl)-diphenylethyl-amino]-propoxy}-phenyl)-diethyl-amine; (2-Chloro-3-trifluoromethyl-benzyl)-{3-[3-(2,5-dimethyl-pyrrol-1-yl)-phenoxy]-propyl}-(2,2-diphenyl-ethyl)-amine; (2-Chloro-3-trifluoromethyl-benzyl)-(2,2-diphenyl-ethyl)-[3-(3-piperazin-1-yl-phenoxy)-propyl]-amine; (2-Chloro-3-trifluoromethyl-benzyl)-((S)-2-phenyl-propyl)-[3-(3-piperazin-1-yl-phenoxy)-propyl]-amine; (2-Chloro-3-trifluoromethyl-benzyl)-(2,2-diphenyl-ethyl)-[(R)-2-methyl-3-(3-piperazin-1-yl-phenoxy)-propyl]-amine, (2-Chloro-3-trifluoromethyl-benzyl)-isobutyl-[3-(3-piperazin-1-yl-phenoxy)-propyl]-amine; [4-(3-{3-[(2-chloro-3-trifluoromethyl-benzyl)-diphenylethyl-amino]-propoxy}-phenyl)-piperazin-1-yl]-acetic acid; [4-(3-{3-[(2-chloro-3-trifluoromethyl-benzyl)-((S)-2-phenyl-propyl)-amino]-propoxy}-phenyl)-piperazin-1-yl]-acetic acid; [4-(3-((R)-[(2-chloro-3-trifluoromethyl-benzyl)-diphenylethyl-amino]-methyl-propoxy}-phenyl)-piperazin-1-yl]-acetic acid; [4-(3-(3-[(2-chloro-3-trifluoromethyl-benzyl)-isobutyl-amino]-propoxy}-phenyl)-piperazin-1-yl]-acetic acid; (2-Chloro-3-trifluoromethyl-benzyl)-(2,2-diphenyl-ethyl)-{3-[3-(4-methyl-piperazin-1-yl)-phenoxy]-propyl}-amine, (2-Chloro-3-trifluoromethyl-benzyl)-(2,2-diphenyl-ethyl)-[3-(3-pyrrolidin-1-yl-phenoxy)-propyl]-amine; (3-(3-[(2-chloro-3-trifluoromethyl-benzyl)-diphenylethyl-amino]-propoxy}-phenylamino)-acetic acid; [(3-{3-[(2-chloro-3-trifluoromethyl-benzyl)-diphenylethyl-amino]-propoxy}-phenyl)-N-methyl-amino]-acetic acid; N-(2,2-Diphenylethyl)-N-(2-chloro-3-trifluoromethylbenzyl)-3-[3-(2-methyl-2-aminopropyl)phenoxy]propylamine, N-(2,2-Diphenylethyl)-N-(2-chloro-3-trifluoromethylbenzyl)-3-(3-[2-hydroxymethyl]phenoxy)propylamine, N-(2,2-Diphenylethyl)-N-(2-chloro-3-trifluoromethylbenzyl)-3-(3-[2-hydroxy-2-methylpropyl]phenoxy)propylamine; N-(2,2-Diphenylethyl)-N-(2-chloro-3-trifluoromethylbenzyl)-3-(3-N-methylsulfonamidophenoxy)propylamine, N-(2-[2-Chlorophenyl]-propyl)-N-(2-chloro-3-trifluoromethylbenzyl)-3-(3-carboxymethylenephenoxy)propylamine, N-(2-[3-Chlorophenyl]-propyl)-N-(2-chloro-3-trifluoromethylbenzyl)-3-(3-carboxymethylenephenoxy)propylamine, N-(2-[4-Chlorophenyl]-propyl)-N-(2-chloro-3-trifluoromethylbenzyl)-3-(3-carboxymethylenephenoxy)propylamine, N-(2-[2-Methoxyphenyl]-propyl)-N-(2-chloro-3-trifluoromethylbenzyl)-3-(3-carboxymethylenephenoxy)propylamine, N-(2-[4-Methoxyphenyl]-propyl)-N-(2-chloro-3-trifluoromethylbenzyl)-3-(3-carboxymethylenephenoxy)propylamine, N-(2-Phenyl-4-methylpentyl)-N-(2-chloro-3-trifluoromethylbenzyl)-3-(3-carboxymethylenephenoxy)propylamine, N-(2-Phenylbutyl)-N-(2-chloro-3-trifluoromethylbenzyl)-3-(3-carboxymethylenephenoxy)propylamine, N-(2-[2-Methyl-2-phenyl]propyl)-N-(2-chloro-3-trifluoromethylbenzyl)-3-(3-carboxymethylenephenoxy)propylamine, N-(2-Phenyl-3-methylbutyl)-N-(2-chloro-3-trifluoromethylbenzyl)-3-(3-carboxymethylenephenoxy)propylamine, N-(2-Phenylhexyl)-N-(2-chloro-3-trifluoromethylbenzyl)-3-(3-carboxymethylenephenoxy)propylamine, N-(2-Phenyl-3-butynyl)-N-(2-chloro-3-trifluoromethylbenzyl)-3-(3-carboxymethylenephenoxy)propylamine; (S)-N-(2-Phenyl-2-methoxyethyl)-N-(2-chloro-3-trifluoromethylbenzyl)-3-(3-carboxymethylenephenoxy)propylamine, (R)-N-(2-Phenyl-2-methoxyethyl)-N-(2-chloro-3-trifluoromethylbenzyl)-3-(3-carboxymethylenephenoxy)propylamine, (R)-N-(2-Phenyl-2-methoxyethyl)-N-2-chloro-3-trifluoromethylbenzyl)-3-(3-[2-hydroxy-2-methylpropyl]phenoxy)propylamine; 2-(3-{3-[[2-Chloro-3-(trifluoromethyl)benzyl](2-methyl-propyl)amino]-propoxy}-phenyl)acetic acid; 1-(3-{3-[(2-Chloro-3-trifluoromethyl-benzyl)-diphenylethyl-amino]-propoxy}-phenyl)-cyclobutanecarboxylic acid; 1-(3-{3-[(2-Chloro-3-trifluoromethyl-benzyl)-diphenylethyl-amino]-propoxy)-phenyl)-cyclopentanecarboxylic acid; 1-(3-{3-[(2-Chloro-3-trifluoromethyl-benzyl)-(2,2-diphenyl-ethyl)-amino]-propoxy}-phenyl)-cyclopropanecarboxylic acid;

and a stereoisomer, a stereoisomeric mixture or racemate thereof and a pharmaceutically acceptable salt or solvate thereof.

Preferred compounds of this invention include:

2-(3-{3-[[2-chloro-3-(trifluoromethyl)benzyl](2,2-dephenylethyl)amino]propoxy}phenyl)-ethanol, (2-chloro-3-trifluoromethyl-benzyl)-(2,2-diphenylethyl)-{3-[3-(1, 2,4-triazol-3-ylmethyl)-phenoxy]-propyl}-amine, (2-chloro-3-trifluoromethyl-benzyl)-(2,2-diphenyl-ethyl)-{3-[3-(1,2,3,4-tetrazol-5-ylmethyl)-phenoxy]-propyl}-amine, (2-chloro-3-trifluoromethyl-benzyl)-(2-cyclohexyl-2-phenyl-ethyl)-{3-[3-(1,2,3,4-tetrazol-5-ylmethyl)-phenoxy]-propyl}-amine, (S)-(2-chloro-3-trifluoromethyl-benzyl)-(2-phenyl-propyl)-{3-[3-(1,2,3,4-tetrazol-3-ylmethyl)-phenoxy]-propyl}-amine, (R)-(2-chloro-3-trifluoromethyl-benzyl)-(2-phenyl-propyl)-{3-[3-(1,2,3,4-tetrazol-3-ylmethyl)-phenoxy]-propyl}-amine, 2-(3-{3-[[2-chloro-3-(trifluoromethyl)benzyl]-benzylamino]propoxy}-phenyl)acetic acid, 2-(3-{3-[[2-chloro-3-(trifluoromethyl)-benzyl]phenethylamino]propoxy}-phenyl)acetic acid, 2-(3-{3-[[2-chloro-3-(trifluoromethyl)benzyl](2-hydroxy-2-phenyl-ethyl)amino]propoxy}-phenyl)acetic acid, 2-(3-{3-[[2-chloro-3-(trifluoromethyl)benzyl](2-acetoxy-2-phenyl-ethyl)amino]propoxy}-phenyl)acetic acid, 2-(3-{3-[[2-chloro-3-(trifluoromethyl)benzyl](2-phenoxy-2-phenyl-ethyl)amino]propoxy}-phenyl)acetic acid, (3-{3-[(2-acetoxy-2-phenylethyl)$_2$-chloro-3-trifluoromethyl-benzyl)-amino]-propoxy}-phenyl)-acetic acid methyl ester, benzoic acid 2-[3-(3-methoxycarbonylmethyl-phenoxy){2-chloro-3-(trifluoromethyl)benzyl}propylamino]-1-phenyl ethyl ester, (3-[(2-chloro-3-trifluoromethyl)benzyl)-(2,2-diphenyl-ethyl)-amino]butyl}phenyl)-acetic acid, 2-(3-{3-[[2-chloro-3-(trifluoromethyl)benzyl](2,2-dephenylethyl)amino]propoxy}phenyl)-ethanol, (2-chloro-3-trifluoromethyl-benzyl)-(2,2-diphenylethyl)-{3-[3-(1,2,4-triazol-3-ylmethyl)-phenoxy]-propyl}-amine, (2-chloro-3-trifluoromethyl-benzyl)-(2,2-diphenyl-ethyl)-{3-[3-(1,2,3,4-tetrazol-5-ylmethyl)-phenoxy]-propyl}-amine, (S)-(2-chloro-3-trifluoromethyl-benzyl)-(2-phenyl-propyl)-{3-[3-(1,2,3,4-tetrazol-3-ylmethyl)-phenoxy]-propyl}-amine, (R)-(2-chloro-3-trifluoromethyl-benzyl)-(2-phenyl-propyl)-{3-[3-(1,2,3,4-tetrazol-3-ylmethyl)-phenoxy]-propyl}-amine, (S)-2-(33-[[2-chloro-3-(trifluoromethyl)benzyl](2-phenyl-propyl)amino]propoxy}-phenyl)acetic acid, furan-2-carboxylic acid N-(33-[(2-Chloro-3-trifluoromethyl-benzyl)-2,2-diphenylethyl-amino]-propoxy}-phenyl)-amide, (R)-2-(3-{3-[[2-chloro-3-(trifluoromethyl)benzyl](2-phenyl-propyl)amino]propoxy}-phenyl)acetic acid, 2-(3-{3-[[2-chloro-3-(trifluoromethyl)benzyl](2-acetoxy-2-phenyl-ethyl)amino]propoxy}-phenyl)acetic acid, (3-{3-[(2-Acetoxy-2-phenyl-ethyl)-(2-chloro-3-trifluoromethyl-benzyl)-amino]-propoxy}-phenyl)-acetic acid methyl ester, (3-(4-[(2-chloro-3-(trifluoromethyl)benzyl)-(2,2-diphenyl-ethyl)-amino]butyl}phenyl)-acetic acid, 1-(3-{3-[(2-chloro-3-trifluoromethyl-benzyl)-diphenyl-ethyl-amino]-propoxy}-phenyl)-cyclobutanecarboxylic acid, N-(2,2-diphenylethyl)-N-(2-chloro-3-trifluoromethylbenzyl)-3-(3-[2-hydroxy-2-methylpropyl]phenoxy)propylamine, (2-chloro-3-trifluoromethyl-benzyl)-(2,2-diphenyl-ethyl)-[3-(3-{2-[(1H-imidazol-2-ylmethyl)-amino]-ethyl}-phenoxy)-propyl]-amine, N-(3-{3-[(2-chloro-3-trifluoromethyl-benzyl)-2,2-diphenyl-ethyl-amino]-propoxy}-phenyl)-methanesulfonamide, N-(3-{3-[(2-chloro-3-trifluoromethyl-benzyl)-2,2-diphenyl-ethyl-amino]-propoxy}-phenyl)-N-methyl-amine,

[2-(3-{3-[(2-chloro-3-trifluoromethyl-benzyl)-diphenyl-ethyl-amino]-propoxy}-phenyl)-ethylamino]-acetic acid, (R)-1-[2-(3-{3-[(2-chloro-3-trifluoromethyl-benzyl)-diphenylethyl-amino]-propoxy}-phenyl)-ethyl]-pyrrolidine-2-carboxylic acid, N-(2-[3-chlorophenyl]-propyl)-N-(2-chloro-3-trifluoromethylbenzyl)-3-(3-carboxymethylenephenoxy)propylamine, (2-chloro-3-trifluoromethyl-benzyl)-{3-[3-(2-morpholin-4-yl-ethyl)-phenoxy]-propyl}-((S)-2-phenyl-propyl amine,

[4-(3-{3-[(2-chloro-3-trifluoromethyl-benzyl)-diphenyl-ethyl-amino]-propoxy}phenyl)-piperazin-1-yl]-acetic acid, 2-(3-{3-[(2-chloro-3-trifluoromethyl-benzyl)-((S)-2-phenyl-propyl)-amino]-propoxy}-phenyl)-2-methyl-propionic acid, (2-chloro-3-trifluoromethyl-benzyl)-(2,2-diphenyl-ethyl)-{3-[3-(4-methyl-piperazin-1-yl)-phenoxy]-propyl}-amine, (3-{(R)-3-[(2-chloro-3-trifluoromethyl-benzyl)-((S)-2-phenyl-propyl)-amino]-butoxy}-phenyl)-acetic acid,

[1-(3-{3-[(2-chloro-3-(trifluoromethyl)-benzyl)-(2,2-diphenylethyl)-amino]-propoxy}-phenyl-piperidine-4-carboxylic acid,

[4-(3-{3-[(2-chloro-3-trifluoromethyl-benzyl)-((S)-2-phenyl-propyl)-amino]-propoxy}-phenyl)-piperazin-1-yl]-acetic acid,

[4-(3-{(R)-[(2-chloro-3-trifluoromethyl-benzyl)-diphenyl-ethyl-amino]-methyl-propoxy}-phenyl)-piperazin-1-yl]-acetic acid, and a stereoisomer, a stereoisomeric mixture or racemate thereof and a pharmaceutically acceptable salt or solvate thereof.

More preferred compounds of this invention include:

2-(3-{3-[[2-chloro-3-(trifluoromethyl)benzyl](2,2-dephenylethyl)amino]propoxy}phenyl)-ethanol, (2-chloro-3-trifluoromethyl-benzyl)-(2,2-diphenylethyl)-{3-[3-(1,2,4-triazol-3-ylmethyl)-phenoxy]-propyl}-amine, (2-chloro-3-trifluoromethyl-benzyl)-(2,2-diphenyl-ethyl)-{3-[3-(1,2,3,4-tetrazol-5-ylmethyl)-phenoxy]-propyl}-amine, (S)-(2-chloro-3-trifluoromethyl-benzyl)-(2-phenyl-propyl)-{3-[3-(1,2,3,4-tetrazol-3-ylmethyl)-phenoxy]-propyl}-amine, (R)-(2-chloro-3-trifluoromethyl-benzyl)-(2-phenyl-propyl)-{3-[3-(1,2,3,4-tetrazol-3-ylmethyl)-phenoxy]-propyl}-amine, (S)-2-(3-{3-[[2-chloro-3-(trifluoromethyl)benzyl](2-phenyl-propyl)amino]propoxy}-phenyl)acetic acid, (R)-2-(3-{3-[[2-chloro-3-(trifluoromethyl)benzyl](2-phenyl-propyl)amino]propoxy}-phenyl)acetic acid, 2-(3-{3-[[2-chloro-3-(trifluoromethyl)benzyl](2-acetoxy-2-phenyl-ethyl)amino]propoxy}-phenyl)acetic acid, (3-{3-[(2-Acetoxy-2-phenyl-ethyl)-(2-chloro-3-trifluoromethyl-benzyl)-amino]-propoxy}-phenyl)-acetic acid methyl ester, (3-{4-[(2-chloro-3-(trifluoromethyl)benzyl)-(2,2-diphenyl-ethyl)-amino]butyl}phenyl)-acetic acid, 1-(3-{3-[(2-chloro-3-trifluoromethyl-benzyl)-diphenyl-ethyl-amino]-propoxy}-phenyl)-cyclobutanecarboxylic acid, N-(2,2-diphenylethyl)-N-(2-chloro-3-trifluoromethylbenzyl)-3-(3-[2-hydroxy-2-methylpropyl]phenoxy)propylamine,
(2-chloro-3-trifluoromethyl-benzyl)-(2,2-diphenyl-ethyl)-[3-(3-{2-[(1H-imidazol-2-ylmethyl)-amino]-ethyl}-phenoxy)-propyl]-amine,
N-(3-{3-[(2-chloro-3-trifluoromethyl-benzyl)-2,2-diphenyl-ethyl-amino]-propoxy}-phenyl)-methanesulfonamide,
N-(3-{3-[(2-chloro-3-trifluoromethyl-benzyl)-2,2-diphenyl-ethyl-amino]-propoxy}-phenyl)-N-methyl-amine,
[2-(3-{3-[(2-chloro-3-trifluoromethyl-benzyl)-diphenyl-ethyl-amino]-propoxy}-phenyl)-ethylamino]-acetic acid,
(R)-1-[2-(3-{3-[(2-chloro-3-trifluoromethyl-benzyl)-diphenylethyl-amino]-propoxy}-phenyl)-ethyl]-pyrrolidine-2-carboxylic acid,
furan-2-carboxylic acid N-(3-{3-[(2-chloro-3-trifluoromethyl-benzyl)-2,2-diphenylethyl-amino]-propoxy}-phenyl)-amide,
N-(2-[3-chlorophenyl]-propyl)-N-(2-chloro-3-trifluoromethylbenzyl)-3-(3-carboxymethylenephenoxy)propylamine,
(2-chloro-3-trifluoromethyl-benzyl)-{3-[3-(2-morpholin-4-yl-ethyl)-phenoxy]-propyl}-((S)-2-phenyl-propyl amine,
[4-(3-{3-[(2-chloro-3-trifluoromethyl-benzyl)-diphenyl-ethyl-amino]-propoxy}-phenyl)-piperazin-1-yl]-acetic acid,
2-(3-{3-[(2-chloro-3-trifluoromethyl-benzyl)-((S)-2-phenyl-propyl)-amino]-propoxy}-phenyl)-2-methyl-propionic acid,
(2-chloro-3-trifluoromethyl-benzyl)-(2,2-diphenyl-ethyl)-{3-[3-(4-methyl-piperazin-1-yl)-phenoxy]-propyl}-amine,
(3-{(R)-3-[(2-chloro-3-trifluoromethyl-benzyl)-((S)-2-phenyl-propyl)-amino]-butoxy}-phenyl)-acetic acid,
[1-(3-{3-[(2-chloro-3-(trifluoromethyl)-benzyl)-(2,2-diphenylethyl)-amino]-propoxy}-phenyl-piperidine-4-carboxylic acid,
[4-(3-{3-[(2-chloro-3-trifluoromethyl-benzyl)-((S)-2-phenyl-propyl)-amino]-propoxy}-phenyl)-piperazin-1-yl]-acetic acid,
[4-(3-{(R)-[(2-chloro-3-trifluoromethyl-benzyl)-diphenyl-ethyl-amino]-methyl-propoxy}-phenyl)-piperazin-1-yl]-acetic acid,
and a stereoisomer, a stereoisomeric mixture or racemate thereof and a pharmaceutically acceptable salt or solvate thereof.

The term "LXR modulator," as used herein, means a small molecule that modulates the biological activities of LXRα and/or LXRβ. More specifically, such an LXR modulator either enhances or inhibits the biological activities of LXR. If such a modulator partially or completely enhances the biological activities of LXR, it is a partial or complete LXR agonist, respectively. If such a modulator partially or completely inhibits the biological activities of LXR, it is a partial or complete LXR agonist, respectively. Preferably, the LXR modulator compounds of this invention are LXR agonists. As used herein, the term "LXR agonist" refers to compounds which achieve at least 20% activation of LXR relative to 24(S),25-epoxycholesterol, the appropriate positive control in the HTRF assay described below in Test Method 1. It should be noted that to show activity in the specific Test Methods described herein, the LXR modulator compound must bind to the LXR nuclear receptor and recruit the specific peptide derived from the coactivator protein, SRC1, to the modulator compound-bound LXR complex. The compounds of this invention that form an LXR-modulator compound-complex may also recruit at least one or more of the other >80 known different nuclear receptor cofactors. Recruiter peptides derived from any of these other nuclear receptor cofactors may be similarly prepared and assayed according to known procedures.

Compounds that are closely structurally related to the compounds of Examples 1-201 have been prepared that do not demonstrate at least 20% recruitment of the SRC1-derived peptide. It is anticipated, however, that such compounds do bind to LXR. It is further anticipated that such an LXR-modulator compound-complex will recruit at least one or more of the other >80 known different nuclear receptor cofactors. Examples of such compounds include:

{3-[[2-Chloro-3-(trifluoromethyl)benzyl](2,2-diphenyl-ethyl)amino]propoxy}benzene having an X—$(CR^1R^2)_p$— group wherein p is 0, k is 0, and X is as follows (the designated position of the X group is relative to the —Y—$(CR^4R^5)_n$— group on the benzene moiety): 4-cyano, 4-isopropyl, 4-methyl, 4-trifluoromethyl, 4-chloro, 3-amino, 4-(phenylamino)-, 4-benzyloxy-, 4-acetyl, 3-(phenylamino)methyl-, 4-phenylaminomethyl-, 4-isopropylaminomethyl-, 4-tert-butoxycarbonyl-N-methyl-amino-, 3,5-di-trifluoromethylphenylcarbonyl-N-methyl-amino-, 4-phenylamidosulfonyl-(Ph-N(H)O$_2$S—), and 4-phenylsulfonylamido-(Ph-SO$_2$N(H)—);

{3-[[2-Chloro-3-(trifluoromethyl)benzyl](2,2-diphenyl-ethyl)amino]propoxy}benzene having an X—$(CR^1R^2)_p$— and an $(R^3)_k$ group, wherein p is 0, k is 1, and X and $R^3$ are as follows (the designated position of the X and $R^3$ groups are relative to the —Y—$(CR^4R^5)_r$-group on the benzene moiety): 2-trifluoromethyl-5-methyl-sulfonylamido-(H$_3$C—SO$_2$N(H)—), 2-trifluoromethyl-5-n-propyl-sulfonylamido-, 2-trifluoromethyl-5-(3-chloro-n-prop-1-yl)-sulfonylamido-, 2-trifluoromethyl-5-trifluoromethyl-sulfonylamido-, 2-trifluoromethyl-5-iso-propyl-sulfonylamido-, 2-methyl-5-tert-butoxycarbonylamino-, 2-methyl-5-iso-propyl-sulfonylamido-, 2-methyl-5-trifluoromethyl-sulfonylamido-, 2-methyl-5-ethyl-sulfonylamido-, 2-methyl-5-(2,2,2-trifluoroethyl)-sulfonylamido-, 4-methyl-3-ethyl-sulfonylamido-, 2-methoxy-5-tert-butoxycarbonylamino-, 2-methoxy-5-tert-butyl-sulfonylamido-, 2-methoxy-5-(2,2,2-trifluoroethyl)-sulfonylamido-, 2-methoxy-5-iso-propyl-sulfonylamido-, and 2-methoxy-5-methyl-sulfonylamido-;

{3-[(R)-3-(2,2-diphenylethyl)amino)-2-methyl-propoxy]-phenyl}-acetic acid having a Q-$(CR^8R^9)_q$— group consisting of Q-(CH$_2$)— wherein Q is furan-2-yl and 5-chloro-thien-2-yl;

{3-[3-(R)-2-(phenylpropylamino)-propoxy}-phenyl)acetic acid, where $R^1$ and $R^2$ are H and having the Q-$(CR^8R^9)_q$— group Q-(CH$_2$)— wherein Q is quinolin-8-yl, 2-methoxy-naphth-1-yl, 3,5-dimethoxy-phenyl-, 3,5-dimethyl-phenyl-, 2,5-dimethoxy-phenyl-, 2,4,6-trimethoxy-phenyl-, 4-(n-hexyloxy)-phenyl-, 4-benzyloxy-phenyl-, 3-(4-methoxy-phenoxy)-phenyl-, 3-methoxy-4-benzyloxy-phenyl-, 4-[(3-N,N-dimethylamino)prop-1-yloxy)-phenyl-, 4-acetylamino-phenyl-; or where $R^1$ and $R^2$ are methyl and Q-$(CR^8R^9)_q$— is the group Q-(CH$_2$)— wherein Q is 2-chloro-3-trifluoromethyl-phenyl-;

{3-[3-(S)-2-(phenylpropylamino)-propoxy}-phenyl}-acetic acid, where $R^1$ and $R^2$ are H and having the Q-$(CR^8R^9)_q$— group Q-(CH$_2$)— wherein Q is 2,6-dimethoxy-phenyl-, 3-cyanophenyl-, furan-2-yl-, and 6-chloro-benzo[1,3]diox-5-yl; and (3-{3-[[2-Chloro-3-(trifluoromethyl)benzyl]-(2-phenyl-propyl)amino]-propoxy}-phenyl)acetic acid where the phenyl moiety of the 2-phenylpropyl group is 3-methoxyphenyl or 2-methoxyphenyl.

The compounds of this invention are useful for a variety of medicinal purposes. The compounds of this invention may be used in methods for the prevention or treatment of LXR mediated diseases and conditions. This invention further provides compounds of this invention for use in the preparation of a medicament for the prevention or treatment of an LXR mediated disease or condition. LXR mediated diseases or conditions include inflammation, cardiovascular disease including atherosclerosis, arteriosclerosis, hypercholesteremia, and hyperlipidemia. In particular, the compounds of this invention are useful in the treatment and prevention of inflammation, cardiovascular disease including atherosclerosis and hypercholesteremia.

The present invention also provides a method for increasing reverse cholesterol transport, compounds of this invention for increasing reverse cholesterol transport and the use of compounds of this invention for the preparation of a medicament for increasing reverse cholesterol transport. Lipoprotein metabolism is a dynamic process comprised of production of triglyceride rich particles from the liver (as VLDL), modification of these lipoprotein particles within the plasma (VLDL to IDL to LDL) and clearance of the particles from the plasma, again by the liver. This process provides the transport of triglycerides and free cholesterol to cells of the body. Reverse cholesterol transport is the proposed mechanism by which peripheral cholesterol is returned to the liver from extra-hepatic tissue. The process is carried out by HDL cholesterol. The combination of lipoprotein production (VLDL, HDL) from the liver, modification of particles (all) within the plasma and subsequent clearance back to the liver, accounts for the steady state cholesterol concentration of the plasma. Without wishing to be bound by any particular theory, it is currently believed that the compounds of this invention increase reverse cholesterol transport by increasing cholesterol efflux from the arteries.

Additionally, this invention provides a method for inhibiting cholesterol absorption, compounds of this invention for inhibiting cholesterol absorption and the use of compounds of this invention for the preparation of a medicament for inhibiting cholesterol absorption. This invention also provides a method for increasing reverse cholesterol transport, compounds of this invention for increasing reverse cholesterol transport and the use of compounds of this invention for the preparation of a medicament for increasing reverse cholesterol transport.

The compounds of this invention may also be useful for the prevention or treatment of inflammation and neurodegenerative diseases or neurological disorders. Accordingly, this invention also provides a method for preventing or treating inflammation (See A. J. Fowler et al., J. Invest. Dermatol., 2003 February, 120 (2): 246-255 and S. B. Joseph, et al. Nat Med., 2003 February, 9 (2): 213-219) and a method for preventing or treating neurodegenerative diseases or neurological disorders, particularly neurodegenerative diseases or disorders characterized by neuron degeneration, neuron injury or impaired plasticity or inflammation in the CNS (as disclosed in U.S. Provisional patent application No. 60/368,424, filed 27 Mar., 2002). Particular diseases or conditions that are characterized by neuron degeneration and inflammation, and thus benefiting from the growth and/or repair of neurons include stroke, Alzheimer's disease, fronto-temporal dementias (tauopathies), peripheral neuropathy, Parkinson's disease, dementia with Lewy bodies, Huntington's disease, amyotrophic lateral sclerosis and multiple sclerosis. Diseases or conditions that are characterized by neuron degeneration and/or impaired plasticity include psychiatric disorders such as schizophrenia and depression. Particular diseases or conditions that are characterized by neuronal injury include those conditions associated with brain and/or spinal cord injury, including trauma.

The methods of the present invention are useful for the treatment of animals including mammals generally and particularly humans. The present invention further provides the use of compounds of this invention for the preparation of a medicament for increasing reverse cholesterol transport The methods of the present invention comprise the step of administering a therapeutically effective amount of the compound of this invention. As used herein, the term "therapeutically effective amount" refers to an amount of the compound of this invention that is sufficient to achieve the stated effect. Accordingly, a therapeutically effective amount of a compound of this invention used in the method for the prevention or treatment of LXR mediated diseases or conditions will be an amount sufficient to prevent or treat the LXR mediated disease or condition. Similarly, a therapeutically effective amount of a compound of this invention for use in the method of increasing reverse cholesterol transport will be an amount sufficient to increase reverse cholesterol transport The amount of a compound of this invention or pharmaceutically acceptable salt or solvate thereof, which is required to achieve the desired biological effect will depend on a number of factors such as the use for which it is intended, the means of administration, and the recipient, and will be ultimately at the discretion of the attendant physician or veterinarian. In general, a typical daily dose for the treatment of LXR mediated diseases and conditions in a human, for instance, may be expected to lie in the range of from about 0.01 mg/kg to about 100 mg/kg. This dose may be administered as a single unit dose or as several separate unit doses or as a continuous infusion. Similar dosages would be applicable for the treatment of other diseases, conditions and therapies including increasing reverse cholesterol transport, and inhibiting cholesterol absorption.

In another embodiment, the present invention provides pharmaceutical compositions comprising a compound of this invention or a pharmaceutically acceptable salt or solvate thereof, as the active ingredient, and at least one pharmaceutical carrier or diluent. These pharmaceutical compositions may be used in the prophylaxis and treatment of the foregoing diseases or conditions and in cardiovascular therapies as mentioned above. The carrier must be pharmaceutically acceptable and must be compatible with, i.e. not have a deleterious effect upon, the other ingredients in the composition. The carrier may be a solid or liquid and is preferably formulated as a unit dose formulation, for example, a tablet which may contain from 0.05 to 95% by weight of the active ingredient.

Possible formulations include those suitable for oral, sublingual, buccal, parenteral (for example subcutaneous, intramuscular, or intravenous), rectal, topical including transdermal, intranasal and inhalation administration. Most suitable means of administration for a particular patient will depend on the nature and severity of the disease or condition being treated or the nature of the therapy being used and on the nature of the active compound, but where possible, oral administration is preferred for the prevention and treatment of LXR mediated diseases and conditions.

Formulations suitable for oral administration may be provided as discrete units, such as tablets, capsules, cachets, lozenges, each containing a predetermined amount of the active compound; as powders or granules; as solutions or suspensions in aqueous or non-aqueous liquids; or as oil-in-water or water-in-oil emulsions.

Formulations suitable for sublingual or buccal administration include lozenges comprising the active compound and, typically a flavored base, such as sugar and acacia or tragacanth and pastilles comprising the active compound in an inert base, such as gelatin and glycerine or sucrose acacia.

Formulations suitable for parenteral administration typically comprise sterile aqueous solutions containing a predetermined concentration of the active compound; the solution is preferably isotonic with the blood of the intended recipient Additional formulations suitable for parenteral administration include formulations containing physiologically suitable co-solvents and/or complexing agents such as surfactants and cyclodextrins. Oil-in-water emulsions are also suitable formulations for parenteral formulations. Although such solutions are preferably administered intravenously, they may also be administered by subcutaneous or intramuscular injection.

Formulations suitable for rectal administration are preferably provided as unit-dose suppositories comprising the active ingredient in one or more solid carriers forming the suppository base, for example, cocoa butter.

Formulations suitable for topical or intranasal application include ointments, creams, lotions, pastes, gels, sprays, aerosols and oils. Suitable carriers for such formulations include petroleum jelly, lanolin, polyethyleneglycols, alcohols, and combinations thereof.

Formulations of the invention may be prepared by any suitable method, typically by uniformly and intimately admixing the active compound with liquids or finely divided solid carriers or both, in the required proportions and then, if necessary, shaping the resulting mixture into the desired shape.

For example a tablet may be prepared by compressing an intimate mixture comprising a powder or granules of the active ingredient and one or more optional ingredients, such as a binder, lubricant, inert diluent, or surface active dispersing agent, or by molding an intimate mixture of powdered active ingredient and inert liquid diluent.

Suitable formulations for administration by inhalation include fine particle dusts or mists which may be generated by means of various types of metered dose pressurized aerosols, nebulisers, or insufflators.

For pulmonary administration via the mouth, the particle size of the powder or droplets is typically in the range 0.5-10 µM, preferably 1-5 µM, to ensure delivery into the bronchial tree. For nasal administration, a particle size in the range 10-500 µM is preferred to ensure retention in the nasal cavity.

Metered dose inhalers are pressurized aerosol dispensers, typically containing a suspension or solution formulation of the active ingredient in a liquefied propellant. During use, these devices discharge the formulation through a valve adapted to deliver a metered volume, typically from 10 to 150 µL, to produce a fine particle spray containing the active ingredient. Suitable propellants include certain chlorofluorocarbon compounds, for example, dichlorodifluoromethane, trichlorofluoromethane, dichlorotetrafluoroethane and mixtures thereof. The formulation may additionally contain one or more co-solvents, for example, ethanol surfactants, such as oleic acid or sorbitan trioleate, anti-oxidants and suitable flavoring agents. Nebulisers are commercially available devices that transform solutions or suspensions of the active ingredient into a therapeutic aerosol mist either by means of acceleration of a compressed gas typically air or oxygen, through a narrow venturi orifice, or by means of ultrasonic agitation. Suitable formulations for use in nebulisers consist of the active ingredient in a liquid carrier and comprising up to 40% w/w of the formulation, preferably less than 20% w/w. The carrier is typically water or a dilute aqueous alcoholic solution, preferably made isotonic with body fluids by the addition of, for example, sodium chloride. Optional additives include preservatives if the formulation is not prepared sterile, for example, methyl hydroxy-benzoate, anti-oxidants, flavoring agents, volatile oils, buffering agents and surfactants.

Suitable formulations for administration by insufflation include finely comminuted powders which may be delivered by means of an insufflator or taken into the nasal cavity in the manner of a snuff. In the insufflator, the powder is contained in capsules or cartridges, typically made of gelatin or plastic, which are either pierced or opened in situ and the powder delivered by air drawn through the device upon inhalation or by means of a manually-operated pump. The powder employed in the insufflator consists either solely of the active ingredient or of a powder blend comprising the active ingredient, a suitable powder diluent, such as lactose, and an optional surfactant. The active ingredient typically comprises from 0.1 to 100 w/w of the formulation.

In addition to the ingredients specifically mentioned above, the formulations of the present invention may include other agents known to those skilled in the art of pharmacy, having regard for the type of formulation in issue. For example, formulations suitable for oral administration may include flavoring agents and formulations suitable for intranasal administration may include perfumes.

General Methods

General Methods

In one embodiment of this invention, the method for the preparation of compounds of Formulas I, II, I-A and II-A comprises the steps of:

(a) reacting an alcohol having the formula: $L'-(CR^4R^5)_n-L$, where L' and L are leaving groups, which may be the same or different, such as a halogen (iodide, bromide or chloride), sulfonate (tosylate, mesylate, triflate, etc.) or is a group that is converted to a leaving group (e.g., an alcohol), with a compound having the formula:

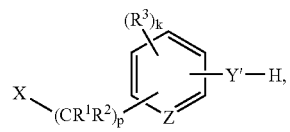

where Y' is —O—, —S—, or —NH— and X is defined as above or a protected form thereof, to form a compound having the formula:

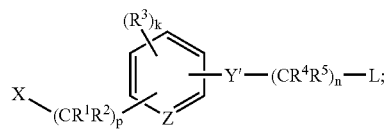

(b) forming a secondary amine by the reductive amination of an aldehyde

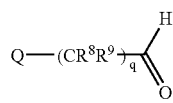

and a primary amine

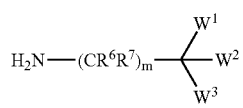

to form

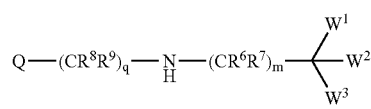

c) coupling the tertiary amine to the product of step a to form a compound having the formula:

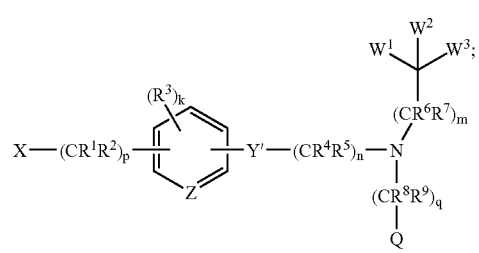

(d) removing any protecting groups; and (e) optionally derivitization of reactive functionality at X The order of the steps can be changed such that a primary amine is coupled to the product of step a prior to the reductive amination of the amide to the aldehyde, or the amine can be coupled to $L^1\text{-}(CR^4R^5)_n\text{-}L$ prior to coupling to an appropriately derivitized ring, e.g.,

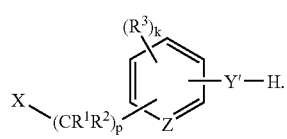

Further analogs prepared by alterations of X are detailed in the experimental text.

Specific Methods

Compounds of Formulas I, II, I-A and II-A of this invention where X is other than a heterocycle and Y is oxygen were prepared by methods analogous to those described in Scheme 1.

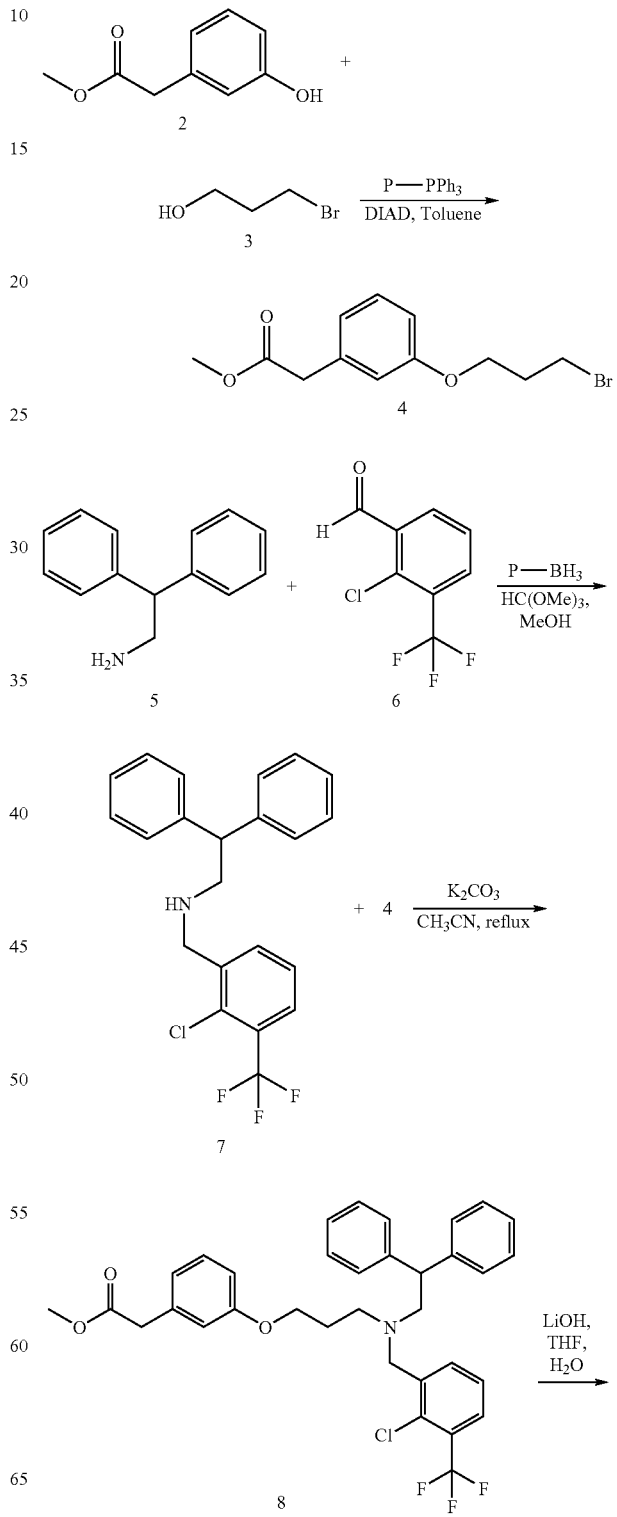

-continued

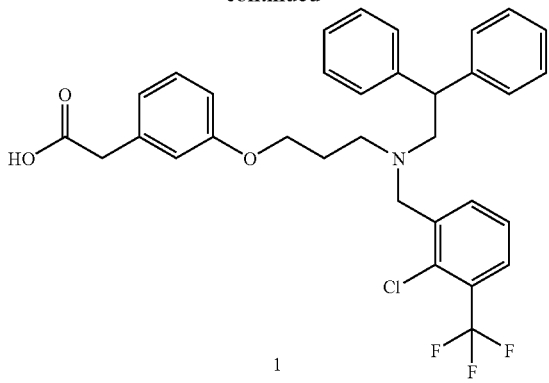

A phenolic nucleophile (2) displaced an alcohol (3), activated with a polymer-bound triphenyl phosphine and diisopropyl azodicarboxylate (DIAD) to give aryl ether (4). A secondary amine (7) was prepared by reductive amination of a primary amine (5) with an aldehyde (6) using polymer bound borohydride resin. The secondary amine (7) then displaced the bromine from aryl-ether (4) to form a tertiary amine (8). The ester of this product was hydrolyzed under basic conditions to afford the free acid (1). The hydrochloride salt of compound 1 was prepared, if desired, by adding HCl in ether.

Each of the above-described methods further include the optional step(s) of forming a pharmaceutically acceptable salt of a compound of this invention, and/or of forming a pharmaceutically acceptable solvate of a compound of this invention or a pharmaceutically acceptable salt thereof.

The following intermediates are useful in the methods described herein to make the compounds of Formulas I, I-A, II and II-A:
{3-[4-(t-butyldimethylsilylhydroxy)but-1-ynyl]phenyl}acetic acid methyl ester,
{3-[4-hydroxybutyl]phenyl}acetic acid methyl ester,
{3-[4-(toluene-4-sulfonyloxy)butyl]phenyl}acetic acid methyl ester,
(S)-(2-chloro-3-trifluoromethyl-benzyl)-(2-phenyl-propyl)-amine,
(R)-(2-chloro-3-trifluoromethyl-benzyl)-(2-phenyl-propyl)-amine,
(2-chloro-3-trifluoromethyl-benzyl)-(naphthalene-1-ylmethyl)-amine,
(2-chloro-3-trifluoromethyl-benzyl)-(phenethyl)-amine,
(2-chloro-3-trifluoromethyl-benzyl)-(benzyl)-amine,
(2-chloro-3-trifluoromethyl-benzylamino)-phenyl-ethanol,
3-(3-benzyloxy-benzyl)-1,2,4-triazole,
3-(3-benzyloxy-benzyl)-ethoxymethyl-1,2,4-triazole,
[3-(ethoxymethyl)-1,2,4-triazol-3-ylmethyl]-phenol,
{3-[3-(3-bromo-propoxy)-benzyl]}(ethoxymethyl)-1,2,4-triazole,
(2-chloro-3-trifluoromethyl-benzyl)-(2,2-diphenyl-ethyl)-{3-[3-(ethoxymethyl)-1,2,4-triazol-3-ylmethyl-phenoxy]-propyl}-amine,
5-(3-benzyloxy-benzyl)-1,2,3,4-tetrazole,
5-(3-benzyloxy-benzyl)-ethoxymethyl-1,2,3,4-tetrazole,
5-(3-hydroxy-benzyl)ethoxymethyl-1,2,3,4-tetrazole,
5-[3-(3-bromo-propoxy)-benzyl]-(ethoxymethyl)-1,2,3,4-tetrazole,
(2-chloro-3-trifluoromethyl-benzyl)-(2,2-diphenyl-ethyl)-{3-[3-(ethoxymethyl-1,2,3,4-tetrazol-5-ylmethyl)-phenoxy]-propyl}-amine, and a stereoisomer, a stereoisomeric mixture or racemate thereof and a pharmaceutically acceptable salt or solvate thereof.

The following Test Methods and Examples are intended for illustration only and are not intended to limit the scope of the invention in any way; the present invention being defined by the claims.

In the Test Methods and Examples, the following terms have the designated meaning: "pRSETa" is a known expression vector available from Invitrogen; "IPTG" means isopropyl β-D-thiogalactopyranoside; "PO$_4$" means phosphate; "PBS" means phosphate buffered saline; "TBS" means tris-buffered saline; EDTA means ethylenediamine tetraacetic acid; "DTT" means dithiothreitol; "FAF-BSA" means fatty-acid free bovine serum albumin; "SRC-1" means steroid receptor coactivator 1; "CS" means charcoal stripped; "nM" means nanomolar; "µM" means micromolar; "mM" means millimolar; "pM" means picomolar; "mmol" means millimoles; "g" means grams; "ng" means nanograms; "mg/ml" means milligram per milliliter; "µL" means microliters; and "mL" means milliliter.

Test Method 1: Ligand Sensing Assay (LiSA) for LXRβ Agonist Activity

This assay measures the recruitment of a peptide derived from the coactivator protein, SRC1, to the agonist-bound LXRβ. Peptides derived from other nuclear receptor cofactors may be similarly prepared and assayed.

To generate the human LXRβ ligand binding domain suitable for LiSA, a modified polyhistidine tag (MKKGH-HHHHHG) (SEQ ID No. 1) was fused in frame to the human LXRβ ligand binding domain (amino acids 185-461 of Genbank accession number U07132) and subcloned into the expression vector pRSETa (Invitrogen) under the control of an IPTG inducible T7 promoter. The human LXRβ ligand binding domain was expressed in *E. coli* strain BL21 (DE3). Ten-liter fermentation batches were grown in Rich PO$_4$ media with 0.1 mg/mL Ampicillin at 25° C. for 12 hours, cooled to 9° C. and held at that temperature for 36 hours to a density of OD600=14. At this cell density, 0.25 mM IPTG was added and induction proceeded for 24 hours at 9° C., to a final OD600=16. Cells were harvested by centrifugation (20 minutes, 3500 g, 4° C.), and concentrated cell slurries were stored in PBS at −80° C.

Typically 25-50 g of cell paste is resuspended in 250-500 mL TBS, pH 8.0 (25 mM Tris, 150 mM NaCl). Cells are lysed by passing 3 times through an APV Rannie MINI-lab homogenizer and cell debris is removed by centrifugation (30 minutes, 20,000 g, 4° C.). The cleared supernatant is filtered through coarse pre-filters, and TBS, pH 8.0, containing 500 mM imidazole is added to obtain a final imidazole concentration of 50 mM. This lysate is loaded onto a column (XK-26, 10 cm) packed with Sepharose [Ni++ charged] Chelation resin (available from Pharmacia) and pre-equilibrated with TBS pH 8.0/50 mM imidazole. After washing to baseline absorbance with equilibration buffer, the column is washed with approximately one column volume of TBS pH −8.0 containing 95 mM imidazole. LXRβLBD (185-461) is eluted with a gradient from 50 to 500 mM imidazole. Column peak fractions are pooled immediately and diluted 5 fold with 25 mM Tris pH 8.0, containing 5% 1,2-propanediol, 0.5 mM EDTA and 5 mM DTT. The diluted protein sample is then loaded onto a column (XK-16, 10 cm)

packed with Poros HQ resin (anion exchange). Afterwashing to baseline absorbance with the dilution buffer the protein is eluted with a gradient from 50-500 mM NaCl. Peak fractions are pooled and concentrated using Centri-prep 10K (Amicon) filter devices and subjected to size exclusion, using a column (XK-26, 90 cm) packed with Superdex-75 resin (Pharmacia) pre-equilibrated with TBS, pH 8.0, containing 5% 1,2-propanediol, 0.5 mM EDTA and 5 mM DTT.

LXRβ protein was diluted to approximately 10 µM in PBS and five-fold molar excess of NHS-LC-Biotin (Pierce) was added in a minimal volume of PBS. This solution was incubated with gentle mixing for 30 minutes at ambient room temperature. The biotinylation modification reaction was stopped by the addition of 2000× molar excess of Tris-HCl, pH 8. The modified LXRβ protein was dialyzed against 4 buffer changes, each of at least 50 volumes, PBS containing 5 mM DTT, 2 mM EDTA and 2% sucrose. The biotinylated LXRβ protein was subjected to mass spectrometric analysis to reveal the extent of modification by the biotinylation reagent. In general, approximately 95% of the protein had at least a single site of biotinylation; and the overall extent of biotinylation followed a normal distribution of multiple sites, ranging from one to nine.

The biotinylated protein was incubated for 20-25 minutes at a concentration of 5 nM in assay buffer (50 mM NaF, 50 mM MOPS-pH 7.5, 0.1 mg/ml FAF-BSA, 0.05 mM CHAPS, 10 mM DTT) with equimolar amounts of streptavidin-AlloPhycoCyanin (APC, Molecular Probes). At the same time, the biotinylated peptide comprising amino acids 676-700 of SRC-1 (CPSSHSSLTERHKILHRLLQEGSPS-CONH2) (SEQ ID No. 2) at a concentration of 10 nM was incubated in assay buffer with a ½ molar amount of streptavidin-labelled Europium (Wallac) for 20-25 minutes. After the initial incubations are completed, a 20 molar excess of biotin was added to each of the solutions to block the unattached streptavidin reagents. After 20 min at room temp, the solutions were mixed yielding a concentration of 5 nM for the dye-labeled LXR protein and 10 nM for SRC-1 peptide.

49 uL of the protein/peptide mixture was added to each well of an assay plate containing 1 ul of test compound serial diluted in 100% DMSO. The final volume in each well was 0.05 mL, and the concentration in the well for the dye-labeled protein and peptide was 5 nM protein and 10 nM SRC1-peptide. The final test compound concentrations were between 33 pM and 20 uM. The plates were incubated at room temp 2-hours and then counted on a Wallac Victor V fluorescent plate reader.

In this assay 1 µM 24(S), 25-epoxycholesterol gave a reading of 20000 fluorescence units over a background reading of 10000 fluorescence units.

Test Method 2: Ligand Sensing Assay for LXRα Agonist Activity

The assay for LXRα was run according to the procedures of Test Method 1, above using his-tagged LXRα ligand binding domain (amino acids 183-447 of Genbank accession number U22662, with the 14$^{th}$ amino acid corrected to A from R). In this assay 1 µM 24(S),25-epoxycholesterol gave a reading of 20000 fluorescence units over a background reading of 10000 fluorescence units.

EXAMPLE 1

2-(3-{3-[[2-Chloro-3-(trifluoromethyl)benzyl](2,2-dephenylethyl)amino]propoxy}phenyl)-ethanol

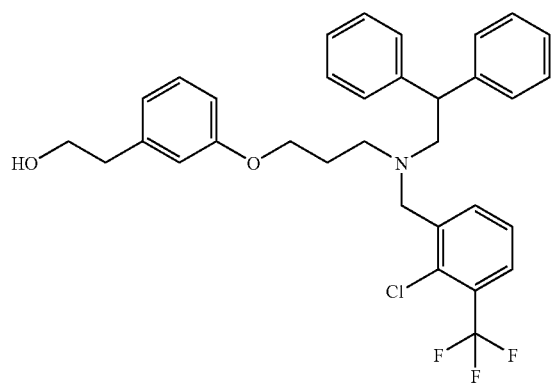

a) Methyl [3-(3-bromopropoxy)phenyl]acetate

A solution of methyl 3-hydroxyphenylacetate (11.3 g, 0.068 mole) in 300 mL of anhydrous toluene was treated with 3-bromopropanol (12.2 g, 0.088 mole). Polymer bound triphenylphosphine (36.0 g, 0.108 mole, 3 mmol/g, Fluka Chemie) was then added, and the mixture reacted for 15 minutes. The reaction mixture was then cooled to 0° C. and diisopropylazodicarboxylate (16.9 g, 0.084 mol) was added in a dropwise fashion. After stirring at RT overnight, the crude reaction mixture was filtered and the solid washed with 100 mL toluene. After concentration of the filtrate in vacuo, the crude product was purified by column chromatography over silica gel (silica gel 60, EM Science) using 15% ethyl acetate:hexane as eluent to afford 15.8 g (81% yield) of the title compound as an oil: $^1$H NMR (CDCl$_3$, 400 MHz) δ 7.23-7.19 (m, 1 H), 6.85-6.7 (m, 3), 4.09-4.06 (t, 2 H, J=5.8), 3.67 (s, 3 H), 3.67-3.56 (m, 4 H), 2.32-2.26 (p, 2 H, J=6.0); MS (ESI) 288 (MH$^+$); TLC (hexanes:ethyl acetate/3:1) R$_f$=0.68. Anal. (C$_{12}$H$_{15}$O$_3$Br) C, H, N.

b) [2-Chloro-3-(trifluoromethyl)benzyl](2,2-diphenylethyl)amine

A solution of 2,2-diphenethylamine (10.0 g, 50.7 mmol) and 2-chloro-3-trifluoromethylbenzaldehyde (10.5 g, 50.7 mmol) in 80 mL of methanol and 40 mL of trimethylorthoformate was stirred at RT for 15 hours whereupon polymer-supported borohydride resin (20.3 g, 55.8 mmol, 2.5 mmol/g, Aldrich) was added in one portion. After stirring at RT for 24 h, the reaction was filtered and the filtrate was concentrated in vacuo. The crude product was purified by column chromatography over silica gel (silica gel 60, EM Science) using ethyl acetate:hexane/40:60 with 1% NH$_4$OH as the eluent to give 11.2 g (57% yield) of the title compound as an oil: $^1$H NMR (CDCl$_3$, 400 MHz) δ 7.57 (d, 1 H. J=8.0), 7.52 (d, 1 H, J=7.6), 7.32-7.15 (m, 11 H), 4.20 (t, 1 H, J=7.6), 3.9 (s, 2 H), 3.22 (d, 2 H, J=7.6); HPLC (Waters symmetry shield, RPq 3.5 micron, 2.1×30 mm, 85:15/water acetonitrile with 0.1% HCOOH to 100% acetonitrile after 4 min, flow rate=0.8 mL/min) t$_R$=2.39 min; MS (ESI) 390 (MH$^+$); TLC (hexanes:ethyl acetate/4:1) R$_f$=0.42.

c) Methyl (3-{3-[[2-Chloro-3-(trifluoromethyl)benzyl](2,2-diphenylethyl)amino]propoxy}-phenyl)acetate A solution of methyl [3-(3-bromopropoxy)phenyl]acetate (1.0 g, 3.48 mmole) and [2-chloro-3-(trifluoromethyl)benzyl]-2,2-diphenylethylamine (1.63 g, 4.18 mmole) in 20 mL of acetonitrile was treated with potassium carbonate (0.72 g, 5.2 mmol). The reaction mixture was heated to reflux and stirred for 4 days. The reaction mixture was filtered, and the filtrate was concentrated in vacuo. The crude product was purified by flash chromatography (silica gel cartridge, Biotage 32-63 um, 60A) with 10% ethyl acetate:hexanes as the eluent to afford 1.69 g (81% yield) of the title compound as a viscous oil: $^1$H NMR (CDCl$_3$, 400 MHz) δ 7.46-7.44 (d, 1H, J=7.7), 7.25-7.14 (m, 12 H), 6.91-6.84 (m, 2 H), 6.666.62 (m, 2 H) 4.154.09 (t, 1 H, J=7.6), 3.78 (s, 1 H), 3.69-3.66 (m, 5 H), 3.59 (S, 2 H), 3.15-3.13 (d, 2 H, J=7.7), 2.72-2.68 (t, 2 H, J=6.6), 1.87-1.80 (m, 2 H); MS (ESI) 597 (MH$^+$); TLC (hexanes:Ethy acetate/9:1) R$_f$=0.36.

d) 2-(33-[[2-Chloro-3-(trifluoromethyl)benzyl](2,2-diphenylethyl)amino]propoxy}-phenyl)acetic acid hydrochloride salt A solution of methyl (3-{3-[[2-chloro-3-(trifluoromethyl)benzyl](2,2-diphenylethyl)amino]propoxy}phenyl)acetate (113 mg, 0.19 mmol) in 1.5 mL of tetrahydrofuran and 1 mL of water was treated with 1N aqueous LiOH (0.29 mL, 0.29 mmol). After stirring at RT for 2 hours, additional 1 N aqueous LiOH (0.29 mL, 0.29 mmol) was added and stirring was continued for 2 hours. The reaction was neutralized with acetic acid (66 μL, 0.58 mmol) and poured into water/Ethyl acetate. The layers were separated and the aqueous layer was extracted with ethyl acetate (3×). The combined organic layers were washed with brine (1×), dried over magnesium sulfate, filtered, and concentrated in vacuo. The crude material was purified by preparative thin layer chromatography (silica gel, 1 mm plates, Merck 20×20 cm silica gel 60 F$_{254}$) eluting with methylene chloride:MeOH (95:5) to afford an oil. The oil was dissolved in diethyl ether and acidified with excess HCl/diethyl ether. The reaction was concentrated in vacuo and dried under reduced pressure to give 65 mg (56% yield) of the title compound as a white solid: $^1$H NMR (C$_5$D$_5$N, 400 MHz) δ 7.60-7.05 (m, 15 H), 7.01 (t, 1 H, J=7.6), 6.84 (dd, 1 H, J=8.4, 2.4), 4.32 (t, 1 H, J=7.6), 3.89 (s, 2 H), 3.77 (s, 2 H), 3.71 (t, 2 H, J=5.6), 3.16 (d, 2 H, J=7.6), 2.65 (t, 2 H, J=6.4), 1.88-1.78 (m, 2 H).

e) 2-(33-[[2-Chloro-3-(trifluoromethyl)benzyl](2,2-dephenylethyl)amino]propoxy}-phenyl)-ethanol A solution of 2-(3-{3-[[2-chloro-3-(trifluoromethyl)benzyl](2,2-diphenylethyl)amino]propoxy}-phenyl)acetic acid hydrochloride (220 mg, 0.36 mmol) in THF (35 ml) at 0° C., was treated with LiAlH$_4$ (1.0 ml of a 1N solution in THF), and the reaction was stirred at 0° for 45 minutes. Ethyl acetate (10 ml) was added, the reaction warmed to RT, and water (20 ml) was added. The mixture was extracted with ethyl acetate. The organic extracts were dried and the solvent removed. The residue was chromatographed over silica gel (hexane/Ethyl acetate:3/7) to give a pure oil (42 mg, 20%). MS (ESI) 568.0 (M+H)$^+$.

EXAMPLE 2

2-(3-{3-[[2-Chloro-3-(trifluoromethyl)benzyl](2,2-diphenylethyl)amino]propoxy}-phenyl)acetic acid, N-oxide

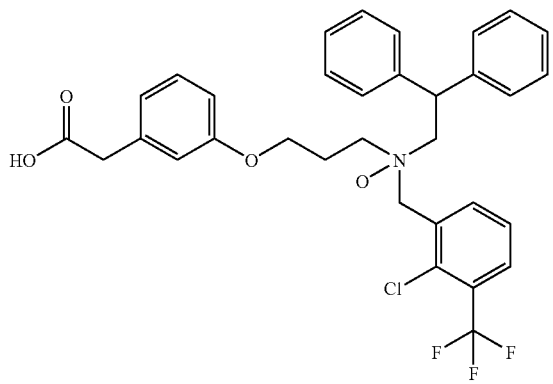

A solution of 2-(3-{3-[[2-chloro-3-(trifluoromethyl)benzyl](2,2-diphenylethyl)amino]propoxy}-phenyl)acetic acid hydrochloride from Example 1d (120 mg, 0.19 mmol) in acetic acid (3 ml) was treated dropwise with H$_2$O$_2$ (1 ml, 30% solution), and the reaction stirred at RT for 16 hr, diluted with water and extracted with CHCl$_3$. The organic extracts were washed with water, dried and evaporated. The residue was crystallized from diethyl ether and gave a pure solid (75 mg, 65%). MS (ESI) 598.0 (M+H)$^+$.

EXAMPLE 3

(3-{3-[[2-Chloro-3-(trifluoromethyl)benzyl](2,2-diphenylethyl)amino]propoxy}-bromobenzene

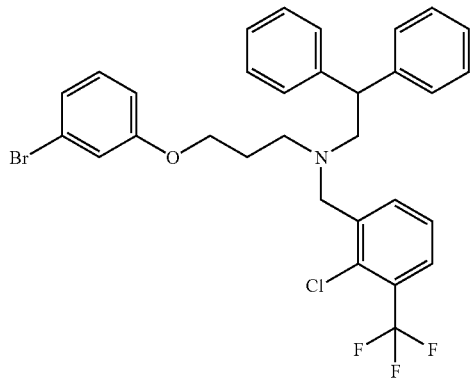

a) 3-(3-Bromopropoxy)bromobenzene

Diethylazodicarboxylate (0.77 g, 3.8 mmol) was added to solution of 3-bromophenol (0.50 g, 3.2 mmol), 3-bromopro panol (0.53 g, 3.8 mmol), triphenylphosphine (1.0 g, 3.8 mmol) and THF (10 mL). The solution was maintained at RT for 16 h and then concentrated in vacuo. The residue was partitioned between methylene chloride and 10% NaHCO$_3$ aq. solution and layers separated. The aqueous layer was extracted with methylene chloride (2×10 mL). The organic layers were combined, dried (MgSO$_4$) and concentrated in vacuo. The crude product was purified by flash column chromatography (100 g silica gel 60, 230-400 mesh, 9:1 hexane:ethyl acetate as eluent) to give 0.63 g (71%) of the title compound as a pale yellow liquid. MS (ESI) 293.0 [M+H]$^+$.

b) (3-{3-[[2-Chloro-3-(trifluoromethyl)benzyl](2,2-diphenylethyl)amino]propoxy}-bromobenzene Potassium carbonate (140 mg, 1.0 mmol) and NaI (82 mg, 0.34 mmol) were added to a solution of 3-(3-bromopropoxy) bromobenzene (100 mg, 0.34 mmol), (2-chloro-3-trifluoromethylbenzyl)(2,2-diphenylethyl)amine and acetonitrile (3 mL). The mixture was heated at reflux for 16 h. The mixture was allowed to cool to RT and concentrated in vacuo. The residue was partitioned between methylene chloride and 10% NaHCO$_3$ aq. solution and layers separated. The aqueous layer was extracted with methylene chloride (2×10 mL). The organic layers were combined, dried (MgSO$_4$) and concentrated in vacuo. The residue was purified by preparative HPLC (YMC CombiPrep ODS-A, 50×20 mm, 20 mL/min, A: 0.1% trifluoroacetic acid in acetonitrile B: 0.1% aqueous trifluoroacetic acid, A: 10 to 90% during 10 min, UV detection at 254 nm) to give 52 mg (29%) of the title compound as an oil. MS (ESI) 639.2 [M+H]$^+$.

EXAMPLE 4

(4-{3-[[2-Chloro-3-(trifluoromethyl)benzyl](2,2-diphenylethyl)amino]propoxy}-bromobenzene

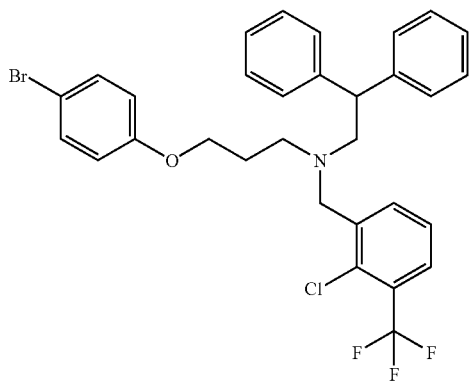

Following the procedure of Example 3, except substituting 4-(3-bromopropoxy)bromobenzene for 3-(3-bromopropoxy)bromobenzene gave the title compound as an oil (23%). MS (ESI) 638.6 [M+H]$^+$.

EXAMPLE 5

(2-Chloro-3-trifluoromethyl-benzyl)-(2,2-diphenylethyl)-{3-[3-(1,2,4-triazol-3-ylmethyl)-phenoxy]-propyl)amine hydrochloride salt

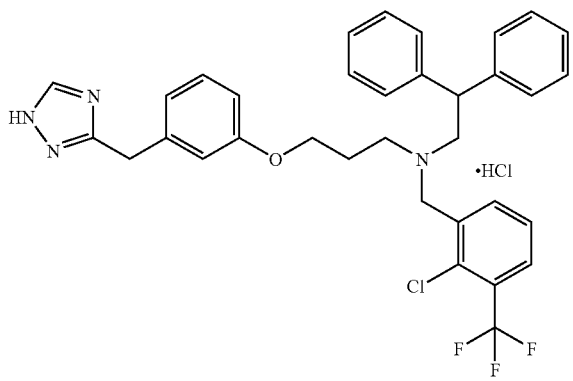

a) 3-(3-Benzyloxy-benzyl)-1,2,4-triazole

To a stirring solution of 3-benzyloxyphenylacetonitrile (5.0 g, 0.022 mole) in methanol (100 mL) was added formic hydrazide (2.69 g, 0.060 mole) and solid potassium carbonate (9.9 g, 0.027 mole). The reaction was heated at reflux and stirred overnight. The mixture was cooled to RT, filtered, and the filtrate was concentrated. The crude product was purified by column chromatography over silica gel (silica gel 60, EM Science) using 75% ethyl acetate:hexane as eluent to afford 1.8 g (30% yield) of the title compound as an oil: MS (ESI) 266.0 (M+H$^+$).

b) 3-(3-Benzyloxy-benzyl)-ethoxymethyl-1,2,4-triazole (Mixture of Regioisomers for Ethoxymethyl Include 1-, 2-, and 4-)

To a stirring solution of 3-(3-benzyloxy-benzyl)-1,2,4-triazole (1.0 g, 0.0037 mole) in DMF (20 mL) at 0° C. was added NaH (0.195 g, 0.0049 mole) and the mixture was stirred for 20 min. To this mixture was added chloromethyl ethyl ether (0.354 g, 0.0037 mole), and the mixture was warmed to RT and stirred overnight. The reaction mixture was poured into water (100 mL) and extracted three times with ethyl acetate. The ethyl acetate extracts were dried over Na$_2$SO$_4$, filtered, and concentrated. The crude product was purified by column chromatography over silica gel (silica gel 60, EM Science) using 60% ethyl acetate:hexane as eluent to afford 1.0 g (89% yield) of the title compounds as an oil: MS (ESI) 324.0 (M+H$^+$).

c) [3-(Ethoxymethyl)-1,2,4-triazol-3-ylmethyl]-phenol (Mixture of Regioisomers for Ethoxymethyl Include 1-, 2-, and 4-)

To a stirring solution of 3-(3-Benzyloxy-benzyl)-ethoxymethyl-1,2,4-triazole (mixture of regioisomers, 1.0 g, 0.0031 mole) in methanol (20 mL) was added palladium on carbon (0.1 g, 10 wt. %). The reaction mixture was stirred at RT under an H$_2$ atmosphere overnight. The crude reaction mixture was filtered, and the filtrate was concentrated in vacuo to give 0.75 g (99% yield) of title compounds as an oil. MS(ESI) 234.0 (M+H$^+$).

d) {3-[3-(3-Bromo-propoxy)-benzyl]}-(ethoxymethyl)-1,2,4-triazole (Mixture of Regioisomers for Ethoxymethyl Include 1-, 2-, and 4-)

A solution of [3-(ethoxymethyl)-1,2,4-triazol-3-ylmethyl]-phenol (mixture of regioisomers, 300 mg, 1.27 mmol) in anhydrous toluene (10 mL) was treated with 3-bromo propanol (230 mg, 1.66 mmol). Polymer bound triphenylphosphine (680 mg, 2.04 mmol, 3 mmol/g, Fluka Chemie) was then added, and the mixture was stirred for 15 minutes. The reaction mixture was then cooled to, 0° C. and diisopropylazodicarboxylate (320 mg, 1.58 mmol) was added in a dropwise fashion. The reaction mixture was stirred at RT overnight, the crude reaction mixture was filtered, and the filtrate was concentrated in vacuo to give 400 mg (88% yield) of title compounds as an oil. MS(ESI) 356.0 (M+2H$^+$).

e) (2,2-Diphenylethyl)(2-chloro-3-trifluoromethylbenzyl)amine

To a stirring solution of 2,2-diphenethylamine (2.0 g, 0.010 mole) and 2-chloro-3-trifluoromethylbenzaldehyde (2.33 g, 0.011 mole) in dichloromethane (20 mL) was added sodium triacetoxyborohydride (2.36° g, 0.011 mole) and acetic acid (2.0 mL). The reaction mixture was stirred overnight. The solvent was removed and the residue was dissolved in ethyl acetate. The ethyl acetate solution was washed with saturated NaHCO$_3$, the ethyl acetate extracts were dried over Na$_2$SO$_4$, filtered, and concentrated. The crude product was subjected to column chromatography over silica gel (silica gel 60, EM Science) using 30% ethyl acetate:hexane as eluent to afford 3.0 g (76% yield) of the title compound as a yellow oil: MS (ESI) 390.0 (M+H$^+$).

f) (2-Chloro-3-trifluoromethyl-benzyl)-(2,2-diphenyl-ethyl)-{3-[3-(ethoxymethyl)-1,2,4-triazol-3-ylmethyl-phenoxy]-propyl}-amine (Mixture of Regioisomers for Ethoxymethyl Include 1-, 2-, and 4-)

A solution of {3-[3-(3-bromo-propoxy)-benzyl]} (ethoxymethyl)-1,2,4-triazole (mixture of regioisomers, 150 mg, 0.421 mmol) and (2,2-diphenylethyl)-(2-chloro-3-trifluoromethyl)amine (164 mg, 0.421 mmol) in acetonitrile (5 ml) was treated with solid potassium carbonate (175 mg, 1.26 mmol) and NaI (189 mg, 1.26 mmol). The reaction mixture was heated to reflux and stirred overnight. The mixture was cooled to RT, filtered, and the filtrate was concentrated. The crude product was purified by preparative HPLC (YMC CombiPrep PDS, 75×30 mm, 25 mL/min, A: acetonitrile B: water, A: 80 to 100% during 10 min, UV detection at 254 nm) to give 98 mg (35% yield) of title compound as a viscous oil. MS (ESI) 663.2 (M$^+$).

g) (2-Chloro-3-trifluoromethyl-benzyl)-2,2-diphenyl-ethyl)-{3-[3-(1,2,4-triazol-3-ylmethyl)-phenoxy]-propyl}-amine hydrochloride salt To a stirring solution of (2-chloro-3-trifluoromethyl-benzyl)-(2,2-diphenyl-ethyl)-{3-[3-(ethoxymethyl-1,2,4-triazol-3-ylmethyl)-phenoxy]-propyl)amine (mixture of regioisomers, 90 mg, 0.135 mmol) in dichloromethane (1.5 mL) was added triethylsilane (157 mg, 1.35 mmol). The reaction mixture was treated with TFA (0.5 mL) and then stirred overnight Solvent was removed and the residue was purified by preparative HPLC (YMC CombiPrep PDS, 75×30 mm, 25 mL/min, A: acetonitrile B: water, A: 60 to 100% during 10 min, UV detection at 254 nm) to give an oil. The oil was dissolved in diethyl ether and acidified with 1.0 M HCl/diethyl ether to give 40 mg (48% yield) of the title compound as a yellow oil. MS (ESI) 605.0 (M$^+$).

EXAMPLE 6

(2-Chloro-3-trifluoromethyl-benzyl)-(2,2-diphenyl-ethyl)-{3-[3-(1,2,3,4-tetrazol-5-ylmethyl)-phenoxy]-propyl}-amine

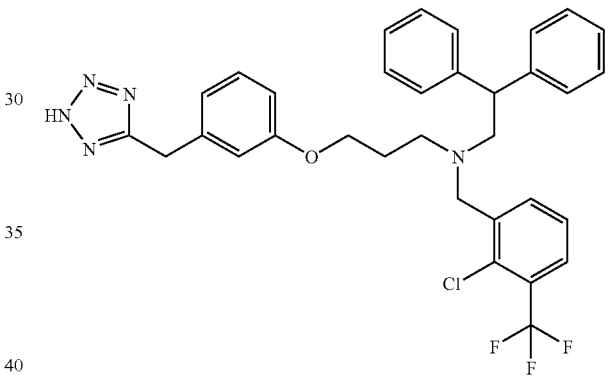

a) 5-(3-Benzyloxy-benzyl)-1,2,3,4-tetrazole

To a stirring solution of 3-benzyloxyphenylacetonitrile (2.0 g, 8.95 mmol) in toluene (17 ml) was added trimethylsilylazide (2.37 g, 17.9 mmol) and di-n-butyltin oxide (0.22 g, 0.9 mmol). The mixture was heated at 110° C. for 48 h, and was concentrated. The reaction mixture was dissolved in ethyl acetate (100 ml) and washed two times with 10% aqueous sodium bicarbonate. The basic extracts were acidified to pH<2 with conc. HCl, and the aqueous layer was extracted with ethyl acetate. The combined organic layers were dried over sodium sulfate, filtered, and concentrated. The crude product (2.0 g, 89%) was used in the next step without further purification. MS (ESI) 267.0 (M+H$^+$).

b) 5-(3-Benzyloxy-benzyl)-ethoxymethyl-1,2,3,4-tetrazole (Mixture of Regioisomers for Ethoxymethyl Include 1- and 2-)

To a stirring solution of 3-(3-benzyloxy-benzyl)-1,2,3,4-tetrazole (2.12 g, 7.96 mmol) in DMF (40 ml) at 0° C. was added NaH (0.38 g, 9.55 mmol). To this mixture was added chloromethyl ethyl ether (0.81 ml, 8.75 mmol), and the solution was stirred at RT overnight. The reaction mixture was poured into water (120 ml) and extracted three times with ethyl acetate. The ethyl acetate extracts were dried over $Na_2SO_4$, filtered, and concentrated. The crude mixture was subjected to column chromatography (silica gel, ethyl acetate/hexane) to provide the title compounds as a mixture of regioisomers as a light yellow oil (1.39 g, 55%). MS (ESI) 324.8 (M+).

c) 5-(3-Hydroxy-benzyl)-ethoxymethyl-1,2,3,4-tetrazole (Mixture of Regioisomers for Ethoxymethyl Include 1- and 2-)

To a stirring solution of 5-(3-benzyloxy-benzyl)-ethoxymethyl-1,2,3,4-tetrazole (mixture of regioisomers, 0.23 g, 0.71 mmol) in MeOH (5 ml) was added palladium on carbon (20 mg). The mixture was stirred for 7 h under $H_2$ atmosphere, filtered, and concentrated. The crude phenol was purified by preparative HPLC (YMC CombiPrep PDS, 75×30 mm, 25 mL/min, acetonitrile:$H_2O$, UV detection at 254 nm) to afford the desired phenol as a clear oil (0.14 g, 84%). MS (ESI) 235.0 (M+H$^+$).

d) 5-[3-(3-Bromo-propoxy)-benzyl]-(ethoxymethyl)-1,2,3,4-tetrazole (Mixture of Regioisomers for Ethoxymethyl Include 1- and 2-)

A solution of 5-(3-hydroxy-benzyl)-ethoxymethyl-1,2,3,4-tetrazole (mixture of regioisomers, 132 mg, 0.56 mmol) in anhydrous toluene (5 ml) was treated with 3-bromo-propanol (117 mg, 0.84 mmol). Polymer bound triphenylphosphine (0.56 mg, 1.7 mmol, 3 mmol/g, Fluka Chemie) was then added, and the mixture stirred for 15 minutes. The reaction mixture was then cooled to 0° C. and diisopropylazodicarboxylate (166 ul, 0.84 mmol) was added dropwise. The reaction mixture was stirred at RT overnight, filtered, and the filtrate was concentrated in vacuo to give 200 mg (100% yield) of a 1:1 mixture of the title compounds as a yellow oil. MS (ESI) 356.8 (M+2H$^+$).

e) (2-Chloro-3-trifluoromethyl-benzyl)-(2,2-diphenyl-ethyl)-{3-[3-(ethoxymethyl-1,2,3,4-tetrazol-5-ylmethyl)-phenoxy]-propyl}-amine (Mixture of Regioisomers for Ethoxymethyl Include 1- and 2-)

A solution of (2-chloro-3-trifluoromethyl-benzyl)-(2,2-diphenyl-ethyl)-{3-[3-(ethoxymethyl-1,2,3,4-tetrazol-5-ylmethyl)-phenoxy]-propyl}-amine (mixture of regioisomers, 0.2 g, 0.56 mmol) and (2,2-diphenylethyl)-(2-chloro-3-trifluoromethyl)amine (0.43 g, 1.12 mmol) in acetonitrile (10 ml) was treated with solid potassium carbonate (0.23 g, 1.7 mmol) and NaI (0.25 g, 1.7 mmol). The reaction was heated at reflux and stirred overnight. The mixture was cooled to RT, filtered, and concentrated. The crude product was purified by preparative HPLC (YMC CombiPrep PDS, 75×30 mm, 25 mL/min, acetonitrile: water, UV detection at 254 nm) to give 125 mg (33% yield) of the title compound as a viscous oil. MS (ESI) 664.2 (M$^+$).

f) (2-Chloro-3-trifluoromethyl-benzyl)-(2,2-diphenyl-ethyl)-{3-[3-(1,2,3,4-tetrazol-5-ylmethyl)-phenoxy]-propyl}-amine To a stirring solution of (2-chloro-3-trifluoromethyl-benzyl)-(2,2-diphenyl-ethyl)-{3-[3-(ethoxymethyl-1,2,3,4-tetrazol-5-ylmethyl)-phenoxy]-propyl}-amine (mixture of regioisomers, 125 mg, 0.19 mmol) in dichloromethane (11 ml) was added triethylsilane (116 mg, 1.08 mmol). The reaction mixture was treated with TFA (3 ml) and then stirred overnight. Solvent was removed and the residue was purified by preparative HPLC (YMC CombiPrep PDS, 75×30 mm, 25 mL/min, acetonitrile:water, UV detection at 254 nm) to afford 50 mg (44%) the title compound as a yellow oil. MS (ESI) 607.0(M+H$^+$).

EXAMPLE 7

(2-Chloro-3-trifluoromethyl-benzyl)-(2-cyclohexyl-2-phenyl-ethyl)-{3-[3-(1,2,3,4-tetrazol-5-ylmethyl)-phenoxy]-propyl)amine

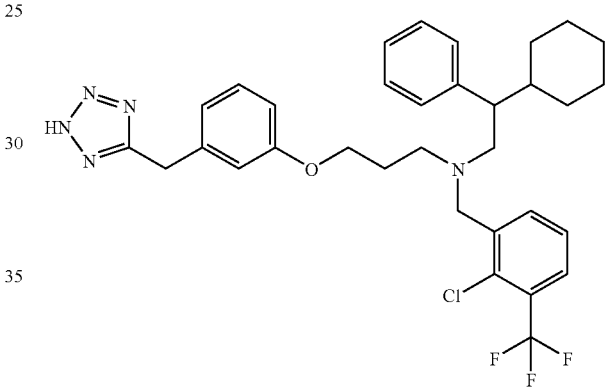

a) 2-Cyclohexyl-2-phenyl-acetic acid Methyl ester

To a stirring solution of 2-cyclohexyl-2-phenyl-acetic acid (2 g, 0.0091 mole) in methanol (100 mL) was added HCl (2 mL), and the mixture was heated at reflux for 5 hours. Methanol was removed, the residue was dissolved in ethyl acetate, and washed with saturated $NaHCO_3$. The organic layer was dried over sodium sulfate, filtered, and concentrated in vacuo to give 2.2 g (99% yield) of the title compound as an oil. MS (ESI) 233.2 (M+H$^+$).

b) 2-Cyclohexyl-2-phenyl-ethanol

To a stirring solution of 2-cyclohexyl-2-phenyl-acetic acid methyl ester (2.2 g, 0.0094 mole) in THF (20 mL) was added 19 mL of a lithium aluminum hydride solution (1.0 M in THF) at 0° C. The reaction mixture was stirred overnight and 10% KOH (8 mL) was added. The mixture was filtered, and then washed with ether. Ether (60 mL) was added to the filtrate and the ethereal solution was washed with water (50 mL). The ether layer was dried over sodium sulfate, filtered, and concentrated to give 1.86 g (97% yield) of the title compound as an oil. 1H-NMR (400 MHz, CDCl$_3$) δ 7.37-7.15 (m, 5H), 3.97 (t, 1H, J=6.0 Hz), 3.86 (t, 1H, J=9.0 Hz), 2.59 (q, 1H, J=4.0 Hz), 1.96-1.03 (m, 11H). The primary alcohol was used without further purification.

c) (2-Azido-1-cyclohexyl-ethyl)-benzene

To a stirring solution of 2-cyclohexyl-2-phenyl-ethanol (0.9 g, 0.00441 mole) and triethylamine (0.536 g, 0.0053 mole) in dichloromethane (10 mL) at 0° C. was added methanesulfonyl chloride (0.606 g, 0.0053 mole). The reaction was stirred at RT for 2 h. The reaction mixture was next poured into water, and extracted three times with dichloromethane. The solvent was removed and DMF (10 mL) was added to the residue. $NaN_3$ (0.57 g, 0.0088 mole) was added to the solution and the mixture was then stirred overnight at RT. The reaction mixture was washed with water and extracted three times with ethyl acetate. The combined organic layers were dried over sodium sulfate, filtered, and concentrated. The crude product was purified by column chromatography over silica gel (silica gel 60, EM Science) using 20% ethyl acetate:hexane as eluent to afford 0.79 g (78% yield) of the title compound as an oil. 1H-NMR (400 MHz, $CDCl_3$) δ 7.26-7.08 (m, 5H), 3.58 (dd, 1H, J=5.2 Hz), 3.48 (dd, 1H, J=8.8 Hz), 2.53 (q, 1H. J=5.2 Hz), 1.87-0.7 (m, 11H).

d) 2-Cyclohexyl-2-phenyl-ethylamine

To a stirring solution of (2-azido-1-cyclohexyl-ethyl)-benzene (700 mg, 3.06 mmol) in methanol (20 mL) was added palladium on carbon (70 mg, 10 wt. %). The mixture was stirred at 50 Psi $H_2$ overnight, filtered, and washed with methanol, and the filtrate was concentrated in vacuo to give 650 mg (99% yield) of title compound as an oil. 1 H-NMR (400 MHz, $CDCl_3$) δ 7.34-7.16 (m, 5H), 3.13 (t, 1H, J=4.5 Hz), 2.92 (t, 1H, J=2.3 Hz), 2.40 (m, 1H), 1.73-0.74 (m, 11H).

e) (2-Cyclohexyl-2-phenyl-ethyl)-(2-chloro-3-trifluoromethyl-benzyl)-amine

Following the procedure in Example 5(e) except 2-cyclohexyl-2-phenyl-ethylamine was used instead of 2,2-diphenethylamine, the title compound was isolated to give 630 mg of a white solid (50% yield). MS (ESI) 396.4 (M+H$^+$).

f) (2-Chloro-3-trifluoromethyl-benzyl)-(2-cyclohexyl-2-phenyl-ethyl)-{3-[3-(ethoxymethyl-1,2,3,4-tetrazol-3-ylmethyl)-phenoxy]-propyl}-amine (Mixture of 1- and 2-ethoxymethyl-tetrazolyl Regioisomers), Following the procedure of Example 6(a)-(f) except (2-cyclohexyl-2-phenyl-ethyl)-(2-chloro-3-trifluoromethyl-benzyl)-amine was used in step e instead of (2,2-diphenyl-ethyl)-(2-chloro-3-trifluoromethyl-benzyl)amine, the title compound was isolated to afford 320 mg of an oil (42%). MS (ESI) 670.2 (M$^+$).

g) (2-Chloro-3-trifluoromethyl-benzyl)-(2-cyclohexyl-2-phenyl-ethyl)-{3-[3-(1,2,3,4-tetrazol-3-ylmethyl)-phenoxy]-propyl}-amine A solution of (2-chloro-3-trifluoromethyl-benzyl)-(2-cyclohexyl-2-phenyl-ethyl)-{3-[3-(½-ethoxymethyl-1,2,3,4-tetrazol-3-ylmethyl)-phenoxy]-propyl}-amine (140 mg, 0.209 mmol) in dichloromethane (2 ml) was added triethylsilane (243 mg, 2.09 mmol). The reaction mixture was treated with TFA (0.6 ml) and then stirred overnight. The crude product was purified by column chromatography over silica gel (silica gel 60, EM Science) using 75% ethyl acetate:hexane as eluent to afford 65 mg (51% yield) of the title compound as an oil: MS (ESI) 612.0 (M$^+$).

EXAMPLE 8

(S)-(2-Chloro-3-trifluoromethyl-benzyl)-(2-phenyl-propyl)-{3-[3-(1,2,3,4-tetrazol-3-ylmethyl)-phenoxy]-propyl}-amine hydrochloride salt

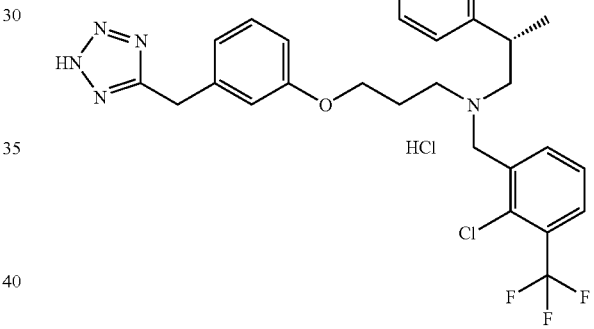

a) (S)-(2-Chloro-3-trifluoromethyl-benzyl)-(2-phenyl-propyl)-amine

Following the procedure of Example 5e except (S)-2-phenyl-propylamine was used instead of 2,2-diphenethylamine, the title compound was isolated to give a white solid (60%). MS (ESI) 328.0 (M+H$^+$).

b) (S)-(2-Chloro-3-trifluoromethyl-benzyl)-(2-phenyl-propyl)-{3-[3-(1,2,3,4-tetrazol-3-ylmethyl)-phenoxy]-propyl}-amine hydrochloride salt Following the procedure of Example 6(a-f) except (S)-(2-chloro-3-trifluoromethyl-benzyl)-(2-phenyl-propyl)-amine was used instead of (2,2-diphenylethyl)-(2-chloro-3-trifluoromethyl)-amine in step e, the title compound was synthesized. The resulting tertiary amine was dissolved in diethyl ether and acidified with 1.0 M HCl/diethyl ether. The reaction mixture was concentrated and dried under reduced pressure to give 59 mg (5% overall yield) of the title compound as a white solid. MS (ESI) 544.0 (M$^+$).

EXAMPLE 9

(R)-(2-Chloro-3-trifluoromethyl-benzyl)-(2-phenyl-propyl)-{3-[3-(1,2,3,4-tetrazol-3-ylmethyl)-phenoxy]-propyl}-amine hydrochloride salt

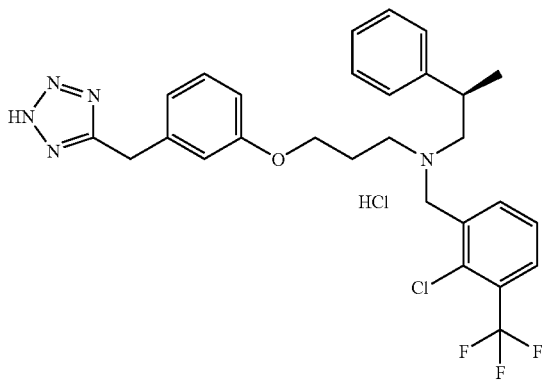

a) (R)-(2-Chloro-3-trifluoromethyl-benzyl)-(2-phenyl-propyl)-amine

Following the procedure of Example 5e except (R)-2-phenyl-propylamine was used instead of 2,2-diphenethylamine, the title compound was isolated to give a white solid (62%). MS (ESI) 328.0 (M+H$^+$).

b) (R)-(2-Chloro-3-trifluoromethyl-benzyl)-(2-phenyl-propyl)-{3-[3-(1,2,3,4-tetrazol-5-ylmethyl)-phenoxy]-propyl}-amine hydrochloride salt Following the procedure of Example 6(a-f) except (R)-(2-chloro-3-trifluoromethyl-benzyl)-(2-phenyl-propyl)-amine was used instead of (2,2-diphenylethyl)-(2-chloro-3-trifluoromethyl)-amine in step e, the title compound was synthesized. The resulting amine was dissolved in diethyl ether and acidified with 1.0 M HCl/diethyl ether. The reaction mixture was concentrated and dried under reduced pressure to give 60 mg (10% overall yield) of the title compound as a white solid. MS (ESI) 544.0 (M$^+$).

EXAMPLE 10

(S)-2-(3-{3-[[2-Chloro-3-(trifluoromethyl)benzyl](2-phenyl-propyl)amino]propoxy}-phenyl)acetic acid hydrochloride salt

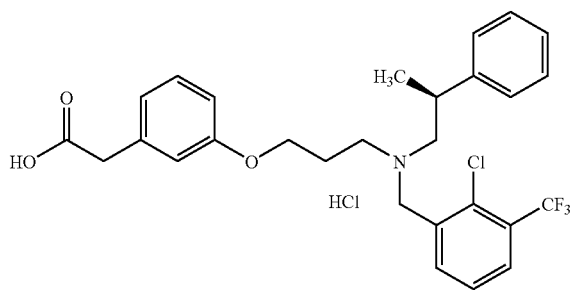

a) (S)-(2-Chloro-3-trifluoromethyl-benzyl)-(2-phenyl-propyl)-amine

To a solution of (S)-2-phenyl propylamine (0.5 g, 3.7 mmol) in dry dichloromethane was added acetic acid followed by 2-chloro-3-trifluoromethylbenzaldehyde (1.1 g, 5.5 mmol) and sodium triacetoxyborohydride (1.5 g, 7.4 mmol). After the resulting mixture was stirred for 1.5 h at RT water was added to quench the reaction. The aqueous layer was extracted with ethyl acetate. The combined organic layers were washed with brine, dried over sodium sulfate, and concentrated in vacuo. The crude mixture was purified by column chromatograph (Ethyl acetate:Hexane/25:75) to give the title compound as an oil (0.55 g, 45%). MS (ESI) 327.6 (M+H)$^+$.

b) (S)-(3-{3-[[2-Chloro-3-(trifluoromethyl)benzyl] (2-phenyl-propyl)amino]propoxy}-phenyl)acetic acid methyl ester A solution of (3-{3-bromo-propoxy}-phenyl)acetic acid methyl ester (0.55 g, 1.5 mmol) and (S)-(2-Chloro-3-trifluoromethyl-benzyl)-(2-phenyl-propyl)-amine (0.55 g, 1.6 mmol) in acetonitrile (10 ml) was treated with solid potassium carbonate(0.4 g, 2.4 mmol). The reaction was heated to reflux and stirred for 48 h. Upon cooling to RT, the reaction was filtered through a pad of celite, washed with ethyl acetate, and the filtrate was concentrated in vacuo. The crude product was purified by column chromatograph (Ethyl acetate:Hexane/20:80) to give the title compound as an oil (0.6 g, 67%). MS (ESI) 534.6 (M+H)$^+$.

c) (S)-2-(3-{3-[[2-Chloro-3-(trifluoromethyl)benzyl] (2-phenyl-propyl)amino]propoxy}-phenyl)acetic acid A solution of (S)-(3-{3-[[2-chloro-3-(trifluoromethyl) benzyl](2-phenyl-propyl)amino]propoxy}-phenyl)acetic acid methyl ester (0.6 g, 1.1 mmol) in THF (9 ml) and water (6 ml) was treated with aqueous LiOH (1.0 N, 1.0 ml, 1.0 mmol). After stirring at RT for 2 h, additional LiOH (1.0 ml, 11.0 mmol) was added and stirring was continued for 2 h. The reaction was neutralized with acetic acid and poured into water and ethyl acetate. The layers were separated and the aqueous layer was extracted with ethyl acetate. The combined organic layers were washed with brine, dried over sodium sulfate and concentrated in vacuo. The crude mixture was purified by HPLC to give the title compound as an oil (0.4 g, 75%). MS (ESI) 520.2 (M+H)$^+$.

d) (S)-2-(3-{3-[[2-Chloro-3-trifluoromethyl)benzyl] (2-phenyl-propyl)amino]propoxy}-phenyl)acetic acid hydrochloride salt To a solution of the (S)-2-(3-{3-[[2-chloro-3-(trifluoromethyl)benzyl](2-phenyl-propyl)amino]propoxy}-phenyl) acetic acid in ethyl ether was added HCl in diethyl ether (1.0M). The suspension was filtered and dried to give the title compound as a white solid (99%). NMR(400 MHz, CD$_3$OD) δ: 8.0 (d, J=4.0 Hz, 1H), 7.9 (d, J=4.0 Hz, 1H), 7.7-7.3 (m, 7H), 7.1 (d, J=8.0 Hz, 1H), 6.8 (m, 2H), 4.1-3.4 (m, 11H), 2.3 (m, 2H), 1.5 (d, J=4.0 Hz, 3H).

EXAMPLE 11

(R)-2-(3-{3-[[2-Chloro-3-trifluoromethyl)benzyl](2-phenyl-propyl)amino]propoxy}-phenyl)acetic acid hydrochloride salt

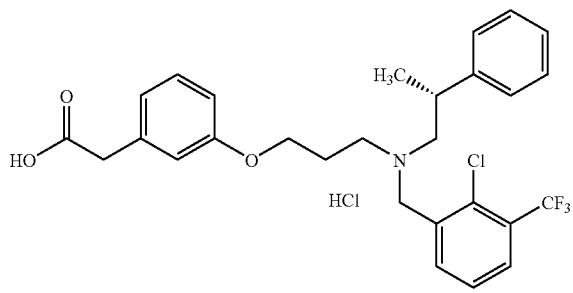

Following the procedure of Example 10 (a-d) except substituting (R)-2-phenyl propylamine for (S)-2-phenyl propylamine in step a, the title compound was obtained as a white solid (0.3 g, 80%). MS (ESI) 520.2 (M+H)+. NMR (400 MHz, CD$_3$OD) δ: 8.0 (d, J=4.0 Hz, 1H), 7.9 (d, J=4.0 Hz, 1H), 7.7-7.3 (m, 7H), 7.1 (d, J=8.0 Hz, 1H), 6.8 (m, 2H), 4.1-3.4 (m, 11H), 2.3 (m, 2H), 1.5 (d, J=4.0 Hz, 3H).

EXAMPLE 12

2-(3-{3-[[2-Chloro-3-(trifluoromethyl)benzyl]naphthalen-1-ylmethyl-amino]propoxy}-phenyl)acetic acid hydrochloride salt

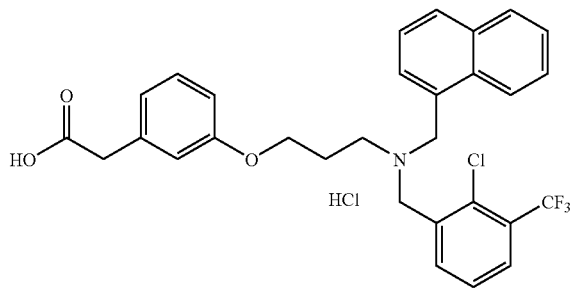

Following the procedure of Example 10 (a-d) except substituting 1-naphthalenemethylamine for (S)-2-phenyl propylamine in step a, the title compound was obtained as a white solid (80%).

EXAMPLE 13

2-(3-{3-[[2-Chloro-3-(trifluoromethyl)benzyl]-benzylamino]propoxy}-phenyl)acetic acid hydrochloride salt

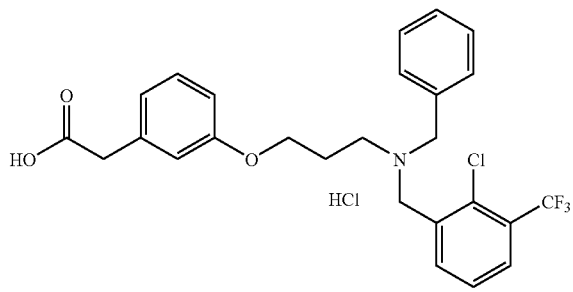

Following the procedure of Example 10 (a-d) except substituting benzylamine for (S)-2-phenyl propylamine in step a, the title compound was obtained as a white solid (80%). MS (ESI) 492.2 (M+H)+.

EXAMPLE 14

2-(3-{3-[[2-Chloro-3-(trifluoromethyl)-benzyl]phenethylamino]propoxy}-phenyl)acetic acid hydrochloride salt

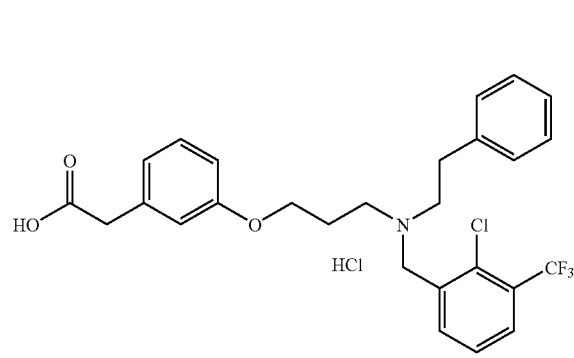

Following the procedure of Example 10 (a-d) except substituting phenethylamine for (S)-2-phenyl propylamine in step a, the title compound was obtained as a white solid (80%). MS (ESI) 506.2 (M+H)+.

EXAMPLE 15

2-(3-{3-[[2-Chloro-3-(trifluoromethyl)benzyl](2-hydroxy-2-phenyl-ethyl)amino]propoxy}-phenyl)acetic acid hydrochloride salt

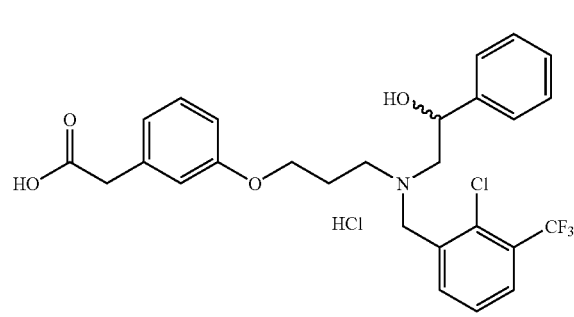

a) 2-(3-{3-[[2-Chloro-3-(trifluoromethyl)benzyl](2-hydroxy-2-phenyl-ethyl)amino]propoxy}-phenyl)acetic acid methyl ester Following the procedure of Example 10 (a-b), except substituting 2-amino-1-phenylethanol for (S)-2-phenyl propylamine for in step a, the title compound was obtained as an oil. (80%) MS (ESI) 536.0 (M+H)+ b) 2-(3-{3-[[2-Chloro-3-(trifluoromethyl)benzyl](2-hydroxy-2-phenyl-ethyl)amino]propoxy}-phenyl)acetic acid Following the procedure of Example 10 (c), the title compound was obtained as an oil. (65%) MS (ESI) 522.2 (M+H)+ c) 2-(3-{3-[[2-Chloro-3-trifluoromethyl)benzyl](2-hydroxy-2-phenyl-ethyl)amino]propoxy}-phenyl) acetic acid hydrochloride salt Following the procedure of Example 10 (d), the title compound was obtained as a white solid (99%). MS (ESI) 522.2 (M+H)$^+$.

EXAMPLE 16

2-(3-{3-[[2-Chloro-3-(trifluoromethyl)benzyl](2-acetoxy-2-phenyl-ethyl)amino]propoxy}-phenyl) acetic acid hydrochloride salt

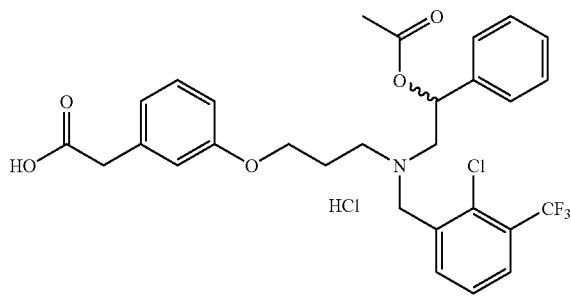

a) 2-(3-{3-[[2-Chloro-3-(trifluoromethyl)benzyl](2-acetoxy-2-phenyl-ethyl)amino]propoxy}-phenyl) acetic acid A solution of 2-(3-{3-[[2-chloro-3-(trifluoromethyl)benzyl](2-hydroxy-2-phenyl-ethyl)amino]propoxy}-phenyl) acetic acid (Example 15 b) in anhydrous toluene (5 ml) was treated with acetic acid (3 mg). Polymer bound triphenylphosphine (30 mg, 3 mmol/g) was then added, and the mixture reacted for 15 min. The reaction mixture was then cooled to 0° C. and diisopropylazodicarboxylate(10 mg, 0.05 mmol) was added dropwise. After stirring at RT overnight the crude mixture was filtered and the solid washed with 10 ml toluene. After concentration of the filtrate in vacuo, the crude product was purified by HPLC to give the title compound as an oil (20 mg, 75%). MS (ESI) 563.8 (M+H)$^+$.

b) 2-(3-{3-[[2-Chloro-3-(trifluoromethyl)benzyl](2-acetoxy-2-phenyl-ethyl)amino]propoxy}-phenyl) acetic acid hydrochloride salt To a solution of 2-(3-{3-[[2-chloro-3-(trifluoromethyl)benzyl](2-acetoxy-2-phenyl-ethyl)amino]propoxy}-phenyl) acetic acid in ethyl ether was added HCl in diethyl ether (1.0M). The suspension was filtered and dried to give the title compound as a white solid (99%). NMR(400 MHz, CD$_3$OD) δ: 7.8 (m, 3H), 7.3 (s, 5H), 7.1 (t, J=4.0 Hz, 1H), 6.7 (m, 3H), 6.1 (m, 1H), 4.0 (m, 2H), 3.6-3.4 (m, 7H), 2.2 (m, 2H), 1.9 (s, 3H), 1.1 (t, J=4.2 Hz, 2H).

EXAMPLE 17

2-(3-{3-[[2-chloro-3-(trifluoromethyl)benzyl](2-phenoxy-2-phenyl-ethyl)amino]propoxy}-phenyl) acetic acid hydrochloride salt

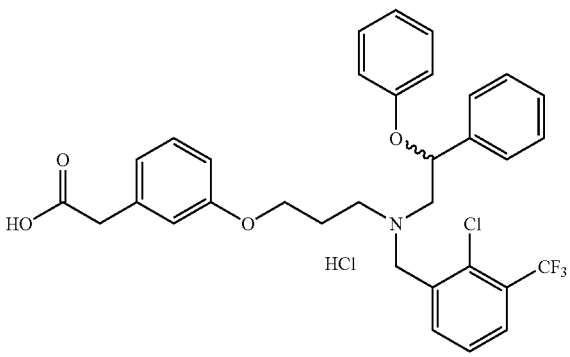

Following the procedure of Example 16 (a-b), except substituting phenol for acetic acid in step a, the title compound was obtained as a white solid (80%). MS (ESI) 597.8 (M+H)$^+$.

EXAMPLE 18

Benzoic acid 2-[3-(3-carboxymethyl-phenoxy){2-chloro-3-(trifluoromethyl)benzyl}propylamino]-1-phenyl ethyl ester hydrochloride salt

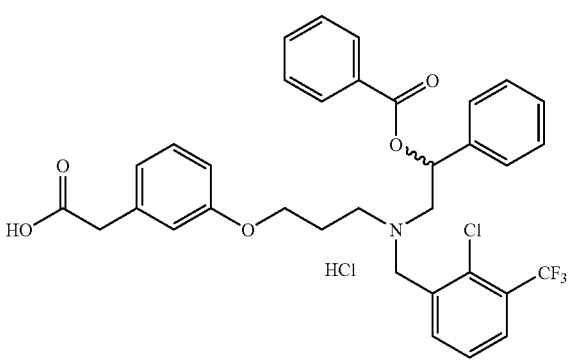

Following the procedure of Example 16 (a-b), except substituting benzoic acid for acetic acid in step a, the title compound was obtained as a white solid (80%). MS (ESI) 626.2 (M+H)$^+$.

EXAMPLE 19

(3-{3-[(2-Acetoxy-2-phenyl-ethyl)-(2-chloro-3-trifluoromethyl-benzyl)-amino]-propoxy}phenyl)-acetic acid methyl ester

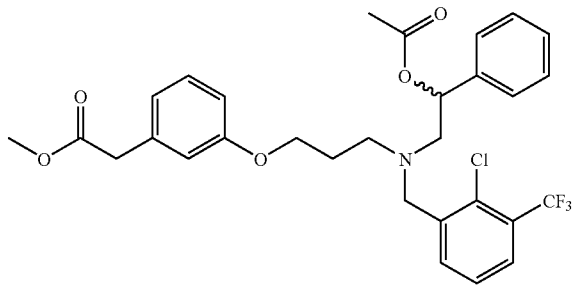

Following the procedure of Example 16 (a) using 2-(3-{3-[[2-chloro-3-(trifluoromethyl)benzyl](2-hydroxy-2-phenyl-ethyl)amino]propoxy}-phenyl)acetic acid methyl ester (Example 15a), the title compound was yielded as a white solid (80%) MS (ESI) 578.0 (M+H)$^+$.

EXAMPLE 20

Benzoic acid 2-[3-(3-methoxycarbonylmethyl-phenoxy){2-chloro-3-(trifluoromethyl)benzyl}propylamino]-1-phenyl ethyl ester

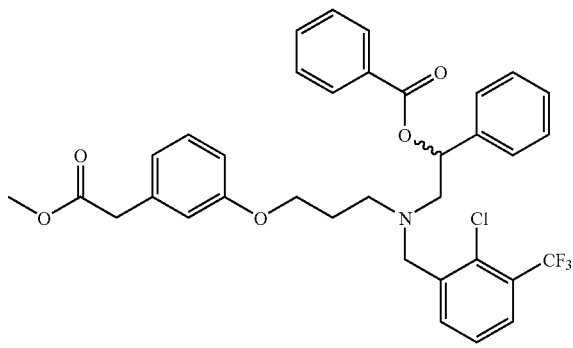

Following the procedure of Example 16 (a), except substituting benzoic acid for acetic acid, and using 2-(3-{3-[[2-chloro-3-(trifluoromethyl)benzyl](2-hydroxy-2-phenyl-ethyl)amino]propoxy}-phenyl)acetic acid methyl ester (Example 15a) as the substrate, the title compound was obtained as a white solid (80%) MS (ESI) 639.4 (M+H)$^+$.

EXAMPLE 21

(3-{4-[(2-Chloro-3-(trifluoromethyl)benzyl)-(2,2-diphenylethyl)-amino]butyl}phenyl)-acetic acid

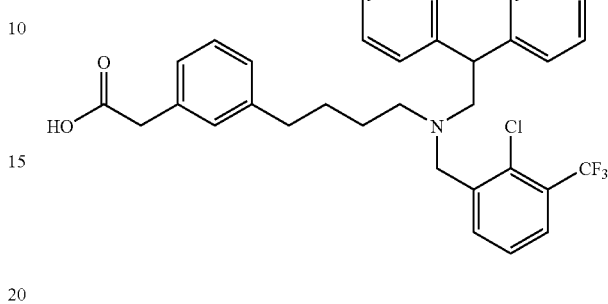

a) 1-(t-Butyldimethylsilyloxy)but-3-yne

A solution of 1-hydroxybut-3-yne (2.0 g, 0.028 mol) and imidazole (2.9 g, 0.043 mol) in DMF (5 ml) was treated with t-butyldimethylsilyl chloride (6.4 g, 0.043 mol). After 24 hr. at RT, the reaction was diluted with water and extracted with diethyl ether. The organic extracts were washed with water, dried, evaporated, and the volatile organics were removed by vacuum to afford the title compound as an oil (4.6 g, 89%). $^1$H NMR (400 MHz, CDCl3): δ 3.67 (t, J=7.1 Hz, 2H), 2.32 (m, 2H), 1.88 (s, 1H), 0.82 (s, 9H), 0.00 (s, 6H).

b) {3-[4-(t-Butyldimethylsilylhydroxy)but-1-ynyl]phenyl}acetic acid methyl ester A mixture of (3-iodo-phenyl)-acetic acid methyl ester (948 mg, 3.4 mmol), 1-(t-butyldimethylsilyloxy)but-3-yne (644 mg, 3.5 mmol), copper(1)iodide (50 mg), and bis(triphenylphosphine)-palladium(II)chloride (50 mg) in Et$_3$N (5 ml) was refluxed, under argon for 2 hr. The reaction was cooled, and the liquid was decanted off, diluted with diethyl ether, and washed with 1N HCl. The organic layer was dried and the solvent was evaporated. The residue was chromatographed on silica gel (hexane/methylene chloride 60/40) to give the title compound as an oil (700 mg, 62%). MS (ESI) 333.0 (M+H)$^+$.

c) {3-[4-Hydroxybutyl]phenyl}acetic acid methyl ester

A solution of {3-[4-(t-butyldimethylsilyloxy)but-1-ynyl]phenyl}acetic acid methyl ester (700 mg, 2.1 mmol) in MeOH (15 ml) was treated with 5% Pd/C (100 mg) and hydrogen gas (1 atm) for 1 hr. The catalyst was filtered, and the solvent evaporated. The residue was dissolved in THF (1 ml), and treated with tetrabutyl ammonium fluoride (2 ml of a 1N solution in THF) for 2 hr. The reaction was diluted with water and extracted with diethyl ether. The organic extracts were washed with water, dried, evaporated, and the volatile organics removed by vacuum to give the title compound as an oil (300 mg, 64%). MS (ESI) 223.2 (M+H)$^+$.

d) {3-[4-(Toluene-4-sulfonyloxy)butyl]phenyl}acetic acid methyl ester

A solution of {3-[4-hydroxybutyl]phenyl)acetic acid methyl ester (300 mg, 1.35 mmol) and p-toluenesulfonyl chloride (513 mg, 2.7 mmol) in pyridine (5 ml) was stirred at RT for 18 hr. The reaction was diluted with water (50 ml) and extracted with diethyl ether. The organic extracts were washed with water and cold 1N HCl, dried, and the solvent evaporated to give the title compound as an oil (322 mg, 63%). MS (ESI) 377.3 (M+H)+.

e) (3-{4-[(2-Chloro-3-trifluoromethyl)benzyl)-(2,2-diphenylethyl)-amino]butyl}phenyl)-acetic acid methyl ester A mixture of {3-[4-(toluene-4-sulfonyloxy)butyl]phenyl}acetic acid methyl ester, (2,2-diphenylethyl)-(2-chloro-3-trifluoromethylbenzyl)amine (73 mg, 0.19 mmol), and potassium carbonate (26 mg, 0.21 mmol) in acetonitrile (5 ml) was stirred and heated to 50° C. for 5 hr. The reaction was cooled, diluted with water, and extracted with diethyl ether. The organic extracts were washed with water, dried, and the solvent removed. The residue was chromatographed over silica gel (hexane/methylene chloride/Diethyl ether:60/40/5) to give the title compound as an oil (35 mg, 31%). MS (ESI) 594.2 (M+H)+.

f) (3-{4-[(2-Chloro-3-(trifluoromethyl)benzyl)-(2,2-diphenylethyl)-amino]butyl}phenyl)-acetic acid A solution of (3-{4-[(2-chloro-3-(trifluoromethyl)benzyl)-(2,2-diphenylethyl)-amino]butyl}phenyl)-acetic acid methyl ester (29 mg, 0.05 mmol) and NaOH (126 mg, 3.15 mmol) in MeOH (3 ml) and water (1 ml) was heated to 50° for 30 minutes. The reaction was cooled, neutralized with aqueous HCl (3.15 mmol), diluted with water and extracted with ethyl acetate. The extracts were dried and the solvent evaporated. Trituration of the residue with cyclohexane gave the title compound as a white powder (19 mg, 65%). MS (ESI) 580.2 (M+H)+.

EXAMPLE 22

Preparation of (3-{3-[(4-Fluoro-3-methyl-benzyl)-((R)-2-phenyl-propyl)-amino]-propoxy}-phenyl)-acetic acid

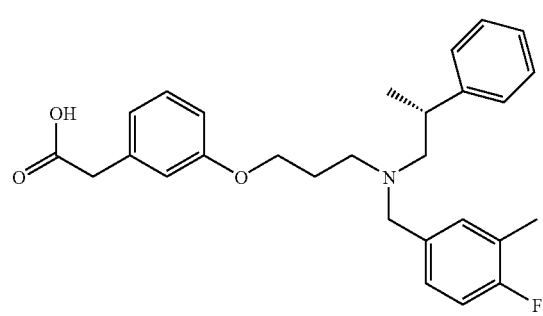

a) {3-[3-((R)-2-Phenyl-propylamino)-propoxy]-phenyl}-acetic acid methyl ester

[3-(3-Bromo-propoxy)-phenyl]-acetic acid methyl ester (11.48 g, 0.04 mole) in acetonitrile (300 mL) was added dropwise over 45 minutes to a mixture of (R)-2-Phenyl-propylamine (1.3 eq., 7.04 g, 0.052 mole), sodium iodide (18.0 g, 0.12 mole), and potassium carbonate (16.6 g, 0.12 mole) in acetonitrile (2000 mL). The mixture was stirred five days. The reaction mixture was filtered and the filter cake washed with acetonitrile (500 mL). The acetonitrile was evaporated and the residue dissolved in methylene chloride and washed with water(2×), dried over magnesium sulfate, filtered and evaporated. The resulting residue was purified by silica gel chromatography (using 3% to 10% methanol/methylene chloride as elutant) to give the title compound (10.19 g, 75%). MS (ESI) 342 (M+H)+.

b) (3-{3-[(4-Fluoro-3-methyl-benzyl)-((R)-2-phenyl-propyl)-amino]-propoxy}-phenyl)-acetic acid To a solution of {3-[3-((R)-2-Phenyl-propylamino)-propoxy]-phenyl}-acetic acid methyl ester (100 mg, 293 mmol) in methanol (1 ml) was added acetic acid (10% by volume) followed by 4-Fluoro-3-methyl-benzaldehyde (121 mg, 879 mmol) and sodium cyanoborohydride (54.5 mg, 879 mmol). After the resulting mixture was stirred for 18 h at RT water was added to quench the reaction. The solution was made basic by the addition of sodium hydroxide and heated for 30 min. The sample concentrated in vacuo and purified by preparative HPLC (YMC CombiPrep ODS-A, 50×20 mm, 20 mL/min, A: 0.1% trifluoroacetic acid in acetonitrile B: 0.1% aqueous trifluoroacetic acid, A: 10 to 90% during 10 min, UV detection at 254 nm) to give the title compound as a solid (71.6 mg, 54%). MS (ESI) 450.0 (M+H)+.

EXAMPLE 23

(3-{3-[Benzo[1,3]dioxol-5-ylmethyl-((R)-2-phenyl-propyl)-amino]-propoxy}-phenyl)-acetic acid

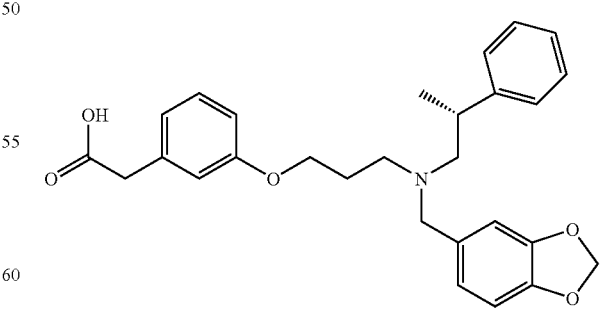

Following the procedure of Example 22 except Benzo[1,3]dioxole-5-carbaldehyde was used instead of 4-Fluoro-3-methyl-benzaldehyde, the title compound was isolated to give a white solid (49%). MS (ESI) 462.0 (M+H+).

EXAMPLE 24

(3-{3-[(4-tert-Butyl-benzyl)-((R)-2-phenyl-propyl)-amino]-propoxy)-phenyl)-acetic acid

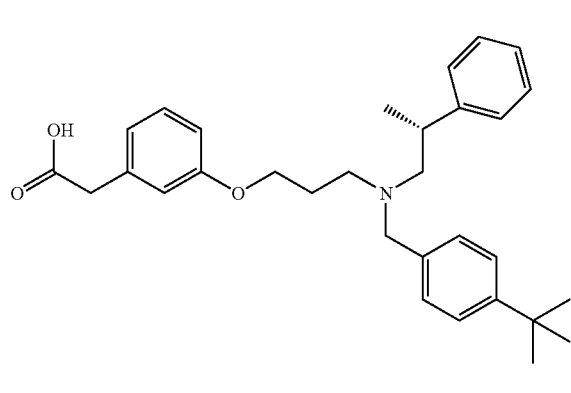

Following the procedure of Example 22 except 4-tert-Butyl-benzaldehyde was used instead of 4-Fluoro-3-methyl-benzaldehyde, the title compound was isolated to give a white solid (31%). MS (ESI) 474.0 (M+H$^+$).

EXAMPLE 25

(3-{3-[(2,3-Dihydro-benzo[1,4]dioxin-6-ylmethyl)-((R)-2-phenyl-propyl)-amino]-propoxy}-phenyl)-acetic acid

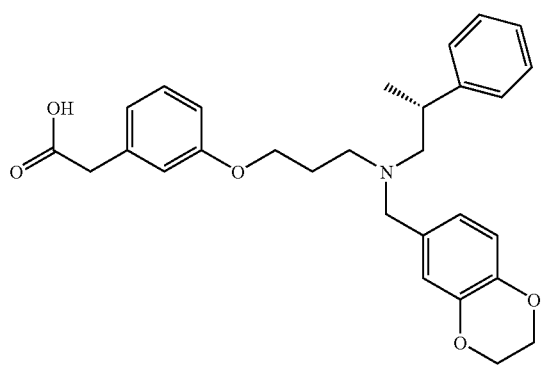

Following the procedure of Example 22 except 2,3-Dihydro-benzo[1,4]dioxine-6-carbaldehyde was used instead of 4-Fluoro-3-methyl-benzaldehyde, the title compound was isolated to give a white solid (97%). MS (ESI) 476.0 (M+H$^+$).

EXAMPLE 26

(3-{3-[(4-Methylsulfanyl-benzyl)-((R)-2-phenyl-propyl)-amino]-propoxy}-phenyl)-acetic acid

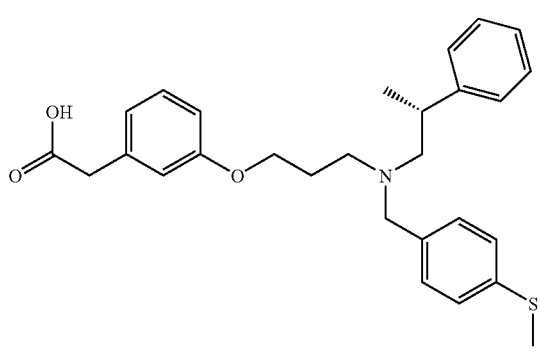

Following the procedure of Example 22, 4-Methylsulfanyl-benzaldehyde was used instead of 4-Fluoro-3-methyl-benzaldehyde, the title compound was isolated to give a white solid (79%). MS (ESI) 464.0 (M+H$^+$).

EXAMPLE 27

(3-{3-[((R)-2-Phenyl-propyl)-(2,4,5-trifluoro-benzyl)-amino]-propoxy}-phenyl)-acetic acid

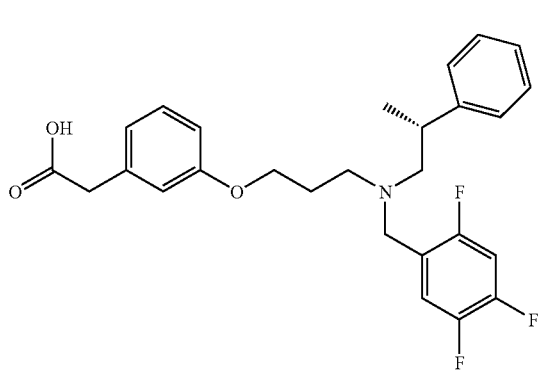

Following the procedure of Example 22, 2,4,5-Trifluoro-benzaldehyde was used instead of 4-Fluoro-3-methyl-benzaldehyde, the title compound was isolated to give a white solid (8.1%). MS (ESI) 472.0 (M+H$^+$).

EXAMPLE 28

(3-{3-[((R)-2-Phenyl-propyl)-(5-piperidin-1-yl-furan-2-ylmethyl)-amino]-propoxy}-phenyl)-acetic acid

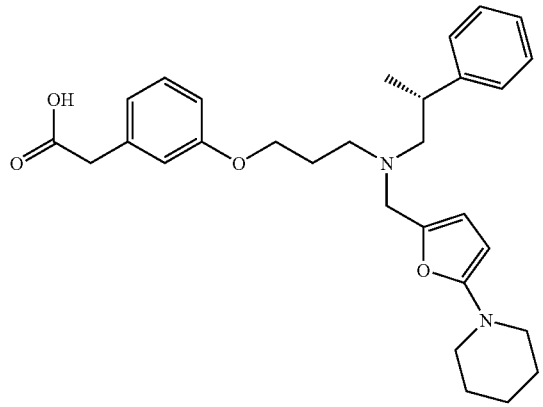

Following the procedure of Example 22, 5-Piperidin-1-yl-furan-2-carbaldehyde was used instead of 4-Fluoro-3-methyl-benzaldehyde, the title compound was isolated to give a white solid (9.9%). MS (ESI) 491.0 (M+H$^+$).

EXAMPLE 29

(3-{3-[(4-Isopropyl-benzyl)-((R)-2-phenyl-propyl)-amino]-propoxy}-phenyl)-acetic acid

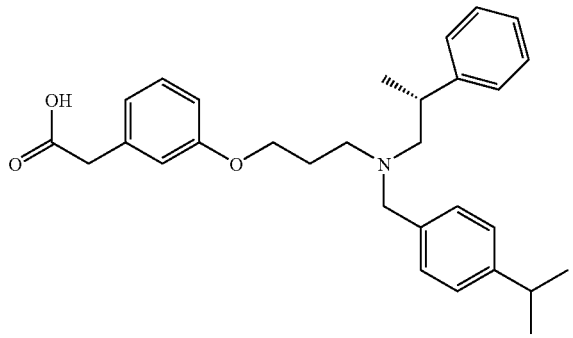

Following the procedure of Example 22, 4-Isopropyl-benzaldehyde used instead of 4-Fluoro-3-methyl-benzaldehyde, the title compound was isolated to give a white solid (16.6%). MS (ESI) 460.0 (M+H$^+$).

EXAMPLE 30

2-(3-{3-[(2-Chloro-3-trifluoromethyl-benzyl)-diphenylethyl-amino]-propoxy}-phenyl)-propane-1,3-diol hydrochloride salt

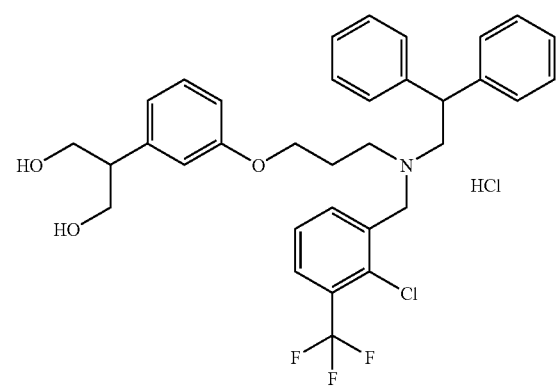

a) (3-{3-[(2-Chloro-3-trifluoromethyl-benzyl)-diphenylethyl-amino]-propoxy}-phenyl)-acetic acid methyl ester To a solution of (3-{3[(2-Chloro-3-trifluoromethyl-benzyl)-diphenylethyl-amino]-propoxy}-phenyl)-acetic acid hydrochloride salt (Example 1d, 0.1 g, 0.2 mmol) in methanol (2 ml) was added concentrated sulfuric acid (2 drops). After the resulting mixture was heated to reflux for 2 h solvent was removed under vacuum. The residue was dissolved in water and neutralized to pH=7. The aqueous layer was extracted with ethyl acetate three times. The combined organic layers were washed with, brine, dried over magnesium sulfate, and concentrated in vacco to give 900 mg (93%) of the title compound as an oil. MS m/e 596.2 (M+H)$^+$.

b) 2-(3-{3-[(2-Chloro-3-trifluoromethyl-benzyl)-diphenylethyl-amino]-propoxy}-phenyl)-malonic acid monomethyl ester To a solution of (3-{3-[(2-Chloro-3-trifluoromethyl-benzyl)-diphenylethyl-amino]-propoxy}-phenyl)-acetic acid methyl ester (97 mg, 0.2 mmol) in dry THF (50 ml) was added lithium diisopropyl amide (400 uL, 1.0 mmol) dropwise at 0° C. After 20 min at 0° C., CO$_2$ gas was bubbled through the mixture as it was warmed to room temperature. The reaction mixture was neutralized with 1N HCl and the residue partitioned between water and ethyl acetate. The combined organic layers were washed with brine, dried over magnesium sulfate and concentrated under vacuum. The crude product was purified by HPLC (YMC CombiPrep ODS-A, 50×20 mm, 20 mumin, A: acetonitrile B: water, A: 60 to 100% during 10 min, UV detection at 254 nm) to give the title compound as an oil (22 mg, 21%). MS m/e 640.2(M+H)$^+$.

c) 2-(3-{3-[(2-Chloro-3-trifluoromethyl-benzyl)-diphenylethyl-amino]-propoxy}-phenyl)-propane-1,3-diol hydrochloride salt To 2-(3-{3-[(2-Chloro-3-trifluoromethyl-benzyl)-diphenylethyl-amino]-propoxy}-phenyl)-malonic acid monomethyl ester (22 mg, 0.03 mmol) in diethyl ether (1 ml) was added lithium aluminum hydride (100 uL) at 0° C. The reaction was allowed to warm to room temperature before the addition of brine and ethyl acetate. The combined organic layers were dried over magnesium sulfate and evaporated. The crude product was purified by HPLC (YMC CombiPrep ODS-A, 50×20 mm, 20 mL/min, A: acetonitrile B: water, A: 60 to 100% during 10 min, UV detection at 254 nm) to give the title compound free amine as an oil. MS m/e 598.2(M+H)$^+$. To a solution of the free amine in diethyl ether was added HCl in diethyl ether (1.0M). The suspension was evaporated and dried to give the title compound as a white solid (2 mg, 10%).

EXAMPLE 31

N-(3-{3-[(2-Chloro-3-trifluoromethyl-benzyl)-2,2-diphenylethyl-amino]-propoxy}-phenyl)-carbamic acid tert-butyl ester

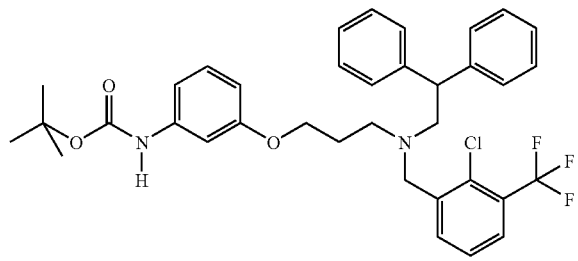

a) N-(3-Hydroxy-phenyl)-carbamic acid tert-butyl ester 3-aminophenol (2.0 g, 18.3 mmol) was dissolved in dioxane (50 mL) and water (25 mL) and treated with triethylamine (3.8 mL, 27.5 mmol) and di-tert-butyl-dicarbonate (6.0 g, 27.5 mmol) at room temperature. The solution was maintained for 18 hours and then the solvent was removed under reduced pressure. The residue was purified by silica gel chromatography (35 g Redisep column, silica, 40 um, 60 Å, 35 mL/min, A: hexanes, B: EtOAc, B: 0% for 5 min, B: 0% to 50% over 30 min; detection at 214 nm) to give 2.7 g (12.9 mmol, 71%) of the title compound as a white solid. $^1$H NMR (CDCl$_3$, 400 MHz) □: 7.2 (m, 2H), 6.8 (m, 1H), 6.5 (m, 2H), 5.8 (bs, 1H), 1.5 (s, 9H);

b) N-(2,2-Diphenylethyl)-N-(3-hydroxy-propyl)-N-(2-chloro-3-trifluoromethyl-benzyl)amine To a stirring solution of 3-bromo-propanol (5.9 mL, 65.4 mmol) in acetonitrile (500 ml) was added NaI (19.6 g, 131 mmol) and K$_2$CO$_3$ (18.1 g, 131 mmol). The mixture was stirred at 85° C. for 1 h, and then N-(2,2-diphenylethyl)-N-(2-chloro-3-trifluoromethyl-benzyl)amine (34.0 g, 87.2 mmol) was added. The reaction mixture was heated at 85° C. overnight. Solvent was removed, the residue was washed with H$_2$O, and extracted twice with EtOAc. The EtOAc extracts were dried over Na$_2$SO$_4$, filtered, and concentrated. The crude mixture was purified by silica gel chromatography (35 g Redisep column, silica, 40 um, 60 Å, 35 mL/min, A: hexanes, B: EtOAc, B: 0% for 2 min, B: 0% to 10% over 10 min; B: 10% for 2 min; B: 10% to 20% over 15 min; B: 20% for 2 min; B: 20% to 30% over 40 min; detection at 214 nm) to give 13.3 g (29.7 mmol, 34%) of the title compound as a white solid. $^1$H NMR (CDCl$_3$, 400 MHz) □: 7.6 (d, J=7.6 Hz, 1H), 7.3-7.1 (m, 12H), 4.2 (t, J=7.6 Hz, 1H), 3.8 (s, 2H), 3.6 (t, J=5.6 Hz, 2H), 3.2 (d, J=7.6 Hz, 2H), 2.8 (t, J=6.0 Hz, 2H), 2.5 (s, 1H), 1.7 (m, 2H);

c) N-(3-{3-[(2-Chloro-3-trifluoromethyl-benzyl)-2,2-diphenylethyl-amino]-propoxy}-phenyl)-carbamic acid tert-butyl ester To a stirring solution of N-(3-Hydroxy-phenyl)-carbamic acid tert-butyl ester (1.9 g, 9.0 mmol) in anhydrous toluene (60 mL) was added N-(2,2-diphenylethyl)-N-(3-hydroxy-propyl)-N-(2-chloro-3-trifluoromethyl-benzyl)amine (2.36 g, 5.3 mmol). Polymer bound triphenylphosphine (2.8 g, 8.4 mmol, 3 mmol/g, Fluka Chemie) was then added, and the mixture stirred for 15 minutes. The reaction mixture was then cooled to 0° C. and diisopropylazodicarboxylate (1.28 mL, 6.5 mmol) was added in a dropwise fashion. After stirring at room temperature for 60 hours, the crude reaction mixture was filtered and the resulting solid was washed with toluene. The filtrate was concentrated and the crude product was purified by silica gel chromatography (35 g Redisep column, silica, 40 um, 60 Å, 35 mL/min, A: hexanes, B: EtOAc, B: 0% for 5 min, B: 0% to 10% over 10 min; B: 10% for 10 min; B: 10% to 30% over 30 min; detection at 214 nm) to give 2.0 g (3.1 mmol, 59% yield) of the title compound as a white foam. MS (ESI) 639.4

EXAMPLE 32

3-{3-[(2-Chloro-3-trifluoromethyl-benzyl)-2,2-diphenylethylamino]-propoxy}-phenylamine

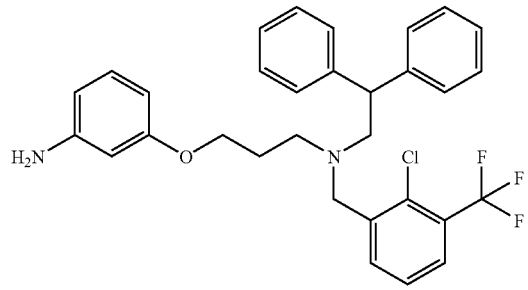

To N-(3-{3-[(2-Chloro-3-trifluoromethyl-benzyl)-2,2-diphenylethyl-amino]-propoxy}-phenyl)-carbamic acid tert-butyl ester (492 mg, 0.77 mmol) dissolved in dioxane (5 mL) was added a 4.0 M solution of HCl in dioxane (5 mL). The solution was maintained for 20 hours after which the solvent was removed under reduced pressure. The residue was dissolved in dichloromethane and washed twice with saturated NaHCO$_3$, dried over Na$_2$SO$_4$, and concentrated to give 0.4 g (0.74 mmol, 96%) of the title compound as a yellow oil. MS (ESI) 539.2

EXAMPLE 33

N-(3-{3-[(2-Chloro-3-trifluoromethyl-benzyl)-2,2-diphenylethyl-amino]-propoxy}-phenyl)-acetamide hydrochloride salt

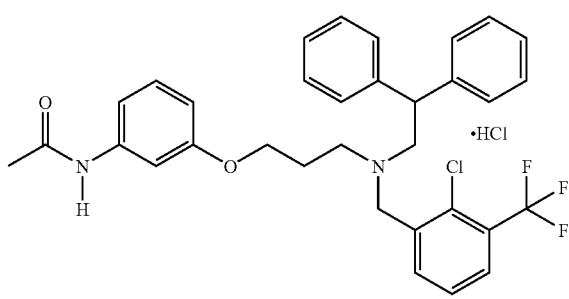

To 3-{3-[(2-Chloro-3-trifluoromethyl-benzyl)-2,2-diphenylethylamino]-propoxy}-phenylamine (80.0 mg, 0.15 mmol) dissolved in anhydrous dichloromethane (1 mL) was added pyridine (18 uL, 0.22 mmol) and acetyl chloride (12.7 uL, 0.18 mmol) at room temperature. The reaction was maintained for 60 hours after which the solvent was removed under reduced pressure. The residue was purified by preparative HPLC (YMC CombiPrep ODS-A, 50×20 mm, 20 mL/min, A: acetonitrile B: water, A: 5 to 95% over 15 min, UV detection at 214 nm and 254 nm) and the resulting residue after solvent removal was treated with aqueous 6N HCl (0.5 mL) and acetonitrile (2 mL). The solvent was removed under reduced pressure to give 41.4 mg (0.07 mmol, 47%) of the title compound as a colorless oil. MS (ESI) 581.0

EXAMPLE 34

Furan-2-carboxylic acid N-(3-{3-[(2-Chloro-3-trifluoromethyl-benzyl)-2,2-diphenylethyl-amino]-propoxy}-phenyl)-amide hydrochloride salt

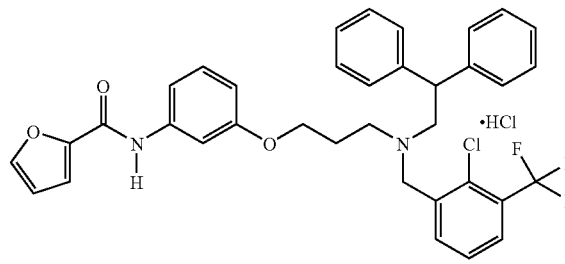

Following the procedure of Example 33 except furan-2-carbonyl chloride was used instead of acetyl chloride, the title compound was isolated to give 61.0 mg (0.096 mmol, 64%) of a colorless oil. MS (ESI) 633.0

EXAMPLE 35

N-(3-{3-[(2-Chloro-3-trifluoromethyl-benzyl)-2,2-diphenylethyl-amino]-propoxy}-phenyl)-methane-sulfonamide hydrochloride salt

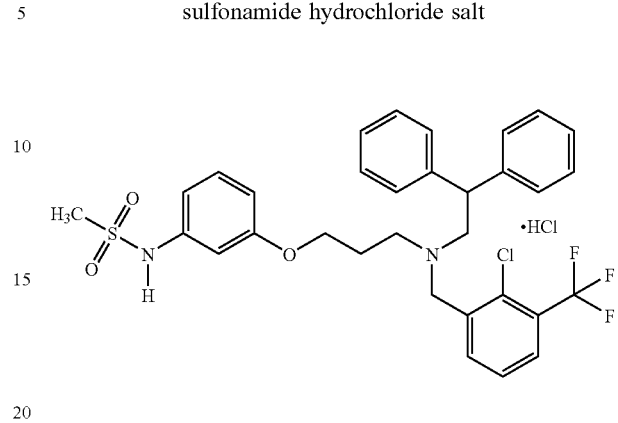

Following the procedure of Example 33 except methanesulfonyl chloride was used instead of acetyl chloride, the title compound was isolated to give 60.2 mg (0.098 mmol, 66%) of a colorless oil. MS (ESI) 617.2

EXAMPLE 36

N-(3-{3-[(2-Chloro-3-trifluoromethyl-benzyl)-2,2-diphenylethyl-amino]-propoxy}phenyl)-benzene-sulfonamide hydrochloride salt

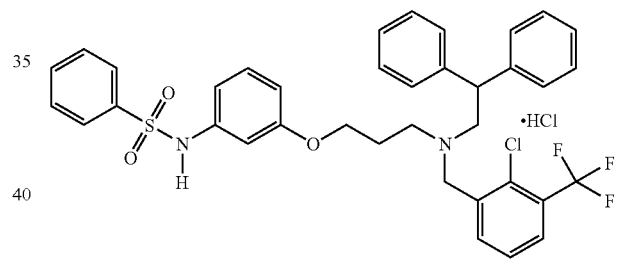

Following the procedure of Example 33 except benzenesulfonyl chloride was used instead of acetyl chloride, the title compound was isolated to give 57.9 mg (0.085 mmol, 58%) of a colorless oil. MS (ESI) 679.0

EXAMPLE 37

1-(2-Chloro-phenyl)-3-(3-{3-[(2-chloro-3-trifluoromethyl-benzyl)-2,2-diphenylethyl-amino]-propoxy}-phenyl)-urea hydrochloride salt

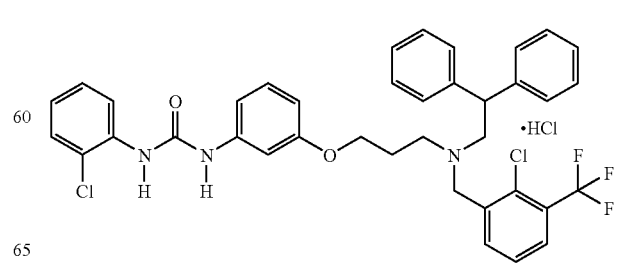

Following the procedure of Example 33 except 2-chlorophenyl isocyanate was used instead of acetyl chloride, the title compound was isolated to give 41.0 mg (0.059 mmol, 40%) of a colorless oil. MS (ESI) 692.4

EXAMPLE 38

N-(3-{3-[(2-Chloro-3-trifluoromethyl-benzyl)-2,2-diphenylethyl-amino]-propoxy}-phenyl)-N-methyl-amine

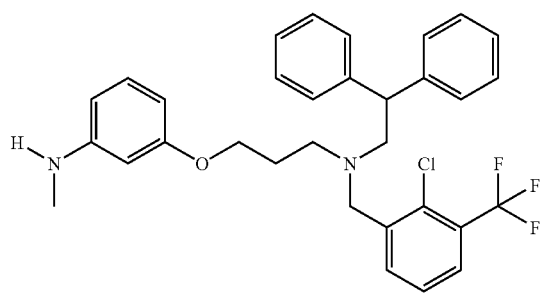

a) N-(3-{3-[(2-Chloro-3-trifluoromethyl-benzyl)-2,2-diphenylethyl-amino]-propoxy}-phenyl)-N-methyl-carbamic acid tert-butyl ester N-(3-{3-[(2-Chloro-3-trifluoromethyl-benzyl)-2,2-diphenylethyl-amino]-propoxy}-phenyl)-carbamic acid tert-butyl ester (1.05 g, 1.64 mmol) was dissolved in anhydrous DMF (10 mL) and cooled to 0° C. under argon. NaH (78.8 mg, 1.97 mmol, 60% dispersion in mineral oil) was added and the mixture stirred at 0° C. for 30 minutes. Methyl iodide (164 uL, 2.63 mmol) was added and the reaction was allowed to warm to room temperature at which point the solution was maintained for 18 hours. The reaction mixture was then poured into H$_2$O and extracted twice with EtOAc. The combined EtOAc extracts were washed with saturated aqueous NaCl, dried over Na$_2$SO$_4$, filtered, and concentrated to a yellow oil which was further purified by silica gel chromatography (10 g Redisep column, silica, 40 um, 60 Å, 35 mL/min, A: hexanes, B: EtOAc, B: 0% for 5 min, B: 0% to 10% over 10 min; B: 10% for 10 min; B: 10% to 30% over 15 min; B: 30% for 10 min; detection at 214 nm) to give 1.05 g (1.63 mmol, 99%) of the title compound as a yellow oil. MS (ESI) 653.2 b) N-(3-{3-[(2-Chloro-3-trifluoromethyl-benzyl)-2,2-diphenylethyl-amino]-propoxy}phenyl)-N-methyl-amine Following the procedure of Example 32 except that N-(3-{3-[(2-Chloro-3-trifluoromethyl-benzyl)-2,2-diphenylethyl-amino]-propoxy}phenyl)-N-methyl-carbamic acid tert-butyl ester was used instead of N-(3-{3-[(2-Chloro-3-trifluoromethyl-benzyl)-2,2-diphenylethyl-amino]-propoxy}-phenyl)-carbamic acid tert-butyl ester, the title compound was isolated to give 422 mg (0.76 mmol, 48%) of a colorless oil. MS (ESI) 553.0

EXAMPLE 39

N-(3-{3-[(2-Chloro-3-trifluoromethyl-benzyl)-2,2-diphenylethyl-amino]-propoxy)-phenyl)-N-methyl-acetamide hydrochloride salt N-(3-{3-[(2-Chloro-3-trifluoromethyl-benzyl)-2,2-diphenylethyl-amino]-propoxy}-phenyl)-N-methyl-amino (54.0 mg, 0.098 mmol) was dissolved in anhydrous dichloromethane (1 mL) and treated with pyridine (12 uL, 0.15 mmol) and acetyl chloride (8.3 uL, 0.12 mmol) at room temperature. The reaction was maintained for 60 hours after which the solvent was removed under reduced pressure. The residue was purified by preparative HPLC (YMC Combi-Prep ODS-A, 50×20 mm, 20 mL/min, A: acetonitrile B: water, A: 5 to 95% over 15 min, UV detection at 214 nm and 254 nm) and the resulting residue after solvent removal was treated with aqueous 6N HCl (0.5 mL) and acetonitrile (2 mL). The solvent was removed under reduced pressure to give 30.3 mg (0.05 mmol, 52%) of the title compound as a colorless oil. MS (ESI) 595.2

EXAMPLE 40

Furan-2-carboxylic acid N-(3-{3-[(2-Chloro-3-trifluoromethyl-benzyl)-2,2-diphenylethyl-amino]-propoxy}-phenyl)-N-methyl-amide hydrochloride salt Following the procedure of Example 39 except furan-2-carbonyl chloride was used instead of acetyl chloride, the title compound was isolated to give 54.1 mg (0.084 mmol, 86%) of a colorless oil. MS (ESI) 647.2

EXAMPLE 41

N-(3-{3-[(2-Chloro-3-trifluoromethyl-benzyl)-2,2-diphenylethyl-amino]-propoxy}-phenyl)-N-methyl-methanesulfonamide hydrochloride salt

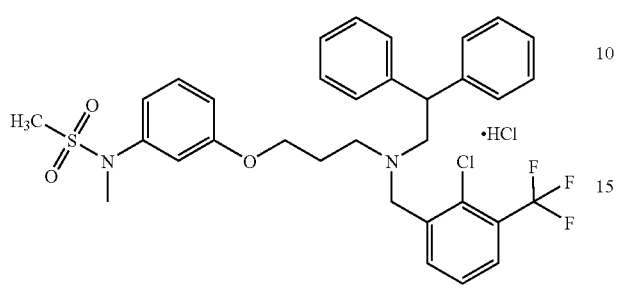

Following the procedure of Example 39 except methanesulfonyl chloride was used instead of acetyl chloride, the title compound was isolated to give 47.9 mg (0.076 mmol, 78%) of a colorless oil. MS (ESI) 631.2

EXAMPLE 42

N-(3-{3-[(2-Chloro-3-trifluoromethyl-benzyl)-2,2-diphenylethyl-amino]-propoxy}-phenyl)-N-methyl-benzenesulfonamide hydrochloride salt

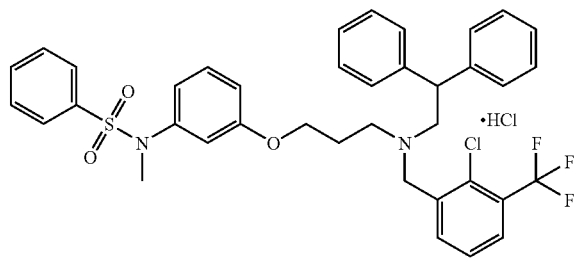

Following the procedure of Example 39 except benzenesulfonyl chloride was used instead of acetyl chloride, the title compound was isolated to give 48.5 mg (0.070 mmol, 72%) of a colorless oil. MS (ESI) 693.0

EXAMPLE 43

3-(2-Chloro-phenyl)-1-(3-{3-[(2-chloro-3-trifluoromethyl-benzyl)-2,2-diphenylethyl-amino]-propoxy}-phenyl)-1-methyl-urea hydrochloride salt

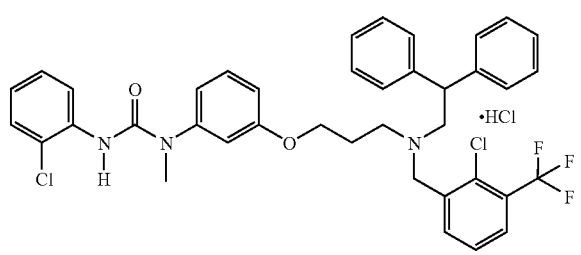

Following the procedure of Example 39 except 2-chlorophenyl isocyanate was used instead of acetyl chloride, the title compound was isolated to give 51.1 mg (0.072 mmol, 74%) of a colorless oil. MS (ESI) 706.0

EXAMPLE 44

Benzo[1,3]dioxole-5-carboxylic acid N-(3-{3-[(2-Chloro-3-trifluoromethyl-benzyl)-2,2-diphenylethyl-amino]-propoxy}-phenyl)-N-methyl-amide hydrochloride salt

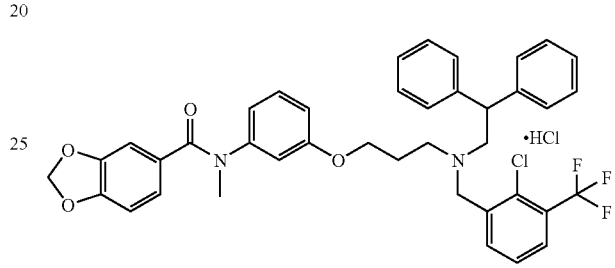

Following the procedure of Example 39 except piperonyloyl chloride was used instead of acetyl chloride, the title compound was isolated to give 58.3 mg (0.083 mmol, 85%) of a colorless oil. MS (ESI) 701.2

EXAMPLE 45

1-(3-{3-[(2-Chloro-3-trifluoromethyl-benzyl)-2,2-diphenylethyl-amino]-propoxy}-phenyl)-3-(3,5-dimethoxy-phenyl)-1-methyl-urea hydrochloride salt

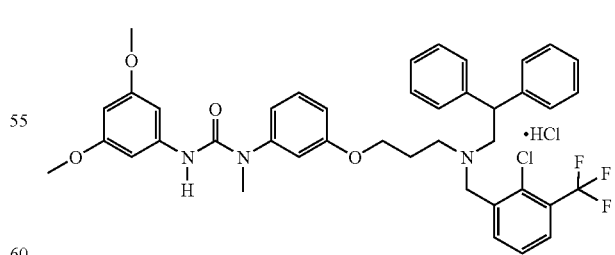

Following the procedure of Example 39 except 3,5-dimethoxyphenyl isocyanate was used instead of acetyl chloride, the title compound was isolated to give 55.8 mg (0.076 mmol, 78%) of a colorless oil. MS (ESI) 732.2

EXAMPLE 46

Propane-1-sulfonic acid (5-{3-[(2-chloro-3-trifluoromethyl-benzyl)-diphenylethyl-amino]-propoxy}-2-methyl-phenyl)-amide

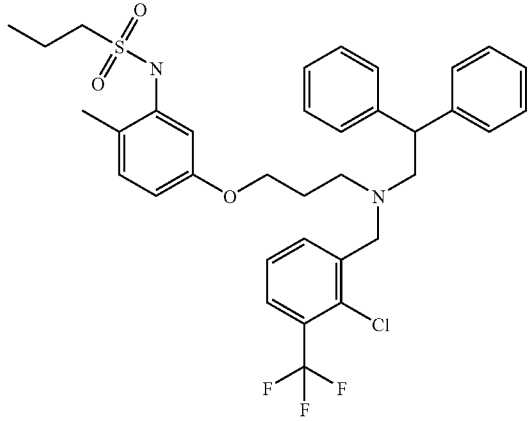

a) Propane-1-sulfonic acid (5-methoxy-2-methyl-phenyl)-amide

To the solution of 5-methoxy-2-methyl-phenylamine (0.118 g, 0.86 mmol) and pyridine (0.1 mL) and $CH_2Cl_2$ (3 mL) at 0° C. was added dropwise propane-1-sulfonyl choride (0.135 g, 0.95 mmol) and the reaction mixture was stirred at RT overnight. The mixture was then concentrated and purified via silica gel chromatography to give the product as an oil (0.145 g, 69%): MS(ES) m/e 244.2 $[M+H]^+$.

b) Propane-1-sulfonic acid (5-hydroxy-2-methyl-phenyl)-amide

To the solution of propane-1-sulfonic acid (5-methoxy-2-methyl-phenyl)-amide. (97 mg, 0.38 mmol) and $CH_2Cl_2$ (3 mL) at 0° C. was added dropwise boron tribromide (0.75 mL, 1M in $CH_2Cl_2$). The reaction mixture was stirred at 0° C. for 1 h then at RT for 1.5 h. The mixture was washed with $H_2O$ and sat. $NaHCO_3$, extracted with $CH_2Cl_2$, dried over $Na_2SO_4$ and concentrated to give the product as a clear oil (47.1 mg, 54%): MS(ES) m/e 230.0 $[M+H]^+$.

c) Propane-1-sulfonic acid (5-{3-[(chloro-trifluoromethyl-benzyl)-diphenylethyl-amino]-propoxy}-2-methyl-phenyl)-amide Following the procedure of Example 31c except propane-1-sulfonic acid (5-hydroxy-2-methyl-phenyl)-amide was used instead of N-(3-Hydroxy-phenyl)-carbamic acid tert-butyl ester, the title compound was obtained as a clear oil (34.3 mg, 27%): MS(ES) m/e 659.4 $[M+H]^+$.

EXAMPLE 47

3-{3-[(2-Chloro-3-trifluoromethyl-benzyl)-diphenylethyl-amino]-propoxy}-2-methyl-phenylamine

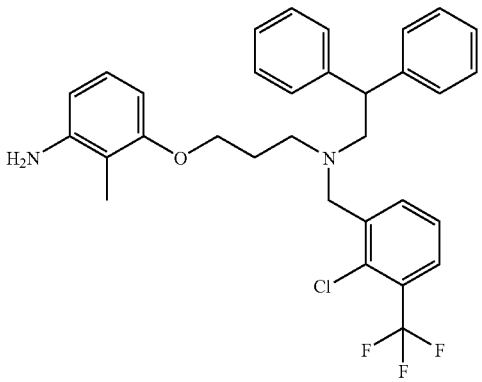

a) (2-Chloro-3-trifluoromethyl-benzyl)-(2,2-diphenyl-ethyl)-[3-(2-methyl-3-nitro-phenoxy)-propyl]-amine Following the procedure of Example 1, step (a-b), except 2-Methyl-3-nitrophenol was used instead of 3-hydroxyphenylacetate in step 1 (a) the title compound was prepared as an oil (2%). MS (ESI) 583.4 ($M^+$).

b) 3-{3-[(2-Chloro-3-trifluoromethyl-benzyl)-diphenylethyl-amino]-propoxy}-2-methyl-phenylamine (2-Chloro-3-trifluoromethyl-benzyl)-(2,2-diphenyl-ethyl)-[3-(2-methyl-3-nitro-phenoxy)-propyl]-amine (300 mg, 0.51 mmol) was dissolved in methanol (100 ml), and hydrogenated with 10% Pd/C (40 mg) at 60 psi at room temperature. After 2.5 h, the reaction mixture was filtered and concentrated in vacuo to give an amber oil, 0.25 g (89%). Flash silica gel chromatography (Supelco Discovery DSC-Si) ($CHCl_3$) afforded the title compound as a pure oil (75%). MS (ESI) 552.5 ($M-H^+$).

EXAMPLE 48

2-Chloro-5-{3-[(2-chloro-3-trifluoromethyl-benzyl)-diphenylethyl-amino]-propoxy}-phenylamine

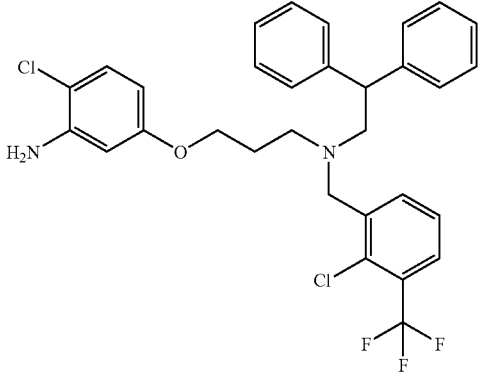

a) (2-Chloro-3-trifluoromethyl-benzyl)-(2,2-diphenyl-ethyl)-[3-(4-chloro-3-nitro-phenoxy)-propyl]-amine Following the procedure of Example 1, step (a-b), except 4-Chloro-3-nitrophenol was used instead of 3-hydroxyphenylacetate in step 1(a) the title compound was prepared as an oil (5%). MS (ESI) 603.2 (M+).

b) 2-Chloro-5-{3-[(2-chloro-3-trifluoromethyl-benzyl)-diphenylethyl-amino]-propoxy}-phenylamine (2-Chloro-3-trifluoromethyl-benzyl)-(2,2-diphenyl-ethyl)-[3-(4-chloro-3-nitro-phenoxy)-propyl]-amine (400 mg, 0.66 mmol) was hydrogenated over 10% Pd/C (40 mg) at 60 psi at room temperature in the presence of 1N HCl-Et$_2$O (10 ml). After 24 h, the reaction mixture was filtered and concentrated in vacuo to give a heavy oil. HPLC purification of the crude amine (Phenomonex Luna Combi HTS, 5 micron C$_{18}$, 275 mm×30 mm, 10% CH$_3$CN—water gradient to 95% CH$_3$CN) afforded the title compound as an oil. Treatment of the free base with 1N HCl-Et$_2$O (excess), followed by filtration and isolation of the resulting precipitate gave the title compound as a brown solid, 18.5 mg (4.3%). MS (ESI) 572.5 (M+).

EXAMPLE 49

3-{3-[(2-Chloro-3-trifluoromethyl-benzyl)-(2,2-diphenyl-ethyl)-amino]-propoxy}-phenyl)-cyclopentyl-amine, dihydrochloride salt

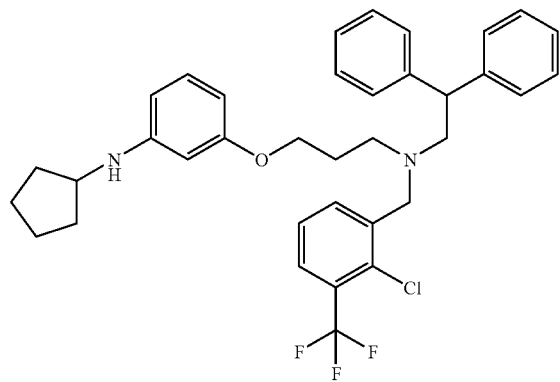

a) (3-(3-[(2-Chloro-3-trifluoromethyl-benzyl)-diphenylethyl-amino]-propoxy}-phenylamine dihydrochloride (3-{3-[(2-Chloro-3-trifluoromethyl-benzyl)-diphenyl-ethyl-amino]-propoxy}-phenyl)-carbamic acid tert-butyl ester, (0.51 g, 0.8 mmol) was stirred overnight at room temperature in a mixture methylene chloride (5 mL) and trifluoroacetic acid (0.5 mL). The solvents were removed in vacuo to yield the crude amine as an oil. The oil was diluted with ether, and 1 N HCl in Et$_2$O was added to precipitate the HCl salt of the product. The title compound was isolated as a cream yellow powder, 0.53 g (100%). MS (ESI) 539 (M+H+).

b) (3-{3-[(2-Chloro-3-trifluoromethyl-benzyl)-(2,2-diphenyl-ethyl)-amino]-propoxy}-phenyl)-cyclopentyl-amine dihydrochloride salt (3-{3-[(2-Chloro-3-trifluoromethyl-benzyl)-diphenyl-ethyl-amino]-propoxy}-phenylamine dihydrochloride (53 mg, 0.086 mmol) was diluted with absolute ethanol (3 mL). Next, both cyclopentanone (7.2 mg, 0.086 mmol) and sodium cyanoborohydride (19.2 mg, 0.3 mmol) were added to the solution. The reaction mixture was stirred at room temperature overnight and concentrated under a stream of argon. Water was added and the reaction mixture was extracted with ethyl acetate. The crude amine was purified by preparative HPLC chromatography (Varian Mega BondElut Si) to afford the title compound as the free base. Addition of 1 N HCl in Et$_2$O gave the title compound as a white powder, 22 mg (42%). MS (ESI) 608 (M+H+).

EXAMPLE 50

(3-{3-[(2-Chloro-3-trifluoromethyl-benzyl)-(2,2-diphenyl-ethyl)-amino]-propoxy}-phenyl)-isopropyl-amine, dihydrochloride salt

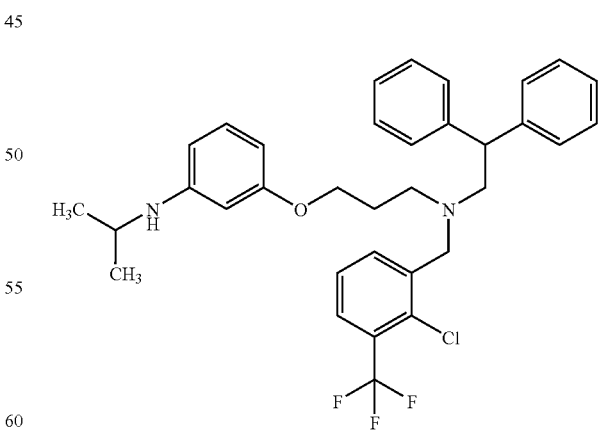

Following the procedure of Example 49, steps (a-b), except acetone was used in step 3(b) instead of cyclopentanone, the title compound was isolated as a white solid, 16 mg (41%). MS (ESI) 582 (M+H+).

EXAMPLE 51

Chloro-3-trifluoromethyl-benzyl)-(2,2-diphenyl-ethyl)-amino]-propoxy}phenyl)-ethyl-amine, dihydrochloride salt

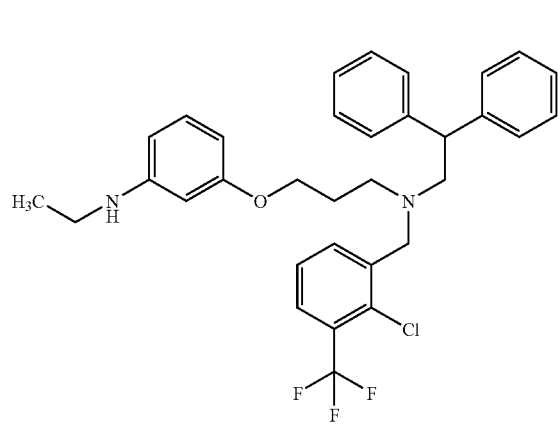

Following the procedure of Example 49, steps (a-b), except acetaldehyde was used in step 3(b) instead of cyclopentanone, the title compound was isolated as a white solid, 10 mg (27%). MS (ESI) 567 (M+H$^+$).

EXAMPLE 52

(3-{3-[(2-Chloro-3-trifluoromethyl-benzyl)-(2,2-diphenyl-ethyl)-amino]-propoxy}-phenyl)-(3-methyl-butyl)-amine dihydrochloride salt

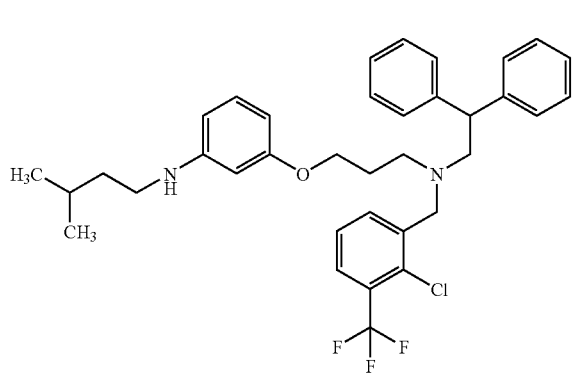

Following the procedure of Example 49, steps (a-b), except 2-methylbutyraldehyde was used in step 3(b) instead of cyclopentanone, the title compound was isolated as a white solid, 7.0 mg (18%). MS (ESI) 609 (M+H$^+$).

EXAMPLE 53

(3-{3-[(2-Chloro-3-trifluoromethyl-benzyl)-diphenylethyl-amino]-propoxy}-phenyl)-isobutyl-amine dihydrochloride salt

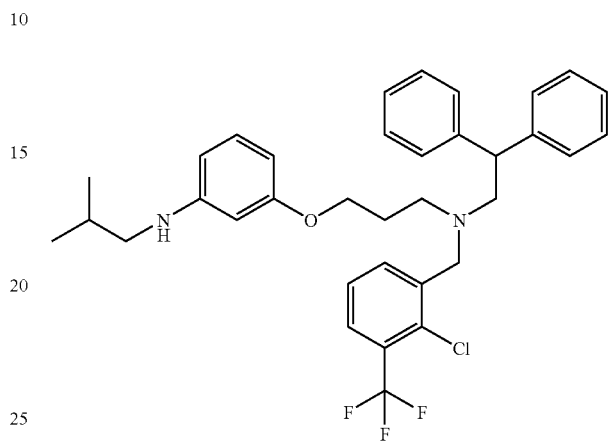

Following the procedure of Example 49, steps (a-b), except 2-isobutyraldehyde was used in step 3(b) instead of cyclopentanone, the title compound was isolated as a white solid, 5 mg (13%). MS (ESI) 595 (M+H$^+$).

EXAMPLE 54

(3-{3-[(2-Chloro-3-trifluoromethyl-benzyl)-(2,2-diphenyl-ethyl)-amino]-propoxy}-phenyl)-(2,2,2-trifluoroethyl)-amine, dihydrochloride salt

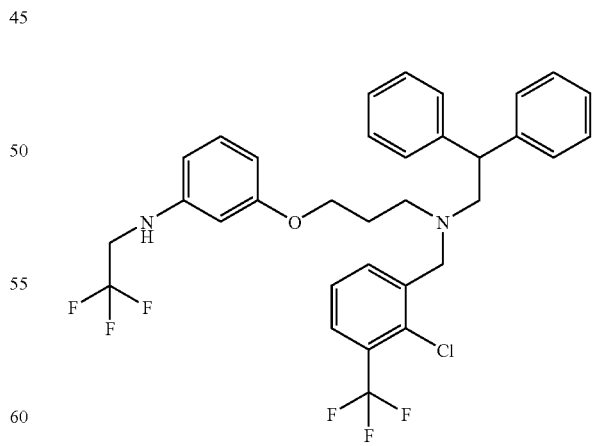

Following the procedure of Example 49, steps (a-b), except 2,2,2-trifluoroacetaldehyde was used in step 3(b) instead of cyclopentanone, the title compound was isolated as a amber oil, 1.7 mg (3.5%). MS (ESI) 621 (M$^+$).

EXAMPLE 55

(3-{3-[(2-Chloro-3-trifluoromethyl-benzyl)-(2,2-diphenyl-ethyl)-amino]-propoxy}-phenyl)-cyclopropylmethy-l-amine dihydrochloride salt

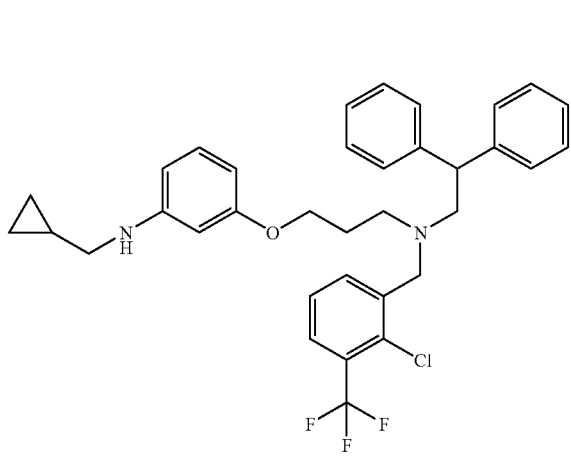

Following the procedure of Example 49, steps (a-b), except cyclopropylcarboxaldehyde was used in step 3(b) instead of cyclopentanone, the title compound was isolated as a white solid, 7.3 mg (19%). MS (ESI) 593 (M+H$^+$).

EXAMPLE 56

(3-{3-[(2-Chloro-3-trifluoromethyl-benzyl)-(2,2-diphenyl-ethyl)-amino]-propoxy}-phenyl)-(2-ethyl-butyl)-amine, dihydrochloride salt

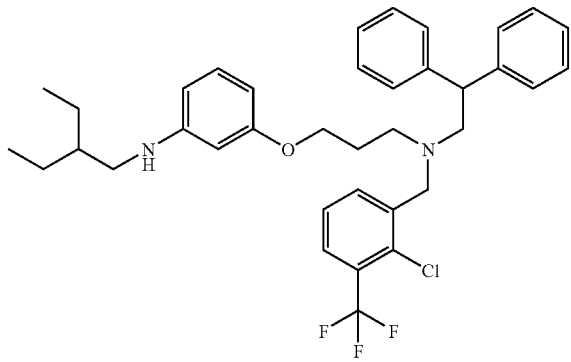

Following the procedure of Example 49, steps (a-b), except 2-ethylbutyraldehyde was used in step 3(b) instead of cyclopentanone, the title compound was isolated as a white solid, 7 mg (17%). MS (ESI) 623 (M+H$^+$).

EXAMPLE 57

(3-{3-[(2-Chloro-3-trifluoromethyl-benzyl)-(2,2-diphenyl-ethyl)-amino]-propoxy}-phenyl)-(2,2-dimethyl-propyl)-amine, dihydrochloride salt

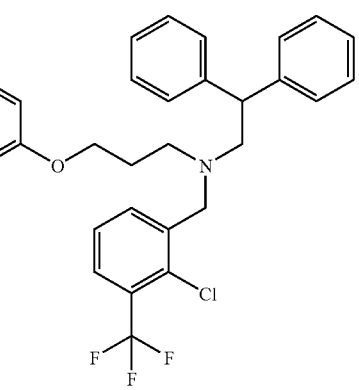

Following the procedure of Example 49, steps (a-b), except isovaleraldehyde was used in step 3(b) instead of cyclopentanone, the title compound was isolated as a white solid, 2.5 mg (6%). MS (ESI) 609 (M+H$^+$).

EXAMPLE 58

(3-{3-[(2-Chloro-3-trifluoromethyl-benzyl)-(2,2-diphenyl-ethyl)-amino]-propoxy}-phenyl)-hexyl-amine dihydrochloride salt

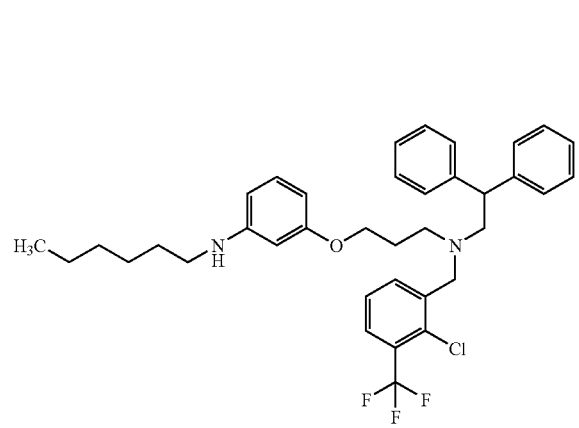

Following the procedure of Example 49, steps (a-b), except valeraldehyde was used in step 3(b) instead of cyclopentanone, the title compound was isolated as a white solid, 4.2 mg (10%). MS (ESI) 623 (M+H$^+$).

EXAMPLE 59

Butyl-(3-{3-[(2-chloro-3-trifluoromethyl-benzyl)-(2,2-diphenyl-ethyl)-amino]-propoxy}-phenyl)-amine dihydrochloride salt

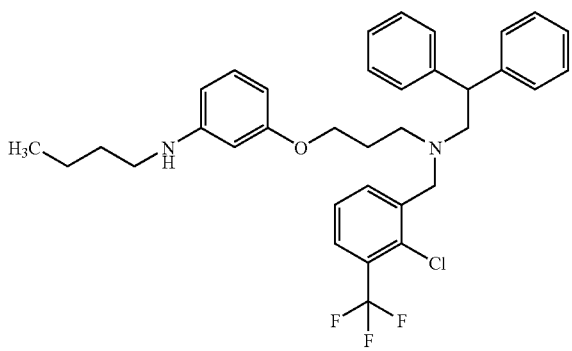

Following the procedure of Example 49, steps (a-b), except butyraldehyde was used in step 3(b) instead of cyclopentanone, the title compound was isolated as a white solid, 7.5 mg (20%). MS (ESI) 595 (M+H$^+$).

EXAMPLE 60

[1-(3-{3-[(2-Chloro-3-(trifluoromethyl)-benzyl)-(2,2-diphenylethyl)-amino]-propoxy}-phenyl-piperidine-4-carboxylic acid dihydrochloride

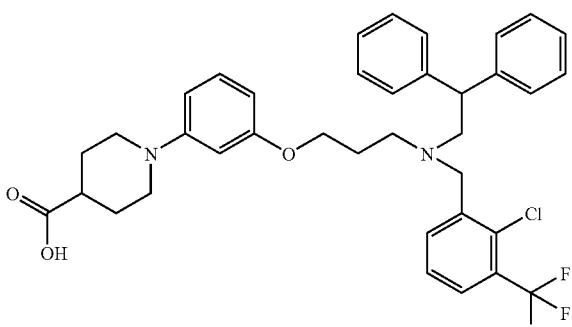

a) 1-(3-Oxo-cyclohex-1-enyl)-piperidine-4-carboxylic acid ethyl ester

The title compound was prepared according to the literature procedure: Lennon, M and Proctor, G. R. *J. Chem. Soc, Perkins Trans.* 1; 2009-2011, 1979.

b) 1-(3-Hydroxy-phenyl)-piperidine-4-carboxylic acid ethyl ester

The title compound was prepared according to the literature procedure above.

c) [1-(3-{3-[(2-Chloro-3-(trifluoromethyl)-benzyl)-(2,2-diphenylethyl)-amino]-propoxy}-phenyl-piperidine-4-carboxylic acid ethyl ester To a stirring solution of 1-(3-hydroxyphenyl)-piperidine-4-carboxylic acid ethyl ester (0.19 g, 0.77 mmol) in 10 mL of anhydrous toluene was added 3-[(2-chloro-3-(trifluoromethyl)-benzyl)-(2,2-diphenyl-ethyl)-amino]-propan-1-ol (0.41 g, 0.92 mmol). Polymer bound triphenyphosphine (0.41 g, 1,23 mmol, 3 mmol/g, Fluka Chemie) was then added, and the mixture was reacted for 15 minutes. The reaction mixture was then cooled to 0° C. and diisopropylazodicarboxylate (0.2 g, 0.96 mmol) was added in a dropwise fashion. After stirring at RT overnight, the crude reaction mixture was filtered and the solid was washed with EtOAc. After concentration of the filtrate in vacuo, the crude product was purified by column chromatography over silica gel (silica gel 60, EM Science) using 10% EtOAc: hexane as eluent to afford 0.32 g (62%) of the title compound as an oil: MS(ESI) 679.0 (M+H$^+$).

d) [1-(3-{3-[(2-Chloro-3-(trifluoromethyl)-benzyl)-(2,2-diphenylethyl)-amino]-propoxy}-phenyl-piperidine-4-carboxylic acid To a stirring solution of [1-3-{[(2-Chloro-3-trifluoromethyl-benzyl)-diphenylethyl-amino]-propoxy)-phenyl-piperidine-4-carboxylic acid ethyl ester (0.32 g, 0.47 mmol) in 7.0 mL of tetrahydrofuran and 3 mL of water was added LiOH (0.042 g, 1 mmol). The reaction mixture was stirred overnight Tetrahydrofuran was removed in vacuo and the residue was diluted with water (3 mL), adjusted to pH=4, with dilute HCl, and extracted with EtOAc. The organic layer was washed with water, brine, dried over MgSO$_4$, filtered, and concentrated in vacuo to give 0.28 g (93%) of an oil. It was dissolved in THF-ether and acidified with 1.0 M HCl/Et$_2$O. More ether was added and filtered to afford the title compound. MS(ESI) 651.0 (M+H$^+$).

EXAMPLE 61

[1-(3-{3-[(2-Chloro-3-(trifluoromethyl)-benzyl)-(2,2-diphenylethyl)-amino]-propoxy}-phenyl-piperidine-4-yl-acetic acid dihydrochloride (GSK-174013A)

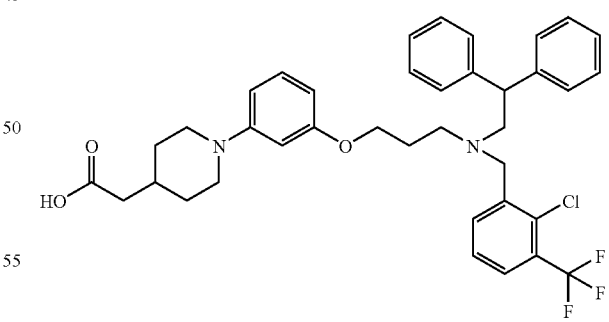

a) Piperidin-4-yl-acetic acid hydrochloride

A mixture of 4-pyridylacetic acid hydrochloride (5 g, 28.8 mmol), glacial acetic acid (100 mL) and PtO$_2$ (0.5 g) was hydrogenated at 50 psi overnight. The solvent was decanted from the catalyst and concentrated in vacuo. Azetroped with toluene twice then washed with ether to give 5 g (97%) of white solid. MS(ESI) 144.0 (M+H$^+$).

b) Piperidin-4-yl-acetic acid methyl ester hydrochloride

To a stirring suspension of piperidin-4-yl-acetic acid hydrochloride in MeOH (15 mL) at −5° C. was added thionyl chloride (1.12 mL, 15.3 mmol) dropwise. The reaction mixture was allowed to reach to RT then heated to 40° C. for 4 h. The reaction mixture was concentrated in vacuo and the resulting white solid was azeotroped with toluene twice. Washed with ether and filtered to give 2.7 g (quantitative yield). MS(ESI) 158.2 (M+H$^+$).

c) [1-(3-Oxo-cyclohex-1-enyl)-piperidin-4-yl]-acetic acid methyl ester

To piperidin-4-yl-acetic acid methyl ester hydrochloride (1.55 g, 8 mmol) was added conc. NH$_4$OH (1 mL). This mixture was stirred for 5 min. and concentrated in vacuo and azetroped with toluene several times. Then fresh toluene (80 mL) and cyclohexane-1,3-dione were added. Refluxed for 3 h with a Dean-Stark Trap. Cooled and concentrated in vacuo. The crude yellow oil was used in the next step without further purification (2.0 g, quantitative yield): MS(ESI) 252.5 (M+H$^+$).

d) [1-(3-Hydroxy-phenyl)-piperidin-4-yl]-acetic acid methyl ester

The title compound was prepared according to the literature procedure (Lennon, M and Proctor, G. R. *J. Chem. Soc, Perkins Trans.* 1;2009-2011 (1979).

The crude product was purified by column chromatography over silica gel (Silica gel 60, EM Science) using 25% EtOAc: hexanes as eluent to afford an oil (33% over two steps). MS(ESI) 250.2 (M+H$^+$)

e) [1-(3-{3-[(2-Chloro-3-(trifluoromethyl)-benzyl)-(2,2-diphenylethyl)-amino]-propoxy}-phenyl-piperidine-4-yl-acetic acid methyl ester Following the procedure of Example 60(c) above except [1-(3-hydroxy-phenyl)-piperidin-4-yl]-acetic acid methyl ester was used in step 60(c). instead of 1-(3-hydroxyphenyl)-piperidin-4-carboxylic acid ethyl ester. The title compound was isolated as an oil (38%). MS(ESI)679.2(M+H$^+$)

f) [1-(3-{[3-(2-Chloro-3-(trifluoromethyl)-benzyl)-(2,2-diphenylethyl)-amino]-propoxy}-phenyl-piperidin-4-yl-acetic acid dihydrochloride Following the procedure of Example 60(d) above except [1-(3-{3-[(2-Chloro-3-(trifluoromethyl)-benzyl)-(2,2-diphenylethyl)-amino]-propoxy}-phenyl-piperidin-4-yl-acetic acid methyl ester was used in step 60(d) instead of [1-(3-{3-[(2-Chloro-3-(trifluoromethyl)-benzyl)-(2,2-diphenylethyl)-amino]-propoxy}-phenyl-piperidine-4-carboxylic acid methyl ester, the title compound was obtained as white solid (81%) MS(ESI) 665.4 (M+H$^+$).

EXAMPLE 62

[4-(3-{3-[(2-Chloro-3-(trifluoromethyl)-benzyl)-(2,2-diphenylethyl-amino]-propoxy}-phenyl)-piperidin-1-yl]-acetic acid dihydrochloride (GSK-130932A)

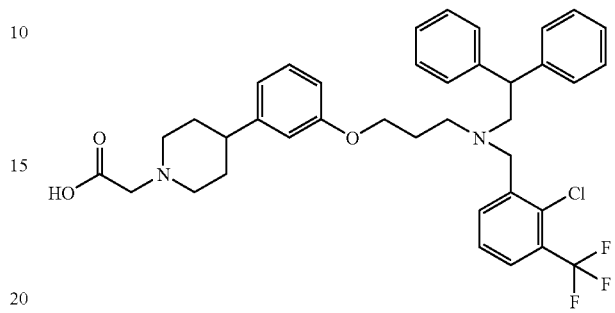

a) 1-Benzyl-4-(3-methoxy phenyl)-piperidin-4-ol

The title compound was prepared according to the literature procedure: Sugg, E. E. and Portoghese, P. S., *J. Med. Chem.* 29, 2028-2033, 1986.

b) 1-Benzyl-4-(3-methoxy phenyl)-1,2,5,6-tetrahydro-pyridine

The title compound was prepared according to the same literature reference above.

c) 4-(3-Methoxy-phenyl)-piperidine

The title compound was prepared according to a literature procedure: Komoto, T., et.al, *Chem. Pharmn. Bull.* 48(12), 1978-1985, 2000.

d) [4-(3-Methoxy-phenyl)-piperidin-1-yl]-acetic acid methyl ester

A mixture of 4-(3-Methoxy-phenyl)-piperidine (0.8 g, 4.2 mmol), methylbromoacetate (1.28 g, 8.38 mmol), diisopropylethylamine (3.7 mL, 21 mmol) and MeOH (40 mL) was refluxed for 3 h. The reaction mixture was concentrated in vacuo, and the residue was partitioned between water and EtOAc and extracted. The organic layer was washed with water, brine, dried and concentrated in vacuo to give the title compound as an oil (1.0 g, 91% yield). MS(ESI) 264.2 (M+H$^+$)

e) [4-(3-Hydroxy-phenyl)-piperidin-1-yl]-acetic acid hydrobromide

A mixture of [4-(3-methoxy-phenyl)-piperidin-1-yl]-acetic acid methyl ester and HBr (48%, 2 mL) was refluxed for 1 h. The reaction mixture was concentrated in vacuo, azeotroped with toluene twice and washed with ether to give white solid (1.2 g, quantitative yield). MS(ESI) 236.0 (M+H$^+$)

f) [4-(3-Hydroxy-phenyl)-piperidin-1-yl]-acetic acid methyl ester

Following the procedure of Example 61(b) above except [4-(3-hydroxy-phenyl)-piperidin-1-yl]-acetic acid hydrobromide was used in step 61 (b) instead of piperidin-4-yl-acetic acid hydrochloride, the title compound was obtained as an off-white solid (0.95 g, 76%). MS(ESI) 250.2 (M+H⁺)

g) [4-(3-{3-[(2-Chloro-3-(trifluoromethyl)-benzyl)-(2,2-diphenylethyl)-amino]-propoxy}-phenyl)-piperidin-1-yl]-acetic acid methyl ester Following the procedure of Example 60(c) except [4-(3-hydroxy-phenyl)-piperidin-1-yl]-acetic acid methyl ester was used in step 60(c) instead of 1-(3-hydroxy-phenyl-piperidin-4-carboxylic acid ethyl ester. The title compound was isolated as an oil (60% yield). MS(ESI) 679.2 (M+H⁺)

h) 4-(3-{3-[(2-Chloro-3-(trifluoromethyl)-benzyl)-(2,2-diphenylethyl)-amino]-propoxy}-phenyl)-piperidin-1-yl]-acetic acid dihydrochloride Following the procedure of Example 60(d) except 4-(3-{3-[(2-Chloro-3-(trifluoromethyl)-benzyl)-(2,2-diphenylethyl)-amino]-propoxy}-phenyl)-piperidin-1-yl]-acetic acid methyl ester was used in step 60(d) instead of [1-(3-{3-[(2-Chloro-3-(trifluoromethyl)-benzyl)-(2,2-diphenylethyl)-amino]-propoxy}-phenyl-piperidine-4-carboxylic acid ethyl ester the title compound was prepared as a white solid (50%). MS(ESI) 665.4 (M+H⁺).

EXAMPLE 63 rac-±-(3-{3-[(2-Chloro-3-trifluoromethyl-benzyl)-(trifluoro-phenyl-propyl)-amino]-propoxy}-phenyl)-acetic acid

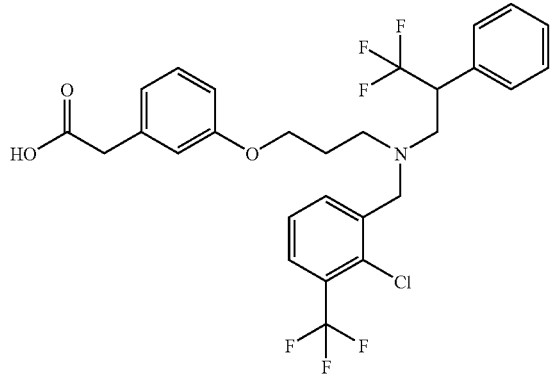

a) rac-±-(2-chloro-3-trifluoromethyl-benzyl)-(trifluoro-phenyl-propyl)-amine To a stirring solution of α,α,α-trifluoromethylphenylacetaldehyde (C. Aaron, D. Dull, J. L. Schmiegel, D. Jaeger, Y. Ohashi, and H. S. Mosher, *J. Org. Chem.* 1967, 32, 2797) (0.70 g, 3.72 mmol) in ethanol (20 mL) was added 2-chloro-3-(α,α,α-trifluoromethyl)benzylamine (R. W. Fuller, B. B. Molloy, W. A. Day, B. W. Roush and M. M. Marsh, *J. Med. Chem.* 1973, 16, 101) (806 mg, 3.84 mmol). To the stirring solution was added a catalytic amount of p-toluenesulfonic acid and sodium cyanoborohydride (0.21 g, 3.34 mmol). The reaction mixture was stirred at room temperature for 1.5 h and then diluted with water. Next, 3N HCl (aqueous) was added to give a clear solution which was extracted with diethyl ether. The aqueous layer was separated and made basic by the addition of 2.5N aqueous NaOH. The basic layer was then extracted with diethyl ether. The combined ether extracts were dried (MgSO₄), filtered, and concentrated in vacuo to give an oil which was purified by flash silica gel chromatography (230-400 mesh, E. Merck) to give the title compound as a light yellow oil, 155 mg (11%). MS (ESI) 382.2 (M+H⁺).

b) rac-±-(3-{3-[(2-Chloro-3-trifluoromethyl-benzyl)-(trifluoro-phenyl-propyl)-amino]-propoxy}-phenyl)-acetic acid Following the procedure of Example 1, steps (a)-(d), except rac-±-(2-Chloro-3-trifluoromethyl-benzyl)-(trifluoro-phenyl-propyl)-amine was used in step 1 (c) instead of [2-chloro-3-(trifluoromethyl)benzyl]-2,2-diphenylethylamine the title compound was synthesized, 17.6 mg (2.5%), as an oil. MS (ESI) 574.5 (M+H⁺).

EXAMPLE 64 rac-±-(3-{3-[(2-Chloro-3-trifluoromethyl-benzyl)-(2-dimethylamino-2-phenyl-ethyl)-amino]-propoxy}-phenyl)-acetic acid

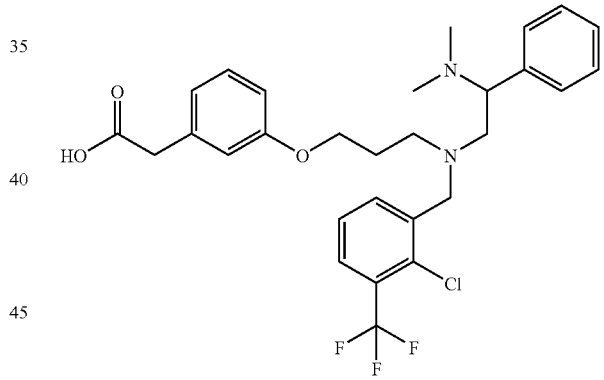

a) rac-±-N²-2-Chloro-3-trifluoromethyl-benzyl)-N¹N¹-dimethyl-1-phenyl-ethane-1,2-diamine To a stirring solution of rac-±-(2-Amino-1-phenethyl) dimethyl amine (500 mg, 3.04 mmol) in methylene chloride (15 mL) was added 2-chloro-3-trifluoromethyl benzaldehyde (0.70 g, 3.35 mmol) and sodium triacetoxyborohydride (0.71 g, 3.35 mmol) and glacial acetic acid (0.5 mL). The reaction mixture was stirred under an argon atmosphere at RT overnight The methylene chloride solvent was removed under a stream of argon and the resulting heavy oil was diluted with ethyl acetate and water. Saturated aqueous sodium bicarbonate was added. The ethyl acetate solution was separated, dried (MgSO₄), filtered, and concentrated in vacuo to afford an oil. Purification by flash silica gel chromatography (230-400 mesh, E. Merck) gave the title compound as an oil, 270 mg (25%). MS (ESI) 563.5 (MH⁺).

b) rac-±-(3-{3-[(2-Chloro-3-trifluoromethyl-benzyl)-(2-dimethylamino-2-phenyl-ethyl)-amino]-propoxy}-phenyl)-acetic acid Following the procedure of Example 1, steps (a)-(d), except rac-±-$N^2$-2-Chloro-3-trifluoromethyl-benzyl)-$N^1N'$-dimethyl-1-phenyl-ethane-1,2-diamine was used in step 1(c) instead of [2-chloro-3-(trifluoromethyl)benzyl]-2,2-diphenylethylamine the title compound was synthesized as a white solid, 26 mg (5.5%). MS (ESI) 549.5 (M+H$^+$).

EXAMPLE 65 rac-±-(3-{3-[(2-Chloro-3-Trifluoromethyl-benzyl)-(2-morpholin-4-yl-2-phenyl-ethyl)-amino]-propoxy}-phenyl)-acetic acid

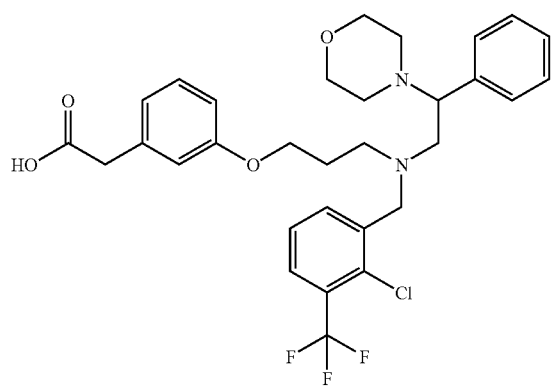

a) rac-±-(2-Chloro-3-trifluoromethyl-benzyl)-(morpholin-4-yl-phenyl-ethyl)-amine Following the procedure (preparation of rac-±-(2-chloro-3-trifluoromethyl-benzyl)-(trifluoro-phenyl-propyl)-amine) of Example 64, step (a) except rac-±-2-Morpholin4-yl-2-phenyl-ethylamine was used in step (a) instead of 2-chloro-3-(α,α,α-trifluoromethyl)benzylamine, and 2-chloro-3-trifluoromethyl benzaldehyde was used instead of (α,α,α-trifluoromethylphenylacetaldehyde, the title compound was sythesized as an oil, 0.27 g (88%); MS (ESI) 399 (M+H$^+$).

b) rac-±-(3-{3-[(2-Chloro-3-trifluoromethyl-benzyl)-(2-morpholin-4-yl-2-phenyl-ethyl)-amino]-propoxy}-phenyl)-acetic acid Following the procedure of Example 1, steps (a)-(d) except rac-±-(2-Chloro-3-trifluoromethyl-benzyl)-(morpholin-4-yl-phenyl-ethyl)-amine was used in step 1(c) instead of [2-chloro-3-(trifluoromethyl)benzyl]-2,2-diphenylethylamine the title compound was synthesized as an oil, 15.2 mg (3%); MS (ESI) 591 (M+H$^+$).

EXAMPLE 66

(2-Chloro-3-trifluoromethyl-benzyl)-(2,2-diphenyl-ethyl)-[3-(6-morpholin-4-yl-pyridin-2-yloxy)-propyl]-amine hydrochloride salt

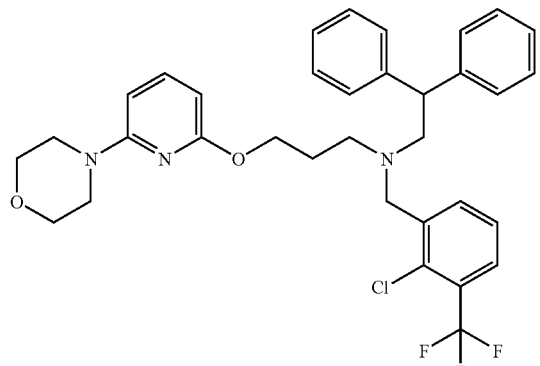

a) 6-Morpholin-4-yl-pyridin-2-ol

To a stirring solution of morpholine (10 ml) was added 6-chloro-2-pyridinol (1.5 g, 11.57 mmol) and the mixture was heated at 90° C. for 60 h. The reaction mixture was cooled to RT and concentrated under reduced pressure (while heating) to afford the title compound as a brown solid (85%. The crude material was used without further purification. MS (ESI) 181.2 (M+H$^+$).

b) (2-Chloro-3-trifluoromethyl-benzyl)-(2,2-diphenyl-ethyl)-[3-(6-morpholin-4-yl-pyridin-2-yloxy)-propyl]-amine hydrochloride salt Following the procedure of Example 6(d), except 6-morpholin-4-yl-pyridin-2-ol and N-(2,2-Diphenylethyl)-N-(3-hydroxy-propyl)-N-(2-chloro-3-trifluoromethyl-benzyl) amine were used instead of 5-(3-hydroxy-benzyl)-ethoxymethyl-1,2,3,4-tetrazole and 3-bromo-propanol in step 6(d), the title compound was synthesized as the free base. The tertiaryamine was then dissolved in diethyl ether and acidified with 1.0 M HCl/diethyl ether to give 90 mg (32% yield) of the title compound as a white solid. MS (ESI) 610.2 (M$^+$).

EXAMPLE 67

[3-(6-Chloro-pyridin-2-yloxy)-propyl]-(2-Chloro-3-trifluoromethyl-benzyl)-(2,2-diphenyl-ethyl)-amine hydrochloride salt

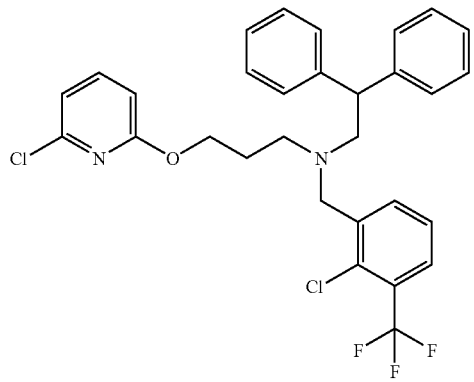

Following the procedure of Example 6(d), except 6-chloro-2-pyridinol (Aldrich) and N-(2,2-Diphenylethyl)-N-(3-hydroxy-propyl)-N-(2-chloro-3-trifluoromethyl-benzyl)amine were used instead of 5-(3-hydroxy-benzyl)-ethoxymethyl-1,2,3,4-tetrazole and 3-bromo-propanol in step 6(d), the title compound was synthesized as the free base. The tertiaryamine was then dissolved in diethyl ether and acidified with 1.0 M HCl/diethyl ether to give 90 mg (32% yield) of the title compound as a white solid. MS (ESI) 559.0 (M+).

EXAMPLE 68

(2-Chloro-3-trifluoromethyl-benzyl)-(2,2-diphenyl-ethyl)-{3-[6-(4-methyl-piperazin-1-yl)-pyridin-2-yloxy]-propyl}-amine dimesylate salt

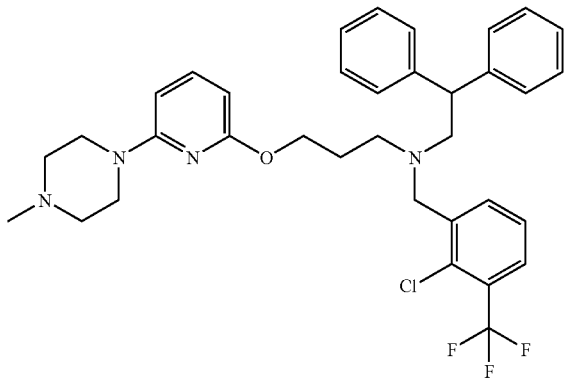

a) 6-(4-Methyl-piperazin-1-yl)-pyridin-2-ol

To a stirring solution of 1-methyl-piperazine (10 ml) was added 6-chloro-2-pyridinol (1.5 g, 11.57 mmol) and the mixture was heated at 90° C. for 60 h. The reaction mixture was cooled to RT and concentrated under reduced pressure (while heating) to afford the title compound as a brown solid (66%). The crude material was used without further purification. MS (ESI) 194.2 (M+H+).

b) (2-Chloro-3-trifluoromethyl-benzyl)-(2,2-diphenyl-ethyl)-{3-[6-(4-methyl-piperazin-1-yl)-pyridin-2-yloxy]-propyl}-amine dimesylate salt Following the procedure of Example 6(d), except 6-(4-methyl-piperazin-1-yl)-pyridin-2-ol and N-(2,2-Diphenylethyl)-N-(3-hydroxy-propyl)-N-(2-chloro-3-trifluoromethyl-benzyl)amine were used instead of 5-(3-hydroxy-benzyl)-ethoxymethyl-1,2,3,4-tetrazole and 3-bromo-propanol in step 6(d), the title compound was synthesized as the free base. The tertiaryamine was then dissolved in dichloromethane and two equivalents of methanesulfonic acid were added to afford the title compound as the dimesylate salt, 47 mg (19% yield), as a white solid. MS (ESI) 623.4 (M+).

EXAMPLE 69

(2-Chloro-3-trifluoromethyl-benzyl)-(2,2-diphenyl-ethyl)-[3-(6-piperazin-1-yl-pyridin-2-yloxy)-propyl]-amine hydrochloride salt

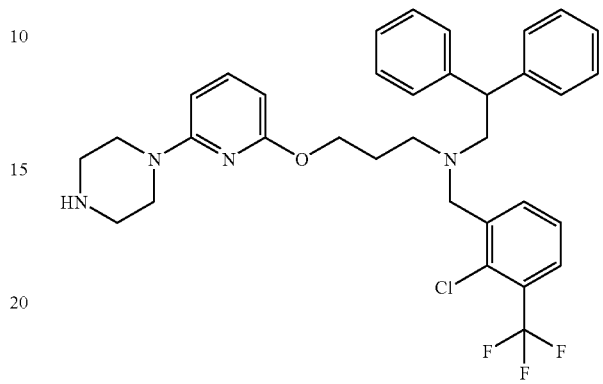

a) 4-(6-Hydroxy-pyridin-2-yl)-piperazine-1-carboxylic acid tert-butyl ester

To a stirring solution of 6-piperazin-1-yl-pyridin-2-ol (0.6 g, 3.30 mmol—Pavia, M. R., Taylor, C. P., Hershenson, F. M., Lobbestael, S. J. *J. Med. Chem.* 1987, 30(7), 1210) in 1,4-dioxane (15 ml) was added t-BOC$_2$O (0.80 g, 3.68 mmol) and H$_2$O (3 ml). The reaction mixture was heated at 75° C. for 8 h and cooled to RT. The heterogenous mixture was filtered and concentrated. Purification by flash silica gel chromatography afforded the title compound as a red solid, 0.90 g (97%). MS (ESI) 280.4 (M+H+).

b) [4-{6-(3-[(2-Chloro-3-trifluoromethyl-benzyl)-(2,2-diphenyl-ethyl)-amino]-propoxy}-pyridin-2-yl)-piperazine-1-carboxylic acid tert-butyl ester Following the procedure of Example 6(d), except 4-(6-Hydroxy-pyridin-2-yl)-piperazine-1-carboxylic acid tert-butyl ester and N-(2,2-Diphenylethyl)-N-(3-hydroxy-propyl)-N-(2-chloro-3-trifluoromethyl-benzyl)amine were used instead of 5-(3-hydroxy-benzyl)-ethoxymethyl-1,2,3,4-tetrazole and 3-bromo-propanol in step 6(d), the title compound was synthesized as the free base, 0.46 g (52% yield), as a white solid. MS (ESI) 709.4 (M+).

c) (2-Chloro-3-trifluoromethyl-benzyl)-(2,2-diphenyl-ethyl)-[3-(6-piperazin-1-yl-pyridin-2-yloxy)-propyl]-amine hydrochloride salt To a stirring solution of [4-{6-(3-[(2-Chloro-3-trifluoromethyl-benzyl)-(2,2-diphenyl-ethyl)-amino]-propoxy}-pyridin-2-yl)-piperazine-1-carboxylic acid tert-butyl ester (40 mg, 0.05 mmol) in methanol (0.8 ml) was added 1 N HCl in Et$_2$O. The reaction mixture was stirred at RT for 4 h and concentrated under vacuum to provide the title compound as an off-white solid, 31 mg (91%). MS (ESI) 609.2 (M+).

EXAMPLE 70

[4-(6-{3-[(2-chloro-3-trifluoromethyl-benzyl)-(2,2-diphenyl-ethyl)-amino]-propoxy}-pyridin-2-yl)-piperazin-1-yl]-acetic acid hydrochloride salt

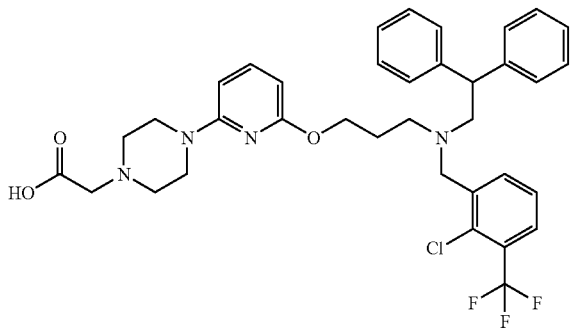

a) [4-(6-{3-[(2-Chloro-3-trifluoromethyl-benzyl)-(2,2-diphenyl-ethyl)-amino]-propoxy}-pyridin-2-yl)-piperazin-1-yl]-acetic acid methyl ester To a stirring solution of (2-Chloro-3-trifluoromethyl-benzyl)-(2,2-diphenyl-ethyl)-[3-(6-piperazin-1-yl-pyridin-2-yloxy)-propyl]-amine hydrochloride (0.1 g, 0.16 mmol) in EtOH (6 ml) was added methyl bromo-acetate (16 uL, 0.17 mmol) and diisopropylethylamine (89 uL, 0.51 mmol). The reaction mixture was stirred for 10 h at RT and then concentrated. Purification by flash silica gel chromatograpy afforded the title compound as a clear oil, 47 mg (42%). MS (ESI) 681.2 (M+).

b) [4-(6-{3-[(2-Chloro-3-trifluoromethyl-benzyl)-(2,2-diphenyl-ethyl)-amino]-propoxy}-pyridin-2-yl)-piperazin-1-yl]-acetic acid hydrochloride salt To a stirring solution of [4-(6{-3-[(2-Chloro-3-trifluoromethyl-benzyl)-(2,2-diphenyl-ethyl)-amino]-propoxy}-pyridin-2-yl)-piperazin-1-yl]-acetic acid methyl ester (46 mg, 0.07 mmol) in THF (2 ml) and H$_2$O (0.5 ml) was added LiOH (6 mg, 0.13 mmol). The reaction mixture was stirred for 24 h at RT and then concentrated. The aqueous mixture was acidified to pH=3 with 1 N HCl (aq) and extracted with EtOAc (three times). The organic extracts were dried over Na$_2$SO$_4$, filtered, and concentrated. The free base was dissolved in dichloromethane and 1 N HCl (Et$_2$O) was added. The solution was concentrated under vacuum to provide the title compound as a white solid, 26 mg (45%). MS (ESI) 667.2 (M+).

EXAMPLE 71

2-(3-{3-[[2-Chloro-3-(trifluoromethyl)benzyl]((S)-2-phenyl-propyl)amino]-(R)-1-methyl-propoxy}-phenyl)acetic acid hydrochloride salt

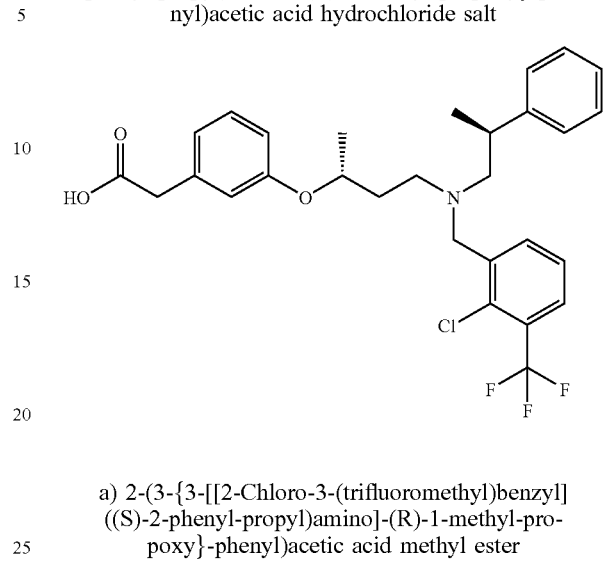

a) 2-(3-{3-[[2-Chloro-3-(trifluoromethyl)benzyl]((S)-2-phenyl-propyl)amino]-(R)-1-methyl-propoxy}-phenyl)acetic acid methyl ester Following the procedure of Example 4(a)-(c), except (S)-(2-Chloro-3-trifluoromethyl-benzyl)-(2-phenyl-propyl)-amine instead of N-(2,2-diphenylethyl)-N-(2-chloro-3-trifluoromethyl)amine in step 4(b) the title compound was obtained as a white powder (10% overall). MS (ESI) 548.0 (M+).

b) 2-(3-{3-[[2-Chloro-3-(trifluoromethyl)benzyl]((S)-2-phenyl-propyl)amino]-(R)-1-methyl-propoxy}-phenyl)acetic acid hydrochloride salt Following the procedure of Example 2, except 2-(3-{3-[[2-Chloro-3-(trifluoromethyl)benzyl]((S)-2-phenyl-propyl)amino]-(R)-1-methyl-propoxy}-phenyl)acetic acid methyl ester was used instead of (R)-2-(3-{3-[[2-chloro-3-(trifluoromethyl)benzyl](2,2-diphenylethyl)amino]-2-methyl-propoxy}-phenyl)acetic acid methyl ester, the title compound was isolated to give a white solid, 65 mg (95% yield). MS(ESI) 534.0(M+).

EXAMPLE 72

2-(3-{3-[[2-Chloro-3-(trifluoromethyl)benzyl]((S)-2-phenyl-propyl)amino]-(R)-1-methyl-propoxy}-phenyl)ethanol

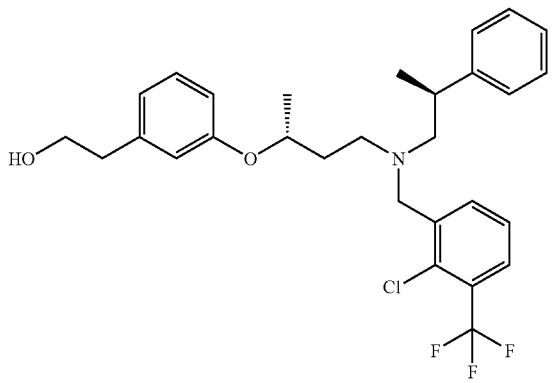

A solution of 2-(3-{3-[[2-Chloro-3-(trifluoromethyl)benzyl]((S)-2-phenyl-propyl)amino]-(R)-1-methyl-propoxy}phenyl)acetic acid methyl ester (20 mg, 0.036 mmol) in THF (1 ml) at 0° C., was treated with LiAlH₄ (100 uL of a 1N solution in THF), and the reaction was stirred at 0° for 45 minutes. Ethyl acetate (1 ml) was added, the reaction warmed to RT, and water (2 ml) was added. The mixture was extracted with ethyl acetate. The organic extracts were dried and the solvent removed. The residue was chromatographed over silica gel (hexane/Ethyl acetate: 3/7) to give the title compound as a pure oil (15 mg, 91%). MS (ESI) 520.0 (M+H)⁺.

EXAMPLE 73

2-(3-{3-[[2-Chloro-3-(trifluoromethyl)benzyl]((S)-2-phenyl-propyl)amino]-(R)-2-methyl-propoxy}-phenyl)acetic acid hydrochloride salt

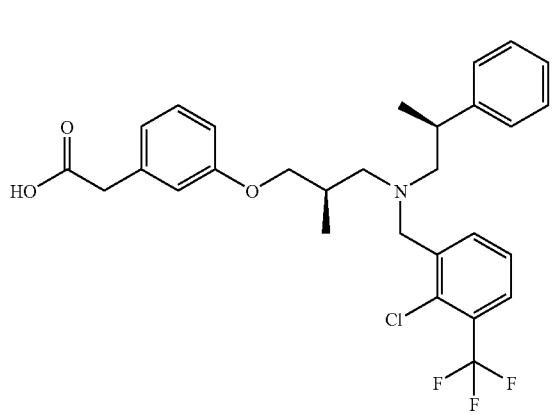

a) 2-(3-{3-[((S)-2-phenyl-propyl)amino](R)-2-methyl-propoxy}-phenyl)acetic acid methyl ester To a stirring solution of (S)-[3-(2-methyl-3-bromopropoxy)phenyl]acetic acid methyl ester (450 mg, 1.49 mmol) and (S)-(−)-β-methylphenylethylamine (214 uL, 1.49 mmol) in acetonitrile (15 mL) was added solid K₂CO₃ (620 mg, 4.5 mmol) and NaI (672 mg, 4.5 mmol). The reaction was heated to reflux and stirred overnight. Upon cooling to room temperature, the reaction was filtered, washed with acetonitrile, and the filtrate was concentrated. The crude product was purified by flash silica gel chromatography (1:1 hexane to EtOAc) to give 268 mg (50% yield) of title compound as a viscous oil. MS(ESI) 356.0 (M+H⁺).

b) 2-(3-{3-[[2-Chloro-3-(trifluoromethyl)benzyl]((S)-2-phenyl-propyl)amino]-(R)-2-methyl-propoxy}-phenyl)acetic acid methyl ester Following the procedure of Example 7(d), except 2-(3-{3-[((S)-2-phenyl-propyl)amino](R)-2-methyl-propoxy}-phenyl)acetic acid methyl ester was used instead of (R)-2-(3-{3-(2,2-diphenylethyl)amino]-3-methyl-propoxy}-phenyl)acetic acid methyl ester in step (d) the title compound was obtained as a white powder, 277 mg (67%). MS (ESI) 548.2 (M⁺).

c) 2-(3-{3-[[2-Chloro-3-(trifluoromethyl)benzyl]((S)-2-phenyl-propyl)amino]-(R)-2-methyl-propoxy}-phenyl)acetic acid hydrochloride salt Following the procedure of Example 2, except 2-(3-{3-[[2-Chloro-3-(trifluoromethyl)benzyl]((S)-2-phenyl-propyl)amino]-(R)-2-methyl-propoxy}-phenyl)acetic acid methyl ester was used instead of (R)-2-(3-{3-[[2-chloro-3-(trifluoromethyl)benzyl](2,2-diphenylethyl)amino]-2-methyl-propoxy}-phenyl)acetic acid methyl ester, the title compound was isolated to give a white solid, 95 mg (97% yield). MS(ESI) 534.2 (M⁺).

EXAMPLE 74

2-(3-{3-[[2-Chloro-3-(trifluoromethyl)benzyl]((S)-2-phenyl-propyl)amino]-(R)-2-methyl-propoxy}-phenyl)ethanol

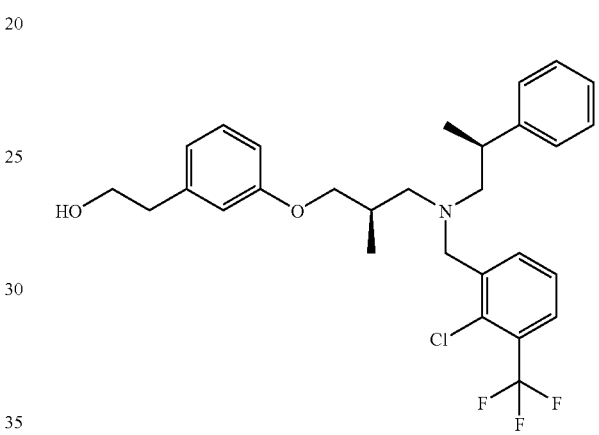

Following the procedure of Example 72 (above) except 2-(3-{3-[[2-Chloro-3-(trifluoromethyl)benzyl]((S)-2-phenyl-propyl)amino]-(R)-2-methyl-propoxy}-phenyl)acetic acid methyl ester was used instead of 2-(3-{3-[[2-Chloro-3-(trifluoromethyl)benzyl]((S)-2-phenyl-propyl)amino]-(R)-1-methyl-propoxy}-phenyl)acetic acid methyl ester, the title compound was isolated to give a white solid, 47 mg (99% yield). MS(ESI) 520.2 (M⁺).

EXAMPLE 75

2-(3-{3-[[2-Chloro-3-(trifluoromethyl)benzyl]((R)-2-phenyl-propyl)amino]-(R)-2-methyl-propoxy}-phenyl)acetic acid hydrochloride salt

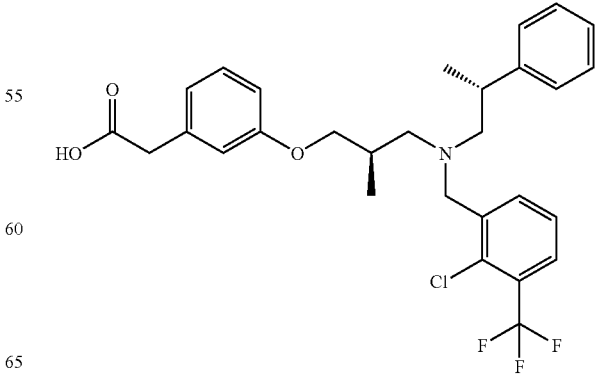

a) 2-(3-{3-[((R)-2-phenyl-propyl)amino]-(R)-2-methyl-propoxy}phenyl)acetic acid methyl ester Following the procedure of Example 73(a) (above) except (R)-(−)-β-methylphenylethylamine was used instead of and (S)-(−)-β-methylphenylethylamine in step (a) the title compound was obtained as a white powder, 270 mg (51%). MS (ESI) 356.0 (M+H⁺).

b) 2-(3-{3-[[2-Chloro-3-(trifluoromethyl)benzyl]((R)-2-phenyl-propyl)amino]-(R)-2-methyl-propoxy}-phenyl)acetic acid methyl ester Following the procedure of Example 7(d), except 2-(3-{3-[((R)-2-phenyl-propyl)amino] (R)-2-methyl-propoxy}-phenyl)acetic acid methyl ester was used instead of (R)-2-(3-{3-(2,2-diphenylethyl)amino]-3-methyl-propoxy}-phenyl)acetic acid methyl ester in step (d) the title compound was obtained as a white powder, 271 mg (66%). MS (ESI) 548.2 (M⁺).

c) 2-(3-{3-[[2-Chloro-3-(trifluoromethyl)benzyl]((R)-2-phenyl-propyl)amino]-(R)-2-methyl-propoxy}-phenyl)acetic acid hydrochloride salt Following the procedure of Example 2, except 2-(3-{3-[[2-Chloro-3-(trifluoromethyl)benzyl]((R)-2-phenyl-propyl)amino]-(R)-2-methyl-propoxy}-phenyl)acetic acid methyl ester was used instead of (R)-2-(3-{3-[[2-chloro-3-(trifluoromethyl)benzyl](2,2-diphenylethyl)amino]-2-methyl-propoxy}-phenyl)acetic acid methyl ester, the title compound was isolated to give a white solid, 140 mg (96% yield). MS(ESI) 534.2 (M⁺).

EXAMPLE 76

2-(3-{3-[[2-Chloro-3-(trifluoromethyl)benzyl]((R)-2-phenyl-propyl)amino]-(R)-2-methyl-propoxy}-phenyl)ethanol

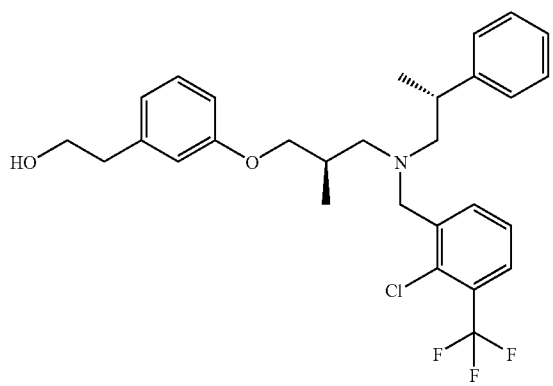

Following the procedure of Example 72 (above) except 2-(3-{3-[[2-Chloro-3-(trifluoromethyl)benzyl]((R)-2-phenyl-propyl)amino]-(R)-2-methyl-propoxy}-phenyl)acetic acid methyl ester was used instead of 2-(3-{3-[[2-Chloro-3-(trifluoromethyl)benzyl]((S)-2-phenyl-propyl)amino]-(R)-1-methyl-propoxy}-phenyl)acetic acid methyl ester, the title compound was isolated to give a white solid, 87 mg (92% yield). MS(ESI) 520.2 (M⁺).

EXAMPLE 77

(R)-2-(3-{3-[[2-Chloro-3-(trifluoromethyl)benzyl](2,2-diphenylethyl)amino]-2-methyl-propoxy}-phenyl)ethanol

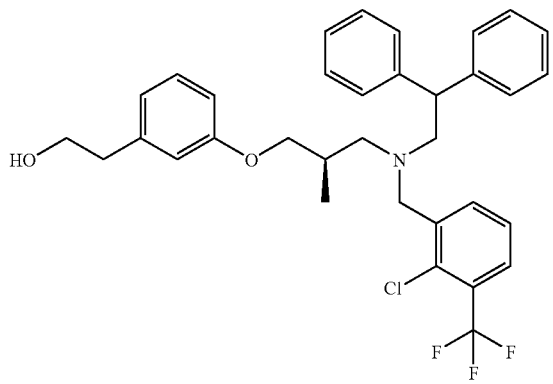

Following the procedure of Example 72 (above) except (R)-2-(3-{3-[[2-Chloro-3-(trifluoromethyl)benzyl](2,2-diphenylethyl)amino]-2-methyl-propoxy}-phenyl)acetic acid methyl ester was used instead of 2-(3-{3-{[2-Chloro-3-(trifluoromethyl)benzyl]((S)-2-phenyl-propyl)amino]-(R)-1-methyl-propoxy}-phenyl)acetic acid methyl ester, the title compound was isolated to give a white solid, 78 mg (59% yield). MS(ESI) 582.4 (M⁺).

EXAMPLE 78

3-{3-[(3-Chloro-2-trifluoromethyl-benzyl)-diphenylethyl-amino]-propoxy-N,N-dimethyl-benzenesulfonamide hydrochloride

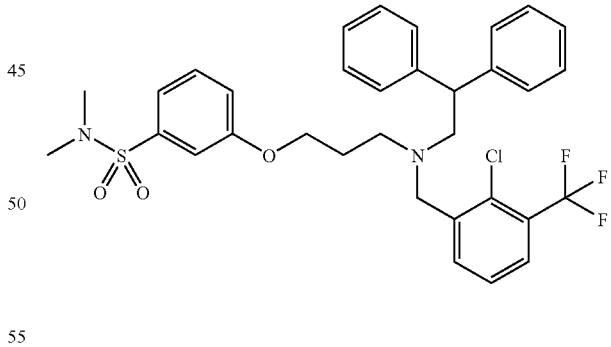

a) 3-Methoxy-N,N,-dimethyl-benzenesulfonamide

Dimethylamine (40% in H₂O, 1 mL) was added to a solution of 3-methoxybenzenesulfonyl chloride (0.50 g, 2.4 mmol) and pyridine (1 mL) in THF (5 mL). The reaction mixture was allowed to stir at rt for 48 h, then was poured into H₂O and extracted with EtOAc. The organic extracts were washed with brine, dried (MgSO₄), filtered and concentrated to give an oil which was chromatographed (10-80% EtOAc in hexane) to give 0.400 g (76%) of the title compound. MS (ESI) 216 (M+H⁺).

b) 3-Hydroxy-N,N,-dimethyl-benzenesulfonamide

A solution of $BBr_3$ (1 M in $CH_2Cl_2$, 2.0 mL, 2.0 mmol) was added dropwise to a −78° C. solution of 3-methoxy-N,N,-dimethyl-benzenesulfonamide (0.15 g, 0.7 mmol) in $CH_2Cl_2$ (2 mL). The mixture was warmed to rt and stirred for 2 h, then cooled to 0° C. and quenched with saturated $NaCO_3$. The aqueous phase was neutralized with saturated $NH_4Cl$ and extracted with EtOAc. The organic extracts were washed with brine, dried ($MgSO_4$), filtered and concentrated to give an oil which was directly in the next step. MS (ESI) 202 (M+H$^+$).

c) 3-{3-[(3-Chloro-2-trifluoromethyl-benzyl)-diphenylethyl-amino}-propoxy-N,N-dimethyl-benzenesulfonamide hydrochloride DIAD (48 uL, 0.24 mmol) was added dropwise to a RT solution of 3-hydroxy-N,N,-dimethyl-benzenesulfonamide (0.040 g, 0.2 mmol), 3-[(3-chloro-2-trifluoromethyl-benzyl)-diphenylethyl-amino]-propan-1-ol (0.088 g, 0.2 mmol) and triphenylphosphine (0.063 g, 0.24 mmol). The mixture was stirred for 48 at rt than was concentrated and purified by reverse phase HPLC to provide a solid which was dissolved in CH2Cl2 and treated with excess 4M HCl in diethyl ether. The mixture was concentrated to provide 35 mg (25%) of the title compound. MS (ESI) 632 (M+H$^+$).

EXAMPLE 79

Cyclopropanecarboxylic acid 3-{3-[(2-chloro-3-trifluoromethyl-benzyl)-diphenylethyl-amino]-propoxy}-benzylamide

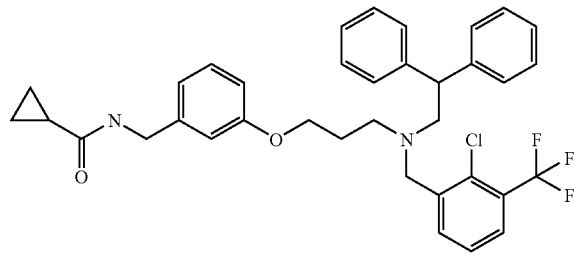

a) (3-Hydroxy-benzyl)-carbamic acid tert butyl ester 3-hydroxybenzylamine (Apin, 1.0 g, 8.1 mmole) was dissolved in DMF(25 ml). Triethylamine (0.33 ml, 2.4 mmole) and $(BOC)_2O$ (1.8 g, 8.1 mmole) were added, the mixture stirred over night at room temperature under argon atmosphere. The reaction was concentrated, chromatographed on silica gel (0 to 20% EtOAc/hexanes) to give the titled compound (400 mg, 22%). MH$^+$223.0 b) (3-{3-[(2-Chloro-3-trifluoromethyl-benzyl)-(2,2-diphenyl-ethyl)-amino]-propoxy}-benzyl)-carbamic acid tert-butyl ester (3-Hydroxy-benzyl)-carbamic acid tert butyl ester was dissolved in THF, triphenylphosphine (0.44 g, 2.2 mmole), 3-{3-[(2-Chloro-3-trifluoromethyl-benzyl)-2,2-diphenyl-ethylamino]-propoxy}-phenylamine (1.0 g, 2.3 mmole) and DIAD (0.43 ml, 2.2 mmole) were added subsequently. The mixture was stirred overnight at room temperature. The reaction was concentrated, chromatographed on silica gel (0 to 15% EtOAc/hexanes) to give the titled compound (0.51 g, 48%). MH$^+$652.0 c) [3-(3-Aminomethyl-phenoxy)-propyl]-(2-chloro-3-trifluoromethyl-benzyl)-(2,2-diphenyl-ethyl)-amine dihydrochloride (3-{3-[(Chloro-trifuoromethyl-benzyl)-(2,2-diphenyl-ethyl)-amino]-propoxy}-benzyl)-carbamic acid tert-butyl ester (530 mg, 0.8 mmole) was treated with 1 M HCl in ether (8 ml). The mixture stirred 2 hours at room temperature under argon atmosphere. Solid precipitated, ether was decanted and solid washed with ether (10 ml) twice, then dried under vacuum. (430 mg, 86%) MH$^+$552.0 d) Cyclopropanecarboxylic acid 3-{3-[(chloro-trifluoromethyl-benzyl)-diphenylethyl-amino]-propoxy}-benzylamide ([3-(3-Aminomethyl-phenoxy)-propyl]-(2-chloro-3-trifluoromethyl-benzyl)-(2,2-diphenyl-ethyl)-amine) (40 mg, 0.06 mmole) was dissolved in CH2Cl2 (1 ml), triethylamine (25 uL) and cyclopropane carbonyl chloride (12.0 mg, 0.12 mmole) were added. The mixture was stirred overnight at room temperature under argon atmosphere, concentrated to dryness in vacuo purified on reversed phase gradient HPLC (YMC CombiPrep ODS-A, 50×20 mm, 20 mL/min, A: 0.1% trifluoroacetic acid in acetonitrile B: 0.1% aqueous trifluoroacetic acid, A: 10 to 90% during 10 min, UV detection at 254 nm) to give a clear film (28 mg, 75%). MH$^+$=621.2.

The following Examples, 80-83, were prepared following the procedure for Example 79 with an alternate acid chloride in step d.

| | Final Compound | Acid Chloride | Structural Data |
|---|---|---|---|
| 80 | N-(3-{3-[(2-Chloro-3-trifluoromethyl-benzyl)-diphenylethyl-amino]-propoxy}-benzyl)-isobutyramide | | MS(ES+) 623.2 [M + H]$^+$ |
| 81 | Acetic acid (3-{3-[(2-chloro-3-trifluoromethyl-benzyl)-diphenylethyl-amino]-propoxy}-benzylcarbamoyl)-methyl ester | | MS(ES+) 653.4 [M + H]$^+$ |
| 82 | N--(3-{3-[(2-Chloro-3-trifluoromethyl-benzyl)-diphenylethyl-amino]-propoxy}-benzyl)-propionamide | | MS(ES+) 609.0 [M + H]$^+$ |
| 83 | 2,5-Dimethyl-2-H-pyrazole-3-carboxylic acid 3-{3-[(2-chloro-3-trifluoromethyl-benzyl)-diphenylethyl-amino]-propoxy}-benzylamide | | MS(ES+) 675.0 [M + H]$^+$ |

EXAMPLE 84

(2-Chloro-3-trifluoromethyl-benzyl)-(2,2-diphenyl-ethyl)-(3-o-tolyloxy-propyl)-amine

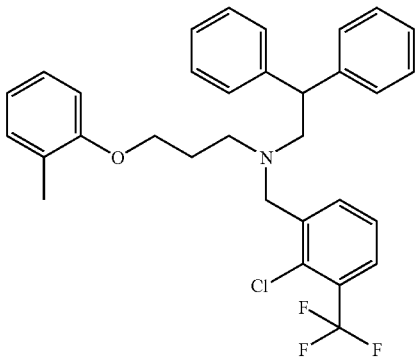

To a solution of 3-[(2-Chloro-3-trifluoromethyl-benzyl)-diphenylethyl-amino]-propan-1-ol (0.065 g, 0.145 mmol) in toluene (4 ml) at ambient temperature was added o-cresol (0.020 g, 0.186 mmol) under Argon with stirring. The mixture was treated with polymer bound $PPh_3$ (0.076 g, 0.228 mmol). After 15 minutes of stirring, the mixture was treated with DIAD (0.036 g, 0.178 mmol) and was stirred at ambient temperature overnight. The reaction mixture was filtered then concentrated, in vacuo, to dryness. The oil was dissolved in DMSO and was purified via reverse-phase HPLC to yield the title compound (0.033 g, 42%); MS (ES+) m/e 539 $[M+H]^+$.

The following Examples, 85-107, were prepared following the procedure for Example 84 with an alternate phenol.

| Example | | Phenol | Characterisation |
|---|---|---|---|
| 85 | 2-{3-[(2-Chloro-3-trifluoromethyl-benzyl)-diphenylethyl-amino]-propoxy}-benzonitrile | 2-Cyanophenol | MS(ES+) m/e 550 $[M + H]^+$ |
| 86 | 3-{3-[(2-Chloro-3-trifluoromethyl-benzyl)-diphenylethyl-amino]-propoxy}-benzonitrile | 3-Cyanophenol | MS(ES+) m/e 550 $[M + H]^+$ |
| 87 | [3-(3-Chloro-phenoxy)-propyl]-(2-chloro-3-trifluoromethyl-benzyl)-(2,2-diphenyl-ethyl)-amine | 3-Chlorophenol | MS(ES+) m/e 559 $[M + H]^+$ |
| 88 | (2-Chloro-3-trifluoromethyl-benzyl)-(2,2-diphenyl-ethyl)-[3-(2-methoxy-phenoxy)-propyl]-amine | 2-Methoxyphenol | MS(ES+) m/e 555 $[M + H]^+$ |
| 89 | [3-(2-Chloro-phenoxy)-propyl]-(2-chloro-3-trifluoromethyl-benzyl)-(2,2-diphenyl-ethyl)-amine | 2-Chlorophenol | MS(ES+) m/e 559 $[M + H]^+$ |
| 90 | (2-Chloro-3-trifluoromethyl-benzyl)-(2,2-diphenyl-ethyl)-(3-phenoxy-propyl)-amine | Phenol | MS(ES+) m/e 525 $[M + H]^+$ |
| 91 | (2-Chloro-3-trifluoromethyl-benzyl)-(2,2-diphenyl-ethyl)-[3-(3-isopropyl-phenoxy)-propyl]-amine | 3-Isopropylphenol | MS(ES+) m/e 567 $[M + H]^+$ |
| 92 | (2-Chloro-3-trifluoromethyl-benzyl)-(2,2-diphenyl-ethyl)-[3-(4-methoxy-phenoxy)-propyl]-amine | 4-Methoxyphenol | MS(ES+) m/e 555 $[M + H]^+$ |
| 93 | 3-{3-[(Chloro-trifluoromethyl-benzyl)-diphenylethyl-amino]-propoxy}-phenol | 3-Hydroxyphenol | MS(ES+) m/e 541 $[M + H]^+$ |
| 94 | 2-{3-[(Chloro-trifluoromethyl-benzyl)-diphenylethyl-amino]-propoxy}-phenol | 2-Hydroxyphenol | MS(ES+) m/e 541 $[M + H]^+$ |
| 95 | 3-{3-[(Chloro-trifluoromethyl-benzyl)-diphenylethyl-amino]-propoxy}-phenylamine | 3-Aminophenol | MS(ES+) m/e 540 $[M + H]^+$ |
| 96 | (2-Chloro-3-trifluoromethyl-benzyl)-(2,2-diphenyl-ethyl)-[3-(3-trifluoromethyl-phenoxy)-propyl]-amine | 3-Trifluoromethylphenol | MS(ES+) m/e 593 $[M + H]^+$ |
| 97 | 1-(3-{3-[(Chloro-trifluoromethyl-benzyl)-diphenylethyl-amino]-propoxy}-phenyl)-ethanone | 3-Hydroxyacetophenone | MS(ES+) m/e 567 $[M + H]^+$ |
| 98 | (3-{3-[(2-Chloro-3-trifluoromethyl-benzyl)-diphenylethyl-amino]-propoxy}-phenyl)-phenyl-amine | 3-Phenylamino-phenol | MS(ES+) m/e 616 $[M + H]^+$ |
| 99 | [3-(Benzo[1,3]dioxol-5-yloxy)-propyl]-(2-chloro-3-trifluoromethyl-benzyl)-(2,2-diphenyl-ethyl)-amine | sesamol | MS(ES+) m/e 569 $[M + H]^+$ |
| 100 | (2-Chloro-3-trifluoromethyl-benzyl)-(2,2-diphenyl-ethyl)-(3-m-tolyloxy-propyl)-amine | m-Cresol | MS(ES+) m/e 539 $[M + H]^+$ |
| 101 | (2-Chloro-3-trifluoromethyl-benzyl)-(2,2-diphenyl-ethyl)-[3-(3-methoxy-phenoxy)-propyl]-amine | 3-Methoxyphenol | MS(ES+) m/e 555 $[M + H]^+$ |
| 102 | (2-Chloro-3-trifluoromethyl-benzyl)-(2,2-diphenyl-ethyl)-[3-(3-isobutyl-phenoxy)-propyl]-amine | 3-Isobutylphenol | MS(ES+) m/e 581 $[M + H]^+$ |
| 103 | [3-(3-Butyl-phenoxy)-propyl]-(2-chloro-3-trifluoromethyl-benzyl)-(2,2-diphenyl-ethyl)-amine | 3-Butylphenol | MS(ES+) m/e 581 $[M + H]^+$ |
| 104 | (2-Chloro-3-trifluoromethyl-benzyl)-{3-[3-(2,2-dimethyl-propyl)-phenoxy]-propyl}-(2,2-diphenyl-ethyl)-amine | 3-(2,2-Dimethyl-propyl)-phenol | MS(ES+) m/e 595 $[M + H]^+$ |

EXAMPLE 105

(4-{3-[(2-Chloro-3-trifluoromethyl-benzyl)-diphenyl-ethyl-amino]-propoxy}-benzyl)-methyl-amine

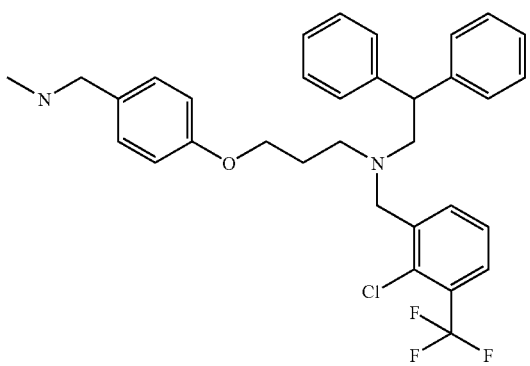

a) 4-{3-[(Chloro-trifluoromethyl-benzyl)-diphenyl-ethyl-amino]-propoxy}-benzaldehyde To a solution of 3-[(Chloro-trifluoromethyl-benzyl)-diphenylethyl-amino]-propan-1-ol (0.500 g, 1.12 mmol) in toluene (4 ml) at ambient temperature was added 4-Hydroxy-benzaldehyde (0.213 g, 1.74 mmol) under Argon with stirring. The mixture was treated with polymer bound $PPh_3$ (0.594 g, 1.782 mmol). After 15 minutes of stirring, the mixture was treated with DIAD (0.273 mL, 1.387 mmol) and was stirred at ambient temperature overnight. The reaction mixture was filtered then concentrated, in-vacuo, to dryness. The oil was dissolved in DMSO and was purified via reverse-phase HPLC to yield the title compound (0.266 g, 43%); MS (ES+) m/e 553 [M+H]⁺.

b) (4-{3-[(2-Chloro-3-trifluoromethyl-benzyl)-diphenylethyl-amino]-propoxy}-benzyl)-methyl-amine A solution of 4-{3-[(2-Chloro-3-trifluoromethyl-benzyl)-diphenylethyl-amino]-propoxy}-benzaldehyde, (0.0443 g, 0.080 mmol) in dichloromethane (1 ml) and AcOH (00.1 mL), was treated with $CH_3NH_2$ (40% solution in $H_2O$, 0.073 mmol) at ambient temperature. To the mixture was added $NaBH(OAc)_3$ (0.017 g, 0.080 mmol), and the reaction was stirred overnight. The reaction mixture was then concentrated, in vacuo, to an oil, which was then dissolved in DMSO and purified via reverse-phase HPLC to afford the title compound (0.007 g, 15%); MS (ES+) m/e 568 [M+H]⁺.

The following Examples, 106-108, were prepared following the procedure for Example 105 step b, with an alternate amine.

| Example | | Amine | Characterisation |
|---|---|---|---|
| 106 | (2-Chloro-3-trifluoromethyl-benzyl)-[3-(4-dimethylamino-methyl-phenoxy)-propyl]-(2,2-diphenyl-ethyl)-amine | Dimethylamine | MS(ES+) m/e 582 [M + H]⁺ |
| 107 | (2-Chloro-3-trifluoromethyl-benzyl)-(2,2-diphenyl-ethyl)-[3-(4-morpholin-4-ylmethyl-phenoxy)-propyl]-amine | Morpholine | MS (ES+) m/e 624 [M + H]⁺ |
| 108 | (2-Chloro-3-trifluoromethyl-benzyl)-(2,2-diphenyl-ethyl)-{3-[4-(4-methyl-piperazin-1-ylmethyl)-phenoxy]-propyl}-amine | N-Methylpiperazine | MS (ES+) m/e 637 [M + H]⁺ |

EXAMPLE 109

(3-{3-[(Chloro-trifluoromethyl-benzyl)-diphenyl-ethyl-amino]-propoxy}-benzyl)-methyl-amine

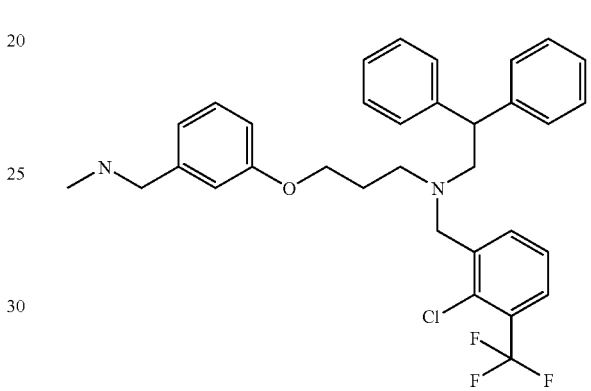

a) 3-{3-[(2-Chloro-3-trifluoromethyl-benzyl)-diphenylethyl-amino]-propoxy}-benzaldehyde To a solution of 3-[(2-Chloro-3-trifluoromethyl-benzyl)-diphenylethyl-amino]-propan-1-ol (0.500 g, 1.12 mmol) in toluene (4 ml) at ambient temperature was added 3-Hydroxy-benzaldehyde (0.213 g, 1.74 mmol) under Argon with stirring. The mixture was treated with polymer bound $PPh_3$ (0.594 g, 1.782 mmol). After 15 minutes of stirring, the mixture was treated with DIAD (0.273 mL, 1.387 mmol) and was stirred at ambient temperature overnight.

The reaction mixture was filtered then concentrated, in-vacuo, to dryness. The oil was dissolved in DMSO and was purified via reverse-phase HPLC to yield the title compound (0.192 g, 31%); MS (ES+) m/e 553 [M+H]⁺.

b) (3-{3-[(Chloro-trifluoromethyl-benzyl)-diphenyl-ethyl-amino]-propoxy}-benzyl)-methyl-amine A solution of 3-{3-[(2-Chloro-3-trifluoromethyl-benzyl)-diphenylethyl-amino]-propoxy}-benzaldehyde, (0.032 g, 0.058 mmol) in dichloromethane (1 ml) and AcOH (0.1 mL), was treated with $CH_3NH_2$ (40% solution in $H_2O$, 0.053 mmol) at ambient temperature. To the mixture was added $NaBH(OAc)_3$ (0.0123 g, 0.058 mmol), and the reaction was stirred overnight. The reaction mixture was then concentrated, in vacuo, to an oil, which was then dissolved in DMSO and purified via reverse-phase HPLC to afford the title compound (0.004 g, 12%); MS (ES+) m/e 568 [M+H]⁺.

The following Examples, 110-113, were prepared following the procedure for Example 109 step b, with an alternate amine.

| Example | Amine | Characterisation |
|---|---|---|
| 110 (2-Chloro-3-trifluoromethyl-benzyl)-[3-(3-dimethylaminomethyl-phenoxy)-propyl]-(2,2-diphenyl-ethyl)-amine | Dimethylamine | MS(ES+) m/e 582 [M + H]+ |
| 111 (2-Chloro-3-trifluoromethyl-benzyl)-(2,2-diphenyl-ethyl)-[3-(3-morpholin-4-ylmethyl-phenoxy)-propyl]-amine | Morpholine | MS (ES+) m/e 624 [M + H]+ |
| 112 (2-Chloro-3-trifluoromethyl-benzyl)-(2,2-diphenyl-ethyl)-{3-[3-(4-methyl-piperazin-1-ylmethyl)-phenoxy]-propyl}-amine | N-Methylpiperazine | MS (ES+) m/e 637 [M + H]+ |
| 113 (3-{3-[(2-Chloro-3-trifluoromethyl-benzyl)-diphenylethyl-amino]-propoxy}-benzyl)-isopropyl-amine | Isopropylamine | MS (ES+) m/e 596 [M + H]+ |

EXAMPLE 114

{3-[(2-Chloro-3-trifluoromethyl-benzyl)-(2,2-diphenyl-ethyl-amino)]-propoxy}-4-trifluoromethyl-phenylamine

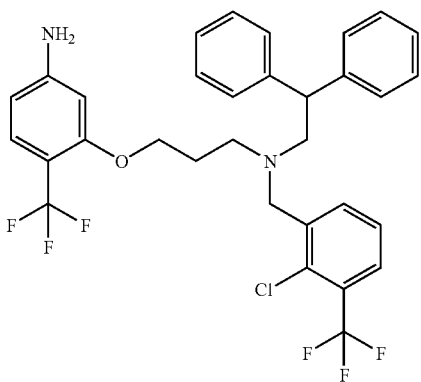

a) 2-Methoxy-4-nitrobenzotrifluoride

Equip a 2 L 3-necked flask with an oil bath, magnetic stirrer, thermocouple, condenser, and addition funnel vented into a caustic scrubber. Charge the flask with 1-methyl-2-pyrrolidinone (NMP) (300 mL, 2 volumes), 2-iodo-5-nitroanisole (145.2 g, 1.00 eq) and copper (I) iodide (14.8 g, 0.15 eq). With stirring, heat the reaction mixture to 80-100° C. Charge the addition funnel with methyl fluorosulfonyl difluoroacetate (200 g, 132 mL, 2.05 eq) and add keeping temperature below 110° C. The mixture is heated for ca. 2 hours then checked by LC to monitor for loss of starting material. The mixture is cooled below 90° C. then water (1400 mL, 9.6 vol) is added and the bath heated to 140° C. Product is collected by azeotropic distillation with a pot temp of 102° C. and head-temp of 90° C. Distillation is stopped when pot temp falls below 101° C. Product is isolated by extraction into 5 volumes tert-butyl methyl ether (TBME), washed with 5 volumes water, and used as a solution in the subsequent stage.

b) 2-Trifluoromethyl-5-nitroaniline

Equip a 1 L 3-necked flask with an oil bath, magnetic stirrer, thermocouple, and distillation apparatus under a stream of nitrogen (2 mL/min). Charge the flask with 2-methoxy-4-nitrobenzotrifluoride/tert-butyl methyl ether (TBME) solution from stage 1 and concentrate to 40% volume (using atmospheric pressure, oil bath at 80° C. Cool the solution below 40° C. and add 1-methyl-2-pyrrolidinone (NMP) (250 mL, 4.8 volumes). Continue distillation at oil bath temp of 80° C., stopping when no further distillate is collected under vacuum. The mixture is cooled to below 40° C. then charge with sodium dihydrogen phosphate hydrate (50 g, 1.6 eq), water (25 g, 6.2 eq), then lithium chloride (50 g, 5.2 eq). The mixture is heated to 130° C. for 16 hours then checked by LC to monitor for loss of starting material. The mixture is cooled below 30° C. then TBME (500 mL, 10 vol) and a mixture of water and conc HCl (500 mL, 4:1 water:conc HCl, 10 vol) is added. The aqueous layers are removed and re-extracted using TBME (150 mL, 3 vol). The combined organics are rinsed with a mixture of water and conc HCl (450 mL, 9:1 water:HCl, 9 vol). The combined organics are concentrated by distillation to 40% volume. Toluene (75 mL, 1.5 vol) is added and distillation continued. Upon no further collection, vacuum is applied to reduce remaining volume to 50%. Heptanes (500 mL, 10 vol) are added and the mixture heated to 90° C. then cooled slowly (8 h) to 25° C. The crystals are isolated by filtration to give 33 g (68%) of an off-white solid.

c) (2-Chloro-3-trifluoromethyl-benzyl)-(2,2-diphenyl-ethyl)-[3-(nitro-trifluoromethyl-phenoxy)-propyl]-amine To a solution of 2-trifluoro-3-nitro-phenol (0.28 g, 1.3 mmol), polymer bound triphenylphosphine (0.82 g, 2.45 mmol, 3 mmol/g, Fluka Chemie), N-(2,2-diphenylethyl)-N-(3-hydroxy-propyl)-N-(2-chloro-3-trifluoromethyl-benzyl) amine (0.35 g, 1.54 mmol), and CH$_2$Cl$_2$ (15 mL), diisopropylazodicarboxylate (0.30 mL, 1.94 mmol) was added and the reaction mixture was stirred overnight. The mixture was then filtered, concentrated, and purified via combiflash to yield the product as a yellow oil (0.69 g, 81%): MS(ES) m/e 637.2 [M+H]+.

d) {3-[(2-Chloro-3-trifluoromethyl-benzyl)-(2,2-diphenyl-ethyl-amino)]-propoxy}-4-trifluoromethyl-phenylamine A solution of (2-chloro-3-trifluoromethyl-benzyl)-(2,2-diphenyl-ethyl)-[3-(nitro-trifluoromethyl-phenoxy)-propyl]-amine (0.28 g, 1.3 mmol), Pd/C (10%) (0.10 g, 0.10 mmol), and MeOH (15 mL) (0.35 g, 1.54 mmol) was treated with H$_2$ (balloon pressure) overnight. The mixture was then filtered, concentrated, and purified via combiflash to yield the product as a yellow oil (0.12 g, 18%): MS(ES) m/e 607.2 [M+H]+

EXAMPLE 115

{3-[(2-Chloro-3-trifluoromethyl-benzyl)-(2,2-diphenyl-ethyl-amino)]-propoxy}-4-methyl-phenylamine

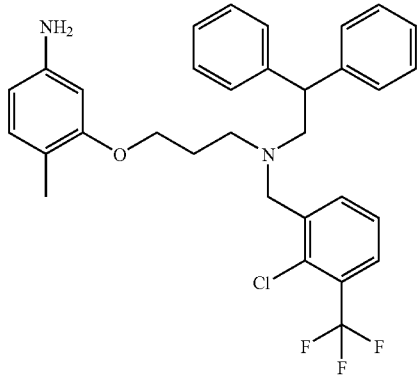

a) {3-[(2-Chloro-3-trifluoromethyl-benzyl)-(2,2-diphenyl-ethyl-amino)]-propoxy}-4-methyl-phenyl carbamic acid tert-butyl ester Following the procedure of Example 114 except substituting (3-hydroxy-4-methyl-phenyl)-carbamic acid tert-butyl ester for 2-trifluoro-3-nitro-phenol in part c, the title compound was obtained as a clear oil (100 mg, 17%): MS(ES) m/e 653.2 [M+H]$^+$.

b) {3-[(2-Chloro-3-trifluoromethyl-benzyl)-(2,2-diphenyl-ethyl-amino)]-propoxy}-4-methyl-phenylamine To a solution of {3-[(2-Chloro-3-trifluoromethyl-benzyl)-(2,2-diphenyl-ethyl-amino)]-propoxy}-4-methyl-phenyl carbamic acid tert-butyl ester (0.09 g, 0.14 mmol) and CH$_2$Cl$_2$ (2 mL), TFA (0.20 mL, 1.2 mmol) was added and the reaction mixture was stirred for 1 h. The mixture was then poured into NaHCO$_3$, extracted with CH$_2$Cl$_2$, dried over Na$_2$SO$_4$, filtered, and concentrated to yield the product as a yellow oil (0.03 g, 39%): MS(ES) m/e 553.2 [M+H]$^+$.

EXAMPLE 116

Ethanesulfonic acid (3-{3-[(2-chloro-3-trifluoromethyl-benzyl)-(2,2-diphenyl-ethyl-amino)]-propoxy}-4-methyl-phenyl)-amide trifluoroacetic acid salt

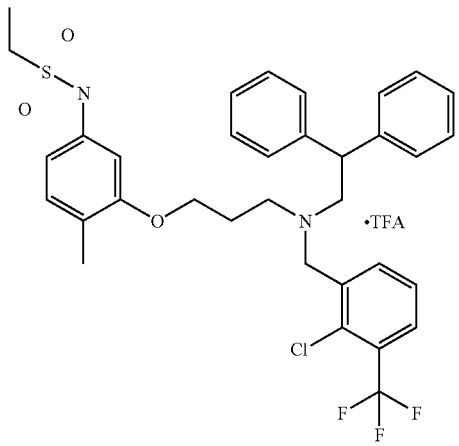

To a solution of {3-[(2-chloro-3-trifluoromethyl-benzyl)-(2,2-diphenyl-ethyl-amino)]-propoxy}-4-methyl-phenylamine (0.02 g, 0.036 mmol), pyridine (0.030 mL, 0.36 mmol), and CH$_2$Cl$_2$ (0.3 mL), ethanesulfonyl chloride (0.02 mL, 0.20) mmol) was added and the reaction mixture was stirred overnight. The mixture was concentrated and purified via preparative HPLC (TMC CombiPrep PDS, 75×30 mm, 25 mL/min, acetonitrile:H$_2$O:TFA, UV detection at 254 nm) to yield the product as a yellow oil (0.02 g, 86%): MS(ES) m/e 645.2 [M+H]$^+$.

EXAMPLE 117

Propane-2-sulfonic acid (3-{3-[(2-chloro-3-trifluoromethyl-benzyl)-(2,2-diphenyl-ethyl-amino)]-propoxy}-4-methyl-phenyl)-amide trifluoroacetic acid salt

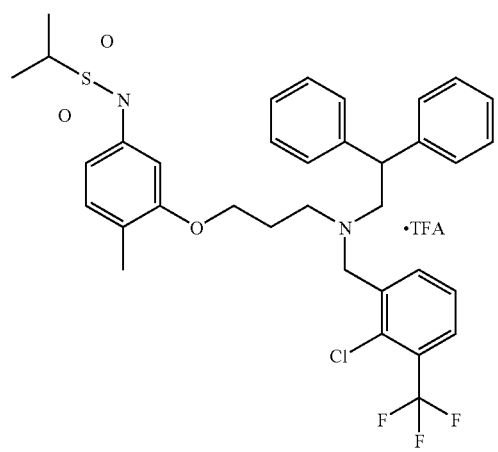

Following the procedure of Example 116 except substituting isopropylsulfonyl chloride for ethanesulfonyl chloride, the title compound was obtained as a yellow oil (20 mg, 84%): MS(ES) m/e 659.0 [M+H]$^+$.

EXAMPLE 118

Methanesulfonic acid (3-{3-[(2-Chloro-3-trifluoromethyl-benzyl)-(2,2-diphenyl-ethyl-amino)]-propoxy)-4-methyl-phenyl)-amide trifluoroacetic acid salt

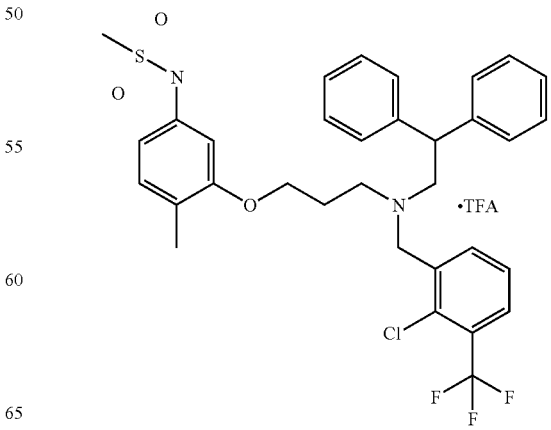

Following the procedure of Example 116 except substituting methanesulfonyl chloride for ethanesulfonyl chloride, the title compound was obtained as a yellow oil (20 mg, 86%): MS(ES) m/e 631.2 [M+H]⁺.

EXAMPLE 119

2,2,2-Trifluoro-ethanesulfonic acid (3-{3-[(2-Chloro-3-trifluoromethyl-benzyl)-(2,2-diphenyl-ethyl-amino)]-propoxy}-4-methyl-phenyl)-amide trifluoroacetic acid salt

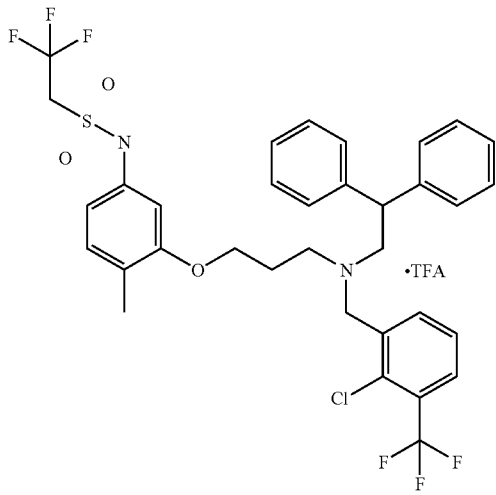

Following the procedure of Example 116 except substituting 2,2,2-trifluoro-ethanesulfonyl chloride for ethanesulfonyl chloride, the title compound was obtained as a yellow oil (22 mg, 87%): MS(ES) m/e 669.2 [M+H]⁺.

EXAMPLE 120

Ethanesulfonic acid (3-{3-[(2-Chloro-3-trifluoromethyl-benzyl)-(2,2-diphenyl-ethyl-amino)]-propoxy}-phenyl)-amide trifluoroacetic acid salt

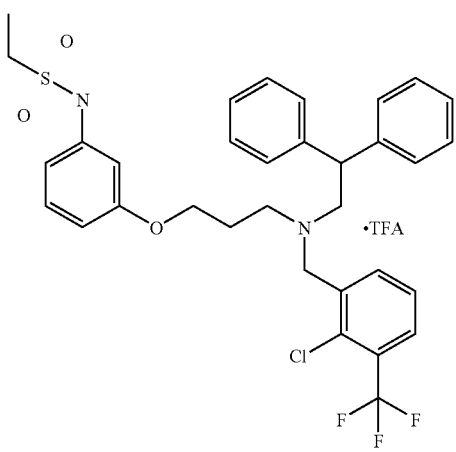

a) (2-Chloro-3-trifluoromethyl-benzyl)-(2,2-diphenyl-ethyl)-[3-(3-nitro-phenoxy)-propyl]-amine Following the procedure of Example 114 except substituting 3-nitro-phenol for 2-trifluoro-3-nitro-phenol in part c, the title compound was obtained as a clear oil (155 mg, 35%): MS(ES) m/e 568.6 [M+H]⁺.

b) 3-{3-[(2-Chloro-3-trifluoromethyl-benzyl)-(2,2-diphenyl-ethyl-amino)]-propoxy}-phenylamine Following the procedure of Example 114 except substituting (2-chloro-3-trifluoromethyl-benzyl)-(2,2-diphenyl-ethyl)-[3-(3-nitro-phenoxy)-propyl]-amine for (2-chloro-3-trifluoromethyl-benzyl)-(2,2-diphenyl-ethyl)-[3-(nitro-trifluoromethyl-phenoxy)-propyl]-amine in part d, the title compound was obtained as a clear oil (125 mg, 91%): MS(ES) m/e 539.2 [M+H]⁺.

c) Ethanesulfonic acid (3-{3-[(2-chloro-3-trifluoromethyl-benzyl)-(2,2-diphenyl-ethyl-amino)]-propoxy}-phenyl)-amide Following the procedure of Example 116 except substituting 3-{3-[(2-Chloro-3-trifluoromethyl-benzyl)-(2,2-diphenyl-ethyl-amino)]-propoxy}-phenylamine for {3-[(2-chloro-3-trifluoromethyl-benzyl)-(2,2-diphenyl-ethyl-amino)]-propoxy}-4-methyl-phenylamine, the title compound was obtained as a yellow oil (23 mg, 79%): MS(ES) m/e 631.2 [M+H]⁺.

EXAMPLE 121

2,2,2-Trifluoro-ethanesulfonic acid (3-{3-[(2-Chloro-3-trifluoromethyl-benzyl)-(2,2-diphenyl-ethyl-amino)]-propoxy}-phenyl)-amide trifluoroacetic acid salt

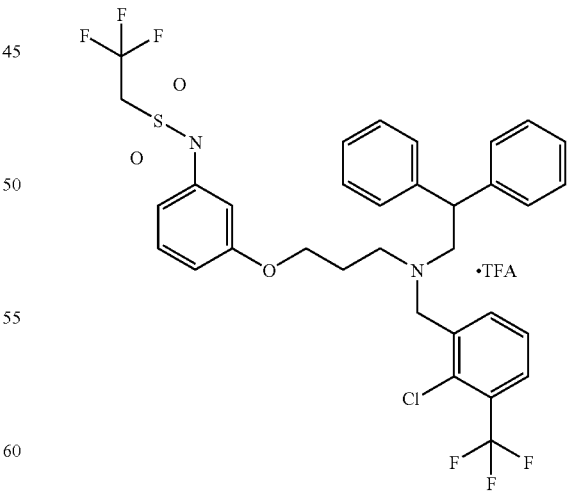

Following the procedure of Example 120 except substituting 2,2,2-trifluoro-ethanesulfonyl chloride for ethanesulfonyl chloride, the title compound was obtained as a yellow oil (25 mg, 79%): MS(ES) m/e 685.2 [M+H]⁺.

EXAMPLE 122

N-(3-{3-[(2-Chloro-3-trifluoromethyl-benzyl)-(2,2-diphenyl-ethyl-amino)]-propoxy}-phenyl)-1,1,1-trifluoro-methanesulfonamide trifluoroacetic acid salt

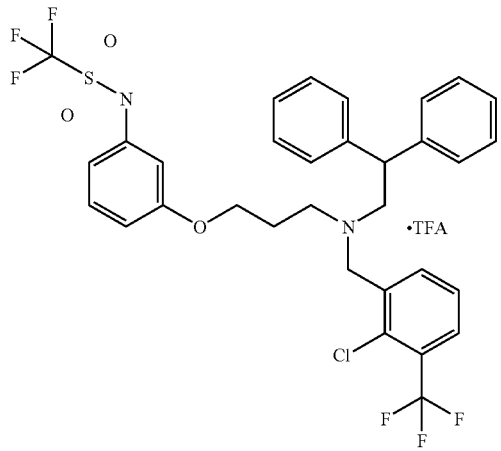

Following the procedure of Example 120 except substituting trifluoro-methanesulfonyl chloride for ethanesulfonyl chloride in part c, the title compound was obtained as a yellow oil (18 mg, 58%): MS(ES) m/e 671.2 [M+H]$^+$.

EXAMPLE 123

Propane-2-sulfonic acid (3-{3-[(2-Chloro-3-trifluoromethyl-benzyl)-(2,2-diphenyl-ethyl-amino)]-propoxy}-phenyl)-amide trifluoroacetic acid salt

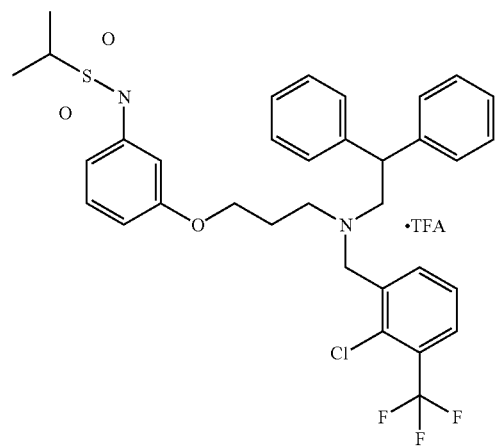

Following the procedure of Example 120 except substituting isopropylsulfonyl chloride for ethanesulfonyl chlorde in part c, the title compound was obtained as a yellow oil (21 mg, 71%): MS(ES) m/e 645.0 [M+H]$^+$.

EXAMPLE 124

{3-[(2-Chloro-3-trifluoromethyl-benzyl)-(2,2-diphenyl-ethyl-amino)]-propoxy}-4-methoxy-phenylamine

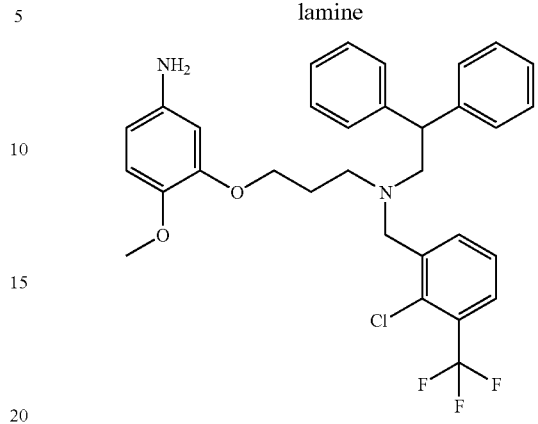

a) {3-[(2-Chloro-3-trifluoromethyl-benzyl)-(2,2-diphenyl-ethyl-amino)]-propoxy}-4-methoxy-phenyl carbamic acid tert-butyl ester Following the procedure of Example 114 except (3-hydroxy-4-methoxy-phenyl)-carbamic acid tert-butyl ester (Charpiot, Brigitte,s et al, *Bioorg. Med. Chem. Lett.*, 1998, 8, 2891-2896) for 2-trifluoro-3-nitro-phenol in part e, the title compound was obtained as a clear oil (110 mg, 12%): MS(ES) m/e 669.0 [M+H]$^+$.

b) {3-[(2-Chloro-3-trifluoromethyl-benzyl)-(2,2-diphenyl-ethyl-amino)]-propoxy}-4-methoxy-phenylamine To a solution of {3-[(2-chloro-3-trifluoromethyl-benzyl)-(2,2-diphenyl-ethyl-amino)]-propoxy}-4-methoxy-phenyl carbamic acid tert-butyl ester (0.05 g, 0.075 mmol) and CH$_2$Cl$_2$ (2 mL), TFA (0.20 mL, 1.2 mmol) was added and the reaction mixture was stirred for 1 h. The mixture was then poured into NaHCO$_3$, extracted with CH$_2$Cl$_2$, dried over Na$_2$SO$_4$, filtered, and concentrated to yield the product as a yellow oil (0.03 g, 70%): MS(ES) m/e 569.4 [M+H]$^+$.

EXAMPLE 125

Ethanesulfonic acid (3-{3-[(2-chloro-3-trifluoromethyl-benzyl)-(2,2-diphenyl-ethyl-amino)]-propoxy}-4-methoxy-phenyl)-amide trifluoroacetic acid salt

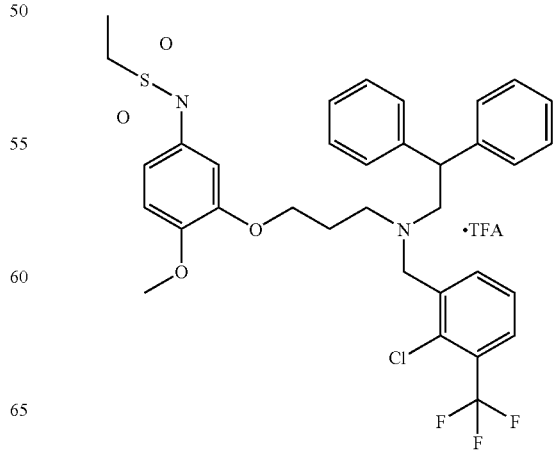

Following the procedure of Example 120 except substituting {3-[(2-chloro-3-trifluoromethyl-benzyl)-(2,2-diphenyl-ethyl-amino)]-propoxy}-4-methoxy-phenylamine for 3-{3-[(2-chloro-3-trifluoromethyl-benzyl)-(2,2-diphenyl-ethyl-amino)]-propoxy}-phenylamine in part c, the title compound was obtained as a yellow oil (21 mg, 71%): MS(ES) m/e 661.4 [M+H]⁺.

EXAMPLE 126

(2-Chloro-3-trifluoromethyl-benzyl)-{3-[3-(2-morpholinyl-4-yl-ethyl)-phenoxy]-propyl}-((S)-2-phenyl-propyl amine hydrochloride salt

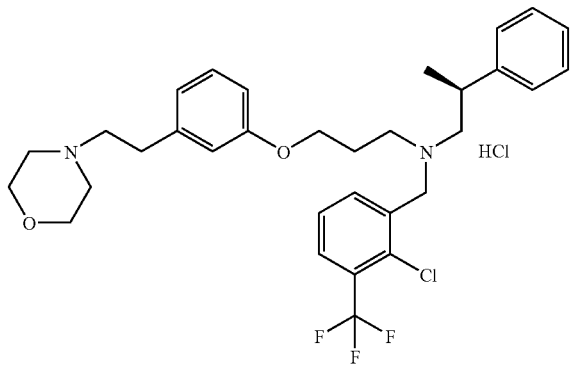

a) (2-chloro-3-trifluoromethyl-benzyl)-((S)-2-phenyl-propyl)-amine

To a solution of (S)-(−)-2-phenyl propylamine (0.5 g, 3.7 mmol) in dry dichloromethane (100 ml) was added acetic acid (2 drops) followed by 2-chloro-3-trifluoromethylbenzaldehyde (1.1 g, 5.5 mmol) and sodium triacetoxyborohydride (1.5 g, 7.4 mmol). After the resulting mixture was stirred for 1.5 h at room temperature, water was added to quench the reaction. The aqueous layer was extracted with ethyl acetate. The combined organic layers was washed with brine, dried over sodium sulfate and concentrated in vacuo. The crude mixture was purified by silica gel column chromatograph using EtOAc:Hexane/25:75 as the eluant to give 0.55 g (45% yield) of the title compound as an oil. MS m/e327.6 (M+H)⁺.

b) (3-{3-[[2-chloro-3-trifluoromethyl-benzyl](S-2-phenyl-propyl)amino]propoxy}-phenyl)acetic acid methyl ester A solution of (3-{3-bromo-propoxy}-phenyl)acetic acid methyl ester (0.55 g, 1.5 mmol) and (2-chloro-3-trifluoromethyl-benzyl)-((S)-2-phenyl-propyl)-amine (0.55 g, 1.6 mmol) in acetonitrile (10 ml) was treated with solid potassium carbonate (0.4 g, 2.4 mmol). The reaction was heated to reflux and stirred for 48 h. Upon cooling to room temperature, the reaction was filtered through a pad of celite, washed with EtOAc, and the filtrate was concentrated in vacuo. The crude product was purified by column chromatograph (EtOAc:Hexane/20:80) to give the title compound as an oil (0.6 g, 67%). MS m/e 534.6 (M+H)⁺.

c) 2-(3-{3-[[2-chloro-3-trifluoromethyl-benzyl](S-2-phenyl-propyl)amino]propoxy}-phenyl)acetic acid A solution of (3-{3-[[2-chloro-3-trifluoromethyl-benzyl](S-2-phenyl-propyl)amino]propoxy}-phenyl)acetic acid methyl ester (0.6 g, 1.1 mmol) in THF (9 ml) and water (6 ml) was added aqueous LiOH (1.0 N, 1.0 ml, 1.0 mmol). After stirring at room temperature for 2 h, additional LiOH (1.0 ml, 1.0 mmol) was added and stirring was continued for 2 h. The reaction was neutralized with AcOH and poured into water and ethyl acetate. The layers were separated and the aqueous layer was extracted with ethyl acetate. The combined organic layers were washed with brine, dried over sodium sulfate and concentrated in vacco. The crude mixture was purified by HPLC to give the title compound as an oil (0.4 g, 75%). MS m/e 520.2 (M+H)⁺.

d) 2-(3-{3-[(2-Chloro-3-trifluoromethyl-benzyl)-((S)-2-phenyl-propyl)-amino]-propoxy}-phenyl)-1-morpholin-4-yl-ethanone To a solution of 2-(3-{3-[[2-chloro-3-(trifluoromethyl)benzyl](S-2-phenyl-propyl)amino]propoxy}-phenyl)acetic acid (100 mg, 0.19 mmol) and morpholine (20 μl) in acetonitrile (20 ml) was added BOP reagent (88 mg, 0.20 mmol) followed by the addition of triethyl amine (2 drops). The reaction mixture was stirred at room temperature overnight and concentrated under vacuum. The residue was partitioned between EtOAc and 5% NaHCO₃. The combined organic layers was dried over sodium sulfate and concentrated to give the title compound as colorless oil (78 mg, 70%). MS m/e 589.2 (M+H)⁺.

e) (2-Chloro-3-trifluoromethyl-benzyl)-{3-[3-(2-morpholin-4-yl-ethyl)-phenoxy]-propyl}-((S)-2-phenyl-propyl amine hydrochloride salt To a solution of 2-(3-{3-[(Chloro-trifluoromethyl-benzyl)-((S)-2-phenyl-propyl)-amino]-propoxy}-phenyl)-1-morpholin-4-yl-ethanone (70 mg, 0.13 mmol) in toluene (20 ml) was added DIBAL (1.5M in toluene, 0.69 ml) dropwise at 0° C. After the reaction mixture was stirred at 0° C. for an additional 30 min it was warmed up to room temperature and stirred over night. The reaction was quenched by adding methanol and the organic layer was washed with water, brine and dried over sodium sulfate. After concentration, the crude mixture was purified by HPLC (YMC CombiPrep ODS-A, 50×20 mm, 20 mL/min, A: acetonitrile B: water, A: 60 to 100% during 10 min, UV detection at 254 nm) to give 35 mg (50% yield) of free amine of the title compound as an oil MS m/e575.2 (M+H)⁺. To a solution of the free amine in diethyl ether was added HCl in diethyl ether (1.0M) to precipitate the amine salt. The suspension was filtered and dried to give the title compound as a white solid.

EXAMPLE 127

(2-Chloro-3-trifluoromethyl-benzyl)-{3-[3-(2-ethylamino-ethyl)-phenoxy]-propyl}-((S)-2-phenyl-propyl)-amine hydrochloride salt

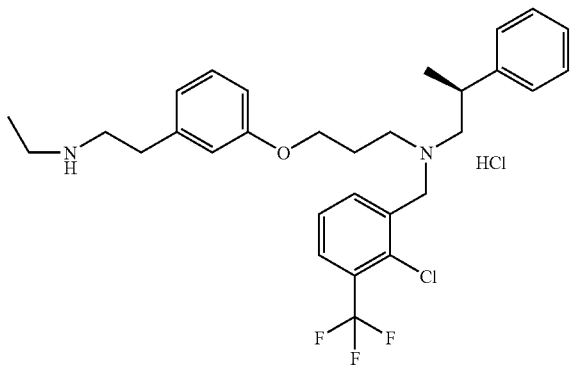

Following the procedure of Example 126 (a-e) except substituting ethylamine for morpholine in step d, the title compound was obtained as a white solid (35 mg, 45%). MS m/e 533.2 (M+H)⁺.

EXAMPLE 128

(3-{(R)-3-[(2-Chloro-3-trifluoromethyl-benzyl)-(S)-2-phenyl-propyl)-amino]-butoxy}-phenyl)-acetic acid hydrochloride salt

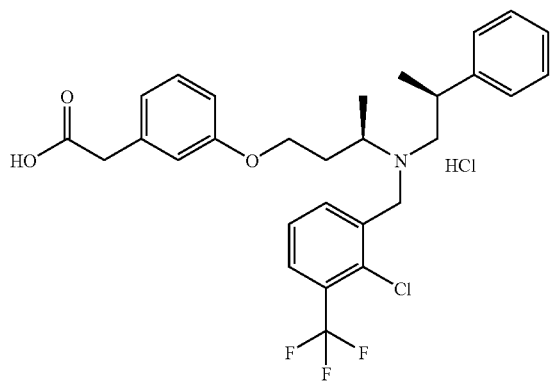

a) (S)-[3-(3-Hydroxy-butoxy)-phenyl]-acetic acid methyl ester

To a stirring solution of (3-hydroxy-phenyl)-acetic acid methyl ester (0.93 g, 0.0056 mole) and toluene-4-sulfonic acid-(S)-3-hydroxy-butyl ester (1.5 g, 0.0061 mole) in anhydrous DMF (10 mL) was added $Cs_2CO_3$ (2.0 g, 0.006 mole). The reaction was heated to 100° C. and stirred for 4 hours. The mixture was cooled to RT and filtered. The filtrate was poured into $H_2O$ (50 mL) and extracted three times with EtOAc. The combined organic layers were dried over sodium sulfate, filtered, and concentrated. The crude product was subjected to column chromatography over silica gel (silica gel 60, EM Science) using 30% EtOAc:hexane as eluent to afford 0.59 g (44% yield) of the title compound as an oil: MS (ESI) 239.0 (M+H⁺).

b) (S)-{3-[3-(Toluene-4-sulfonyloxy)-butoxy]-phenyl}-acetic acid methyl ester

To a stirring solution of (S)-[3-(3-hydroxy-butoxy)-phenyl]-acetic acid methyl ester (589 mg, 2.47 mmol) and triethylamine (376 mg, 3.71 mmol) in dichloromethane (10 mL) at 0° C. was added p-toluenesulfonyl chloride (944 mg, 4.95 mmol). The reaction was then stirred at RT for 30 min. and refluxed overnight. The reaction mixture was poured into $H_2O$ (40 mL) and extracted three times with dichloromethane. The combined organic extracts were dried over sodium sulfate, filtered, and concentrated. The crude product was purified by column chromatography over silica gel (silica gel 60, EM Science) using 15% EtOAc:hexane as eluent to afford 0.61 g (63% yield) of the title compound as an oil: MS (ESI) (M+H⁺).

c) {3-[(R)-3-((S)-2-Phenyl-propylamino)-butoxy]-phenyl}-acetic acid methyl ester A solution of {3-[(S)-3-(Toluene-4-sulfonyloxy)-butoxy]-phenyl}-acetic acid methyl ester (0.2 g, 0.51 mmol) and (S)-2-Phenyl-propylamine (0.19, 0.77 mmol) in acetonitrile (30 ml) was treated with solid potassium carbonate (0.149, 1.02 mmol). The reaction was heated to reflux and stirred for six days. Upon cooling to room temperature, the reaction was filtered through a pad of celite, washed with EtOAc, and the filtrate was concentrated in vacuo. The crude product was purified by column chromatograph (EtOAc:Hexane/20:80) to give the title compound as an oil (0.12 g, 40%). MS m/e 356.6 (M+H)⁺.

d) (3-{(R)-3-[(2-Chloro-3-trifluoromethyl-benzyl)-((S)-2-phenyl-propyl)-amino]-butoxy}-phenyl)-acetic acid methyl ester To a solution of {3-[(R)-3-((S)-2-Phenyl-propylamino)-butoxy]-phenyl}-acetic acid methyl ester (0.12 g, 0.34 mmol) in dry dichloromethane was added acetic acid followed by 2-chloro-3-trifluoromethylbenzaldehyde (0.1 g, 0.51 mmol) and sodium triacetoxyborohydride (0.149, 0.68 mmol). After the resulting mixture was stirred at room temperature overnight water was added to quench the reaction. The aqueous layer was extracted with ethyl acetate. The combined organic layers was washed with brine, dried over sodium sulfate and concentrated in vacco. The crude mixture was purified by silica gel column chromatography using EtOAc:Hexane/25:75 as the eluent to give 50 mg (40% yield) of the title compound as an oil MS m/e 548.4 (M+H)⁺.

e) (3-{(R)-3-[(2-Chloro-3-trifluoromethyl-benzyl)-((S)-2-phenyl-propyl)-amino]-butoxy}-phenyl)-acetic acid hydrochloride salt A solution of compound (3-{(R)-3-[(2-Chloro-3-trifluoromethyl-benzyl)-((S)-2-phenyl-propyl)-amino]-butoxy}-phenyl)-acetic acid methyl ester (50 mg, 0.1 mmol) in THF (9 ml) and water (6 ml) was treated with aqueous LiOH (1.0 N, 1.0 ml, 1.0 mmol). After stirring at room temperature for 2 h, additional LiOH (1.0 ml, 1.0 mmol) was added and stirring was continued for 2 h. The reaction was neutralized with AcOH and poured into water and ethyl acetate. The aqueous layer was extracted with EtOAc and the combined organic layers were washed with brine, dried over sodium sulfate and concentrated in vacco. The crude mixture was purified by HPLC (YMC CombiPrep ODS-A, 50×20 mm, 20 mL/min, A: acetonitrile B: water, A: 60 to 100% during 10 min, v detection at 254 nm) to give the free acid of title compound as an oil (40 mg, 75%). MS m/e 534.2 (M+H)+. To a solution of the free amine in diethyl ether was added HCl in diethyl ether (1.0M) to precipitate the HCl salt. The suspension was filtered and dried to give the title compound as a white solid.

EXAMPLE 129

(3-{(S)-3-[(2-Chloro-3-trifluoromethyl-benzyl)-((S)-2-phenyl-propyl)-amino]-butoxy}-phenyl)-acetic acid hydrochloride salt

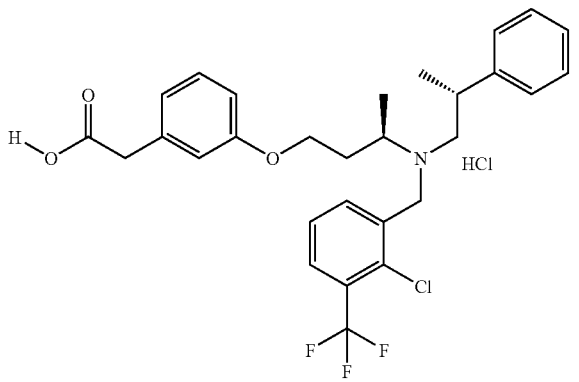

Following the procedure of Example 128 except toluene-4-sulfonic acid-(R)-3-hydroxy-butyl ester was used instead of toluene-4-sulfonic acid-(S)-3-hydroxy-butyl ester in step a, the title compound was obtained as a white solid (35 mg, 30%). MS (ESI): 534.2 (M+H)+

EXAMPLE 130

2-(3-{3-[(2-Chloro-3-trifluoromethyl-benzyl)-((S)-2-phenyl-propyl)-amino]-propoxy}-phenyl)-ethanol hydrochloride salt

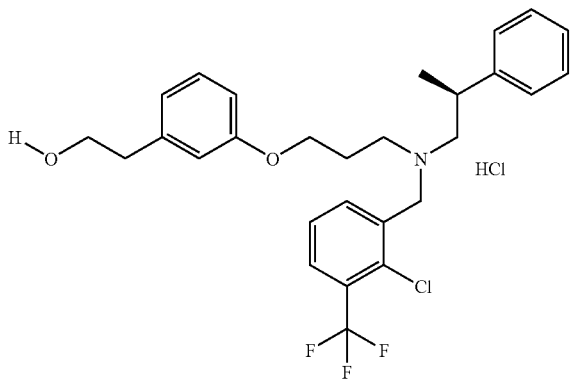

To a solution of (3-{3-[(2-Chloro-3-trifluoromethyl-benzyl)(S)-2-phenyl-propyl)-amino]-butoxy}-phenyl)-acetic acid methyl ester (Example 10c, 90 mg, 1.7 mmol) in THF (40 ml) was added LiAlH4 (0.4 ml, 1.0M in THF). The reaction mixture was heated to reflux for 1.5 h. After the mixture was cooled to room temperature water was added to quench the reaction which was then filtered. The filtrate was concentrated and the crude product was purified by silica gel column chromatograph using EtOAc:Hexane/25:75 as the eluent to give 30 mg (40% yield) of free amine of the title compound as an oil MS m/e506.4 (M+H)+. To a solution of the free amine in diethyl ether was added HCl in diethyl ether (1.0M) to precipitate HCl salt. The suspension was filtered and dried to give the title compound as a white solid.

EXAMPLE 131

2-(3-{3-[(2-Chloro-3-trifluoromethyl-benzyl)-((S)-2-phenyl-propyl)-amino]-propoxy}-phenyl)-2-methyl-propionic acid hydrochloride salt

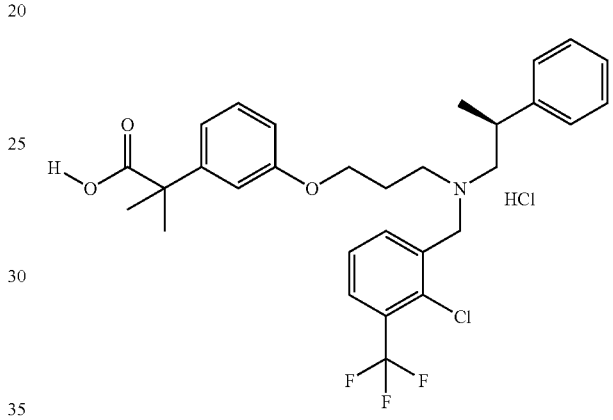

a) (3-{3-[(2-Chloro-3-trifluoromethyl-benzyl)-((S)-2-phenyl-propyl)-amino]-propoxy}-phenyl)-acetic acid methyl ester To a solution of (3-{3-[(2-Chloro-3-trifluoromethyl-benzyl)-((S)-2-phenyl-propyl)-amino]-propoxy}-phenyl)-acetic acid (Example 10, 0.5 g, 3.7 mmol) in methanol (300 ml) was added concentrated hydrochloric acid (10 ml). After the resulting mixture was heated to reflux for 2 h solvent was removed under vacuum. The residue was dissolved in water and neutralized to pH=7. The aqueous layer was extracted with ethyl acetate. The combined organic layers were washed with saturated sodium bicarbonate, brine, dried over sodium sulfate, and concentrated in vacco to give the title compound as colorless oil (0.5 g, 90%). MS m/e 534.6 (M+H)+.

b) 2-(3-{3-[(2-Chloro-3-trifluoromethyl-benzyl)-((S)-2-phenyl-propyl)-amino]-propoxy}-phenyl)-2-methyl-propionic acid methyl ester To a solution of (3-{3-[(2-Chloro-3-trifluoromethyl-benzyl)-diphenylethyl-amino]-propoxy}-phenyl)-acetic acid methyl ester (70 mg, 0.12 mmol) in dry THF (50 ml) was added lithium diisopropyl amide (1.7 ml, 1.2 mmol) dropwise when it was cooled to −78° C. After the reaction mixture was stirred at −78° C. for additional 1 h iodoethane (0.4 ml) was added. The reaction was warmed to room temperature over 4 h followed by quenching with saturated ammonium chloride (10 ml). Solvent was removed and the residue was partitioned between water and ethyl acetate. The combined organic layers were washed with brine, dried over sodium sulfate and concentrated under vacuum. The residue was purified by silica gel column chromatograph (EtOAc: Hexane/20:80) to give the title compound as an oil (37.2 mg, 50%). MS m/e 562.2 (M+H)+.

c) 2-(3-{3-[(2-Chloro-3-trifluoromethyl-benzyl)-((S)-2-phenyl-propyl)-amino]-propoxy}-phenyl)-2-methyl-propionic acid hydrochloride salt A solution of 2-(3-{3-[(2-Chloro-3-trifluoromethyl-benzyl)-((S)-2-phenyl-propyl)-amino]-propoxy}-phenyl)-2-methyl-propionic acid methyl ester (30 mg, 0.05 mmol) in DMF (9 ml) was treated with LiCl (20 mg, 0.46 mmol). The resulting reaction mixture was heated to reflux overnight and concentrated under vacuum. The crude product was purified by HPLC (YMC CombiPrep ODS-A, 50×20 mm, 20 mL/min, A: acetonitrile B: water, A: 60 to 100% during 10 min, UV detection at 254 nm) to give the title compound free amine as an oil (15 mg, 45%). MS m/e 548.2(M+H)+. To a solution of the free amine in diethyl ether was added HCl in diethyl ether (1.0M) to precipitate the amine salt. The suspension was filtered and dried to give the title compound as a white solid.

EXAMPLE 132

2-(3-{3-[(2-Chloro-3-trifluoromethyl-benzyl)-((R)-2-phenyl-propyl)-amino]-propoxy}-phenyl)-2-methyl-propionic acid hydrochloride salt

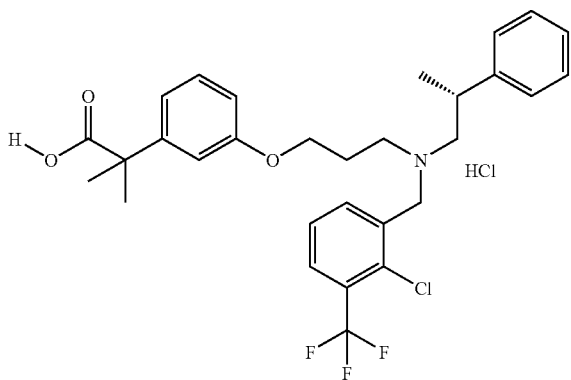

Following the procedure of Example 131 except substituting (3-{3-[(Chloro-trifluoromethyl-benzyl)-((R)-2-phenyl-propyl)-amino]-propoxy}-phenyl)-acetic acid (Example 11) for (3-(3-[(2-Chloro-3-trifluoromethyl-benzyl)-((S)-2-phenyl-propyl)-amino]-propoxy}-phenyl)-acetic acid in step a, the title compound was obtained as a white solid (25 mg, 35%). MS (ESI): 548.2 (M+H)+.

EXAMPLE 133

(3-{3-[(2-Chloro-3-trifluoromethyl-benzyl)-(2-thiophen-3-yl-propyl)-amino]-propoxy}-phenyl)-acetic acid hydrochloride salt

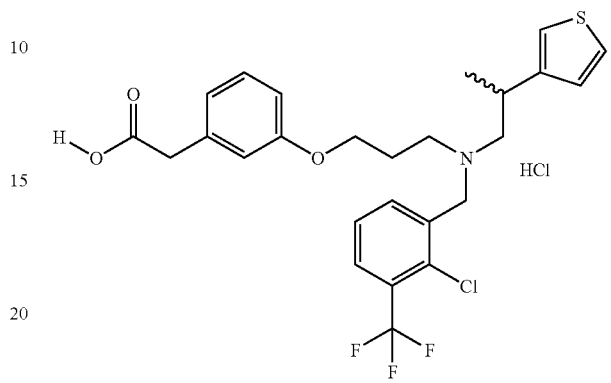

a) 2-thiophen-3-yl-propionaldehyde

A solution of methoxymethyldiphenyl phosphonium chloride (4 g, 11.9 mmol) in anhydrous ethanol (50 ml) was cooled to 0° C. and sodium ethoxide (0.8 g, 8.25 mmol) was added. After the mixture had warmed to room temperature, 1-thiophen-3-yl-ethanone (0.7 g, 5.9 mmol) was added and the reaction mixture was heated to 120° C. for 30 min in Microwave. The mixture was filtered and the filtrate was concentrated. The crude product was purified by silica gel column chromatograph using EtOAc:Hexane/20:80 as the eluent to give 0.5 g (54.5% yield) 3-((E or Z)-2-methoxy-1-methyl-vinyl)-thiophene. The solution of 3-((E or Z)-2-methoxy-1-methyl-vinyl)-thiophene in THF:HCl: H₂O (10 ml total, 9:0.5:1) was heated to 150° C. for 30 min in microwave. After the mixture was concentrated the residue was partitioned between EtOAc and water. The combined organic layers were washed with sodium bicarbonate, water, brine, dried over sodium sulfate and concentrated to give the title compound as an oil 250 mg (30%).

b) {3-[3-(2-chloro-3-trifluoromethyl-benzylamino)-propoxy]-phenyl}-acetic acid methyl ester A solution of [3-(3-bromo-propoxy)-phenyl]-acetic acid methyl ester (1.5 g, 5.26 mmol) and 2-chloro-3-trifluoromethyl-benzylamine (1 g, 4.77 mmol) in acetonitrile (300 ml) was treated with solid potassium carbonate (0.79 g, 5.74 mmol). The reaction was heated to reflux and stirred overnight. Upon cooling to room temperature, the reaction was filtered through a pad of celite, washed with EtOAc, and the filtrate was concentrated in vacuo. The crude product was purified by column chromatograph (EtOAc:Hexane/30:90) to give the title compound as an oil (1.5 g, 50%). MS m/e 402.2 (M+H)+.

c) (3-{3-[(2-Chloro-3-trifluoromethyl-benzyl)-(2-thiophen-3-yl-propyl)-amino]-propoxy}-phenyl)-acetic acid methyl ester To a solution of {3-[3-(2-chloro-3-trifluoromethyl-benzylamino)-propoxy]-phenyl}-acetic acid methyl ester (70 mg, 0.17 mmol) in dry dichloromethane (20 ml) was added acetic acid (2 drops) followed by 2-thiophen-3-yl-propionaldehyde (26 mg, 0.19 mmol) and sodium triacetoxyborohydride (72 mg, 0.34 mmol). After the resulting mixture was stirred at room temperature overnight, water was added to quench the reaction. The aqueous layer was extracted with ethyl acetate. The combined organic layers was washed with brine, dried over sodium sulfate and concentrated in vacco. The crude mixture was purified by HPLC (YMC CombiPrep ODS-A, 50×20 mm, 20 mL/min, A: acetonitrile B: water, A: 60 to 100% during 10 min, UV detection at 254 nm) to give 50 mg (32% yield) of the title compound as an oil MS m/e 541.4 (M+H)⁺.

d) (3-{3-[(Chloro-trifluoromethyl-benzyl)-(2-thiophen-3-yl-propyl)-amino]-propoxy}-phenyl)-acetic acid hydrochloride salt A solution of (3-{3-[(2-Chloro-3-trifluoromethyl-benzyl)-(2-thiophen-3-yl-propyl)-amino]-propoxy}-phenyl)-acetic acid methyl ester (30 mg, 0.07 mmol) in THF (9 ml) and water (6 ml) was treated with aqueous LiOH (1.0 N, 1.0 ml, 1.0 mmol). After stirring at room temperature for 2 h, additional LiOH (1.0 ml, 1.0 mmol) was added and stirring was continued for 2 h. The reaction was neutralized with AcOH and poured into water and ethyl acetate. The aqueous layer was extracted with EtOAc and the combined organic layers were washed with brine, dried over sodium sulfate and concentrated in vacco. The crude mixture was purified by HPLC (YMC CombiPrep ODS-A, 50×20 mm, 20 mL/min, A: acetonitrile B: water, A: 60 to 100% during 10 min, UV detection at 254 nm) to give the free acid of title compound as an oil (25 mg, 75%). MS m/e 527.2 (M+H)⁺. To a solution of the free amine in diethyl ether was added HCl in diethyl ether (1.0M) to precipitate HCl salt. The suspension was filtered and dried to give the title compound as a white solid.

EXAMPLE 134

2-(3-{3-[(2-Chloro-3-trifluoromethyl-benzyl)-(2-thiophen-3-yl-propyl)-amino]-propoxy}-phenyl)-ethanol hydrochloride salt

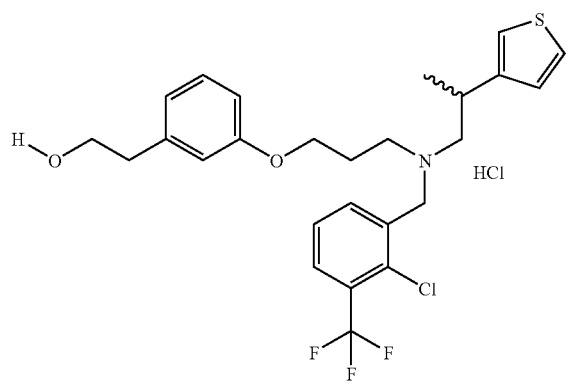

a) The procedure of Example 131 (a-c) was used to make (3-{3-[(2-Chloro-3-trifluoromethyl-benzyl)-(2-thiophen-3-yl-propyl)-amino]-propoxy}-phenyl)-acetic acid methyl ester b) 2-(3-{3-[(2-Chloro-3-trifluoromethyl-benzyl)-(2-thiophen-3-yl-propyl)-amino]-propoxy}-phenyl)-ethanol hydrochloride salt To a solution of (3-{3-[(2-Chloro-3-trifluoromethyl-benzyl)-(2-thiophen-3-yl-propyl)-amino]-propoxy}-phenyl)-acetic acid methyl ester (50 mg, 0.1 mmol) in THF (20 ml) was added LiAlH₄ (0.2 ml, 11.0M in diethyl ether). After the reaction mixture was heated to reflux for 4 h it was cooled down to room temperature followed by the addition of NaOH (1 ml, 2N) to quench the reaction. The reaction mixture was filtered and the filtrate was concentrated. The crude product was purified by HPLC (YMC CombiPrep ODS-A, 50×20 mm, 20 mL/min, A: acetonitrile B: water, A: 60 to 100% during 10 min, UV detection at 254 nm) to give the free amine of the title compound as an oil (25 mg, 40%). MS m/e 512.2 (M+H)⁺. To a solution of the free amine in diethyl ether was added HCl in diethyl ether (1.0M) to precipitate the HCl salt The suspension was filtered and dried to give the title compound as a white solid.

EXAMPLE 135

(3-{3-[(2-Chloro-3-trifluoromethyl-benzyl)-(2-thiophen-2-yl-propyl)-amino]-propoxy}-phenyl)-acetic acid hydrochloride salt

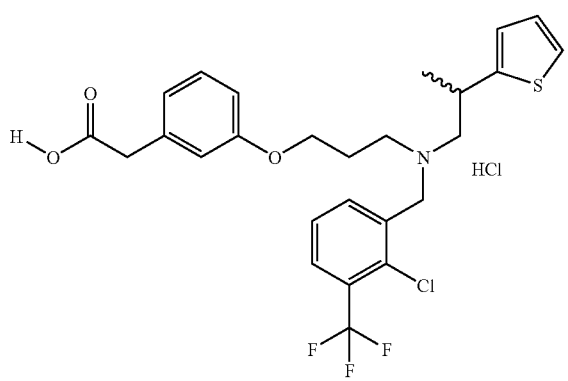

a) 2-thiophen-2-yl-propionaldehyde

To a solution of diethylisocyanomethylphosphonate in diethyl ether (40 ml) was added butyl lithium (6.9 ml, 1.6M in hexane) dropwise at −60° C. After the reaction mixture was stirred at −60° C. for additional 15 min a solution of 2-acetylthiophene (1.26 g, 10 mmol) in diethyl ether (10 ml) was added at the same temperature. The reaction mixture was warmed up to 0° C. and was stirred for 1.5 h. Concentrated HCl (15 ml) was added at 0° C. and then ice bath was removed. After the resulting mixture was stirred at room temperature overnight it was poured to cold water (20 ml).

The organic layer was washed with water, sat. sodium bicarbonate, brine, dried over sodium sulfate and concentrated. The crude product was used in the next step without purification.

b) (2-chloro-3-trifluoromethyl-benzyl)-(2-thiophen-2-yl-propyl)-amine

To a solution of 2-thiophen-2-yl-propionaldehyde (100 mg, 0.7 mmol) in dry dichloromethane (20 ml) was added 2-chloro-3-trifluoromethyl-benzylamine (30 mg, 0.14 mmol) followed by the addition of sodium triacetoxyborohydride (60.5 mg, 0.28 mmol). After the resulting mixture was stirred at room temperature overnight water was added to quench the reaction. The aqueous layer was extracted with ethyl acetate. The combined organic layers was washed with brine, dried over sodium sulfate and concentrated in vacco. The crude mixture was purified by silica gel column chromatograph using EtOAc:Hexane/25:75 as the eluent to give 50 mg (40% yield) of the title compound as an oil. MS m/e 334.4 (M+H)+.

c) (3-{3-[(2-chloro-3-trifluoromethyl-benzyl)-(2-thiophen-2-yl-propyl)-amino]-propoxy}-phenyl)-acetic acid methyl ester A solution of (3-{3-bromo-propoxy}-phenyl)acetic acid methyl ester (41 mg, 0.14 mmol) and (2-chloro-3-trifluoromethyl-benzyl)-(2-thiophen-2-yl-propyl)-amine (50 mg, 10.14 mmol) in acetonitrile (10 ml) was treated with solid potassium carbonate (24.9 mg, 0.18 mmol). The reaction was heated to reflux and stirred for 48 h. Upon cooling to room temperature, the reaction was filtered through a pad of celite, washed with EtOAc, and the filtrate was concentrated in vacuo. The crude product was purified by column chromatograph (EtOAc:Hexane/20:80) to give the title compound as an oil (25 mg, 30%). MS m/e 540.6 (M+H)+.

d) (3-{3-[(2-Chloro-3-trifluoromethyl-benzyl)-(2-thiophen-2-yl-propyl)-amino]-propoxy}-phenyl)-acetic acid hydrochloride salt A solution of (3-{3-[(2-chloro-3-trifluoromethyl-benzyl)-(2-thiophen-2-yl-propyl)-amino]-propoxy}-phenyl)-acetic acid methyl ester (25 mg, 0.05 mmol) in THF (9 ml) and water (6 ml) was treated with aqueous LiOH (1.0 N, 0.29 ml, 1.0 mmol). After stirring at room temperature for 2 h, additional LiOH (0.29 ml, 1.0 mmol) was added and stirring was continued for 2 h. The reaction was neutralized with AcOH and poured into water and ethyl acetate. The layers were separated and the aqueous layer was extracted with EtOAc. The combined organic layers were washed with brine, dried over sodium sulfate and concentrated in vacco. The crude mixture was purified by HPLC to give the free amine of title compound as an oil (15 mg, 58%). MS m/e 520.2 (M+H)+. To a solution of the free amine in diethyl ether was added HCl in diethyl ether (1.0M) to precipitate HCl salt The suspension was filtered and dried to give the title compound as a white solid.

EXAMPLE 136

(3-{3-[(2-Chloro-3-trifluoromethyl-benzyl)-(2-pyridin-2-yl-propyl)-amino]-propoxy}-phenyl)-acetic acid hydrochloride salt

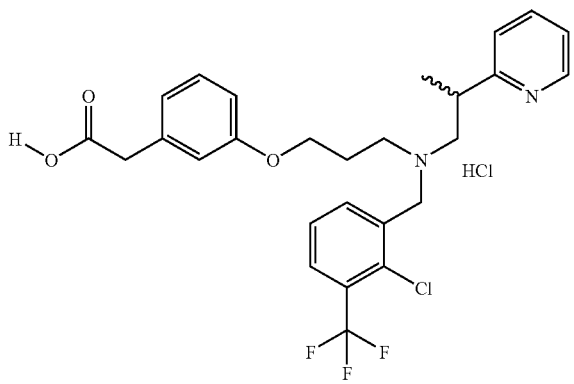

Following the procedure of Example 133 a-d, except substituting 1-pyridin-2-yl-ethanone for 2-acetylthiophene in step a, the title compound was obtained as a white solid (15 mg, 50%). MS (ESI): 522.0 (M+H)+

EXAMPLE 137

[3-(3-{(2-Chloro-3-trifluoromethyl-benzyl)-[2-(4-methyl-pyridin-2-yl)-propyl]-amino}-propoxy)-phenyl]-acetic acid hydrochloride salt

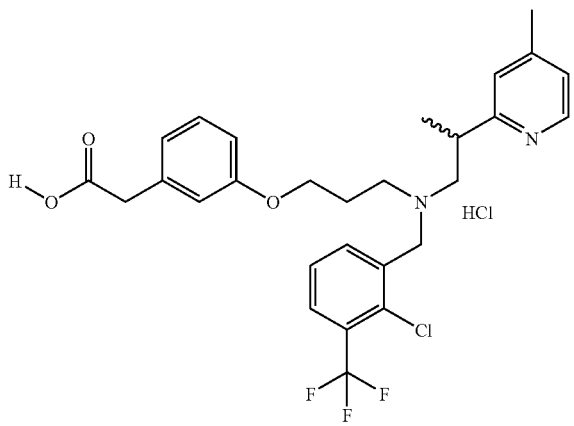

Following the procedure of Example 133 a-d, except substituting 1-(4-methyl-pyridin-2-yl)-ethanone for 2-acetylthiophene in step a, the title compound was obtained as a white solid (15 mg, 50%). MS (ESI): 535.0 (M+H)+.

EXAMPLE 138

[3-(3-{(2-Chloro-3-trifluoromethyl-benzyl)-[3,3,3-trifluoro-2-(1H-pyrrol-2-yl)-propyl]-amino}-propoxy)-phenyl]-acetic acid hydrochloride salt

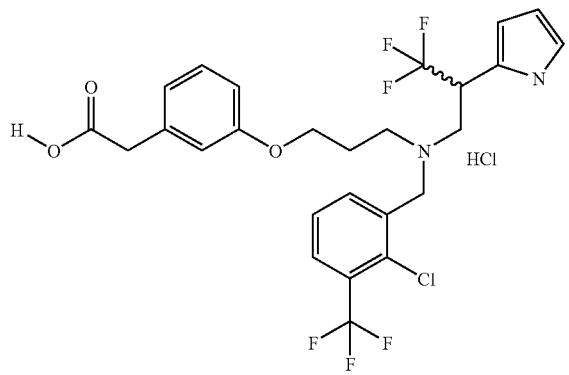

Following the procedure of Example 126 a-c, except substituting 3,3,3-trifluoro-2-(1H-pyrrol-2-yl)-propylamine for (S)-(−)-2-phenyl propylamine in step a, the title compound was obtained as a white solid (15 mg, 50%). MS (ESI): 563.6 (M+H)$^+$

Intermediate 1

2-(3-{3-[(2-Chloro-3-(trifluoromethyl)-benzyl)-(2,2-diphenylethyl)-amino]-propoxy}phenyl)-1-morpholin-4-yl-ethanone hydrochloride salt

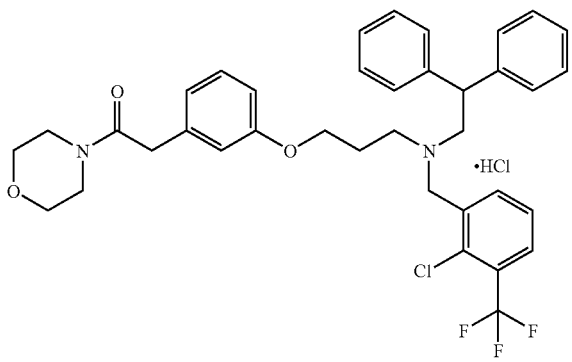

a) Methyl [3-(3-bromopropoxy)phenyl]acetate

A solution of methyl 3-hydroxyphenylacetate (11.3 g, 0.068 mole) in 300 mL of anhydrous toluene was treated with 3-bromopropanol (12.2 g, 0.088 mole). Polymer bound triphenylphosphine (36.0 g, 0.108 mole, 3 mmol/g, Fluka Chemie) was then added, and the mixture reacted for 15 minutes. The reaction mixture was then cooled to 0° C. and diisopropylazodicarboxylate (16.9 g, 0.084 mol) was added in a dropwise fashion. After stirring at room temperature overnight, the crude reaction mixture was filtered and the solid washed with 100 mL toluene. After concentration of the filtrate in vacuo, the crude product was purified by column chromatography over silica gel (silica gel 60, EM Science) using 15% EtOAc:hexane as eluent to afford 15.8 g (81% yield) of the title compound as an oil:
$^1$H NMR (CDCl$_3$, 400 MHz) δ 7.23-7.19 (m, 1 H), 6.85-6.7 (m, 3), 4.09-4.06 (t, 2 H. J=5.8), 3.67 (s, 3 H) 3.67-3.56 (m, 4 H), 2.32-2.26 (p, 2 H, J=6.0); MS (ESP+) m/e 288 (MH$^+$); TLC (hexanes:EtOAc/3:1) R$_f$=0.68. Anal. (C$_{12}$H$_{15}$O$_3$Br) C, H, N.

b) N-[2-Chloro-3-(trifluoromethyl)benzyl]-N-(2,2-diphenylethyl)amine

A solution of 2,2-diphenethylamine (10.0 g, 50.7 mmol) and 2-chloro-3-trifluoromethylbenzaldehyde (10.5 g, 50.7 mmol) in 80 mL of methanol and 40 mL of trimethylorthoformate was stirred at room temperature for 15 hours whereupon polymer-supported borohydride resin (20.3 g, 55.8 mmol, 2.5 mmol/g, Aldrich) was added in one portion. After stirring at room temperature for 24 h, the reaction was filtered and the filtrate was concentrated in vacuo. The crude product was purified by column chromatography over silica gel (silica gel 60, EM Science) using EtOAc:hexane/40:60 with 1% NH$_4$OH as the eluent to give 11.2 g (57% yield) of the title compound as an oil: $^1$H NMR (CDCl$_3$, 400 MHz) δ 7.57 (d, 1 H, J=8.0), 7.52 (d, 1 H, J=7.6), 7.32-7.15 (m, 11 H), 4.20 (t, 1 H, J=7.6), 3.94 (s, 2 H), 3.22 (d, 2 H, J=7.6); HPLC (Waters symmetry shield, RPq 3.5 micron, 2.1×30 mm, 85:15/H$_2$O:CH$_3$CN with 0.1% HCOOH to 100% CH$_3$CN after 4 min, flow rate=0.8 mL/min) t$_R$=2.39 min; MS (ESP+) m/e 390 (MH$^+$); TLC (hexanes:EtOAc/4:1) R$_f$=0.42.

c) Methyl (3-{3-[[2-Chloro-3-(trifluoromethyl)benzyl](2,2-diphenylethyl)amino]propoxy}phenyl)acetate A solution of methyl [3-(3-bromopropoxy)phenyl]acetate (1.0 g, 3.48 mmole) and N-[2-chloro-3-(trifluoromethyl)benzyl]-2,2-diphenylethanamine (1.63 g, 4.18 mmole) in 20 mL of acetonitrile was treated with potassium carbonate (0.72 g, 5.2 mmol). The reaction mixture was heated to reflux and stirred for 4 days. The reaction mixture was filtered, and the filtrate was concentrated in vacuo. The crude product was purified by flash chromatography (silica gel cartridge, Biotage 32-63 um, 60A) with 10% EtOAc:hexanes as the eluent to afford 1.69 g (81% yield) of the title compound as a viscous oil: $^1$H NMR (CDCl$_3$, 400 MHz) δ 7.46-7.44 (d, 1 H, J=7.7), 7.25-7.14 (m, 12 H), 6.91-6.84 (m, 2 H), 6.66-6.62 (m, 2 H), 4.15-4.09 (t, 1 H. J=7.6), 3.78 (s, 1 H), 3.69-3.66 (m, 5 H), 3.59(S, 2 H), 3.15-3.13 (d, 2 H, J=7.7), 2.72-2.68 (t, 2 H, J=6.6), 1.87-1.80 (m, 2 H); MS (ESP+) m/e 597 (MH$^+$); TLC (hexanes:EtOAc/9:1) R$_f$=0.36.

d) 2-(3-{3-[[2-Chloro-3-(trifluoromethyl)benzyl](2,2-diphenylethyl)amino]propoxy}-phenyl)acetic acid hydrochloride salt A solution of methyl (3-{3-[[2-chloro-3-(trifluoromethyl)benzyl](2,2-diphenylethyl)amino]propoxy}phenyl)acetate (113 mg, 0.19 mmol) in 1.5 mL of tetrahydrofuran and 1 mL of water was treated with 1 N aqueous LiOH (0.29 mL, 0.29 mmol). After stirring at room temperature for 2 hours, additional 1N aqueous LiOH (0.29 mL, 0.29 mmol) was added and stirring was continued for 2 hours. The reaction was neutralized with AcOH (66 μL, 0.58 mmol) and poured into H$_2$O/EtOAc. The layers were separated and the aqueous layer was extracted with EtOAc (3×). The combined organic layers were washed with brine (1×), dried over magnesium sulfate, filtered, and concentrated in vacuo. The crude material was purified by preparative thin layer chromatography (silica gel, 1 mm plates, Merck 20×20 cm silica gel 60 $F_{254}$) eluting with $CH_2Cl_2$:MeOH (95:5) to afford an oil. The oil was dissolved in $Et_2O$ and acidified with excess $HCl/Et_2O$. The reaction was concentrated in vacuo and dried under reduced pressure to give 65 mg (56% yield) of the title compound as a white solid: H NMR ($C_5D_5N$, 400 MHz) δ 7.60-7.05 (m, 15 H), 7.01 (t, 1 H, J=7.6), 6.84 (dd, 1 H, J=8.4, 2.4), 4.32 (t, 1 H, J=7.6), 3.89 (s, 2 H), 3.77 (s, 2 H), 3.71 (t, 2 H, J=5.6), 3.16 (d, 2 H, J=7.6), 2.65 (t, 2 H, J=6.4), 1.88-1.78 (m, 2 H).

e) 2-(3-{3-[(2-Chloro-3-(trifluoromethyl)-benzyl)-(2,2-diphenylethyl)-amino]-propoxy}phenyl)-1-morpholin-4-yl-ethanone hydrochloride salt 2-{3-[[2-chloro-3-(trifluoromethyl)benzyl)(2,2-diphenylethyl)-amino]-propoxy}-phenyl acetic acid (50 mg, 0.086 mmole) and morpholine (8.7 mg, 0.10 mmole) were dissolved in $CH_3CN$ (2 ml). BOP reagent (44 mg, 0.10 mmole) was added followed by $Et_3N$ (20 mg, 0.20 mmole). The resultant mixture was stirred at room temperature for 2 h. The mixture was concentrated under reduced pressure. The residue was partitioned between EtOAc and aqueous $Na_2CO_3$ (5%) solution. The organic layer was separated, dried over $MgSO_4$ and concentrated. In cases where the product required further purification, a preparative Gilson HPLC was used (YMC CombiPrep ODS-A, 50×20 mm, 20 m/min, 30-90% $CH_3CN$ over 15 minutes). The HCl salt was made by adding HCl (in ether) to an ether solution of the product and then evaporation of the solvent to give a yellow solid (32 mg, 54%). MS(ES) m/e 651.2 $[M+H]^+$.

Following the procedure from Intermediate 1, the following amides were prepared:

| In. | Amine | Compound Name | M/S |
|---|---|---|---|
| 2 | 4-methyl-piperazine | 2-(3-{3-[(2-Chloro-3-(trifluoro-methyl)-benzyl)-(2,2-diphenylethyl)-amino]-propoxy}phenyl)-1-(4-methyl-piperazin-1-yl)-ethanone hydrochloride salt | 664.2 (M + H⁺) |
| 3 | methylamine | 2-(3-{3-[(2-Chloro-3-(trifluoro-methyl)-benzyl)-(2,2-diphenylethyl)-amino]-propoxy}phenyl)-N-methyl-acetamide hydrochloride salt | 595.2 (M + H⁺) |
| 4 | (1H-Imidazol-2-yl)-methylamine | 2-(3-{3-[(2-chloro-3-trifluoromethyl-benzyl)-diphenylethyl-amino]-propoxy}-phenyl)-N-(1H-imidazol-2-ylmethyl)-acetamide hydrochloride salt | 661.4 (M⁺) |
| 5 | (5-Bromo-thiophen-2-yl)-methylamine | N-(5-Bromo-thiophen-2-ylmethyl)-2-(3-{3-[(2-chloro-3-trifluoromethyl-benzyl)-diphenylethyl-amino]-propoxy}-phenyl)-acetamide hydrochloride salt | 755.2 (M − H)⁺ |
| 6 | Thiophen-2-yl-methylamine | 2-(3-{3-[(2-chloro-3-trifluoromethyl-benzyl)-diphenylethyl-amino]-propoxy}-phenyl)-N-thiophen-2-ylmethyl-acetamide hydrochloride salt | 677.2 (M⁺) |
| 7 | ethylamine | 2-(3-{3-[(2-Chloro-3-(trifluoro-methyl)-benzyl)-(2,2-diphenylethyl)-amino]-propoxy}phenyl)-N-ethyl-acetamide hydrochloride salt | 609.2 (M + H⁺) |
| 8 | dimethylamine | 2-(3-{3-[(2-Chloro-3-(trifluoro-methyl)-benzyl)-(2,2-diphenylethyl)-amino]-propoxy}phenyl)-N,N-di-methyl-acetamide hydrochloride salt | 609.4 (M + H⁺) |
| 9 | pyrrolidine | 2-(3-{3-[(2-Chloro-3-(trifluoro-methyl)-benzyl)-(2,2-diphenylethyl)-amino]-propoxy}phenyl)-1-pyrrolidin-1-yl-ethanone hydrochloride salt | 635.4 (M + H⁺) |

Intermediate 10

(R)-2-(3-{3-[(2-Chloro-3-trifluoromethyl)-benzyl)-(2,2-diphenylethyl)-amino]-2-methyl-propoxy}phenyl)-1-morpholin-4-yl-ethanone hydrochloride salt

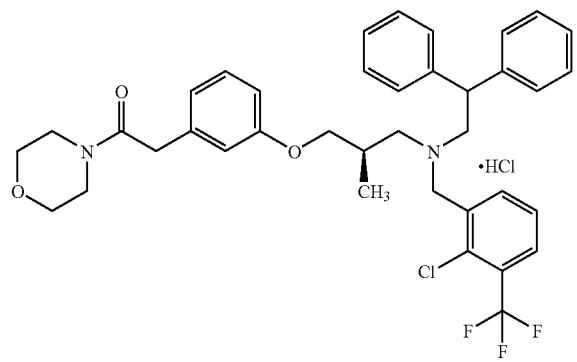

a) (3-Hydroxy-phenyl)-acetic acid methyl ester

To a stirring solution of (3-hydroxy-phenyl)-acetic acid (4.3 g, 0.028 mole) in methanol (30 mL) was added $H_2SO_4$ (1 mL) and the mixture was heated to reflux for 2 hours. The solvent was removed, the residue was washed with $H_2O$, and extracted three times with EtOAc (ethyl acetate). The combined organic layers were dried over $Na_2SO_4$, filtered, and concentrated to give 4.7 g (99% yield) of the title compound as an oil. MS (ESI) 167.0(M+H⁺).

b) (S)-[3-(2-Methyl-3-bromopropoxy)phenyl]acetic acid methyl ester

To a stirring solution of (3-hydroxy-phenyl)-acetic acid methyl ester (0.75 g, 0.0045 mole) in anhydrous toluene (30 mL) was added (S)-(+)-3-bromo-2-methyl-1-propanol (0.90 g, 0.0059 mole). Polymer bound triphenylphosphine (2.4 g, 0.0072 mole, 3 mmol/g, Fluka Chemie) was then added, and the mixture was stirred for 15 minutes. The reaction mixture was then cooled to 0° C. and diisopropylazodicarboxylate (1.1 g, 0.00560 mole) was added In a dropwise fashion. After stirring at room temperature overnight, the crude reaction mixture was filtered, and the solid washed with toluene. After concentration of the filtrate in vacuo, the crude product was purified by column chromatography over silica gel (silica gel 60, EM Science) using 15% EtOAc:hexane as eluent to afford 0.86 g (63% yield) of the title compound as an oil: MS (ESI) 303.0 (M+2H⁺).

c) N-(2,2-Diphenylethyl)-N-(2-chloro-3-trifluoromethyl-benzyl)amine

To a stirring solution of 2,2-diphenethylamine (2.0 g, 0.010 mole) and 2-chloro-3-trifluoromethylbenzaldehyde (2.33 g, 0.011 mole) in dichloromethane (20 mL) was added sodium triacetoxyborohydride (2.36 g, 0.011 mole) and acetic acid (2.0 mL). The reaction mixture was stirred overnight Solvent was removed, the residue was washed with saturated NaHCO$_3$, and extracted three times with EtOAc. The organic extracts were dried over Na$_2$SO$_4$, filtered, and concentrated. The crude mixture was subjected to column chromatography over silica gel (silica gel 60, EM Science) using 30% EtOAc:hexane as eluent to afford 3.0 g (76% yield) of the title compound as a yellow oil: MS (ESI) 390.0 (M+H$^+$).

d) (R)-2-(3-{3-[[2-Chloro-3-(trifluoromethyl)benzyl](2,2-diphenylethyl)amino]-2-methyl-propoxy}-phenyl)acetic acid methyl ester To a stirring solution of (S)-[3-(2-methyl-3-bromopropoxy)phenyl]acetic acid methyl ester (100 mg, 0.33 mmol) and N-(2,2-diphenylethyl)-N-(2-chloro-3-trifluoromethyl)amine (130 mg, 0.33 mmol) in acetonitrile (5 mL) was added solid K$_2$CO$_3$ (138 mg, 1.0 mmol) and NaI (149 mg, 1.0 mmol). The reaction was heated to reflux and stirred overnight Upon cooling to room temperature, the reaction was filtered, washed with acetonitrile, and the filtrate was concentrated. The crude product was purified by preparative HPLC (TMC CombiPrep PDS, 75×30 mm, 25 mL/min, acetonitrile:H$_2$O, UV detection at 254 nm) to give 29 mg (14% yield) of title compound as a viscous oil. MS(ESI) 610.2(M$^+$).

e) (R)-2-(3-{3-[[2-Chloro-3-(trifluoromethyl)benzyl](2,2-diphenylethyl)amino]-2-methyl-propoxy}-phenyl)acetic acid hydrochloride salt To a stirring solution of (R)-2-(3-{3-[[2-chloro-3-(trifluoromethyl)benzyl](2,2-diphenylethyl)amino]-2-methyl-propoxy}-phenyl)acetic acid methyl ester (22 mg, 0.0361 mmol) in THF (0.75 ml) and water (0.25 ml) was treated with LiOH (3.0 mg, 0.072 mmol). The reaction mixture was stirred overnight at RT. The reaction mixture was concentrated and 3 N HCl (aq.) was added until the pH was less than two. The aqueous layer was extracted three times with EtOAc, the combined organic layers were dried over sodium sulfate, filtered, and concentrated. The resulting amine/carboxylic acid was dissolved in Et$_2$O (diethylether) and acidified with 1.0 M HCl/Et$_2$O. The reaction mixture was concentrated in vacuo and dried under reduced pressure to give 18 mg (78% yield) of the title compound as a white solid. MS(ESI) 596.0(M$^+$).

f) (R)-2-(3-{3-[(2-Chloro-3-(trifluoromethyl)-benzyl)-(2,2-diphenylethyl)-amino]-2-methyl-propoxy}phenyl)-1-morpholin-4-yl-ethanone hydrochloride salt Following the procedure of Intermediate 1 step (e) except (R)-2-(3-{3-[[2-Chloro-3-(trifluoromethyl)benzyl](2,2-diphenylethyl)amino]-2-methyl-propoxy}-phenyl)acetic acid was used instead of 2-(3-{3-[[2-chloro-3-(trifluoromethyl)benzyl)(2,2-diphenylethyl)-amino]-propoxy}-phenyl acetic acid in step 1(e) the title compound was prepared as a white solid.
MS(ESI) 665.4 (M$^+$).

Intermediate 11

2-(3-{(R)-3-[(2-chloro-3-trifluoromethyl-benzyl)-diphenylethyl-amino]-butoxy}-phenyl)-1-morpholin-4-yl-ethanone hydrochloride salt

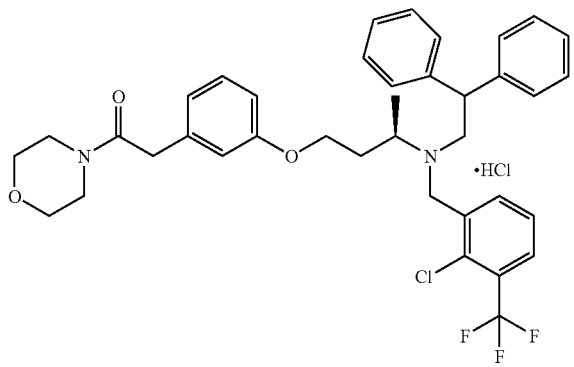

a) (S)-[3-(3-Hydroxy-butoxy)-phenyl]-acetic acid methyl ester

To a stirring solution of (3-hydroxy-phenyl)-acetic acid methyl ester (0.93 g, 0.0056 mole) and toluene-4-sulfonic acid-(S)-3-hydroxy-butyl ester (1.5 g, 0.0061 mole) in anhydrous DMF (10 mL) was added Cs$_2$CO$_3$ (2.0 g, 0.006 mole). The reaction was heated to 100° C. and stirred for 4 hours. The mixture was cooled to RT and filtered. The filtrate was poured into H$_2$O (50 mL) and extracted three times with EtOAc. The combined organic layers were dried over sodium sulfate, filtered, and concentrated. The crude product was subjected to column chromatography over silica gel (silica gel 60, EM Science) using 30% EtOAc:hexane as eluent to afford 0.59 g (44% yield) of the title compound as an oil: MS (ESI) 239.0 (M+H$^+$).

b) (S)-{3-[3-(Toluene-4-sulfonyloxy)-butoxy]-phenyl}-acetic acid methyl ester To a stirring solution of (S)-[3-(3-hydroxy-butoxy)-phenyl]-acetic acid methyl ester (589 mg, 2.47 mmol) and triethylamine (376 mg, 3.71 mmol) in dichloromethane (10 mL) at 0° C. was added p-toluenesulfonyl chloride (944 mg, 4.95 mmol). The reaction was then stirred at RT for 30 min. and refluxed overnight. The reaction mixture was poured into H$_2$O (40 mL) and extracted three times with dichloromethane. The combined organic extracts were dried over sodium sulfate, filtered, and concentrated. The crude product was purified by column chromatography over silica gel (silica gel 60, EM Science) using 15% EtOAc:hexane as eluent to afford 0.61 g (63% yield) of the title compound as an oil: MS (ESI) (M+H$^+$).

c) (R)-2-(3-{3-[(2,2-Diphenylethyl)amino]-3-methyl-propoxy}-phenyl)acetic acid methyl ester To a stirring solution of 2,2-diphenethylamine (151 mg, 0.765 mmol) and (S){3-[3-(toluene-4-sulfonyloxy)-butoxy]-phenyl)-acetic acid methyl ester (300 mg, 0.765 mmol) in 5 mL acetonitrile was treated with solid K$_2$CO$_3$ (317 mg, 2.30 mmol). The reaction was heated to reflux and stirred for 48 hours. Upon cooling to room temperature, the reaction was filtered, washed with acetonitrile, and the filtrate was concentrated. The crude product was purified by column chromatography over silica gel (silica gel 60, EM Science) using 50% EtOAc:hexane as eluent to afford 200 mg (63% yield) of the title compound as an oil: MS (ESI) 418.2 (M+H$^+$).

d) (R)-2-(3-{3-[[2-Chloro-3-(trifluoromethyl)benzyl](2,2-diphenylethyl)amino]-3-methyl-propoxy}-phenyl)acetic acid methyl ester To a stirring solution of (R)-2-(3-{3-(2,2-diphenylethyl)amino]-3-methyl-propoxy}-phenyl)acetic acid methyl ester (150 mg, 0.359 mmol) and 2-chloro-3-trifluoromethylbenzaldehyde (164 mg, 0.79 mmol) in dichloromethane (5 ml) was added sodium triacetoxyborohydride (168 mg, 0.79 mmol) and acetic acid (10 drops). The reaction mixture was stirred at RT for three days. Solvent was next removed, the residue was dissolved in EtOAc, and then washed with saturated aqueous NaHCO$_3$. The EtOAc layer was dried over Na$_2$SO$_4$, filtered, and concentrated. The crude mixture was purified by preparative HPLC (TMC CombiPrep PDS, 75×30 mm, 25 mL/min, acetonitrile:H$_2$O, UV detection at 254 nm) to give 140 mg (64%) of the title compound as a viscous oil. MS(ESI) 610.0(M$^+$).

e) (R)-2-(3-{3-[[2-Chloro-3-(trifluoromethyl)benzyl](2,2-diphenylethyl)amino]-3-methyl-propoxy}-phenyl)acetic acid hydrochloride salt Following the procedure of Intermediate 8 step(e) except (R)-2-(3-{3-[[2-chloro-3-(trifluoromethyl)benzyl](2,2-diphenylethyl)amino]-3-methyl-propoxy}-phenyl)acetic acid methyl ester was used instead of (R)-2-(3-{3-[[2-chloro-3-(trifluoromethyl)benzyl](2,2-diphenylethyl)amino]-2-methyl-propoxy}-phenyl)acetic acid methyl ester in step 8(e), the title compound was isolated to give a white solid (100 mg, 89%). MS(ESI) 596.0 (M$^+$).

f) 2-(3-{(R)-3-[(2-chloro-3-trifluoromethyl-benzyl)-diphenylethyl-amino]-butoxy}-phenyl)-1-morpholin-4-yl-ethanone hydrochloride salt Following the procedure of Intermediate 1 step (e) except (R)-2-(3-{3-[[2-Chloro-3-(trifluoromethyl)benzyl](2,2-diphenylethyl)aminod-3-methyl-propoxy}-phenyl)acetic acid was used instead of 2-(3-(3-[[2-chloro-3-(trifluoromethyl)benzyl](2,2-diphenylethyl)-amino]-propoxy}-phenyl acetic acid in step 1(e) the title compound was prepared as a white solid.
MS(ESI) 665.4 (M$^+$).

EXAMPLE 139 (METHOD A)

(2-Chloro-3-trifluoromethyl-benzyl)-(2,2-diphenyl-ethyl)-(3-{3-[2-(4-methyl-piperazin-1-yl)-ethyl]-phenoxy}-propyl)-amine hydrochloride salt A solution of 2-(3-{3-[(2-chloro-3-trifluoromethyl-benzyl)-diphenylethyl-amino]-propoxy}-phenyl)-1-(4-methyl-piperazin-1-yl)-ethanone (108 mg, 0.162 mmol) (Intermediate 2 above) and 15 ml anhydrous toluene (Aldrich) was cooled down to −40° C. in a dry ice-acetonitrile bath. To this solution was added 4 eq of DIBAL-H (0.45 ml of a 1.5M solution in toluene, Aldrich) in a dropwise fashion. The resulting mixture was allowed to warm up to room temperature and stirred overnight. The reaction was then quenched with water. The reaction mixture was concentrated in vacuo, and extracted with EtOAc (3×). The combined organic layers were washed with brine (1×), dried over sodium sulfate, filtered and concentrated in vacuo. The crude product was purified by column chromatography over silica gel (silica gel 60, EM science) using 5% MeOH:dichloromethane as eluent). The free base was dissolved in dichloromethane, 1 eq. of HCl (1M in Et$_2$O, Aldrich) was added, and the mixture was concentrated to afford the title compound as a solid (78 mg, 70%). MS(ES) m/e 650.4 (M$^+$).

EXAMPLE 140 (METHOD B)

(2-Chloro-3-trifluoromethyl-benzyl)-(2,2-diphenyl-ethyl)-{3-[3-(2-methylamino-ethyl)-phenoxy]-propyl}-amine hydrochloride salt To a stirring solution of 2-(3-{3-[(2-chloro-3-trifluoromethyl-benzyl)-diphenylethyl-amino]-propoxy}-phenyl)-N-methyl-acetamide (101 mg, 0.17 mmol) (Intermediate 3 above) in anhydrous THF (10 mL) was added BH$_3$ THF (0.34 ml, 1 M solution in THF). The resulting solution was then heated to reflux for 1.5 hours. Aqeous HCl (0.34 ml. 6 M) was then added to the reaction and the mixture was heated at reflux for 30 min. After cooling to RT, the reaction mixture was concentrated in vacuo and extracted with EtOAc (3×). The combined organic layers were washed with brine (1×), dried over sodium sulfate, filtered and concentrated in vacuo. The crude product was purified by column chromatography over silica gel (silica gel 60, EM science) using 5% MeOH:dichloro-methane as eluent. The free base was dissolved in dichloromethane, 1 eq. of HCl (1M in Et$_2$O) was added, and the mixture was evaporated to afford the title compound as a white solid (52 mg, 50%). MS(ES) m/e 581.4 (M$^+$).

EXAMPLE 141-149

Following the same procedure (method A or B) as in Example 139 or 140 the following 9 amines were prepared from the corresponding amides:

| Ex. # & method | Amide | Chemical Name | MS |
|---|---|---|---|
| 141 A | In. 4 | (2-Chloro-3-trifluoromethyl-benzyl)-(2,2-diphenyl-ethyl)-[3-(3-{2-[(1H-imidazol-2-ylmethyl)-amino] -ethyl}-phenoxy)-propyl]-amine hydrochloride salt | 647.4 (M$^+$) |
| 142 A | In. 7 | (2-Chloro-3-trifluoromethyl-benzyl)-(2,2-diphenyl-ethyl)-{3-[3-(2-ethylamino-ethyl)-phenoxy]-propyl}-amine hydrochloride salt | 595.4 (M$^+$) |
| 143 A | In. 5 | [3-(3-{2-[(5-Bromo-thiophen-2-ylmethyl)-amino]-ethyl}-phenoxy)-propyl]-(2-chloro-3-trifluoromethyl-benzyl)-(2,2-diphenyl-ethyl)-amine hydrochloride salt | 741.2 [M − H]$^+$ |
| 144 A | In. 6 | (2-Chloro-3-trifluoromethyl-benzyl)-(2,2-diphenyl-ethyl)-[3-(3-{2-[(thiophen-2-ylmethyl)-amino]-ethyl}-phenoxy)-propyl]-amine hydrochloride salt | 663.4 (M$^+$) |
| 145 B | In. 8 | (2-Chloro-3-trifluoromethyl-benzyl)-{3-[3-(2-dimethylamino-ethyl)-phenoxy]-propyl}-(2,2-diphenyl-ethyl)-amine hydrochloride salt | 595.2 (M$^+$) |

-continued

| Ex. # & method | Amide | Chemical Name | MS |
|---|---|---|---|
| 146 B | In. 9 | (2-Chloro-3-trifluoromethyl-benzyl)-(2,2-diphenyl-ethyl)-{3-[3-(2-pyrrolidin-1-yl-ethyl)-phenoxy]-propyl}-amine hydrochloride salt | 621.4 (M+) |
| 147 B | In. 1 | (2-Chloro-3-trifluoromethyl-benzyl)-(2,2-diphenyl-ethyl)-{3-[3-(2-morpholin-4-yl-ethyl)-phenoxy]-propyl}-amine hydrochloride salt | 637.6 (M+) |
| 148 A | In. 11 | (2-Chloro-3-trifluoromethyl-benzyl)-(2,2-diphenyl-ethyl)-{(R)-1-methyl-3-[3-(2-morpholin-4-yl-ethyl)-phenoxy]-propyl}-amine hydrochloride salt | 653.1 (M+) |
| 149 A | In. 10 | (2-Chloro-3-trifluoromethyl-benzyl)-(2,2-diphenyl-ethyl)-{(R)-2-methyl-3-[3-(2-morpholin-4-yl-ethyl)-phenoxy]-propyl}-amine hydrochloride salt | 653.4 (M+) |

EXAMPLE 150

{3-[3-(2-Amino-ethyl)-phenoxy]-propyl}-(2-chloro-3-trifluoromethyl-benzyl)-(2,2-diphenyl-ethyl)-amine hydrochloride salt

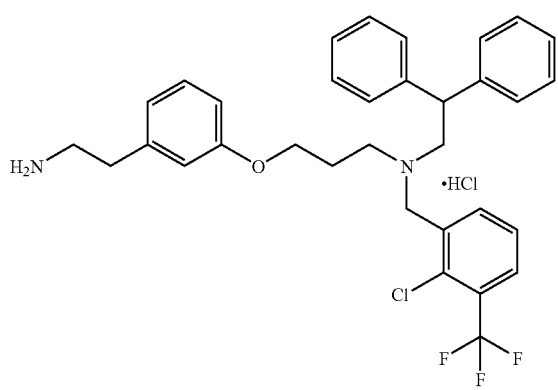

a) 2-(3-{3-[(2-chloro-3-trifluoromethyl-benzyl)-diphenylethyl-amino]-propoxy}-phenyl)-acetamide Following the procedure of Intermediate 1 (a)-(e) except ammonia (1M in methanol) was substituted for morpholine in step 1(e), the title compound was obtained as an oil (84.6 mg, 90%). MS(ES) m/e 581.4 (M+).

b) {3-[3-(2-Amino-ethyl)-phenoxy]-propyl}-(2-chloro-3-trifluoromethyl-benzyl)-(2,2-diphenyl-ethyl)-amine hydrochloride salt Following the procedure of Example 140 except 2-(3-{3-[(2-chloro-3-trifluoromethyl-benzyl)-diphenylethyl-amino]-propoxy}-phenyl)-acetamide was used instead of 2-(3-{3-[(2-chloro-3-trifluoromethyl-benzyl)-diphenylethyl-amino]-propoxy}-phenyl)-N-methyl-acetamide, the title compound was obtained as a solid (40 mg, 45%). MS(ES) m/e 567.2 (M+).

EXAMPLE 151

[2-(3-{3-[(2-chloro-3-trifluoromethyl-benzyl)-diphenylethyl-amino]-propoxy}-phenyl)-ethyl]-isopropyl-amine hydrochloride salt

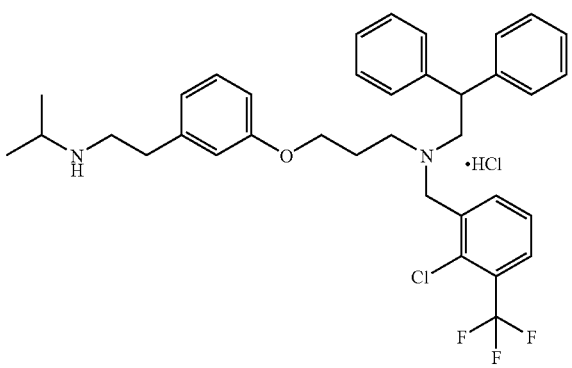

Following the procedure of Example 150 step (a)-(b) except isopropylamine was substituted for ammonia in step (a), the title compound was obtained as a solid (50 mg, 48% for two steps). MS(ES) m/e 609.2 (M+).

EXAMPLE 152

[2-(3-{3-[(2-Chloro-3-trifluoromethyl-benzyl)-diphenylethyl-amino]-propoxy}-phenyl)-ethyl]-propyl-amine hydrochloride salt

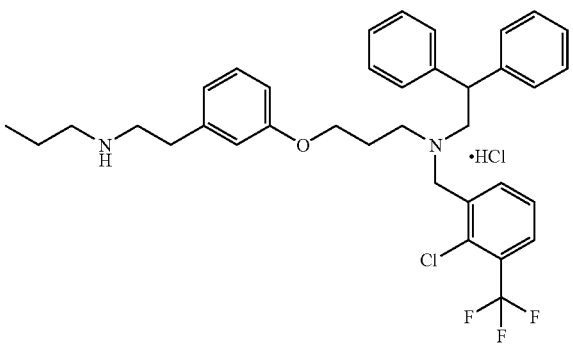

Following the procedure of Example 150 (a)-(b) except n-propylamine was substituted for ammonia in step (a), the title compound was obtained as a solid (45 mg, 43% for two steps). MS(ES) m/e 609.2 (M+).

EXAMPLE 153

2-[2-(3-{3-[(2-chloro-3-trifluoromethyl-benzyl)-diphenylethyl-amino]-propoxy}-phenyl)-ethylamino]-ethanol hydrochloride salt

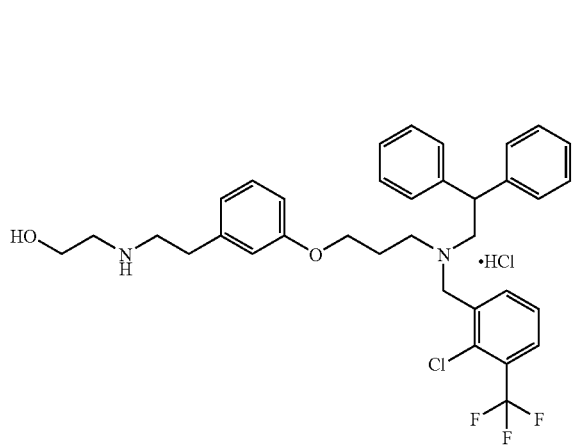

Following the procedure of Example 150 (a)-(b) except amino-acetic acid tert-butyl ester for ammonia in step (a), the title compound was obtained as a solid (44.7 mg, 42.7% for two steps). MS(ES) m/e 611.4 (M$^+$).

EXAMPLE 154

(2-Chloro-3-trifluoromethyl-benzyl)-(2,2-diphenylethyl)-[3-(3-{2-[(1-methyl-1H-imidazol-2-ylmethyl)-amino]-ethyl}-phenoxy)-propyl]-amine hydrochloride salt

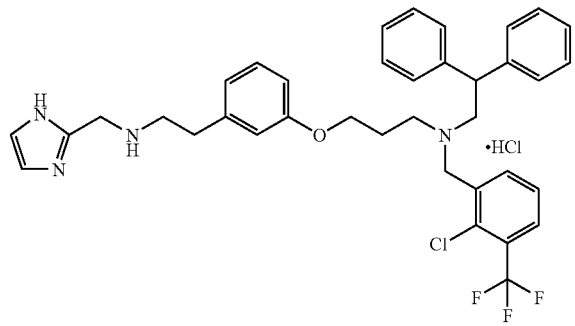

Following the procedure of Example 150 (a)-(b) except (1-Methyl-1H-imidazol-2-yl)-methylamine was substituted for ammonia in step (a), the title compound was obtained as a solid (84 mg, 74% for two steps). MS(ES) m/e 661.0 (M$^+$).

EXAMPLE 155

(2-Chloro-3-trifluoromethyl-benzyl)-(2,2-diphenylethyl)-{3-[3-(2-thiomorpholin-4-yl-ethyl)-phenoxy]-propyl}-amine hydrochloride salt

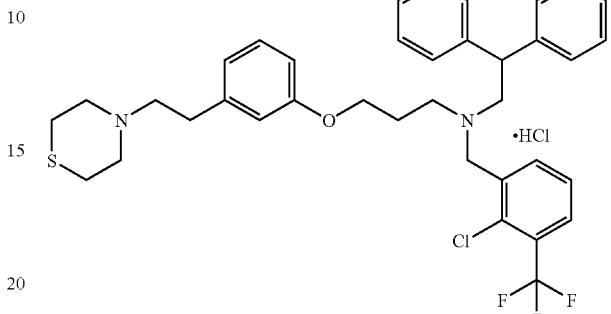

a) 2-(3-{3-[(2-chloro-3-trifluoromethyl-benzyl)-diphenylethyl-amino]-propoxy}-phenyl)-1-thiomorpholin-4-yl-ethanone Following the procedure of Intermediate 1 (a)-(e) except thiomorpholine was substituted for morpholine in step 1(e), the title compound was obtained as an oil (107 mg, 99%). MS(ES) m/e 667.4 (M$^+$).

b) {3-[3-(2-Amino-ethyl)-phenoxy]-propyl}-(2-chloro-3-trifluoromethyl-benzyl)-(2,2-diphenylethyl)-amine hydrochloride salt Following the procedure of Example 139 except 2-(3-{3-[(2-chloro-3-trifluoromethyl-benzyl)-diphenylethyl-amino]-propoxy}-phenyl)-1-thiomorpholin-4-yl-ethanone was used instead of 2-(3-{3-[(2-chloro-3-trifluoromethyl-benzyl)-diphenylethyl-amino]-propoxy}-phenyl)-1-(4-methyl-piperazin-1-yl)-ethanone, the title compound was obtained as a solid (73 mg, 65%). MS(ES) m/e 653.4 (M$^+$).

EXAMPLE 156

[2-(3-{3-[(2-chloro-3-trifluoromethyl-benzyl)-diphenylethyl-amino]-propoxy}-phenyl)-ethylamino]-acetic acid hydrochloride salt

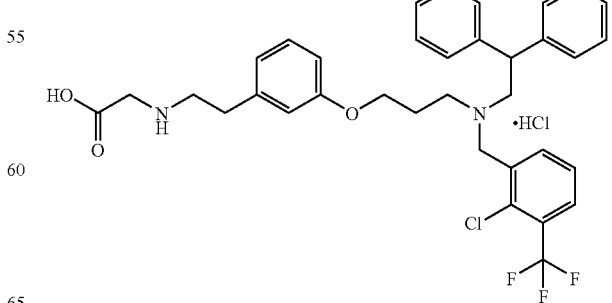

a) (3-{3-[(2-chloro-3-trifluoromethyl-benzyl)-diphenylethyl-amino]-propoxy}-phenyl)-acetaldehyde A solution of (3-{3-[(2-chloro-3-trifluoromethyl-benzyl)-diphenylethyl-amino]-propoxy}-phenyl)-acetic acid methyl ester (350 mg, 1.68 mmole) in anhydrous toluene (20 ml) was cooled down to −40° C. in a dry ice/acetonitrile bath. DIBAL-H (1.25 ml, 1.5M solution in toluene, Aldrich) was added in a dropwise fashion. The resulting mixture was stirred at −40° C. for 3 hours and then quenched with 0.01N HCl (aq.). The crude material was concentrated in vacuo and then extracted with EtOAc (3×). The combined organic layers were washed with brine (1×), dried over sodium sulfate, filtered and concentrated in vacuo. Preparative HPLC (YMC, 75×30 mm, 25 ml/min, 70-100% $CH_3CN$) afforded the title compound as an oil, 0.15 g (45%). MS(ES) m/e 566.2 ($M^+$).

b) [2-(3-{3-[(2-chloro-3-trifluoromethyl-benzyl)-diphenylethyl-amino]-propoxy}-phenyl)-ethylamino]-acetic acid methyl ester To a solution of (3-{3-[(2-chloro-3-trifluoromethyl-benzyl)-diphenylethyl-amino]-propoxy}-phenyl)-acetaldehyde (76 mg, 0.13 mmol) and glycine methyl ester (34 mg, 0.27 mmol) in 1,2-dichloroethane (15 ml) was stirred as room temperature for 10 minutes, and sodium triacetoxyborohydride (57 mg, 0.27 mmol) was added. Next two drops of glacial acetic acid was added. The reaction mixture was stirred at room temperature for 18 hour and then quenched with 0.01N aqueous HCl (15 ml) The biphasic mixture was separated and the aqueous layer was extracted with dichloromethane (3×). The organic layers were combined with the 1,2-dichloroethane solution and were washed with brine (1×), dried over sodium sulphate, filtered and concentrated in vacuo. Preparative HPLC (YMC 75×30 mm, 25 ml/min, 90-100% $CH_3CN$) afforded title compound as an oil, 70 mg (81%).

c) [2-(3-{3-[(2-chloro-3-trifluoromethyl-benzyl)-diphenylethyl-amino]-propoxy}-phenyl)-ethylamino]-acetic acid hydrochloride salt To a stirring solution of [2-(3-{3-[(2-chloro-3-trifluoromethyl-benzyl)-diphenylethyl-amino]-propoxy}-phenyl)-ethylamino]-acetic acid methyl ester (70 mg, 0.11 mmol) in THF (10 ml) and water (3.3 ml) was added lithium hydroxide monohydrate (12 mg, 0.28 mmol). The resulting mixture was stirred at room temperature for 18 hours and acidified with HCl (0.5 ml, 1 M in water). The crude mixture was concentrated in vacuo and then extracted with EtOAc (3×). The combined organic layers were washed with brine (1×), dried over sodium sulfate, filtered and concentrated in vacuo. Preparative HPLC (YMC 75×30 mm, 25 ml/min, 25-100% $CH_3CN$) afforded the title compound as the free base. The diamine was treated with 1 M HCl in $Et_2O$ (0.11 ml, 0.11 mmol), and the $Et_2O$ was evaporated to afford the title compound as an off-white solid, 31 mg (45%). MS(ES) m/e 625.4 ($M^+$).

EXAMPLE 157

[2-(3-{(R)-3-[(2-chloro-3-trifluoromethyl-benzyl)-diphenylethyl-amino]-butoxy}-phenyl)-ethylamino]-acetic acid hydrochloride salt

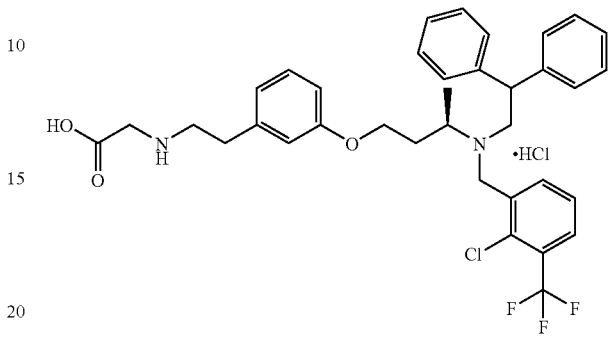

Following the procedure of Example 156 steps (a)-(c) except (R)-2-(3-{3-[[2-Chloro-3-(trifuoromethyl)benzyl](2,2-diphenylethyl)amino]-3-methyl-propoxy}-phenyl)acetic acid methyl ester was used in step (a) instead of (3-{3-[(2-chloro-3-trifluoromethyl-benzyl)-diphenylethyl-amino]-propoxy}-phenyl)-acetic acid methyl ester, the title compound was obtained as a solid. MS(ES) m/e 639.2 ($M^+$)

EXAMPLE 158-160

The following compound were prepared in analogous fashion to Example 157 steps (a)-(c) by substituting for glycine methyl ester in step (b):

| Ex | Amino Esters | Chemical Names | M/S |
|---|---|---|---|
| 158 | N-Methylamino-acetic acid methyl ester | {[2-(3-{3-[(2-chloro-3-trifluoromethyl-benzyl)-diphenylethyl-amino]-propoxy}-phenyl)-ethyl]-methyl-amino}-acetic acid hydrochloride salt | 639.4 ($M^+$) |
| 159 | 2-Amino-2-methyl-propionic acid methyl ester | 2-[2-(3-{3-[(2-chloro-3-trifluoromethyl-benzyl)-diphenylethyl-amino]-propoxy}-phenyl)-ethylamino]-2-methyl-propionic acid hydrochloride salt | 653.4 ($M^+$) |
| 160 | (S)-2-Amino-propionic acid methyl ester | (S)-2-[2-(3-{3-[(2-chloro-3-trifluoro-methyl-benzyl)-diphenylethyl-amino]-propoxy}-phenyl)-ethylamino]-propionic acid hydrochloride salt | 639.4 ($M^+$) |

EXAMPLES 161-162

The following compound were prepared in analogous fashion to Example 157 steps (a)-(b) except (R)-pyrrolidine-2-carboxylic acid and (S)-pyrrolidine-2-carboxylic acid were substituted for glycine methyl ester in step (b):

| Ex | Amino Acid | Chemical Name | MS |
|---|---|---|---|
| 161 | (R)-Pyrrolidine-2-carboxylic acid | (R)-1-[2-(3-{3-[(2-chloro-3-trifluoromethyl-benzyl)-diphenylethyl-amino]-propoxy}-phenyl)-ethyl]-pyrrolidine-2-carboxylic acid hydrochloride salt | 665.4 ($M^+$) |

-continued

| Ex | Amino Acid | Chemical Name | MS |
|---|---|---|---|
| 162 | (S)-Pyrrolidine-2-carboxylic acid | (S)-1-[2-(3-{3-[(2-chloro-3-trifluoromethyl-benzyl)-diphenylethyl-amino]-propoxy}-phenyl)-ethyl]-pyrrolidine-2-carboxylic acid hydrochloride salt | 665.4 (M$^+$) |

EXAMPLE 163

[2-(3-{3-[(2-chloro-3-trifluoromethyl-benzyl)-diphenylethyl-amino]-propoxy}-phenyl)-ethyl]-pyrimidin-2-yl-amine hydrochloride salt

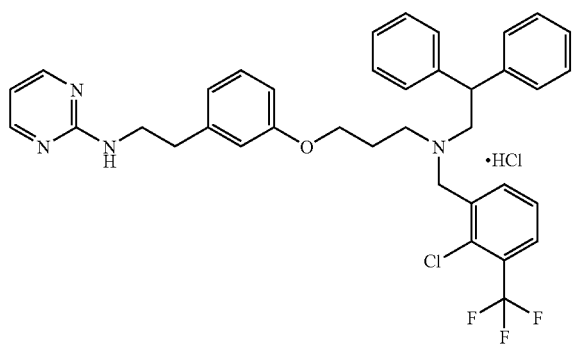

To a stirring solution of {3-[3-(2-amino-ethyl)-phenoxy]-propyl}-(2-chloro-3-trifluoromethyl-benzyl)-(2,2-diphenyl-ethyl)-amine (57 mg, 0.1 mml, Example 150) and 2-Chloro-pyrimidine (97 mg, 0.85 mmol) in ethanol (10 mL) was added triethylamine (0.5 ml, 3.75 mmol). The resulting solution was refluxed for 72 hours and then concentrated in vacuo. Purification by preparative HPLC (YMC 75×30 mm, 25 m/min, 95-100% CH$_3$CN) afforded the desired pyrimidine product. The free base was treated with 1 M HCl in Et$_2$O (0.1 ml) and the mixture was concentrated in vacuo to afford the title compound as a solid, 44 mg (64%). MS(ES) m/e 645.4 (M$^+$).

EXAMPLE 164

2-Chloro-3-trifluoromethyl-benzyl)-(2,2-diphenyl-ethyl)-[3-(3-morpholin-4-yl-phenoxy)-propyl]-amine hydrochloride salt

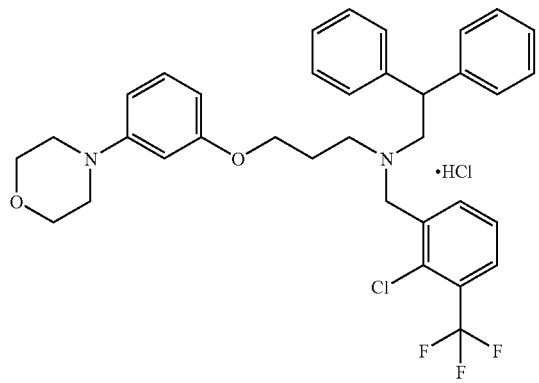

a) (2,2-Diphenylethyl)(2-chloro-3-trifluoromethyl-benzyl)amine

To a stirring solution of 2,2-diphenethylamine (2.0 g, 0.010 mole) and 2-chloro-3-trifluoromethylbenzaldehyde (2.33 g, 0.011 mole) in dichloromethane (20 mL) was added sodium triacetoxyborohydride (2.36 g, 0.011 mole) and acetic acid (2.0 mL). The reaction mixture was stirred overnight. The solvent was removed and the residue was dissolved in ethyl acetate. The ethyl acetate solution was washed with saturated NaHCO$_3$, the ethyl acetate extracts were dried over Na$_2$SO$_4$, filtered, and concentrated. The crude product was subjected to column chromatography over silica gel (silica gel 60, EM Science) using 30% ethyl acetate:hexane as eluent to afford 3.0 g (76% yield) of the title compound as a yellow oil: MS (ESI) 390.0 (M+H$^+$).

b) N-(2,2-Diphenylethyl)-N-(3-hydroxy-propyl)-N-(2-chloro-3-trifluoromethyl-benzyl)amine To a stirring solution of 3-bromo-propanol (77 ul, 0.84 mmol) in acetonitrile (10 ml) was added NaI (0.25 g, 1.7 mmol) and K$_2$CO$_3$ (0.23 g, 1.7 mmol). The mixture was stirred at 85° C. for 1 h, and then N-(2,2-diphenylethyl)-N-(2-chloro-3-trifluoromethyl-benzyl)amine (0.43 g, 1.12 mmol) was added. The reaction mixture was heated at 85° C. overnight. Solvent was removed, the residue was washed with H$_2$O, and extracted twice with EtOAc. The EtOAc extracts were dried over Na$_2$SO$_4$, filtered, and concentrated. The crude mixture was purified by preparative HPLC (TMC CombiPrep PDS, 75×30 mm, 25 mL/min, acetonitrile:H$_2$O, UV detection at 254 nm) to give 225 mg (60%) of the title compound as a white solid. MS (ESI) 448.0 (M+H$^+$).

c) (2-Chloro-3-trifluoromethyl-benzyl)-(2,2-diphenyl-ethyl)-[3-(3-morpholin-4-yl-phenoxy)-propyl]-amine hydrochloride salt A stirring solution of 3-[(2-chloro-3-trifluoromethyl-benzyl)-(2,2-diphenyl-ethyl)-amino]-propan-1-ol (282 mg, 0.38 mmol) in toluene (25 mL) was treated with 3-morpholin-4-yl-phenol (75 mg, 0.42 mmol). Polymer bound triphenylphosphine (224 mg, 0.67 mmol, 3 mmol/g, Fluka Chemie) was then added, and the mixture was stirred for 15 minutes. The reaction mixture was then cooled to 0° C. and diisopropylazodicarboxylate (127 mg, 0.63 mmol) was added in a dropwise fashion. After stirring at room temperature overnight, the crude reaction mixture was filtered and the solid washed with toluene (25 mL). The filtrate was concentrated in vacuo. Purification by preparative HPLC (YMC 75×30 mm, 25 ml/min, 85-100% CH$_3$CN over) led to the isolation of the morpholine product. The free base was treated with 1 M HCl in Et$_2$O (0.1 ml) and the mixture was concentrated in vacuo to afford the title compound as a solid, 104 mg (41%). MS(ES) m/e 609.4 (M$^+$).

EXAMPLE 165-167

Following the same procedure of Example 164 (a)-(c), except substituting the below-named starting alcohol for 3-morpholin-4-yl-phenol in step (c), the following compounds were prepared:

| Ex. | starting alcohol | chemical name | M/S |
|---|---|---|---|
| 165 | 3-Piperidin-1-yl-phenol | (2-Chloro-3-trifluoromethyl-benzyl)-(2,2-diphenyl-ethyl)-[3-(3-piperidin-1-yl-phenoxy)-propyl]-amine hydrochloride salt | 607.4 (M$^+$) |
| 166 | 3-Diethylamino-phenol | (3-{3-[(2-chloro-3-trifluoromethyl-benzyl)-diphenylethyl-amino]-propoxy}-phenyl)-diethyl-amine hydrochloride salt | 595.4 (M$^+$) |
| 167 | 3-(2,5-Dimethyl-pyrrol-1-yl)-phenol | (2-Chloro-3-trifluoromethyl-benzyl)-{3-[3-(2,5-dimethyl-pyrrol-1-yl)-phenoxy]-propyl}-(2,2-diphenyl-ethyl)-amine | 617.2 (M$^+$) |

EXAMPLE 168

(2-Chloro-3-trifluoromethyl-benzyl)-(2,2-diphenyl-ethyl)-[3-(3-piperazin-1-yl-phenoxy)-propyl]-amine hydrochloride salt

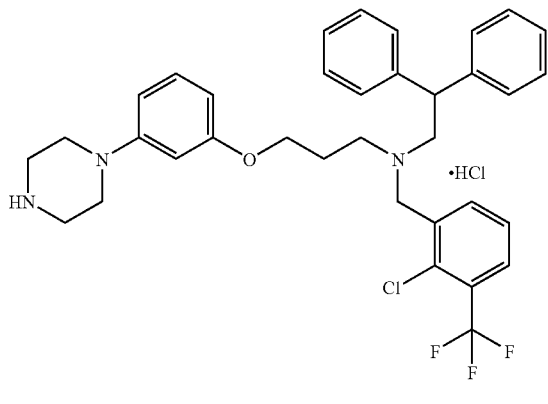

a) 4-(3-Hydroxy-phenyl)-piperazine-1-carboxylic acid tert-butyl ester

To a stirring solution of 3-piperazin-1-yl-phenol (1.50 g, 8.43 mmol) in 1,4-dioxane (25 mL) was added di-t-butyl dicarbonate (2.02 g, 9.26 mmol). The resulting mixture was stirred at room temperature for 36 hours and then concentrated in vacuo. The crude product was dissolved in EtOAc and washed with saturated aqueous sodium bicarbonate solution (1×) and brine (1×). The EtOAc layer was dried over sodium sulfate, filtered and concentrated in vacuo to afford the title compound as a light yellow solid, 2.05 g (86%). MS(ES) m/e 279.4 (M+H$^+$).

b) 4-(3-{3-[(2-chloro-3-trifluoromethyl-benzyl)-diphenylethyl-amino]-propoxy}-phenyl)-piperazine-1-carboxylic acid tert-butyl ester To a stirring solution of 3-[(2-chloro-3-trifluoromethyl-benzyl)-(2,2-diphenyl-ethyl)-amino]-propan-1-ol (448 mg, 1.0 mmol) in toluene (30 mL) was added 4-(3-hydroxy-phenyl)-piperazine-1-carboxylic acid tert-butyl ester (419 mg, 1.50 mmol). Polymer bound triphenylphosphine (500 mg, 1.50 mmol, 3 mmol/g, Fluka Chemie) was then added, and the mixture stirred for 15 minutes. The reaction mixture was then cooled to 0° C. and diisopropylazodicarboxylate (303 mg, 1.50 mmol) was added in a dropwise fashion. After stirring at room temperature overnight, the crude reaction mixture was filtered and the solid washed with toluene. Concentration of the filtrate in vacuo followed by purification by flash silica gel chromatography (silica gel 60, EM science; 15% EtOAc:hexane) afforded title compound as an oil (0.59 g, 84%). MS(ES) m/e 708.4 (M$^+$).

c) (2-Chloro-3-trifluoromethyl-benzyl)-(2,2-diphenyl-ethyl)-[3-(3-piperazin-1-yl-phenoxy)-propyl]-amine hydrochloride salt A solution of 4-(3-{3-[(2-chloro-3-trifluoromethyl-benzyl)-diphenylethyl-amino]-propoxy}-phenyl)-piperazine-1-carboxylic acid tert-butyl ester (475 mg, 0.67 mmol) in a 1:1 mixture of 3M HCl (aq.) and methanol (30 mL total) was stirred at room temperature for 18 hours. The mixture was concentrated in vacuo, and the crude material was dissolved in EtOAc. The EtOAc solution was washed with saturated aqueous sodium bicarbonate solution (3×) and brine (1×), dried over sodium sulfate, and filtered. The EtOAc extracts were concentrated and the crude piperazine was treated with 1 M HCl (Et$_2$O) to afford the title compound as a solid, 415 mg (100%). MS(ES) m/e 608.4 (M$^+$).

EXAMPLE 169

(2-Chloro-3-trifluoromethyl-benzyl)-((S)-2-phenyl-propyl)-[3-(3-piperazin-1-yl-phenoxy)-propyl]-amine hydrochloride salt

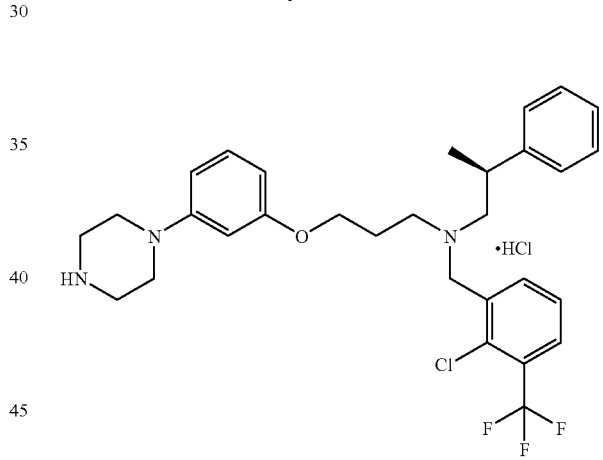

a) 3-[(2-chloro-3-trifluoromethyl-benzyl)-((S)-2-phenyl-propyl)-amino]-propan-1-ol Following the procedure of Example 164 step(b) except (S)-(2-Chloro-3-trifluoromethyl-benzyl)-(2-phenyl-propyl)-amine (Example 10(a) was used in step (b) instead of 2,2-diphenylethylamine the title compound was prepared as a clear oil (30%). MS (ESI) 385.8 (M$^+$).

b) (2-Chloro-3-trifluoromethyl-benzyl)-((S)-2-phenyl-propyl)-[3-(3-piperazin-1-yl-phenoxy)-propyl]-amine hydrochloride salt Following the procedure for Example 168 steps (a)-(c) except 3-[(2-chloro-3-trifluoromethyl-benzyl)-((S)-2-phenyl-propyl)-amino]-propan-1-ol was used in step (b) instead of 3-[(2-chloro-3-trifluoromethyl-benzyl)-(2,2-diphenyl-ethyl)-amino]-propan-1-ol the title compound was synthesized as a white solid, 199 mg (68%). MS (ESI) 546.0 (M$^+$).

EXAMPLE 170

(2-Chloro-3-trifluoromethyl-benzyl)-(2,2-diphenyl-ethyl)-[(R)-2-methyl-3-(3-piperazin-1-yl-phenoxy)-propyl]-amine hydrochloride

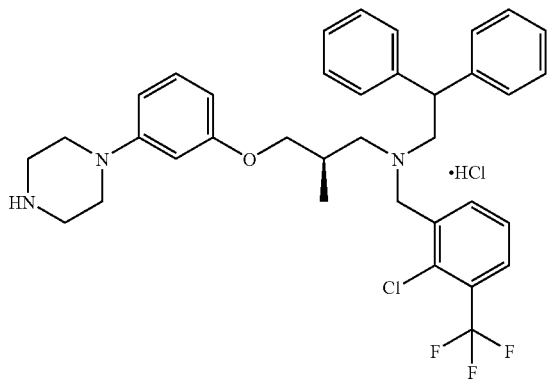

a) N-(2,2-Diphenylethyl)-N-((R)-2-Methyl-3-hydroxy-propyl)-N-(2-chloro-3-trifluoromethyl-benzyl) amine Following the procedure of Example 164 steps (a)-(b) except (S)-3-bromo-2-methyl-propanol was used in step (b) instead of 3-bromo-propanol the title compound was prepared as a yellow oil (25%). MS (ESI) 461.9 (M+).

b) (2-Chloro-3-trifluoromethyl-benzyl)-(2,2-diphenyl-ethyl)-[(R)-2-methyl-3-(3-piperazin-1-yl-phenoxy)-propyl]-amine hydrochloride Following the procedure for Example 168 steps (a)-(c) except N-(2,2-diphenylethyl)-N-((R)-2-methyl-3-hydroxy-propyl)-N-(2-chloro-3-trifluoromethyl-benzyl)amine was used in step (b) instead of 3-[(2-chloro-3-trifluoromethyl-benzyl)-(2,2-diphenyl-ethyl)-amino]-propan-1-ol the title compound was synthesized as a white solid, 153 mg (57%). MS (ESI) 622.4 (M+).

EXAMPLE 171

(2-Chloro-3-trifluoromethyl-benzyl)-isobutyl-[3-(3-piperazin-1-yl-phenoxy)-propyl]-amine hydrochloride salt

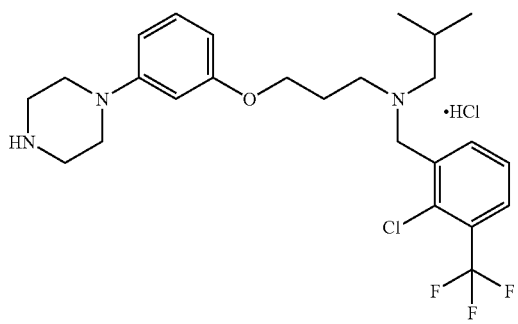

a) 3-[(2-chloro-3-trifluoromethyl-benzyl)-isobutyl-amino]-propan-1-ol

Following the procedure of Example 164 steps (a)-(b) except i-butyl-amine was used in step (a) instead of 2,2-diphenethylamine the title compound was prepared as a clear oil (25%). MS (ESI) 324.2 (M+H+).

b) (2-Chloro-3-trifluoromethyl-benzyl)-isobutyl-[3-(3-piperazin-1-yl-phenoxy)-propyl]-amine hydrochloride salt Following the procedure for Example 168 steps (a)-(c) except 3-[(2-chloro-3-trifluoromethyl-benzyl)-isobutyl-amino]-propan-1-ol was used in step (b) instead of 3-[(2-chloro-3-trifluoromethyl-benzyl)-(2,2-diphenyl-ethyl)-amino]-propan-1-ol the title compound was synthesized as a white solid, 192 mg (60%). MS (ESI) 484.2 (M+).

EXAMPLE 172

[4-(3-{3-[(2-Chloro-3-trifluoromethyl-benzyl)-diphenylethyl-amino]-propoxy}-phenyl)-piperazin-1-yl]-acetic acid hydrochloride salt

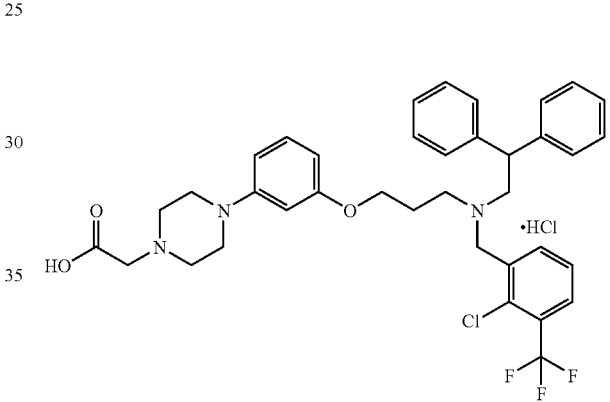

a) [4-(3-{3-[(2-chloro-3-trifluoromethyl-benzyl)-diphenylethyl-amino]-propoxy}-phenyl)-piperazin-1-yl]-acetic acid methyl ester To a solution of (2-chloro-3-trifluoromethyl-benzyl)-(2,2-diphenyl-ethyl)-[3-(3-piperazin-1-yl-phenoxy)-propyl]-amine hydrochloride (114 mg, 0.187 mmol—Example 168) in methanol (15 mL) was treated with bromo-acetic acid methyl ester (57 mg, 0.375 mmol) and diisopropyl-ethylamine (48 mg, 0.375 mmol). The resulting solution was heated at 50° C. for 3 hours, cooled to room temperature, and concentrated. The crude material was dissolved in EtOAc and washed with water (1×). The organic layer was then washed with brine (1×), dried over sodium sulfate, and filtered. The EtOAc was concentrated and the sample was dried under vacuum to title compound as an oil (99 mg, 78%). MS(ES) m/e 622.2 ([M−COOCH3]+).

b) [4-(3-{3-[(2-chloro-3-trifluoromethyl-benzyl)-diphenylethyl-amino]-propoxy}-phenyl)-piperazin-1-yl]-acetic acid hydrochloride salt To a stirring solution of [4-(3-{3-[(2-chloro-3-trifluoromethyl-benzyl)-diphenylethyl-amino]-propoxy}-phenyl)-piperazin-1-yl]-acetic acid methyl ester (99 mg, 0.146 mmol) in a mixture of THF and water (3:1; 12 ml) was added lithium hydroxide monohydrate (8 mg, 0.192 mmol). The resulting mixture was stirred at room temperature for 18 hours and then acidified with 1 M aqueous HCl (0.2 ml). The mixture was concentrated in vacuo, water (5 mL) was added, and the crude material was extracted with EtOAc (3×). The combined organic layers were washed with brine (1×), dried over sodium sulfate, and filtered. The organic layer was concentrated, and the crude amine was treated with 1 M HCl (Et$_2$O). The resulting precipitate was dried under vacuum to afford the title compound as a solid (87 mg, 97%). MS(ES) m/e 666.0 (M$^+$).

Following the procedure of Example 172 (a)-(b) except NH-piperazines from Examples 173, 174, and 175 were used in step 172(a) instead of (2-chloro-3-trifluoromethyl-benzyl)-(2,2-diphenyl-ethyl)-[3-(3-piperazin-1-yl-phenoxy)-propyl]-amine, the following compounds were prepared:

| Ex. | Free base of | Chemical Name | MS |
|---|---|---|---|
| 173 | Example 169 | [4-(3-{3-[(2-chloro-3-trifluoromethyl-benzyl)-((S)-2-phenyl-propyl)-amino]-propoxy}-phenyl)-piperazin-1-yl]-acetic acid hydrochloride salt | 604.0 (M$^+$) |
| 174 | Example 170 | [4-(3-{(R)-[(2-chloro-3-trifluoromethyl-benzyl)-diphenylethyl-amino]-methyl-propoxy}-phenyl)-piperazin-1-yl]-acetic acid hydrochloride salt | 680.2 (M$^+$) |
| 175 | Example 171 | [4-(3-{3-[(2-chloro-3-trifluoromethyl-benzyl)-isobutyl-amino]-propoxy}-phenyl)-piperazin-1-yl]-acetic acid hydrochloride salt | 542.2 (M$^+$) |

EXAMPLE 176

(2-Chloro-3-trifluoromethyl-benzyl)-(2,2-diphenyl-ethyl)-{3-[3-(4-methyl-piperazin-1-yl)-phenoxy]-propyl}-amine methanesulfonate

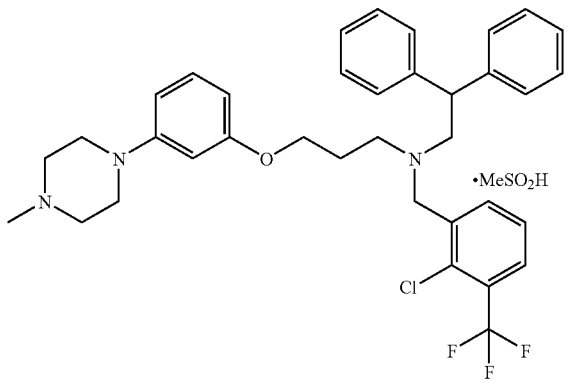

To a stirring solution of (2-chloro-3-trifluoromethyl-benzyl)-(2,2-diphenyl-ethyl)-[3-(3-piperazin-1-yl-phenoxy)-propyl]-amine (150 mg, 2.46 mmol) in anhydrous DMF (20 ml) was added iodomethane (16.8 uL, 2.71 mmol) and diisopropylethylamine (86 uL, 4.93 mmol). The resulting solution was heated at 50° C. for 4 hours and then concentrated. Purification by flash silica gel chromatography (silica gel 60, EM science; 3% MeOH and 0.5% NH$_2$OH in CH$_2$Cl$_2$) afforded the N-methylated product. The amine was dissolved in CH$_2$Cl$_2$ and methansulfonic acid (2 equivalents) was added. The methylene chloride solution was concentrated and the resulting bis-methanesulfonate salt was dried under vacuum to yield the title compound as a solid, 56 mg (37%). MS(ES) m/e 622.4 (M$^+$).

EXAMPLE 177

(2-Chloro-3-trifluoromethyl-benzyl)-(2,2-diphenyl-ethyl)-[3-(3-pyrrolidin-1-yl-phenoxy)-propyl]-amine hydrochloride salt

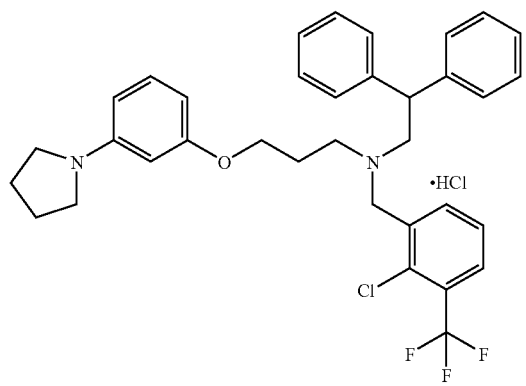

a) 1-(3-Methoxy-phenyl)-pyrrolidine

To a stirring solution of 3-methoxy-phenylamine (571 mg, 4.6 mmol) in anhydrous toluene (40 ml) was added 1,4-dibromo-butane (1.0 g, 4.6 mmol) and diisopropylethylamine (0.59 g, 4.6 mmol). The resulting solution was heated to reflux for 24 hours and then concentrated in vacuo. The crude material was purified by column chromatography over silica gel (silica gel 60, EM science, 5% EtOAc:hexanes) and the title compound was obtained as an oil (754 mg, 92%). MS(ES) m/e 178.4 ([M+H]$^+$).

b) 3-Pyrrolidin-1-yl-phenol

To a stirring solution of 1-(3-methoxy-phenyl)-pyrrolidine (354 mg, 2 mmol) in dichloromethane (30 ml) at 0° C. was added BBr$_3$ (4.0 ml, 4 mmol, 1 M solution in dichloromethane) in a dropwise fashion. The resulting solution was stirred over night at room temperature and then poured into ice water (30 ml). The aqueous mixture was extracted with dichloromethane (3×). The combine organic layers were washed with brine (1×), dried over sodium sulfate, and filtered. The dichloromethane filtrate was concentrated to afford the title compound as an oil (317 mg, 97%). MS(ES) m/e 164.2 ([M+H]$^+$).

c) (2-Chloro-3-trifluoromethyl-benzyl)-(2,2-diphenyl-ethyl)-[3-(3-pyrrolidin-1-yl-phenoxy)-propyl]-amine hydrochloride salt Following the procedure of Example 164 (a)-(c) except 3-pyrrolidin-1-yl-phenol was used instead of 3-morpholin-4-yl-phenol in step (c) the title compound was obtained as a solid. MS(ES) m/e 593.2 (M$^+$).

EXAMPLE 178

(3-{3-[(2-chloro-3-trifluoromethyl-benzyl)-diphenyl-ethyl-amino]-propoxy}-phenylamino)-acetic acid hydrochloride salt

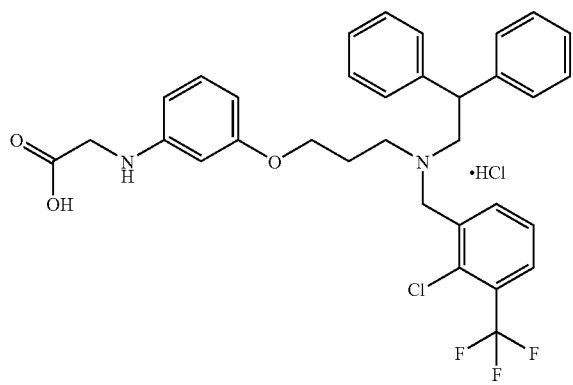

a) [tert-Butoxycarbonyl-(3-{3-[(2-chloro-3-trifluoromethyl-benzyl)-diphenylethyl-amino]-propoxy}-phenyl)-amino]-acetic acid methyl ester To a solution of sodium hydride (18.8 mg, 0.47 mmol, 60% in mineral oil) in anhydrous DMF (10 mL) at 0° C. and DMSO (10 ml) was added dropwise a solution of (3-{3-[(2-chloro-3-trifluoromethyl-benzyl)-diphenylethyl-amino]-propoxy}-phenyl)-carbamic acid tert-butyl ester (150 mg, 0.235 mmol) in DMF (5 ml). The solution was stirred at 0° C. for 20 minutes and was then treated with bromo-acetic acid methyl ester (72 mg 0.47 mmol). The resulting solution was warmed to room temperature and stirred for 6 hours. The reaction mixture was poured into ice water (30 ml). The mixture was extracted with EtOAC (3×) and the combine organic layers were washed with saturated aqueous sodium bicarbonate (2×), brine (×), dried over sodium sulphate, and filtered. The ethyl acetate filtrate was concentrated to afford the title compound as an oil. MS(ES) m/e 711.2 (M$^+$).

b) (3-{3-[(2-chloro-3-trifluoromethyl-benzyl)-diphenylethyl-amino]-propoxy}-phenylamino)-acetic acid methyl ester To a solution of [tert-butoxycarbonyl-(3-{3-[(2-chloro-3-trifluoromethyl-benzyl)-diphenylethyl-amino]-propoxy)phenyl)-amino]-acetic acid methyl in 4 M aqueous HCl (7.5 ml) and methanol (7.5 ml) was stirred at room temperature for 18 hours and was then concentrated in vacuo. The resulting mixture was dissolved in EtOAc and the combine organic layers were washed with saturated aqueous sodium bicarbonate solution (2×), brine (1×), dried over sodium sulfate, and filtered. The ethyl acetate filtrate was concentrated to afford the title compound as an oil. MS(ES) m/e 611.2 (M$^+$).

c) (3-{3-[(2-chloro-3-trifluoromethyl-benzyl)-diphenylethyl-amino]-propoxy}-phenylamino)-acetic acid Hydrochloride To a stirring solution of (3-{3-[(2-chloro-3-trifluoromethyl-benzyl)-diphenylethyl-amino]-propoxy}-phenylamino)-acetic acid methyl ester in THF (6 ml) and water (2 ml) was added lithium hydroxide monohydrate (20 mg, 0.47 mmol) and the mixture was stirred at room temperature for 6 hours. The reaction mixture was acidified with 1 M aqueous HCl (0.5 mL). The aqueous mixture was concentrated in vacuo and the crude material was dissolved in EtOAc. The ethyl acetate solution was washed with brine (1×), dried over sodium sulfate, and filtered. The organic layer was concentrated, and the crude amine was treated with 1 M HCl (Et$_2$O). The resulting precipitate was dried under vacuum to afford the title compound as a solid. MS(ES) m/e 597.4 (M$^+$).

EXAMPLE 179

[(3-{3-[(2-chloro-3-trifluoromethyl-benzyl)-diphenylethyl-amino]-propoxy}-phenyl)-N-methyl-amino]-acetic acid hydrochloride salt

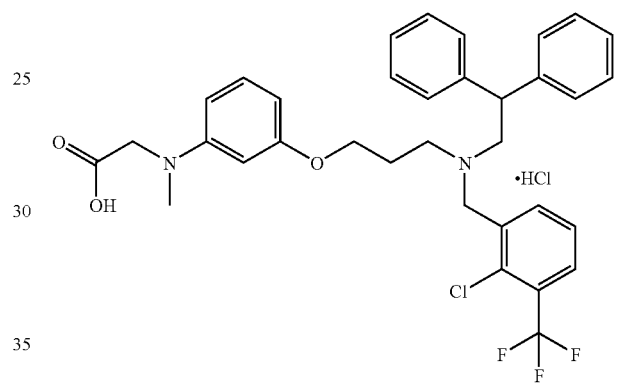

a) [(3-{3-[(2-chloro-3-trifluoromethyl-benzyl)-diphenylethyl-amino]-propoxy}-phenyl)-N-methyl-amino]-acetic acid methyl ester A solution of (3-{3-[(2-chloro-3-trifluoromethyl-benzyl)-diphenylethyl-amino]-propoxy}-phenyl)-N-methyl-amine (81 mg, 0.15 mmol) in methanol (15 ml) was treated with bromo-acetic acid methyl ester (46 mg, 0.30 mmol) diisopropylethylamine (46 mg, 0.36 mmol). The resulting solution was heated at 50° C. for 4 hours, cooled down and concentrated. The crude material was dissolved in EtOAc and washed with brine (1×), dried over sodium sulfate, and filtered. The filtrate was concentrated to afford title compound as an oil (70 mg, 76%). MS(ES) m/e 625.2 (M$^+$).

b) [(3-{3-[(2-chloro-3-trifluoromethyl-benzyl)-diphenylethyl-amino]-propoxy}-phenyl)-N-methyl-amino]-acetic acid hydrochloride salt Following the procedure of Example 178 step (c) except [(3-{3-[(2-chloro-3-trifluoromethyl-benzyl)-diphenylethyl-amino]-propoxy}-phenyl)-N-methyl-amino]-acetic acid methyl ester was used in step (c) instead of (3-{3-[(2-chloro-3-trifluoromethyl-benzyl)-diphenylethyl-amino]-propoxy}phenylamino)-acetic acid methyl ester the title compound was obtained as a solid, 65 mg (96%). MS (ES) m/e 611.2 (M$^+$).

EXAMPLE 180

N-(2,2-Diphenylethyl)-N-(2-chloro-3-trifluoromethylbenzyl)-3-[3-(2-methyl-2-aminopropyl)phenoxy]propylamine, dihydrochloride

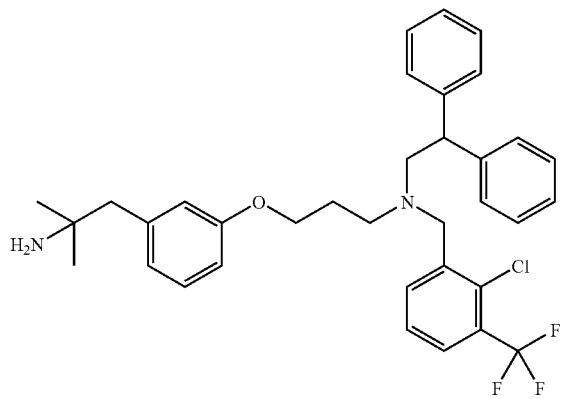

a. 2,2-Dimethyl-3-(3-benzyloxyphenyl)propionic acid

A solution of diisopropylamine (1.55 mL, 11.9 mmole) in 20 mL of THF was cooled to −78° and treated with n-BuLi (6.5 mL 1.6N solution in hexane, 10.4 mmole). After 10 minutes, a solution of isobutyric acid (436 mg, 4.96 mmole) in 3 mL of THF was added, followed by HMPA (1.74 mL, 10 mmole). The reaction was allowed to warm to 23°, then heated at 55° for 30 minutes. The reaction was cooled to −78° and a solution of 3-benzyloxybenzyl chloride (1.15 g, 4.96 mmole) in 6 mL of THF was added. The reaction was warmed to 23° for 30 minutes, then heated at 55° for 30 minutes. The reaction was cooled, diluted with $H_2O$, acidified with 3N HCl, and extracted with $Et_2O$. The extracts were washed three times with $H_2O$, dried and the solvent removed, and gave the titled compound as a white powder, 1.2 g (85% yield). MS (ESI) 285 ($MH^+$).

b. Methyl 2,2-dimethyl-3-(3-benzyloxyphenyl)propionate

A solution of 2,2-dimethyl-3-(3-benzyloxyphenyl)propionic acid (400 mg, 1.4 mmole) in 20 mL of MeOH and 0.5 mL conc. $H_2SO_4$ was refluxed for 18 hours. The reaction was cooled, diluted with $H_2O$ and extracted with $Et_2O$. The extracts were washed with $H_2O$, three times with aqueous $NaHCO_3$, dried, and the solvent evaporated. The residue was chromatographed over a silica gel column, and elution with a mixture of $CH_2Cl_2$, hexane and MeOH (50:50:1) gave the titled compound, 208 mg (50% yield). MS (ESI) 299 ($MH^+$).

c. Methyl 2,2-dimethyl-3-(3-hydroxyphenyl)propionate

A solution of methyl 2,2-dimethyl-3-(3-benzyloxyphenyl)propionate (208 mg, 0.7 mmole) in 10 mL of MeOH and 1 mL of 1N HCl was treated with 10% Pd/C (100 mg) and hydrogenated on a Parr shaker with 50 psi $H_2$ pressure for 1 hour. The catalyst was filtered, and the filtrate was concentrated, diluted with $H_2O$ and extracted with $Et_2O$. The extracts were washed with $H_2O$, dried and the solvent removed, and gave the titled product, 140 mg (97% yield). MS (ESI) 209 ($MH^+$).

d. Methyl N-(2,2-diphenylethyl)-N-(2-chloro-3-trufluoromethylbenzyl)-2,2-dimethyl-3-(3-aminopropoxy)phenylpropionate A solution of methyl 2,2-dimethyl-3-(3-hydroxyphenyl)propionate (135 mg, 0.65 mmole) and N-(2,2-Diphenylethyl)-N-(2-chloro-3-trifluoromethylbenzyl)-3-hydroxypropylamine (290 mg, 0.65 mmole) in 8 mL of THF was treated with $Ph_3P$ (170 mg, 0.65 mmole) and diisopropylazodicarboxylate (135 mg, 0.65 mmole) and stirred for 16 hours. The reaction was diluted with $H_2O$ and extracted with $Et_2O$. The extracts were washed with $H_2O$, dried, and the solvent removed. The residue was chromatographed on a silica gel column, and elution with 30% EtOAc in hexane gave the titled compound, 200 mg (50%). MS (ESI) 639 ($MH^+$).

e. N-(2,2-Diphenylethyl)-N-(2-chloro-3-trifluoromethylbenzyl)-2,2-dimethyl-3-(3-aminopropoxy)phenylpropionic acid A solution of methyl N-(2,2-diphenylethyl)-N-(2-chloro-3-trifluoromethylbenzyl)-2,2-dimethyl-3-(3-aminopropoxy)phenylpropionate (195 mg, 0.3 mmole) in 10 mL of MeOH, 1 mL of $H_2O$ and 2 mL 2.5N NaOH was refluxed for 5 hours. The reaction was cooled, diluted with $H_2O$ and acidified with 3N HCl to pH 5.1. The mixture was extracted with EtOAc, the extracts were washed with $H_2O$, dried and evaporated, and gave the titled compound, 172 mg (92% yield). MS (ESI) 625 ($MH^+$).

f. N-(2,2-Diphenylethyl)-N-(2-chloro-3-trifluoromethylbenzyl)-3-[3-(2-methyl-2-aminopropyl)phenoxy]propylamine, dihydrochloride A solution of N-(2,2-Diphenylethyl)-N-(2-chloro-3-trifluoromethylbenzyl)-2,2-dimethyl-3-(3-aminopropoxy)phenylpropionic acid, hydrochloride (158 mg, 0.24 mmole) in 10 mL of $Me_2CO$ was treated with $Et_3N$ (56 mg, 0.55 mmole) and cooled in an ice bath. A solution of isobutylchloroformate (37 mg, 0.27 mmole) in 2 ml of $Me_2CO$ was added dropwise to the cold solution, and the reaction was stirred at 0° for 30 minutes. A solution of $NaN_3$ (40 mg, 0.6 mmole) in 2 mL of $H_2O$ was added to the cold solution, and stirring was continued for 30 minutes. The reaction was diluted with $H_2O$, and extracted with $Et_2O$. The extracts were washed with $H_2O$, and dried. The ethereal solution of the acyl azide was slowly added with stirring to 50 mL of refluxing toluene. After the addition, the toluene solution is stirred at 105° for 30 minutes, and all the solvents are removed. The residue is dissolved in 5 mL of dioxane, treated with 5 mL of 6N HCl and heated at 100° for 30 minutes. The reaction was cooled, diluted with $H_2O$, made basic with aqueous NaOH and extracted with $Et_2O$. The extracts were washed with $H_2O$, dried, and the solvents removed. The residue was chromatographed on a silica gel column and the product was eluted with 10% MeOH in EtOAc. The chromatographed product was converted to the dihydrochloride salt in Et₂O and isopropanol with 4N HCl in dioxane, and gave the titled product, 78 mg (55% yield). MS (ESI) 596 (MH⁺).

EXAMPLE 181

N-(2,2-Diphenylethyl)-N-(2-chloro-3-trifluoromethylbenzyl)-3-(3-[2-hydroxymethyl]phenoxy)propylamine hydrochloride

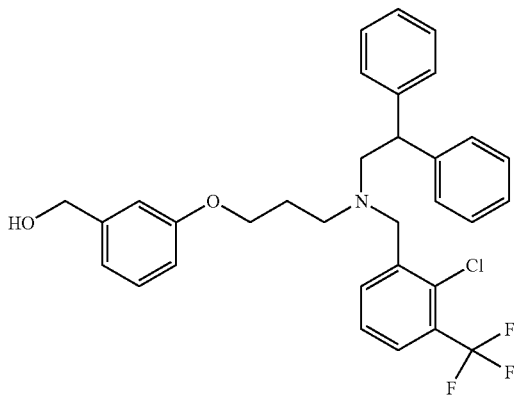

a. N-(2,2-Diphenylethyl)-N-(2-chloro-3-trifluoromethylbenzyl)-3-(3-carbomethoxyphenoxy)propylamine A solution of N-(2,2-Diphenylethyl)-N-(2-chloro-3-trifluoromethylbenzyl)-3-hydroxypropylamine (186 mg, 0.42 mmole) and methyl 3-hydroxybenzoate (63 mg, 0.42 mmole) in 15 mL of THF was treated with Ph₃P (110 mg, 0.42 mmole) and diisopropylazodicarboxylate (93 mg, 0.46 mmole). The reaction was stirred for 18 hours, diluted with H₂O, and extracted with Et₂O. The extracts were washed with H₂O, dried, and the solvent evaporated. The residue was chromatographed on a silica gel column, and elution with 10% EtOAc in hexane gave the titled product, 64 mg (26% yield). MS (ESI) 583 (MH⁺).

b. N-(2,2-Diphenylethyl)-N-(2-chloro-3-trifluoromethylbenzyl)-3-(3-[2-hydroxymethyl]phenoxy)propylamine A solution of N-(2,2-Diphenylethyl)-N-(2-chloro-3-trifluoromethylbenzyl)-3-(3-carbomethoxyphenoxy)propylamine (52 mg, 0.09 mmole) in 5 mL of Et₂O at 0° was treated with LiAlH₄ (0.5 mL of a 1N solution in THF). The reaction was stirred at 0° for 30 minutes, 1 mL of EtOAc was added, and the reaction was allowed to warm to 23° for 30 minutes, diluted with H₂O and extracted with Et₂O. The extracts were washed with H₂O, dried and the solvent removed. The residue was dissolved in Et₂O, the solution was treated with 4N HCl in dioxane. The precipitated solid was filtered, washed with Et₂O and dried, and gave the titled compound, 27 mg (52%). MS (ESI) 555 (MH⁺).

EXAMPLE 182

N-(2,2-Diphenylethyl)-N-2-chloro-3-trifluoromethylbenzyl)-3-(3-[2-hydroxy-2-methylpropyl]phenoxy)propylamine

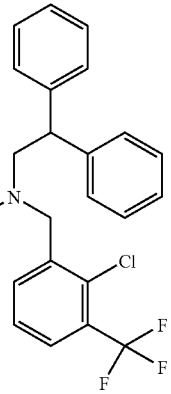

A solution of MeMgl (5 mmole) in 10 mL of Et₂O was treated with a solution of methyl (3-{3-[[2-chloro-3-trifluoromethylbenzyl](2,2-diphenylethyl)amino]propoxy}-phenyl)acetate (120 mg, 0.2 mmole) in 2 mL of Et₂O. The reaction was heated, and concentrated to 3 mL, and stirred at 23° for 30 minutes. The reaction was diluted with cold, aqueous NH₄Cl and extracted with Et₂O. The extracts were washed with H₂O, dried, and the solvent removed. The residue was chromatographed on a silica gel column, eluted with a mixture of CH₂Cl₂, hexane and MeOH (50:50:1), and gave the titled product, 92 mg (77% yield). MS (ESI) 597 (MH⁺).

EXAMPLE 183

N-(2,2-Diphenylethyl)-N-(2-chloro-3-trifluoromethylbenzyl)-3-(3-N-methylsulfonamidophenoxy)propylamine, hydrochloride

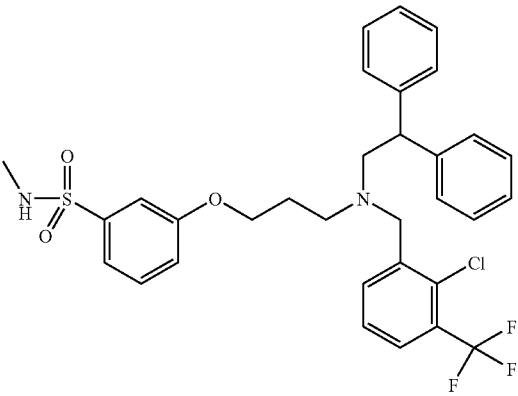

a. N-Methyl-3-nitrobenzene sulfonamide

A solution of MeNH₂ (10 mL of a 2N solution in THF) and 10 mL of H₂O was treated with a solution of 3-nitrobenzene sulfonyl chloride (884 mg, 4 mmole) in 4 mL of THF. The reaction was stirred for 2 hours, diluted with H$_2$O and extracted with Et$_2$O. The extracts were washed with H$_2$O, 0.1N HCl, aqueous NaHCO$_3$, dried, and the solvent removed, and gave the titled product, 608 mg (70%). MS (ESI) 217 (MH$^+$).

b. N-Methyl-3-aminobenzene sulfonamide

A solution of N-methyl-3-nitrobenzene sulfonamide (608 mg, 2.8 mmole) in 30 mL of MeOH and 5 mL of EtOAc was treated with 10% Pd/C (100 mg) and hydrogenated at 1 atmosphere H$_2$ pressure for 16 hours. The catalyst was filtered, and the filtrate evaporated. The residue was dissolved in EtOAc, washed with H$_2$O, dried and the solvent removed, and gave the titled product, 498 mg (96%). MS (ESI) 187 (MH$^+$).

c. N-Methyl-3-hydroxybenzene sulfonamide

N-Methyl-3-aminobenzene sulfonamide (488 mg, 2.62 mmole) was dissolved in a mixture of 10 mL of H$_2$O and 2 mL of conc. H$_2$SO$_4$, and was cooled to −5°. A solution of NaNO$_2$ (207 mg, 3 mmole) in 2 mL of H$_2$O was added dropwise at such a rate that the temperature doesn't exceed 0°. The reaction was stirred for 10 minutes, urea (100 mg) was added, and the reaction was stirred an additional 10 minutes. The cold solution of diazo compound was slowly added with stirring to a 0° solution of Cu(NO$_3$)$_2$ dihydrate (10.3 g, 43 mmole) and Cu$_2$O (363 mg) in 100 mL of H$_2$O. Stirring was continued for 30 minutes as the temperature was allowed to warm to 23°. The heterogeneous reaction was extracted with Et$_2$O, and the extracts were extracted with 0.2N NaOH. The basic extracts were washed with Et$_2$O, acidified, and extracted with CH$_2$Cl$_2$. The extracts were dried, and the solvent removed. The residue was chromatographed on a silica gel column, and elution with 50% EtOAc in hexane gave the titled product, 175 mg (36%). MS (ESI) 188 (MH$^+$).

d. 3-Chloro-1-propanol tosylate

A solution of 3-chloro-1-propanol (1.88 g, 20 mmole) in 20 ml of pyridine was treated at 0° with tosyl chloride (7.6 g, 40 mmole). The solution was warmed to 23°, and stirred 16 hours. The reaction was diluted with 100 mL of H$_2$O and stirred for 90 minutes, and extracted with Et$_2$O. The extracts were washed with 1N HCl, dried, and the solvents thoroughly removed, and gave the titled product, 2.3 g (46%). MS (ESI) 188 (MH$^+$).

e. N-Methyl-3-(3-chloropropoxy)benzene sulfonamide

N-Methyl-3-hydroxybenzene sulfonamide (175 mg, 0.94 mmole) in 15 mL of DMF was treated with Cs$_2$CO$_3$ (305 mg, 0.94 mmole), and stirred for 45 minutes. A solution of 3-Chloro-1-propanol tosylate (223 mg, 0.90 mmole) in 3 mL of DMF was added. The reaction was heated at 55° for 3 hours, and stirred at 23° for 16 hours. The reaction was diluted with H$_2$O and extracted with Et$_2$O. The extracts were washed with H$_2$O, dried and the solvent removed. The residue was chromatographed on a silica gel column, and elution with 30% EtOAc in hexane gave the titled product, 75 mg (30%). MS (ESI) 264 (MH$^+$).

f. N-Methyl-3-(3-iodopropoxy)benzene sulfonamide

A solution of N-methyl-3-(3-chloropropoxy)benzene sulfonamide (75 mg, 0.28 mmole) in 10 mL of Me$_2$CO was treated with NaI (200 mg) and the mixture was refluxed for 32 hours. The reaction was diluted with H$_2$O, extracted with Et$_2$O. The extracts were washed with H$_2$O, aqueous NaHSO$_3$, dried, and the solvent removed, and gave the titled compound, 96 mg (95%). MS (ESI) 356 (MH$^+$).

g. N-(2,2-Diphenylethyl)-N-(2-chloro-3-trifluoromethylbenzyl)-3-(3-N-methylsulfonamidophenoxy) propylamine, hydrochloride A solution of N-methyl-3-(3-iodopropoxy)benzene sulfonamide (96 mg, 0.27 mmole) and N-(2-chloro-3-trifluoromethylbenzyl)-2,2-diphenylethylamine (105 mg, 0.27 mmole) in 7 mL of MeCN was treated with excess NaHCO$_3$, and the mixture refluxed for 18 hours. The solvents were evaporated, and the residue taken up in EtOAc. The EtOAc was washed with aqueous NH$_4$Cl, H$_2$O, dried and the solvent removed. The residue was chromatographed on a silica gel column, and elution with 30% EtOAc in hexane afforded the titled compound, 66 mg (40% yield). The hydrochloride salt was formed by treating a solution of the titled compound in a mixture of Et$_2$O and isopropanol with 4N HCl in dioxane. MS (ESI) 618 (MH$^+$).

EXAMPLE 184

N-(2-[2-Chlorophenyl]-propyl)-N-(2-chloro-3-trifluoromethylbenzyl)-3-(3-carboxymethylenephenoxy)propylamine, hydrochloride

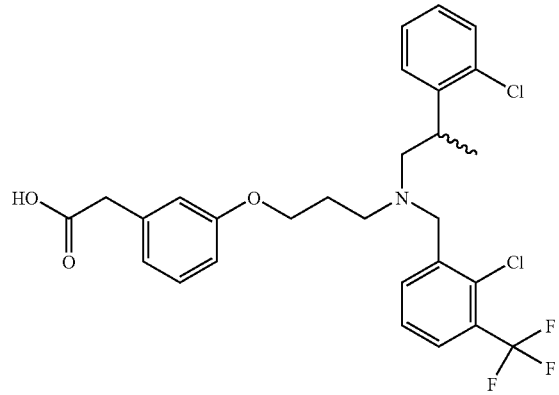

a. 2-(2-Chlorophenyl)propionic acid

A solution of diisopropylamine (1.6 mL, 12 mmole) in 20 mL of THF at −78° was treated with n-BuLi (7.5 mL of a 1.6N solution in hexane, 12 mmole). The solution was stirred 10 minutes, and then treated with HMPA (2.16 mL, 12 mmole), and stirred an additional 2 minutes. A solution of o-chlorophenylacetic acid (850 mg, 5 mmole) in 4 mL of THF was added, the reaction was warmed to 23°, stirred 45 minutes, warmed to 50° and stirred for 5 minutes, and then cooled to 0°. MeI (1 mL) was added, the reaction was warmed to 23°, and stirred for 30 minutes. The reaction was diluted with H$_2$O, acidified with HCl, and extracted with Et$_2$O. The extracts were washed with 0.1N HCl, H$_2$O, aqueous NaHSO₃, dried, and the solvent removed, and gave the titled compounds as a white crystalline solid, 603 mg (66% yield). MS (ESI) 185 (MH⁺).

b. N-(2-Chloro-3-trifluoromethylbenzyl)-2-(2-chlorophenyl)propionamide

A solution of 2-(2-chlorophenyl)propionic acid (350 mg, 1.9 mmole) and 2-chloro-3-trifluoromethylbenzylamine (398 mg, 1.9 mmole) in 5 mL of dichloroethane was treated with diisopropylcarbodiimide (0.3 mL, 1.9 mmole) and the reaction was stirred for 16 hours. The solvent was removed, and the residue taken up in Et₂O. The Et₂O was washed with H₂O, 0.1N HCl, and aqueous Na₂CO₃, dried and the solvent removed. Recrystallization from a mixture of CH₂Cl₂ and hexane gave the titled compound, 265 mg (37% yield). MS (ESI) 376 (MH⁺).

c. N-(2-Chloro-3-trifluoromethylbenzyl)-2-(2-chlorophenyl)propylamine

A solution of N-(2-chloro-3-trifluoromethylbenzyl)-2-(2-chlorophenyl)propionamide (265 mg, 0.7 mmole) in 40 mL of toluene was treated with diisobutyl aluminum hydride (5 mL of a 1N solution in hexane), and the reaction was stirred for 90 minutes. The reaction was diluted with 20 mL of Et₂O, a concentrated aqueous solution of Rochelle salt was added, and the mixture stirred for 60 minutes, at which time the emulsion had broken apart. The organic layer was separated, washed with H₂O, aqueous Rochelle salt, dried and the solvent removed, and gave the titled compound, 221 mg (87%). MS (ESI) 362 (MH⁺).

d. Methyl 3-(3-chloropropyloxy)-phenyl acetate

A solution of methyl 3-hydroxyphenylacetate (2.55 g, 15.4 mmole) and 3-chloro-1-propanol (1.45 g, 15.4 mmole) in 25 m[of THF was treated with Ph₃P (4.04 g, 15.4 mmole) and diisopropylazodicarboxylate (3.42 g, 16.9 mmole), and the mixture was stirred for 18 hours. The reaction was diluted with H₂O and extracted with Et₂O. The extracts were washed with 0.1N NaOH, 0.1N HCl, and H₂O. The extracts were dried and the solvent removed. Chromatography on a silica gel column and elution with 10% EtOAc in hexane gave the titled compound, 1.94 g (52% yield). MS (ESI) 243 (MH⁺).

e. Methyl 3-(3-iodopropyloxy)-phenyl acetate

A solution of methyl 3-(3-chloropropyloxy)-phenyl acetate (1.92 g, 7.9 mmole) in 50 mL of Me₂CO was treated with NaI (3.6 g, 24 mmole), and the mixture was refluxed for 24 hours. The reaction was diluted with H₂O and extracted with Et₂O. The extracts were washed with H₂O, aqueous NaHSO₃, dried, and the solvent removed, and gave the titled compound, 2.48 g (94% yield). MS (ESI) 335 (MH⁺).

f. N-(2-[2-Chlorophenyl]-propyl)-N-(2-chloro-3-trifluoromethylbenzyl)-3-(3-carbomethoxymethylenephenoxy)propylamine A solution of N-(2-chloro-3-trifluoromethylbenzyl)-2-(2-chlorophenyl)propylamine (220 mg, 0.6 mmole) and methyl 3-(3-iodopropyloxy)-phenyl acetate (163 mg, 0.48 mmole) in 15 mL of MeCN was treated with K₂CO₃ (165 mg, 1.2 mmole), and the mixture was refluxed for 16 hours. The solvent was removed, and the residue was taken up in Et₂O. The Et₂O was washed with H₂O, aqueous NaHSO₃, dried and the solvent removed. The residue was chromatographed on a silica gel column, and elution with 30% EtOAc in hexane gave the titled compound, 90 mg (33% yield). MS (ESI) 568 (MH⁺).

g. N-(2-[2-Chlorophenyl]-propyl)-N-(2-chloro-3-trifluoromethylbenzyl)-3-(3-carboxymethylenephenoxy)propylamine, hydrochloride A solution of N-(2-[2-Chlorophenyl]-propyl)-N-(2-chloro-3-trifluoromethylbenzyl)-3-(3-carbomethoxymethylenephenoxy)propylamine (80 mg, 0.14 mmole) in 5 mL of MeOH was treated with 1 mL of H₂O and 0.5 mL of 2.5N NaOH, and heated to 500 for 30 minutes. The reaction was diluted with H₂O, and acidified to pH 4, and extracted with EtOAc. The extracts were washed with H₂O, dried, and the solvent removed. The residue was dissolved in Et₂O, a small amount of isopropanol was added, and treated with 4N HCl in dioxane. The precipitated solid was filtered, washed with Et₂O and dried, and gave the titled compound, 65 mg (81%). MS (ESI) 554 (MH⁺).

EXAMPLE 185

N-(2-[3-Chlorophenyl]-propyl)-N-(2-chloro-3-trifluoromethylbenzyl)-3-(3-carboxymethylenephenoxy)propylamine, hydrochloride

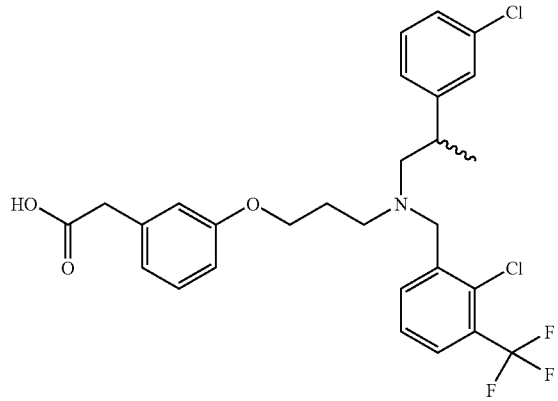

a. 2-(3-Chlorophenyl)propionic acid

The titled compound was prepared from m-chlorophenylacetic acid in 57% yield in the same manner as the preparation of 2-(2-Chlorophenyl)propionic acid in Example 184a. MS (ESI) 185 (MH⁺).

b. N-(3-Chloro-3-trifluoromethylbenzyl)-2-(2-chlorophenyl)propionamide

The titled compound was prepared from 2-(3-Chlorophenyl)propionic acid in 22% yield in the same manner as the preparation of N-(2-Chloro-3-trifluoromethylbenzyl)-2-(2-chlorophenyl)propionamide in Example 184b. MS (ESI) 376 (MH⁺).

c. N-(2-Chloro-3-trifluoromethylbenzyl)-2-(2-chlorophenyl)propylamine

The titled compound was prepared from N-(2-chloro-3-trifluoromethylbenzyl)-2-(2-chlorophenyl)propionamide in 61% yield in the same manner as the preparation of N-(2-chloro-3-trifluoromethylbenzyl)-2-(2-chlorophenyl)propylamine in Example 184c. MS (ESI) 362 (MH+).

d. N-(2-[3-Chlorophenyl]-propyl)-N-(2-chloro-3-trifluoromethylbenzyl)-3-(3-carbomethoxymethylenephenoxy)propylamine The titled compound was prepared from N-(2-Chloro-3-trifluoromethylbenzyl)-2-(2-chlorophenyl)propylamine in 49% yield in the same manner as the preparation of N-(2-[2-Chlorophenyl]-propyl)-N-(2-chloro-3-trifluoromethylbenzyl)-3-(3-carbomethoxymethylenephenoxy)propylamine in Example 184f. MS (ESI) 568 (MH+).

e. N-(2-[3-Chlorophenyl]-propyl)-N-(2-chloro-3-trifluoromethylbenzyl)-3-(3-carboxymethylenephenoxy)propylamine, hydrochloride The titled compound was prepared from N-(2-[3-Chlorophenyl]-propyl)-N(2-chloro-3-trifluoromethylbenzyl)-3-(3-carbomethoxymethylenephenoxy)propylamine in 48% yield in the same manner as the preparation of N-(2-[2-Chlorophenyl]-propyl)-N-(2-chloro-3-trifluoromethylbenzyl)-3-(3-carboxymethylenephenoxy)propylamine in Example 184g. MS (ESI) 554 (MH+).

EXAMPLE 186

N-(2-[4-Chlorophenyl]-propyl)-N-(2-chloro-3-trifluoromethylbenzyl)-3-(3-carboxymethylenephenoxy)propylamine, hydrochloride

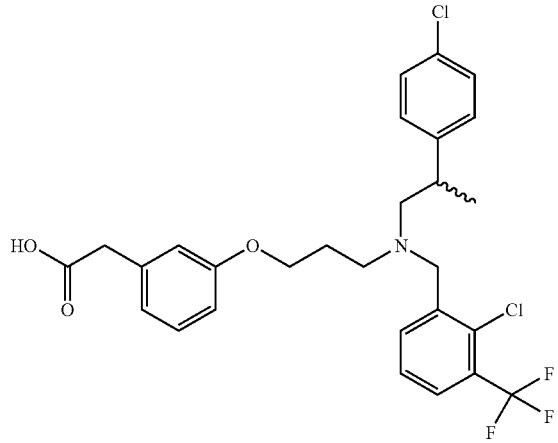

a. 2-(4-Chlorophenyl)propionic acid

The titled compound was prepared from p-chlorophenylacetic acid in 73% yield in the same manner as the preparation of 2-(2-Chlorophenyl)propionic acid in Example 184a. MS (ESI) 185 (MH+).

b. N-(2-Chloro-3-trifluoromethylbenzyl)-2-(4-chlorophenyl)propionamide

The titled compound was prepared from 2-(4-Chlorophenyl)propionic acid in 32% yield in the same manner as the preparation of N-(2-Chloro-3-trifluoromethylbenzyl)-2-(2-chlorophenyl)propionamide in Example 184b. MS (ESI) 376 (MH+).

c. N-(2-Chloro-3-trifluoromethylbenzyl)-2-(4-chlorophenyl)propylamine

The titled compound was prepared from N-(2-chloro-3-trifluoromethylbenzyl)-2-(4-chlorophenyl)propionamide in 94% yield in the same manner as the preparation of N-(2-chloro-3-trifluoromethylbenzyl)-2-(2-chlorophenyl)propylamine in Example 184c. MS (ESI) 362 (MH+).

d. N-(2-[4-Chlorophenyl]-propyl)-N-(2-chloro-3-trifluoromethylbenzyl)-3-(3-carbomethoxymethylenephenoxy)propylamine The titled compound was prepared from N-(2-Chloro-3-trifluoromethylbenzyl)-2-(4-chlorophenyl)propylamine in 33% yield in the same manner as the preparation of N-(2-[2-Chlorophenyl]-propyl)-N-(2-chloro-3-trifluoromethylbenzyl)-3-(3-carbomethoxymethylenephenoxy)propylamine in Example 184f. MS (ESI) 568 (MH+).

e. N-(2-[4-Chlorophenyl]-propyl)-N-(2-chloro-3-trifluoromethylbenzyl)-3-(3-carboxymethylenephenoxy)propylamine, hydrochloride The titled compound was prepared from N-(2-[4-Chlorophenyl]-propyl)-N-(2-chloro-3-trifluoromethylbenzyl)-3-(3-carbomethoxymethylenephenoxy)propylamine in 55% yield in the same manner as the preparation of N-(2-(2-Chlorophenyl]-propyl)-N-(2-chloro-3-trifluoromethylbenzyl)-3-(3-carboxymethylenephenoxy)propylamine in Example 184g. MS (ESI) 554 (MH+).

EXAMPLE 187

N-(2-[2-Methoxyphenyl]-propyl)-N-(2-chloro-3-trifluoromethylbenzyl)-3-(3-carboxymethylenephenoxy)propylamine, hydrochloride

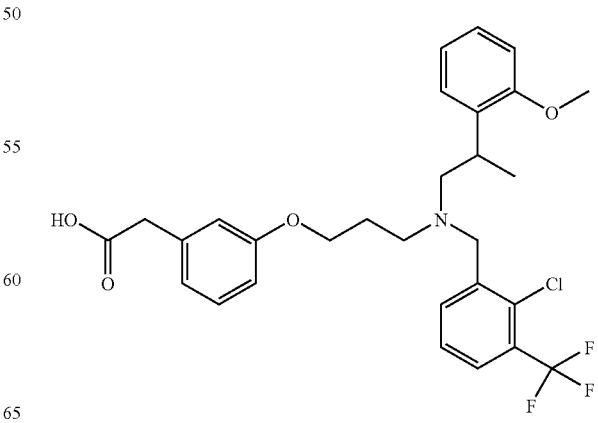

a. 2-(2-Methoxyphenyl)propionic acid

The titled compound was prepared from o-methoxyphenylacetic acid in 39% yield in the same manner as the preparation of 2-(2-Chlorophenyl)propionic acid in Example 184a.
MS (ESI) 181 (MH⁺).

b. N-(2-Chloro-3-trifluoromethylbenzyl)-2-(2-methoxyphenyl)propionamide

The titled compound was prepared from 22-methoxyphenyl)propionic acid in 42% yield in the same manner as the preparation of N-(2-Chloro-3-trifluoromethylbenzyl)-2-(2-chlorophenyl)propionamide in Example 184b. MS (ESI) 372 (MH⁺).

c. N-(2-Chloro-3-trifluoromethylbenzyl)-2-(2-methoxyphenyl)propylamine

The titled compound was prepared from N-(2-chloro-3-trifluoromethylbenzyl)-2-(2-methoxyphenyl)propionamide in 28% yield in the same manner as the preparation of N-(2-chloro-3-trifluoromethylbenzyl)-2-(2-chlorophenyl)propylamine in Example 184c. MS (ESI) 358 (MH⁺).

d. N-(2-[2-Methoxyphenyl]-propyl)-N-(2-chloro-3-trifluoromethylbenzyl)-3-(3-carbomethoxymethylenephenoxy)propylamine The titled compound was prepared from N-(2-Chloro-3-trifluoromethylbenzyl)-2-(2-methoxyphenyl)propylamine in 90% yield in the same manner as the preparation of N-(2-[2-Chlorophenyl]-propyl)-N-(2-chloro-3-trifluoromethylbenzyl)-3-(3-carbomethoxymethylenephenoxy)propylamine in Example 184f. MS (ESI) 564 (MH⁺).

e. N-(2-[2-Methoxyphenyl]-propyl)-N-(2-chloro-3-trifluoromethylbenzyl)-3-(3-carboxymethylenephenoxy)propylamine, hydrochloride The titled compound was prepared from N-(2-[2-methoxyphenyl]-propyl)-N-(2-chloro-3-trifluoromethylbenzyl)-3-(3-carbomethoxymethylenephenoxy)propylamine in 62% yield in the same manner as the preparation of N-(2-[2-Chlorophenyl]-propyl)-N-(2-chloro-3-trifluoromethylbenzyl)-3-(3-carboxymethylenephenoxy)propylamine in Example 184g. MS (ESI) 550 (MH⁺).

EXAMPLE 188

N-(2-[4-Methoxyphenyl]-propyl)-N-(2-chloro-3-trifluoromethylbenzyl)-3-(3-carboxymethylenephenoxy)propylamine, hydrochloride

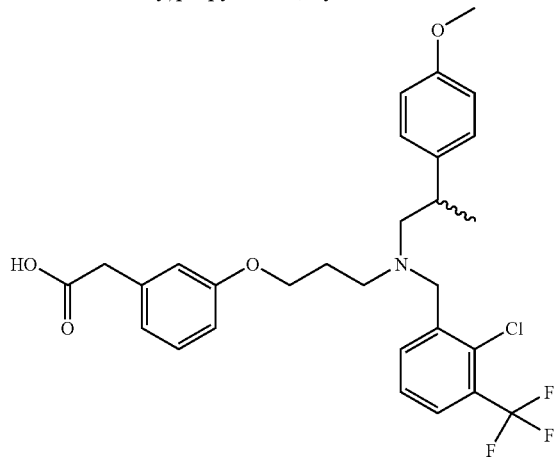

a. 2-(4-Methoxyphenyl)propionic acid

The titled compound was prepared from p-methoxyphenylacetic acid in 73% yield in the same manner as the preparation of 22-chlorophenyl)propionic acid in Example 184a. MS (ESI) 181 (MH⁺)

b. 2-(4-Methoxyphenyl)propionamide

A solution of 2-(4-methoxyphenyl)propionic acid (230 mg, 1.28 mmole) in 10 mL of benzene and 1 drop of DMF was treated with oxalyl chloride (0.5 mL). The reaction was stirred at 23° for 1 hour, and the solvents were evaporated. The residue was dissolved in 5 mL of Me₂CO and added to a stirred mixture of 5 mL of Me₂CO and 5 mL of 28% NH₄OH. After 1 hour, the reaction was diluted with H₂O, and the solid filtered. Recrystallization from EtOH gave the titled compound, 146 mg (64% yield). MS (ESI) 181 (MH⁺)

c. 2-(4-Methoxyphenyl)propylamine, hydrochloride

A solution of 2-(4-methoxyphenyl)propionamide (550 mg, 3.07 mmole) in 15 mL of THF was treated with BH₃ (15 mL of a 1N solution in THF), and the reaction was refluxed for 12 hours, cooled, and MeOH was added, and the solvents were removed. The residue was dissolved in 5 mL of dioxane, treated with 10 mL of 6N HCl and refluxed for 2 hours. The reaction was cooled, diluted with H₂O, and washed with Et₂O. The aqueous layer was basified and extracted with Et₂O. The extracts were washed with H₂O, dried, and the solvent evaporated. The residue was converted to the HCl salt, and recrystallization from a mixture of Et₂O and isopropanol gave the titled compound, 318 mg (52% yield). MS (ESI) 166 (MH⁺)

d. N-(2-Chloro-3-trifluoromethylbenzyl)-2-(4-methoxyphenyl)propylamine

A solution of 2-(4-methoxyphenyl)propylamine (183 mg, 1.11 mmole) and 2-chloro-3-trifluoromethylbenzaldehyde (230 mg, 1.11 mmole) in 10 mL of MeOH was treated with a crystal of p-toluenesulfonic acid hydrate, and stirred for 30 minutes. The reaction was diluted with Et₂O, and washed with aqueous NaHCO₃. The extracts were dried, and the solvent removed. A solution of the residue in 10 mL of MeOH was cooled to 0° and treated with excess NaBH4. The reaction was warmed to 23° and stirred for 30 minutes. The reaction was diluted with H₂O and extracted with Et₂O. The extracts were washed with H₂O, dried and the solvent removed, and gave the titled compound, 305 mg (77% yield). MS (ESI) 358 (MH⁺)

e. N-(2-[4-Methoxyphenyl]-propyl)-N-(2-chloro-3-trifluoromethylbenzyl)-3-(3-carbomethoxymethylenephenoxy)propylamine The titled compound was prepared from N-(2-Chloro-3-trifluoromethylbenzyl)-2-(4-methoxyphenyl)propylamine in 26% yield in the same manner as the preparation of N-(2-[2-Chlorophenyl]-propyl)-N-(2-chloro-3-trifluoromethylbenzyl)-3-(3-carbomethoxymethylenephenoxy)propylamine in Example 184f. MS (ESI) 564 (MH⁺)

f. N-(2-[4-Methoxyphenyl]-propyl)-N-(2-chloro-3-trifluoromethylbenzyl)-3-(3-carboxymethylenephenoxy)propylamine, hydrochloride The titled compound was prepared from N-(2-[4-methoxyphenyl]-propyl)-N-(2-chloro-3-trifluoromethylbenzyl)-

3-(3-carbomethoxymethylenephenoxy)propylamine in 66% yield in the same manner as the preparation of N-(2-[2-Chlorophenyl]-propyl)-N-(2-chloro-3-trifluoromethylbenzyl)-3-(3-carboxymethylenephenoxy)propylamine in Example 184g. MS (ESI) 550 (MH+)

EXAMPLE 189

N-(2-Phenyl-4-methylpentyl)-N-(2-chloro-3-trifluoromethylbenzyl)-3-(3-carboxymethylenephenoxy)propylamine, hydrochloride

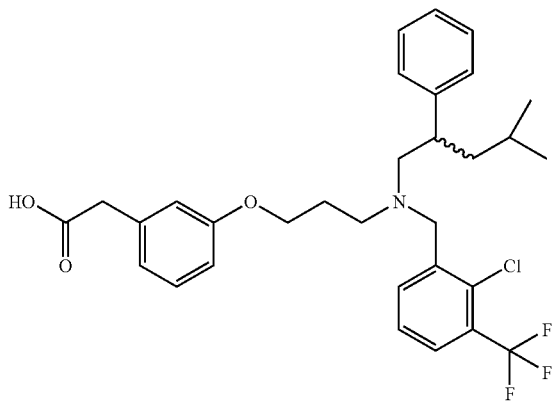

a. Diethyl 2-phenyl-2-(2-methyl-2-propenyl)malonate

NaH (440 mg of a 60% dispersion in mineral oil, 11 mmole) was washed free of mineral oil, and suspended in 20 mL of DMF. This was treated with a solution of diethyl phenylmalonate (2.36 g, 10 mmole) in 10 mL of DMF, and the reaction was stirred for 15 minutes, at which time the solution was clear. 2-Methylallyl bromide (2.0 mL) was added, and stirring continued for 1 hour. The reaction was diluted with H₂O and extracted with Et₂O. The extracts were washed with H₂O, dried and the solvent removed and gave the titled compound, 2.85 g (95% yield). MS (ESI) 291 (MH+)

b. Methyl 2-phenyl-4-methyl-4-pentenoic acid

A solution of diethyl 2-phenyl-2-(2-methyl-2-propenyl)malonate (1.63 g, 5.6 mmole) in 20 mL of EtOH and 5 mL of H₂O was treated with NaOH (2 g), and refluxed for 3 hours. The reaction was cooled, diluted with H₂O, and washed with Et₂O. The aqueous layer was acidified and extracted with CH₂Cl₂. The extracts were dried and evaporated. The residue was dissolved in 5 mL of dimethylacetamide and heated to 125° for 1 hour. The reaction was cooled, diluted with H₂O, acified, and extracted with Et₂O. The extracts were washed with H₂O, dried, and the solvent removed. The residue was dissolved in 10 mL of MEOH, a drop of concentrated H₂SO₄ was added, and stirred for 24 hours. The reaction was diluted with H₂O, and extracted with Et₂O. The extracts were washed with H₂O, aqueous NaHCO₃, dried and the solvent removed, and gave the titled compound, 953 mg (83%). MS (ESI) 205 (MH+)

c. 2-Phenyl-4-methylpentanoic acid

A solution of methyl 2-phenyl-4-methyl-4-pentenoic acid (850 mg, 4.15 mmole) in 10 mL of MeOHwas treated with 5 mL of 2.5N NaOH and heated to 50° for 30 minutes. The reaction was cooled, diluted with H₂O and washed with Et₂O. The aqueous phase was acified, and extracted with CH₂Cl₂. The extracts were washed with H₂O, dried and the solvent removed. The residue was dissolved in 25 mL of EtOAc, and hydrogenated over a 10% Pd/C catalyst, at 1 atmosphere H₂ pressure, for 2 hours. The catalyst was filtered and the solvent removed and gave the titled compound, 647 mg (81%). MS (ESI) 193 (MH+)

d. 2-Phenyl-4-methylpentanoic acid amide

The titled compound was prepared from 2-phenyl-4-methylpentanoic acid in 94% yield in the same manner as the preparation of 2-(4-Methoxyphenyl)propionamide in Example 188b. MS (ESI) 192 (MH+)

e. 2-Phenyl-4-methylpentylamine

The titled compound was prepared from 2-phenyl-4-methylpentanoic acid amide in 51% yield in the same manner as the preparation of 2-(4-methoxyphenyl)propylamine in Example 188c. MS (ESI) 178 (MH+)

f. N-(2-Chloro-3-trifluoromethylbenzyl)-2-phenyl-4-methylpentylamine

The titled compound was prepared from 2-Phenyl-4-methylpentylamine in 77% yield in the same manner as the preparation of N-(2-Chloro-3-trifluoromethylbenzyl)-2-(4-methoxyphenyl)propylamine in Example 188d. MS (ESI) 370 (MH+)

g. N-(2-Phenyl-4-methylpentyl)-N-(2-chloro-3-trifluoromethylbenzyl)-3-(3-carbomethoxymethylenephenoxy)propylamine The titled compound was prepared from N-(2-chloro-3-trifluoromethylbenzyl)-2-phenyl-4-methylpentylamine in 34% yield in the same manner as the preparation of N-(2-[4-methoxyphenyl]-propyl)-N-(2-chloro-3-trifluoromethylbenzyl)-3-(3-carbomethoxymethylenephenoxy)propylamine in Example 188e. MS (ESI) 576 (MH+)

h. N-(2-Phenyl-4-methylpentyl)-N-(2-chloro-3-trifluoromethylbenzyl)-3-(3-carboxymethylenephenoxy)propylamine, hydrochloride The titled compound was prepared from N-(2-phenyl-4-methylpentyl)-N-(2-chloro-3-trifluoromethylbenzyl)-3-(3-carbomethoxymethylenephenoxy)propylamine in 74% yield in the same manner as the preparation of N-(2-[4-Methoxyphenyl]-propyl)-N-(2-chloro-3-trifluoromethylbenzyl)-3-(3-carboxymethylenephenoxy)propylamine, hydrochloride in Example 188f. MS (ESI) 562 (MH+)

i. (R)-N-(2-Phenyl-4-methylpentyl)-N-(2-chloro-3-trifluoromethylbenzyl)-3-(3-carboxymethylenephenoxy)propylamine, trifluoroacetate and (S)-N-(2-Phenyl-4-methylpentyl)-N-(2-chloro-3-trifluoromethylbenzyl)-3-(3-carboxymethylenephenoxy)propylamine, trifluoroacetate The enantiomers of racemic N-(2-Phenyl-4-methylpentyl)-N-(2-chloro-3-trifluoromethylbenzyl)-3-(3-carboxymethylenephenoxy)propylamine were separated on a Chiralcel OJ Preparative HPLC column, 21 mm ID×250 mm, elution with 25:75:0.1-EtOH:hexane:TFA, 15 ml/min.

EXAMPLE 190

N-(2-Phenylbutyl)-N-(2-chloro-3-trifluoromethylbenzyl)-3-(3-carboxymethylenephenoxy)propylamine, hydrochloride

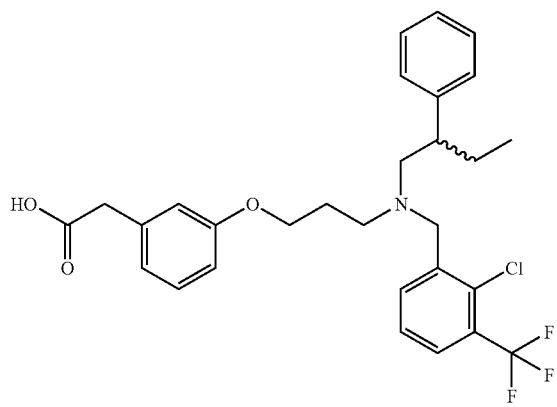

a. The titled compound was prepared from 2-phenylbutylamine (Acta. Pharmaceutica Nordica (1992), 4(2), 105-9) in the same manner as the preparation of N-(2-Phenyl-4-methylpentyl)-N-(2-chloro-3-trifluoromethylbenzyl)-3-(3-carboxymethylenephenoxy)propylamine, hydrochloride, Example 189 e-h. MS (ESI) 534 (MH$^+$)

b. (R)-N-2-Phenylbutyl)-N-(2-chloro-3-trifluormmethylbenzyl)-3-(3-carboxymethylenephenoxy)propylamine, trifluoroacetate and (S)-N-(2-Phenylbutyl)-N-2-chloro-3-trifluoromethylbenzyl)-3-(3-carboxymethylenephenoxy)propylamine, trifluoroacetate The enantiomers of racemic N-(2-phenylbutyl)-N-(2-chloro-3-trifluoromethylbenzyl)-3-(3-carboxymethylenephenoxy)propylamine were separated on a Chiralcel OJ Preparative HPLC column, 21 mm ID×250 mm, elution with 25:75:0.1-EtOH:hexane:TFA, 15 ml/min.

EXAMPLE 191

N-(2-[2-Methyl-2-phenyl]propyl)-N-(2-chloro-3-trifluoromethylbenzyl)-3-(3-carboxymethylenephenoxy)propylamine, hydrochloride

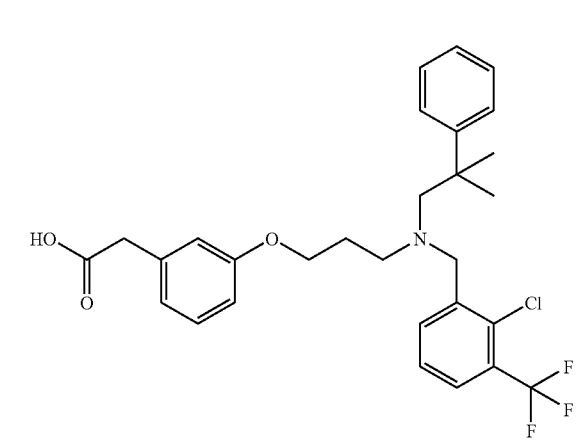

The titled compound was prepared from 2-phenyl-2-methylpropylamine (Acta. Pharmaceutica Nordica (1992), 4(2), 105-9) in the same manner as the preparation of N-(2-Phenyl-4-methylpentyl)-N-(2-chloro-3-trifluoromethylbenzyl)-3-(3-carboxymethylenephenoxy)propylamine, hydrochloride, Example 189e-h. MS (ESI) 534 (MH$^+$)

EXAMPLE 192

N-(2-Phenyl-3-methylbutyl)-N-(2-chloro-3-trifluoromethylbenzyl)-3-(3-carboxymethylenephenoxy)propylamine, hydrochloride

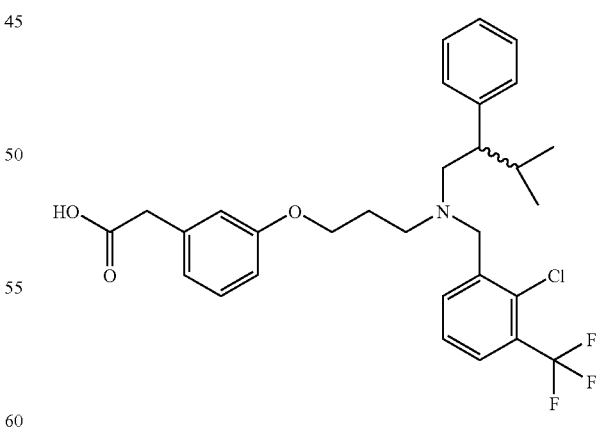

The titled compound was prepared from 2-phenyl-3-methylbutylamine (Acta. Pharmaceutica Nordica (1992), 4(2), 105-9) in the same manner as the preparation of N-(2-Phenyl-4-methylpentyl)-N-(2-chloro-3-trifluoromethylbenzyl)-3-(3-carboxymethylenephenoxy)propylamine, hydrochloride, Example 189e-h. MS (ESI) 548 (MH$^+$).

EXAMPLE 193

N-(2-Phenylhexyl)-N-(2-chloro-3-trifluoromethyl-benzyl)-3-(3-carboxymethylenephenoxy)propylamine, hydrochloride

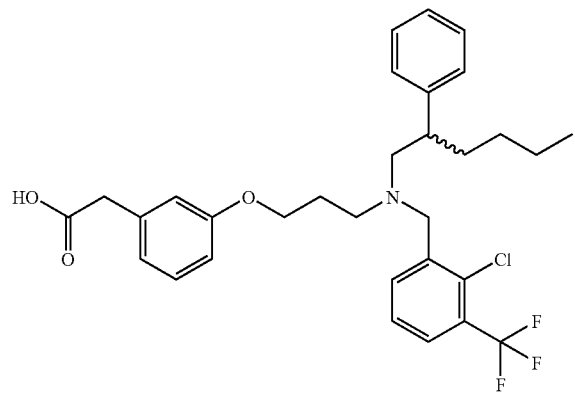

The titled compound was prepared from 2-phenylhexylamine (J. Chem. Soc. Perk. Trans. 1: Organic and Biorganic Chemistry (1976), (1), 33-8) in the same manner as the preparation of N-(2-Phenyl-4-methylpentyl)-N-(2-chloro-3-trifluoromethylbenzyl)-3-(3-carboxymethylenephenoxy)propylamine, hydrochloride, Example 189e-h. MS (ESI) 562 (MH$^+$)

EXAMPLE 194

N-(2-Phenyl-3-butynyl)-N-(2-chloro-3-trifluoromethylbenzyl)-3-(3-carboxymethylenephenoxy)propylamine

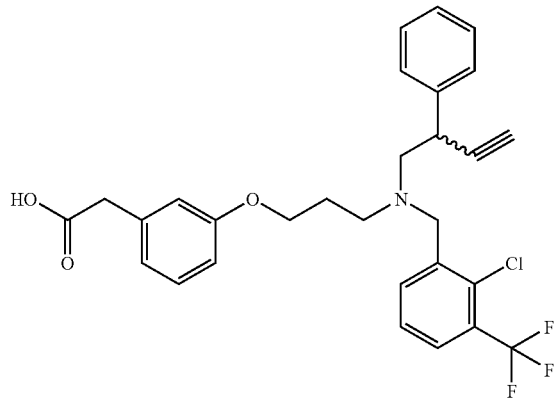

The titled compound was prepared from 2-ethynylphenethylamine (J. Med. Chem. (1988), 31(4), 704-6) in the same manner as the preparation of N-(2-Phenyl-4-methylpentyl)-N-(2-chloro-3-trifluoromethylbenzyl)-3-(3-carboxymethylenephenoxy)propylamine, hydrochloride, Example 189e-h. MS (ESI) 530 (MH$^+$)

EXAMPLE 195

(S)-N-(2-Phenyl-2-methoxyethyl)-N-(2-chloro-3-trifluoromethylbenzyl)-3-(3-carboxymethylenephenoxy)propylamine, hydrochloride

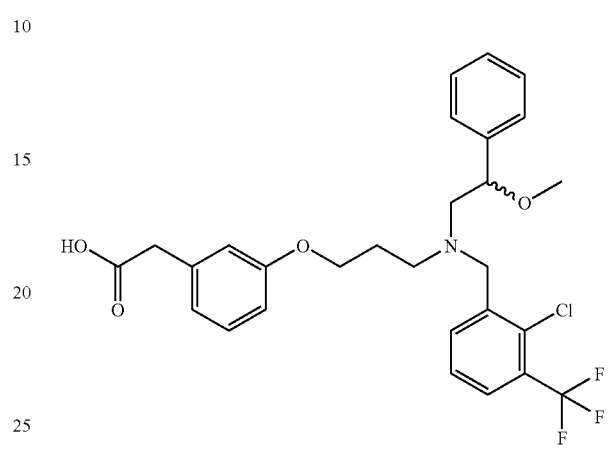

The titled compound was prepared from (S)-2-methoxyphenethyl amine (Eur. J. Med. Chem. (1995), 30(12), 949-54) in the same manner as the preparation of N-(2-Phenyl-4-methylpentyl)-N-(2-chloro-3-trifluoromethylbenzyl)-3-(3-carboxymethylenephenoxy)propylamine, hydrochloride, Example 189e-h. MS (ESI) 536 (MH$^+$)

EXAMPLE 196

(R)-N-(2-Phenyl-2-methoxyethyl)-N-(2-chloro-3-trifluoromethylbenzyl)-3-(3-carboxymethylenephenoxy)propylamine, hydrochloride

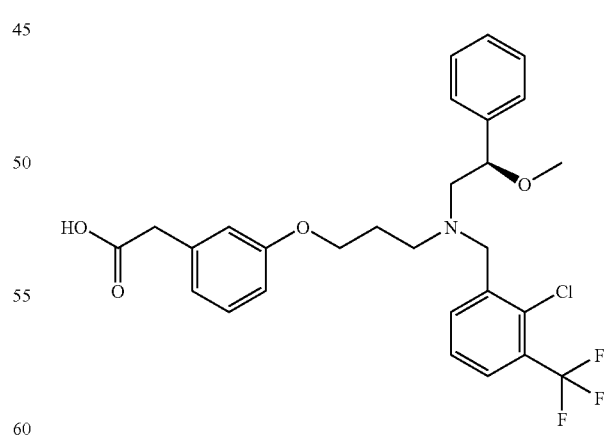

The titled compound was prepared from (R)-2-methoxyphenethyl amine (Eur. J. Med. Chem. (1995), 30(12), 949-54) in the same manner as the preparation of N-(2-Phenyl-4-methylpentyl)-N-(2-chloro-3-trifluoromethylbenzyl)-3-(3-carboxymethylenephenoxy)propylamine, hydrochloride, Example 189e-h. MS (ESI) 536 (MH$^+$)

EXAMPLE 197

(R)-N-(2-Phenyl-2-methoxyethyl)-N-(2-chloro-3-trifluoromethylbenzyl)-3-(3-[2-hydroxy-2-methylpropyl]phenoxy)propylamine

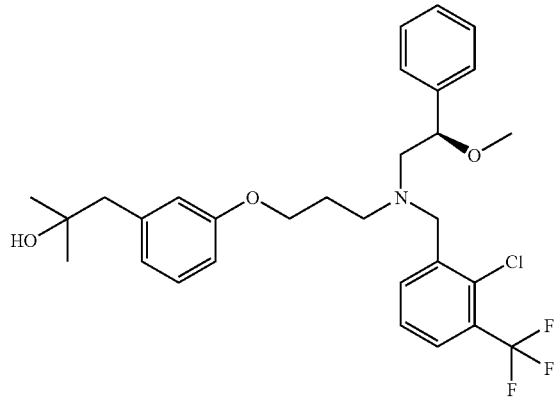

The titled compound was prepared from (R)-N-(2-phenyl-2-methoxyethyl)-N-(2-chloro-3-trifluoromethylbenzyl)-3-(3-carbomethoxymethylenephenoxy)propylamine in 44% yield in the same manner as the preparation of N-(2,2-Diphenylethyl)-N-(2-chloro-3-trifluoromethylbenzyl)-3-(3-[2-hydroxy-2-methylpropyl]phenoxy)propylamine in Example 182. MS (ESI) 550 (MH+)

EXAMPLE 198

2-(3-{3-[[2-Chloro-3-(trifluoromethyl)benzyl](2-methyl-propyl)amino]-propoxy}-phenyl)acetic acid hydrochloride salt

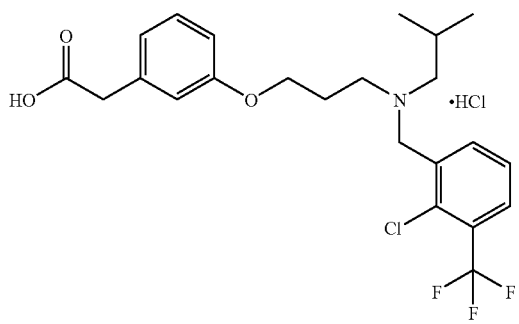

Following the procedure of Intermediate 1 (a)-(e) except isobutylamine was used in step 1(b) instead of 2,2-diphenylethylamine the title compound was prepared as a white solid (7.5% overall). MS (ESI) 458.2 (M+H+).

EXAMPLE 199

1-(3-{3-[(2-Chloro-3-trifluoromethyl-benzyl)-diphenylethyl-amino]-propoxy}-phenyl)-cyclobutanecarboxylic acid hydrochloride salt

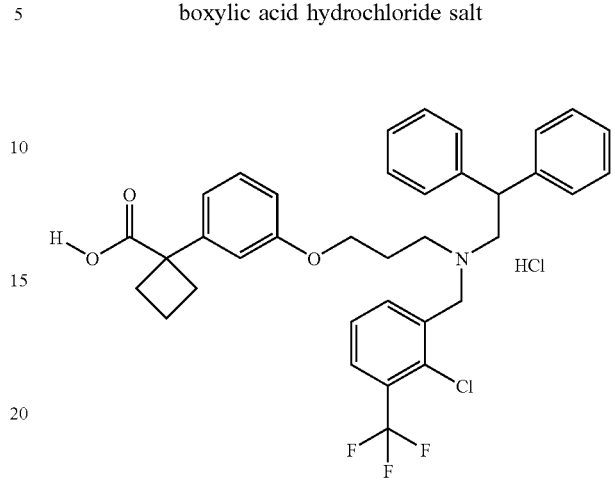

a) (3-{3-[(2-Chloro-3-trifluoromethyl-benzyl)-diphenylethyl-amino]-propoxy}-phenyl)-acetic acid methyl ester To a solution of (3-{3-[(2-Chloro-3-trifluoromethyl-benzyl)-diphenylethyl-amino]-propoxy}-phenyl)-acetic acid (0.5 g, 3.7 mmol) in methanol (300 ml) was added concentrated hydrochloric acid (10 ml). After the resulting mixture was heated to reflux for 2 h solvent was removed under vacuum. The residue was dissolved in water and neutralized to pH=7. The aqueous layer was extracted with ethyl acetate. The combined organic layers were washed with saturated sodium bicarbonate, brine, dried over sodium sulfate, and concentrated in vacco to give the title compound as colorless oil (0.5 g, 90%). MS m/e 596.6 (M+H)+.

b) 1-(3-{3-[(2-Chloro-3-trifluoromethyl-benzyl)-diphenylethyl-amino]-propoxy}-phenyl)-cyclobutanecarboxylic acid methyl ester To a solution of (3-{3-[(2-Chloro-3-trifluoromethyl-benzyl)-diphenylethyl-amino]-propoxy}-phenyl)-acetic acid methyl ester (100 mg, 0.17 mmol) in dry THF (50 ml) was added lithium diisopropylamide (1.26 ml, 0.5 mmol) dropwise with cooling to −78° C. After the reaction mixture was stirred at −78° C. for an additional 1 h, diiodo-propane (152 mg, 0.51 mmol) was added. The reaction was warmed to room temperature over 4 h followed by quenching with saturated ammonium chloride (10 ml). Solvent was removed and the residue was partitioned between water and ethyl acetate. The combined organic layers were washed with brine, dried over sodium sulfate and concentrated under vacuum. The residue was purified by silica gel column chromatograph (EtOAc:Hexane/20:80) to give the title compound as an oil (40 mg, 50%). MS m/e 636.2 (M+H)+.

c) 1-(3-{3-[(2-Chloro-3-trifluoromethyl-benzyl)-diphenylethyl-amino]-propoxy}-phenyl)-cyclobutanecarboxylic acid hyrdochloride salt A solution of 1-(3-{3-[(2-Chloro-3-trifluoromethyl-benzyl)-diphenylethyl-amino]-propoxy}-phenyl)-cyclobutanecarboxylic acid methyl ester (40 mg, 0.06 mmol) in DMF (9 ml) was treated with LiCl (20 mg, 0.46 mmol). The resulting reaction mixture was heated to reflux overnight and concentrated under vacuum. The crude product was purified by HPLC (YMC CombiPrep ODS-A, 50×20 mm, 20 mL/min, A: acetonitrile B: water, A: 60 to 100% during 10 min, W detection at 254 nm) to give the title compound, the free amine as an oil (20 mg, 50%). MS m/e 622.2 (M+H)+. To a solution of the free amine in diethyl ether was added HCl in diethyl ether (1.0M) to precipitate the amine salt. The suspension was filtered and dried to give the title compound as a white solid.

EXAMPLE 200

1-(3-{3-[(2-Chloro-3-trifluoromethyl-benzyl)-diphenylethyl-amino]-propoxy}-phenyl)-cyclopentanecarboxylic acid hydrochloride salt

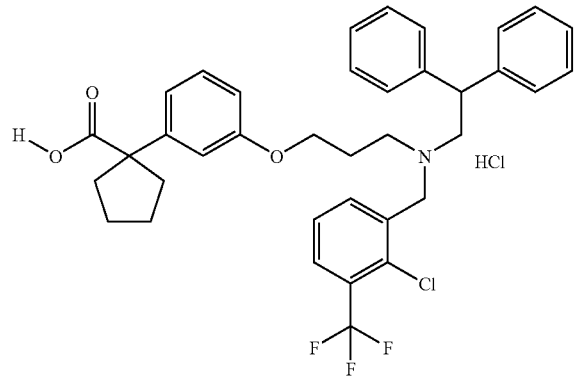

Following the procedure of Example 199 except substituting 1,4-diiodo-butane for iodoethane in step b, the title compound was obtained as a white solid (15 mg, 35%). MS (ESI): 637.2 (M+H)+.

EXAMPLE 201

1-(3-{3-[(2-Chloro-3-trifluoromethyl-benzyl)-(2,2-diphenyl-ethyl)-amino]-propoxy}-phenyl)-cyclopropanecarboxylic acid hydrochloride salt

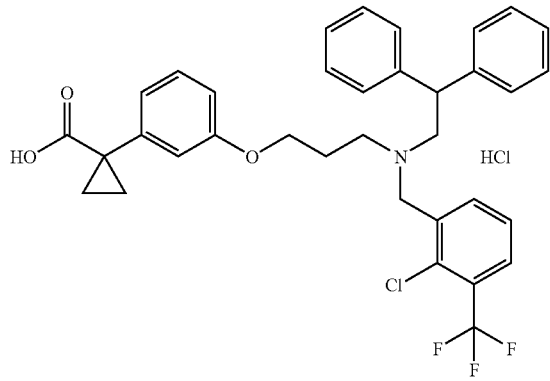

a) (3-Benzyloxy-phenyl)-acetic acid methyl ester

To a solution of 3-phenoxy-acetic acid methyl ester (2.0 g, 12 mmol) in dry acetone (60 mL) with potassium carbonate (3.3 g, 24 mmol) was added benzylbromide (2.1 ml, 18 mmol). The reaction mixture was heated to reflux for 1 h. After cooling, the solvent was evaporated, water was added and the organic products were extracted into ethyl acetate, washed with brine, dried (MgSO4), and evaporated. The residue was purified by column chromatography over silica gel (silica gel 60, EM Science) using a gradient of 5-30% ethyl acetate:hexane as eluent to afford 2.1 g (66% yield) of the title compound as an oil. $^1$H NMR (CDCl$_3$, 400 MHz) δ 7.45-7.25 (m, 6 H), 6.95-6.90 (m, 3 H), 5.09 (s, 2 H), 3.72 (s, 3 H), 3.63 (s, 2 H).

b) 2-(3-Benzyloxy-phenyl)-3-oxo-succinic acid diethyl ester

Intermediates b-c were prepared following the procedure of Jefford, C. W.; Kubota, T.; Zaslona, A. *Helvetica Chimica Acta* 1986, 69(8), 2048-2061. Dry ethanol (4 ml) was added to sodium (120 mg) while cooling to 0 C. After the bubbling ceased, diethyl oxylate (532 uL, 3.9 mmol) was added in ethanol (1 ml) followed by (3-Benzyloxy-phenyl)-acetic acid methyl ester (1.0 g, 3.9 mmol). This mixture was stirred and allowed to warm to RT overnight. The solvent was evaporated, the residue taken up in water and diethyl ether. The aqueous layer was collected and neutralized, then the product was extracted into methylene chloride which was dried (MgSO4), and evaporated to afford 1.28 g (89% yield) of the title compound as an oil: MS (ESI) 371.2 (M+H+).

c) 2-(3-Benzyloxy-phenyl)-acrylic acid ethyl ester

To 2-(3-Benzyloxy-phenyl)-3-oxo-succinic acid diethyl ester (1.28 g, 3.6 mmol) in water (5 ml) was added formaldehyde (600 uL, 37% solution, 6.6 mmol) and potassium carbonate (0.37 g, 2.7 mmol). The reaction was stirred vigorously overnight The organic products were extracted into diethyl ether which was dried (MgSO4), and evaporated. The residue was purified by column chromatography over silica gel (silica gel 60, EM Science) using 5% ethyl acetate:hexane as eluent to afford 0.99 g (55% yield) of the title compound as an oil. $^1$H NMR (CDCl$_3$, 400 MHz) δ 7.48-7.27 (m, 6H), 7.10-6.97 (m, 3H), 6.35 (s, 1H), 5.90 (s, 1H), 5.10 (s, 2H), 4.30 (q, J=7.2 Hz, 2H), 1.36 (t, J=7.2 Hz, 3H).

d) 1-(3-Benzyloxy-phenyl)-2,2-dibromo-cyclopropanecarboxylic acid ethyl ester

Intermediates d-e were prepared following the procedure of Kirmse, W.; Rode, J. *Chem. Ber.* 1986, 119, 3694-3703. To absolution of 2-(3-benzyloxy-phenyl)-acrylic acid ethyl ester (250 mg, 0.89 mmol) in methylene chloride (283 uL) was added bromoform (100 uL, 1.1 mmol), benzyltriethyl ammonium chloride (2.6 mg), and sodium hydroxide (50% aqueous solution, 167 uL). The reaction was stirred at room temperature for 48 hours and then the product was extracted into diethyl ether, dried (MgSO4), and evaporated. This material was further purified by filtration through a plug of silica gel using diethyl ether as the eluant to give 358 mg (89% yield) of the title compounds as a white solid. MS (ESI) 454.8 (M+H+).

e) 1-(3-Hydroxy-phenyl)-cyclopropanecarboxylic acid ethyl ester

To a solution of 1-(3-Benzyloxy-phenyl)-2,2-dibromo-cyclopropanecarboxylic acid ethyl ester (282 mg, 0.62 mmol) in diethyl ether (1 ml) was added tributyltin hydride (420 uL, 1.5 mmol). Additional tin was added with stirring over 48 hours to try to push the reaction to completion. After evaporation, purification by column chromatography over silica gel (silica gel 60, EM Science) using a gradient of 1-5% ethyl acetate:hexane as eluent was used to afford 200 mg of 13-Benzyloxy-phenyl)-cyclopropanecarboxylic acid ethyl ester and a mono-brominated contaminant as an oil: MS (ESI) 297.2 (M+H$^+$).

To this mixture was added palladium on carbon (10 w %, 100 mg), methanol (10 ml), and hydrogen was applied at 50 psi using a parr shaker over 4 hours. The reaction was filtered through celite and the solvent evaporated. The residue was purified by preparative HPLC (YMC Combi-Prep ODS-A, 50×20 mm, 20 mL/min, A: acetonitrile B: water, A: 10 to 90% during 10 min, UV detection at 254 nm) to give 25 mg (20% over 2 steps) of the title compound as an oil. MS (ESI) 207.0 [M+H]$^+$.

f) (2-Chloro-3-trifluoromethyl-benzyl)-diphenyl

To a solution of 2,2-Diphenyl-ethylamine (1.149, 5.7 mmol) in dry dichloromethane (300 ml) was added acetic acid followed by 2-chloro-3-trifluoromethylbenzaldehyde (1.0 g, 4.8 mmol) and sodium triacetoxyborohydride (2.03 g, 9.6 mmol). After the resulting mixture was stirred for 1.5 h at room temperature water was added to quench the reaction. The aqueous layer was extracted with ethyl acetate. The combined organic layers were washed with brine, dried over sodium sulfate, and concentrated in vacco. The crude mixture was purified by silica gel column chromatograph (EtOAc:Hexane/25:75) to give the title compound as an oil 1.7 g. (yield 76%). MS m/e 387.2 (M+H)$^+$.

g) (3-Bromo-propyl)-(2-chloro-3-trifluoromethyl-benzyl)diphenylethyl-amine

A solution of compound (2-Chloro-3-trifluoromethyl-benzyl)-diphenylethyl-amine (2.5 g, 6.5 mmol) and 1,3-dibromo propane (3.2 ml, 32 mmol) in acetonitrile (300 ml) was treated with solid potassium carbonate (1.8 g, 13 mmol). The reaction was heated to reflux and stirred for 48 h. Upon cooling to room temperature, the reaction was filtered through a pad of celite, washed with EtOAc, and the filtrate was concentrated in vacuo. The crude product was purified by column chromatography (EtOAc:Hexane/20:80) to give the title compound as an oil (2.2 g, 67%). MS m/e 510.6 (M+H)$^+$.

h) 1-(3-{3-[3-Chloro-2-trifluoromethyl-benzyl-(2,2-diphenyl-ethyl)-amino]-propoxy)phenyl)-cyclopropanecarboxylic acid ethyl ester To a solution of 1-(3-Hydroxy-phenyl)-cyclopropanecarboxylic acid ethyl ester (25 mg, 0.12 mmol) in acetonitrile (2 ml) was added potassium carbonate (37 mg, 0.24 mmol) and (3-Bromo-propyl)-(2-chloro-3-trifluoromethyl-benzyl)-(2,2-diphenyl-ethyl)-amine (68 mg, 0.13 mmol). The mixture was heated to reflux overnight After cooling, the solvent was evaporated, water was added and the organic products were extracted into ethyl acetate, washed with brine, dried (MgSO4), and evaporated. Further purification by column chromatography over silica gel (silica gel 60, EM Science) using 5% ethyl acetate:hexane as eluent was used to afford 65 mg (84% yield) of the titled compound as an oil: MS (ESI) 636.2 (M+H$^+$).

i) 1-(3-{3-[(2-Chloro-3-trifluoromethyl-benzyl)-(2,2-diphenyl-ethyl)-amino]-propoxy}-phenyl)-cyclopropanecarboxylic acid hydrochloride salt To a solution of 1(3-{3-[2-Chloro-3-trifluoromethyl-benzyl-(2,2-diphenyl-ethyl)-amino]-propoxy}-phenyl)-cyclopropanecarboxylic acid ethyl ester (65 mg, 0.12 mmol) in THF (1 ml) and methanol (4 ml) was added lithium hydroxide (2N aq., 1 ml). The reaction was stirred at RT overnight. Acidic water was added to neutralize the solution and the organic products were extracted into ethyl acetate, washed with brine, dried (MgSO4), and evaporated. The residue was purified by preparative HPLC (YMC CombiPrep ODS-A, 50×20 mm, 20 mL/min, A: acetonitrile B: water, A: 10 to 90% during 10 min, UV detection at 254 nm) to give 17 mg (27%) of the title compound as an oil. The oil was dissolved in methanol, and HCl in diethyl ether was added, the solvents were evaporated to form the hydrochloride salt as a solid. MS (ESI) 608.0 [M+H]$^+$.

The above description fully discloses how to make and use the present invention. However, this invention is not limited to the particular embodiments described hereinabove, but includes all modification thereof within the scope of the appended claims and their equivalents. Those skilled in the art will recognize through routine experimentation that various changes and modifications can be made without departing from the scope of this invention. The various references to journals, patents and other patent applications that are cited herein are incorporated by reference herein as though fully set forth.

What is claimed is:

1. A compound of Formula I:

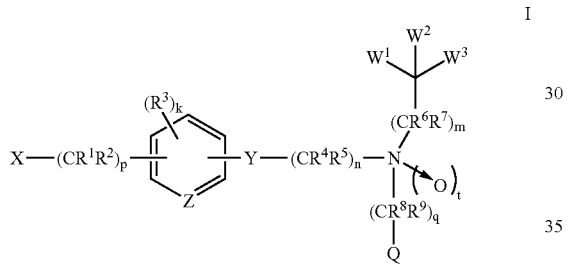

I wherein:

X is selected from $C_1$-$C_8$ alkyl, halo, —$OR^{10}$, —$NR^{14}R^{15}$, nitro, cyano, —$COOR^{10}$, —$COR^{13}$, —$OCOR^{13}$, —$N(R^{17})COR^{13}$, —$N(R^{17})CONR^{14}R^{15}$, —$N(R^{17})COOR^{13}$, —$SO_3H$, —$SO_2NR^{14}R^{15}$, —$C(=NR^{17})NR^{14}R^{15}$, —$N(R^{17})SO_2R^{16}$, and a 5 or 6-membered heterocyclic group;

or X and an adjacent $R^3$, taken together with the atoms to which they are bonded, form an alkylenedioxy moiety;

Z is CH, $CR^3$ or N, wherein when Z is CH or $CR^3$, k is 0-4 and t is 0 or 1, and when Z is N, k is 0-3 and t is 0;

Y is selected from —O—, —S—, —$N(R^{10})$-, and —$C(R^4)(R^5)$—;

$W^1$ is selected from $C_3$-$C_8$ cycloalkyl, aryl and Het, wherein said $C_3$-$C_8$ cycloalkyl, aryl and Het are optionally unsubstituted or substituted with one or more groups independently selected from halo, cyano, nitro, $C_1$-$C_6$ alkyl, $C_3$-$C_6$ alkenyl, $C_3$-$C_6$ alkynyl, —$C_0$-$C_6$ alkyl-$CO_2R^{10}$, —$C_0$-$C_6$ alkyl-$C(O)SR^{10}$, —$C_0$-$C_6$ alkyl-$CONR^{11}R^{12}$, —$C_0$-$C_6$ alkyl-$COR^{13}$, —$C_0$-$C_6$ alkyl-$NR^{11}R^{12}$, —$C_0$-$C_6$ alkyl-$SR^{10}$, —$C_0$-$C_6$ alkyl-$OR^{10}$, —$C_0$-$C_6$ alkyl-$SO_3H$, —$C_0$-$C_6$ alkyl-$SO_2NR^{11}R^{12}$, —$C_0$-$C_6$ alkyl-$SO_2R^{10}$, —$C_0$-$C_6$ alkyl-$SOR^{13}$, —$C_0$-$C_6$ alkyl-$OCOR^{13}$, —$C_0$-$C_6$ alkyl-$OC(O)NR^{11}R^{12}$, —$C_0$-$C_6$ alkyl-$OC(O)OR^{13}$, —$C_0$-$C_6$ alkyl-$NR^{11}C(O)OR^{13}$, —$C_0$-$C_6$ alkyl-$NR^{11}C(O)NR^{11}R^{12}$, and —$C_0$-$C_6$ alkyl-$NR^{11}COR^{13}$, where said $C_1$-$C_6$ alkyl, is optionally unsubstituted or substituted by one or more halo substituents;

$W^2$ is selected from H, halo, $C_1$-$C_6$ alkyl, $C_2$-$C_6$ alkenyl, $C_2$-$C_6$ alkynyl, —$C_0$-$C_6$ alkyl-$NR^{11}R^{12}$, —$C_0$-$C_6$ alkyl-$SR^{10}$, —$C_0$-$C_6$ alkyl-$OR^{10}$, —$C_0$-$C_6$ alkyl-$CO_2R^{10}$, —$C_0$-$C_6$ alkyl-$C(O)SR^{10}$, —$C_0$-$C_6$ alkyl-$CONR^{11}R^{12}$, —$C_0$-$C_6$ alkyl-$COR^{13}$, —$C_0$-$C_6$ alkyl-$OCOR^{13}$, —$C_0$-$C_6$ alkyl-$OCONR^{11}R^{12}$, —$C_0$-$C_6$ alkyl-$NR^{11}CONR^{11}R^{12}$, —$C_0$-$C_6$ alkyl-$NR^{11}COR^{13}$, —$C_0$-$C_6$ alkyl-Het, —$C_0$-$C_6$ alkyl-aryl and —$C_0$-$C_6$ alkyl-$C_3$-$C_7$ cycloalkyl, wherein said $C_1$-$C_6$ alkyl is optionally unsubstituted or substituted by one or more halo substituents, and wherein the $C_3$-$C_7$ cycloalkyl, aryl and Het moieties of said —$C_0$-$C_6$ alkyl-Het, —$C_0$-$C_6$ alkyl-aryl and —$C_0$-$C_6$ alkyl-$C_3$-$C_7$ cycloalkyl are optionally unsubstituted or substituted with one or more groups independently selected from halo, cyano, nitro, $C_1$-$C_6$ alkyl, $C_3$-$C_6$ alkenyl, $C_3$-$C_6$ alkynyl, —$C_0$-$C_6$ alkyl-$CO_2R^{10}$, —$C_0$-$C_6$ alkyl-$C(O)SR^{10}$, —$C_0$-$C_6$ alkyl-$CONR^{11}R^{12}$, —$C_0$-$C_6$ alkyl-$COR^{13}$, —$C_0$-$C_6$ alkyl-$NR^{11}R^{12}$, —$C_0$-$C_6$ alkyl-$SR^{10}$, —$C_0$-$C_6$ alkyl-$OR^{10}$, —$C_0$-$C_6$ alkyl-$SO_3H$, —$C_0$-$C_6$ alkyl-$SO_2NR^{11}R^{12}$, —$C_0$-$C_6$ alkyl-$SO_2R^{10}$, —$C_0$-$C_6$ alkyl-$SOR^{13}$, —$C_0$-$C_6$ alkyl-$OCOR^{13}$, —$C_0$-$C_6$ alkyl-$OC(O)NR^{11}R^{12}$, —$C_0$-$C_6$ alkyl-$OC(O)OR^{13}$, —$C_0$-$C_6$ alkyl-$NR^{11}C(O)OR^{13}$, —$C_0$-$C_6$ alkyl-$NR^{11}C(O)NR^{11}R^{12}$, and —$C_0$-$C_6$ alkyl-$NR^{11}COR^{13}$, where said $C_1$-$C_6$ alkyl, is optionally unsubstituted or substituted by one or more halo substituents;

$W^3$ is selected from the group consisting of: H, halo, $C_1$-$C_6$ alkyl, —$C_0$-$C_6$ alkyl-$NR^{11}R^{12}$, —$C_0$-$C_6$ alkyl-$SR^{10}$, —$C_0$-$C_6$ alkyl-$OR^{10}$, —$C_0$-$C_6$ alkyl-$CO_2R^{10}$, —$C_0$-$C_6$ alkyl-$C(O)SR^{10}$, —$C_0$-$C_6$ alkyl-$CONR^{11}R^{12}$, —$C_0$-$C_6$ alkyl-$COR^{13}$, —$C_0$-$C_6$ alkyl-$OCOR^{13}$, —$C_0$-$C_6$ alkyl-$OCONR^{11}R^{12}$, —$C_0$-$C_6$ alkyl-$NR^{11}CONR^{11}R^{12}$, —$C_0$-$C_6$ alkyl-$NR^{11}COR^{13}$, —$C_0$-$C_6$ alkyl-Het, —$C_1$-$C_6$ alkyl-aryl and —$C_1$-$C_6$ alkyl-$C_3$-$C_7$ cycloalkyl, wherein said $C_1$-$C_6$ alkyl is optionally unsubstituted or substituted by one or more halo substituents;

Q is selected from $C_3$-$C_8$ cycloalkyl, Ar and Het; wherein said $C_3$-$C_8$ cycloalkyl, Ar and Het are optionally unsubstituted or substituted with one or more groups independently selected from halo, cyano, nitro, $C_1$-$C_6$ alkyl, $C_3$-$C_6$ alkenyl, $C_3$-$C_6$ alkynyl, —$C_0$-$C_6$ alkyl-$CO_2R^{10}$, —$C_0$-$C_6$ alkyl-C(O)$SR^{10}$, —$C_0$-$C_6$ alkyl-$CONR^{11}R^{12}$, —$C_0$-$C_6$ alkyl-$COR^{13}$, —$C_0$-$C_6$ alkyl-$NR^{11}R^{12}$, —$C_0$-$C_6$ alkyl-$SR^{10}$, —$C_0$-$C_6$ alkyl-$OR^{10}$, —$C_0$-$C_6$ alkyl-$SO_3H$, —$C_0$-$C_6$ alkyl-$SO_2NR^{11}R^{12}$, —$C_0$-$C_6$ alkyl-$SO_2R^{10}$, —$C_0$-$C_6$ alkyl-$SOR^{13}$, —$C_0$-$C_6$ alkyl-$OCOR^{13}$, —$C_0$-$C_6$ alkyl-OC(O)$NR^{11}R^{12}$, —$C_0$-$C_6$ alkyl-OC(O)$OR^{13}$, —$C_0$-$C_6$ alkyl-$NR^{11}$C(O)$OR^{13}$, —$C_0$-$C_6$ alkyl-$NR^{11}$C(O)$NR^{11}R^{12}$, and —$C_0$-$C_6$ alkyl-$NR^{11}COR^{13}$, where said $C_1$-$C_6$ alkyl is optionally unsubstituted or substituted by one or more halo substituents;

p is 0-8;

n is 3;

m is 0 or 1;

q is 0 or 1;

t is 0 or 1;

each $R^1$ and $R^2$ are independently selected from H, halo, $C_1$-$C_6$ alkyl, $C_3$-$C_6$ alkenyl, $C_3$-$C_6$ alkynyl, —$C_0$-$C_6$ alkyl-$NR^{11}R^{12}$, —$C_0$-$C_6$ alkyl-$OR^{10}$, —$C_0$-$C_6$ alkyl-$SR^{10}$, —$C_1$-$C_6$ alkyl-Het, —$C_1$-$C_6$ alkyl-Ar and —$C_1$-$C_6$ alkyl-$C_3$-$C_7$ cycloalkyl, or $R^1$ and $R^2$ together with the carbon to which they are attached form a 3-5 membered carbocyclic or heterocyclic ring, wherein said heterocyclic ring contains one, or more heteroatoms selected from N, O, and S, where any of said $C_1$-$C_6$ alkyl is optionally unsubstituted or substituted by one or more halo substituents;

each $R^3$ is the same or different and is independently selected from halo, cyano, nitro, $C_1$-$C_6$ alkyl, $C_3$-$C_6$ alkenyl, $C_3$-$C_6$ alkynyl, —$C_0$-$C_6$ alkyl-Ar, —$C_0$-$C_6$ alkyl-Het, —$C_0$-$C_6$ alkyl-$C_3$-$C_7$ cycloalkyl, —$C_0$-$C_6$ alkyl-$CO_2R^{10}$, —$C_0$-$C_6$ alkyl-C(O)$SR^{10}$, —$C_0$-$C_6$ alkyl-$CONR^{11}R^{12}$, —$C_0$-$C_6$ alkyl-$COR^{13}$, —$C_0$-$C_6$ alkyl-$NR^{11}R^{12}$, —$C_0$-$C_6$ alkyl-$SR^{10}$, —$C_0$-$C_6$ alkyl-$OR^{10}$, —$C_0$-$C_6$ alkyl-$SO_3H$, —$C_0$-$C_6$ alkyl-$SO_2NR^{11}R^{12}$, —$C_0$-$C_6$ alkyl-$SO_2R^{10}$, —$C_0$-$C_6$ alkyl-$SOR^{13}$, —$C_0$-$C_6$ alkyl-$OCOR^{13}$, —$C_0$-$C_6$ alkyl-OC(O)$NR^{11}R^{12}$, —$C_0$-$C_6$ alkyl-OC(O)$OR^{13}$, —$C_0$-$C_6$ alkyl-$NR^{11}$C(O)$OR^{13}$, —$C_0$-$C_6$ alkyl-$NR^{11}$C(O)$NR^{11}R^{12}$, and —$C_0$-$C_6$ alkyl-$NR^{11}COR^{13}$, wherein said $C_1$-$C_6$ alkyl is optionally unsubstituted or substituted by one or more halo substituents;

each $R^4$ and $R^5$ is independently selected from H, halo, $C_1$-$C_6$ alkyl, —$C_0$-$C_6$ alkyl-Het, —$C_0$-$C_6$ alkyl-Ar and —$C_0$-$C_6$ alkyl-$C_3$-$C_7$ cycloalkyl;

$R^6$ and $R^7$ are each independently selected from H, halo, $C_1$-$C_6$ alkyl, —$C_0$-$C_6$ alkyl-Het, —$C_0$-$C_6$ alkyl-Ar and —$C_0$-$C_6$ alkyl-$C_3$-$C_7$ cycloalkyl;

$R^8$ and $R^9$ are each independently selected from H, halo, $C_1$-$C_6$ alkyl, —$C_0$-$C_6$ alkyl-Het, —$C_0$-$C_6$ alkyl-Ar and —$C_0$-$C_6$ alkyl-$C_3$-$C_7$ cycloalkyl;

$R^{10}$ is selected from H, $C_1$-$C_6$ alkyl, $C_3$-$C_6$ alkenyl, $C_3$-$C_6$ alkynyl, —$C_0$-$C_6$ alkyl-Ar, —$C_0$-$C_6$ alkyl-Het and —$C_0$-$C_6$ alkyl-$C_3$-$C_7$ cycloalkyl;

each $R^{11}$ and each $R^{12}$ are independently selected from H, $C_1$-$C_6$ alkyl, $C_3$-$C_6$ alkenyl, $C_3$-$C_6$ alkynyl, —$C_0$-$C_6$ alkyl-Ar, —$C_0$-$C_6$ alkyl-Het and —$C_0$-$C_6$ alkyl-$C_3$-$C_7$ cycloalkyl, or $R^{11}$ and $R^{12}$ together with the nitrogen to which they are attached form a 4-7 membered heterocyclic ring which optionally contains one or more additional heteroatoms selected from N, O, and S;

$R^{13}$ is selected from $C_1$-$C_6$ alkyl, $C_3$-$C_6$ alkenyl, $C_3$-$C_6$ alkynyl, —$C_0$-$C_6$ alkyl-Ar, —$C_0$-$C_6$ alkyl-Het and —$C_0$-$C_6$ alkyl-$C_3$-$C_7$ cycloalkyl;

$R^{14}$ and $R^{15}$ are each independently from H, $C_1$-$C_6$ alkyl, $C_3$-$C_6$ alkenyl, $C_3$-$C_6$ alkynyl, —$C_0$-$C_6$ alkyl-Ar, —$C_0$-$C_6$ alkyl-Het, —$C_0$-$C_6$ alkyl-$C_3$-$C_7$ cycloalkyl, —$C_0$-$C_6$ alkyl-O—Ar, —$C_0$-$C_6$ alkyl-O-Het, —$C_0$-$C_6$ alkyl-O—$C_3$-$C_7$ cycloalkyl, —$C_0$-$C_6$ alkyl-S(O)$_x$—$C_1$-$C_6$ alkyl, —$C_0$-$C_6$ alkyl-S(O)$_x$—Ar, —$C_0$-$C_6$ alkyl-S(O)$_x$-Het, —$C_0$-$C_6$ alkyl-S(O)$_x$—$C_3$-$C_7$ cycloalkyl, —$C_0$-$C_6$ alkyl-NH-Het, —$C_0$-$C_6$ alkyl-NH—$C_3$-$C_7$ cycloalkyl, —$C_0$-$C_6$ alkyl-N($C_1$-$C_4$ alkyl)-Ar, —$C_0$-$C_6$ alkyl-N($C_1$-$C_4$ alkyl)-Het, —$C_0$-$C_6$ alkyl-N($C_1$-$C_4$ alkyl)-$C_3$-$C_7$ cycloalkyl, —$C_0$-$C_6$ alkyl-Ar, —$C_0$-$C_6$ alkyl-Het and —$C_0$-$C_6$ alkyl-$C_3$-$C_7$ cycloalkyl, where x is 0, 1 or 2, or $R^{14}$ and $R^{15}$, together with the nitrogen to which they are attached, form a 4-7 membered heterocyclic ring which optionally contains one or more additional heteroatoms selected from N, O, and S, wherein said $C_1$-$C_6$ alkyl is optionally substituted by one or more of the substituents independently selected from the group halo, —OH, —SH, —$NH_2$, —NH(unsubstituted $C_1$-$C_6$ alkyl), —N(unsubstituted $C_1$-$C_6$ alkyl)(unsubstituted $C_1$-$C_6$ alkyl), unsubstituted —$OC_1$-$C_6$ alkyl, —$CO_2H$, —$CO_2$(unsubstituted $C_1$-$C_6$ alkyl), —$CONH_2$, —CONH(unsubstituted $C_1$-$C_6$ alkyl), —CON(unsubstituted $C_1$-$C_6$ alkyl)(unsubstituted $C_1$-$C_6$ alkyl), —$SO_3H$, —$SO_2NH_2$, —$SO_2NH$(unsubstituted $C_1$-$C_6$ alkyl) and —$SO_2N$(unsubstituted $C_1$-$C_6$ alkyl)(unsubstituted $C_1$-$C_6$ alkyl);

$R^{16}$ is $C_1$-$C_6$ alkyl, —$C_0$-$C_6$ alkyl-Ar or —$C_0$-$C_6$ alkyl-Het; and $R^{17}$ is H, $C_1$-$C_6$ alkyl, —$C_0$-$C_6$ alkyl-Ar or —$C_0$-$C_6$ alkyl-Het;

wherein each Ar or aryl independently represent a substituted or unsubstituted carbocyclic aromatic group, which may be optionally fused to another carbocyclic aromatic group moiety or to a cycloalkyl group moiety, wherein said Ar or aryl is optionally substituted by one or more of the substituents independently selected from the group halo, cyano, $C_1$-$C_6$ alkyl, $C_1$-$C_6$ haloalkyl, —$C_0$-$C_6$ alkyl-OH, —$C_0$-$C_6$ alkyl-SH, —$C_0$-$C_6$ alkyl-NR'R", $C_3$-$C_6$ alkenyl, —$OC_1$-$C_6$alkyl, —$OC_1$-$C_6$ alkenyl, —$C_0$-$C_6$ alkyl-COR', —$C_0$-$C_6$ alkyl-$CO_2R'$, —$C_0$-$C_6$ alkyl-CONR'R", —$OC_0$-$C_6$ alkyl-$CO_2H$, —$OC_2$-$C_6$ alkyl-NR'R", —$C_0$-$C_6$ alkyl-C(=NR')NR'R", and —$C_0$-$C_6$ alkyl-$SO_2NR'R"$, wherein each R' and R" are independently selected from H and unsubstituted $C_1$-$C_6$ alkyl, each Het independently represents a monocyclic 5- to 7-membered, a bicyclic 7- to 10-membered or a tricyclic 11- to 18-membered heterocyclic ring group which is saturated, unsaturated or aromatic, and consists of carbon atoms and from one to three heteroatoms selected from N, O and S, wherein the N or S heteroatoms of said Het are optionally oxidized or the N heteroatom is optionally quaternized, wherein said Het is optionally unsubstituted or substituted by one or more of the substituents independently selected from the group halo, cyano, $C_1$-$C_6$ alkyl (which specifically includes $C_1$-$C_6$ haloalkyl, —$C_0$-$C_6$ alkyl-OH, —$C_0$-$C_6$ alkyl-SH and —$C_0$-$C_6$ alkyl-NR'R"), $C_3$-$C_6$ alkenyl, oxo, —$OC_1$-$C_6$alkyl, —$OC_1$-$C_6$ alkenyl, —$C_0$-$C_6$ alkyl-COR', —$C_0$-$C_6$ alkyl-$CO_2R'$, —$C_0$-$C_6$ alkyl-CONR'R", —$OC_0$-$C_6$ alkyl-$CO_2H$, —$OC_2$-$C_6$ alkyl-NR'R", —$C_0$-$C_6$ alkyl-C(=NR')NR'R" and —$C_0$-$C_6$ alkyl-$SO_2NR'R"$, wherein each R' and R" are independently selected from H and unsubstituted $C_1$-$C_6$ alkyl;

provided that X is not $COOR^{10}$ when Y is —O—, p is 0-8, n is 3, m is 1, q is 0 or 1, t is 0, each $R^1$ and $R^2$ is independently selected from H, $C_1$-$C_6$ alkyl, —OH, —O—$C_1$-$C_6$ alkyl, —SH, and —S—$C_1$-$C_6$ alkyl, each $R^4$, $R^5$, $R^6$, $R^7$, $R^8$ and $R^9$ are independently H or $C_1$-$C_4$ alkyl, k is 0 or 1, $W^3$ is H, $W^1$ and $W^2$ are each independently selected from $C_3$-$C_8$ cycloalkyl and aryl and $R^3$ and Q are as defined above; or provided that the compound is not 5-[3-[[(3,4-dichlorophenyl)methyl][2-(2-naphthalenyl) ethyl]amino]propoxy]-3-methoxy-1,2-benzenedicarboxylic acid, or 5-[3-[[(3,4-dichlorophenyl)methyl][2-(2-naphthalenyl) ethyl]amino]propoxy]-3-methoxy-1,2-benzenedicarboxylic acid, dimethyl ester;

or a pharmaceutically acceptable salt or hydrate thereof.

2. The compound according to claim 1, wherein p is 0, 1 or 2.

3. The compound according to claim 1, wherein t is 0.

4. The compound according to claim 1, wherein $R^1$ and $R^2$ are independently H or $C_1$-$C_4$ alkyl or $R^1$ and $R^2$ together with the carbon to which they are attached form a 3-5 membered carbocyclic ring.

5. The compound according to claim 1, wherein k is 0 or 1.

6. The compound according to claim 1, wherein $R^3$ is selected from halo, $C_1$-$C_4$ alkyl and $C_1$-$C_4$ alkoxy.

7. The compound according to claim 1, wherein X is selected from $C_1$-$C_6$ alkyl, halo, —$OR^{10}$, —$NR^{14}R^{15}$, cyano, —$COR^{13}$, —$COOR^{10}$, —$OCOR^{13}$, —$N(R^{17})$ $CONR^{14}R^{15}$, —$N(R^{17})COR^{13}$, —$SO_2NR^{14}R^{15}$, —$N(R^{17})$ $SO_2R^{16}$, and a 5 or 6-membered heterocyclic group or X and an adjacent $R^3$, taken together with the atoms to which they are bonded, form an alkylenedioxy moiety.

8. The compound according to claim 7, wherein $R^{10}$ is H, $C_1$-$C_4$ alkyl or phenyl; $R^{13}$ is H, $C_1$-$C_4$ alkyl, —$C_0$-$C_4$ alkyl-$C_3$-$C_7$ cycloalkyl, or —$C_0$-$C_4$ alkyl-phenyl; $R^{14}$ and $R^{15}$ are each independently selected from H, $C_1$-$C_6$ alkyl, —$C_0$-$C_4$ alkyl-Ar, —$C_0$-$C_4$ alkyl-Het, —$C_0$-$C_4$ alkyl-$C_3$-$C_7$ cycloalkyl, —$C_0$-$C_4$ alkyl-O—Ar, —$C_0$-$C_4$ alkyl-O-Het, —$C_0$-$C_4$ alkyl-O—$C_3$-$C_7$ cycloalkyl, —$C_0$-$C_4$ alkyl-S(O)$_2$— $C_1$-$C_4$ alkyl, —$C_0$-$C_4$ alkyl-S(O)$_2$—Ar, —$C_0$-$C_4$ alkyl-S(O)$_2$-Het, —$C_0$-$C_4$ alkyl-S(O)$_2$—$C_3$-$C_7$ cycloalkyl, —$C_0$-$C_4$ alkyl-NH—Ar, —$C_0$-$C_4$ alkyl-NH-Het, —$C_0$-$C_4$ alkyl-NH—$C_3$-$C_7$ cycloalkyl, —$C_0$-$C_4$ alkyl-N($C_1$-$C_4$ alkyl)-Ar, —$C_0$-$C_4$ alkyl-N($C_1$-$C_4$ alkyl)-Het, —$C_0$-$C_4$ alkyl-N($C_1$-$C_4$ alkyl)-$C_3$-$C_7$ cycloalkyl, —$C_0$-$C_4$ alkyl-Ar, —$C_0$-$C_4$ alkyl-Het and —$C_0$-$C_4$ alkyl-$C_3$-$C_7$ cycloalkyl, or $R^{14}$ and $R^{15}$, together with the nitrogen to which they are attached, form a 4-7 membered heterocyclic ring which optionally contains one or more additional heteroatoms selected from N, O, and S, wherein said $C_1$-$C_6$ alkyl is optionally substituted by one or more of the substituents independently selected from the group halo, —OH, —SH, —$NH_2$, —NH(unsubstituted $C_1$-$C_4$ alkyl), —N(unsubstituted $C_1$-$C_4$ alkyl)(unsubstituted $C_1$-$C_4$ alkyl), unsubstituted —$OC_1$-$C_4$ alkyl, —$CO_2H$, —$CO_2$(unsubstituted $C_1$-$C_4$ alkyl), —$CONH_2$, —CONH(unsubstituted $C_1$-$C_4$ alkyl), —CON(unsubstituted $C_1$-$C_4$ alkyl)(unsubstituted $C_1$-$C_4$ alkyl), —$SO_3H$, —$SO_2NH_2$, —$SO_2NH$(unsubstituted $C_1$-$C_4$ alkyl) and —$SO_2N$(unsubstituted $C_1$-$C_4$ alkyl)(unsubstituted $C_1$-$C_4$ alkyl); $R^{16}$ is $C_1$-$C_4$ alkyl or phenyl; and $R^{17}$ is H or $C_1$-$C_4$ alkyl.

9. The compound according to claim 1 wherein each $R^4$ and $R^5$ are independently selected from H and $C_1$-$C_3$ alkyl.

10. The compound according to claim 1, wherein $R^8$ and $R^9$ are each H.

11. The compound according to claim 1, wherein Q is a substituted or unsubstituted phenyl or furanyl group or a benzo[1,3]dioxyl or benzo[1,4]dioxyl group containing one, two or three substituents selected from halo, $C_1$-$C_4$ alkyl; $C_1$-$C_4$ alkylthio; or —$NR^{Q1}R^{Q2}$, where $R^{Q1}$ and $R^{Q2}$ taken together with the nitrogen to which they are attached form a 4-7 membered heterocyclic ring, which may optionally contain one or more additional heteroatoms selected form N, O and S.

12. The compound according to claim 11, wherein said substituents are selected from fluoro, chloro, trifluoromethyl, tert-butyl, isopropyl, methylthio and piperidin-1-yl.

13. The compound according to claim 1, wherein m is 0 or m is 1 and $R^6$ and $R^7$ are each H.

14. The compound according to claim 1, wherein $W^1$ is phenyl, naphthyl, thienyl, pyridyl, furanyl, pyrrolyl, cyclohexyl, cyclopentyl, morpholinyl, or pyrrolidinyl, where each phenyl, naphthyl, thienyl, pyridyl, furanyl, pyrrolyl, cyclohexyl, cyclopentyl, morpholinyl, or pyrrolidinyl may be optionally substituted from 1 to 3 times with one or more of the substituents independently selected from $C_1$-$C_4$ alkyl, —OH, halo, —O—$C_1$-$C_4$ alkyl, and —$C_1$-$C_4$ haloalkyl.

15. The compound according to claim 1, wherein $W^2$ is $C_1$-$C_4$ alkyl, $C_2$-$C_4$ alkynyl, $C_3$-$C_6$ cycloalkyl, aryl, Het hydroxy, aryloxy-, $C_1$-$C_4$ alkoxy-, —$OCOC_1$-$C_4$ alkyl, —OCOaryl, or —$NR^{W1}R^{W2}$, where $R^{W1}$ and $R^{W2}$ are independently H or $C_1$-$C_4$ alkyl or taken together with the nitrogen to which they are attached form a 4-7 membered heterocyclic ring, which may optionally contain one or more additional heteroatoms selected form N, O and S.

16. The compound according to claim 1, wherein $W^3$ is H or $C_1$-$C_4$ alkyl.

17. The compound according to claim 1, wherein X is selected from $C_1$-$C_6$ alkyl, halo, —$OR^{10}$, —$NR^{14}R^{15}$, cyano, —$COR^{13}$, —$COOR^{10}$, —$OCOR^{13}$, —$N(R^{17})$ $CONR^{14}R^{15}$, —$N(R^{17})COR^{13}$, —$SO_2NR^{14}R^{15}$, —$N(R^{17})$ $SO_2R^{16}$, and a 5 or 6-membered heterocyclic group or X and an adjacent $R^3$, taken together with the atoms to which they are bonded, form an alkylenedioxy moiety, where $R^{10}$ is H, $C_1$-$C_4$ alkyl or phenyl, $R^{13}$ is H, $C_1$-$C_4$ alkyl, —$C_0$-$C_4$ alkyl-$C_3$-$C_7$ cycloalkyl, or —$C_0$-$C_4$ alkyl-phenyl, $R^{14}$ and $R^{15}$ are each independently selected from H, $C_1$-$C_6$ alkyl, —$C_0$-$C_4$ alkyl-Ar, —$C_0$-$C_4$ alkyl-Het, —$C_0$-$C_4$ alkyl-$C_3$-$C_7$ cycloalkyl, —$C_0$-$C_4$ alkyl-O—Ar, —$C_0$-$C_4$ alkyl-O-Het, —$C_0$-$C_4$ alkyl-O—$C_3$-$C_7$ cycloalkyl, —$C_0$-$C_4$ alkyl-S(O)$_2$- $C_1$-$C_4$ alkyl, —$C_0$-$C_4$ alkyl-S(O)$_2$—Ar, —$C_0$-$C_4$ alkyl-S(O)$_2$-Het, —$C_0$-$C_4$ alkyl-S(O)$_2$-$C_3$-$C_7$ cycloalkyl, —$C_0$-$C_4$ alkyl-NH—Ar, —$C_0$-$C_4$ alkyl-NH-Het, —$C_0$-$C_4$ alkyl-NH—$C_3$-$C_7$ cycloalkyl, —$C_0$-$C_4$ alkyl-N($C_1$-$C_4$ alkyl)-Ar, —$C_0$-$C_4$ alkyl-N($C_1$-$C_4$ alkyl)-Het, —$C_0$-$C_4$ alkyl-N($C_1$-$C_4$ alkyl)-$C_3$-$C_7$ cycloalkyl, —$C_0$-$C_4$ alkyl-Ar, —$C_0$-$C_4$ alkyl-Het and —$C_0$-$C_4$ alkyl-$C_3$-$C_7$ cycloalkyl, or $R^{14}$ and $R^{15}$, together with the nitrogen to which they are attached, form a 4-7 membered heterocyclic ring which optionally contains one or more additional heteroatoms selected from N, O, and S, wherein said $C_1$-$C_6$ alkyl is optionally substituted by one or more of the substituents independently selected from the group halo, —OH, —SH, —$NH_2$, —NH(unsubstituted $C_1$-$C_4$ alkyl), —N(unsubstituted $C_1$-$C_4$ alkyl)(unsubstituted $C_1$-$C_4$ alkyl), unsubstituted —$OC_1$-$C_4$ alkyl, —$CO_2H$, —$CO_2$(unsubstituted $C_1$-$C_4$ alkyl), —$CONH_2$, —CONH(unsubstituted $C_1$-$C_4$ alkyl), —CON(unsubstituted $C_1$-$C_4$ alkyl)(unsubstituted $C_1$-$C_4$ alkyl), —$SO_3H$, —$SO_2NH_2$, —$SO_2NH$(unsubstituted $C_1$-$C_4$ alkyl) and —$SO_2N$(unsubstituted $C_1$-$C_4$ alkyl)(unsubstituted $C_1$-$C_4$ alkyl), $R^{16}$ is $C_1$-$C_4$ alkyl or phenyl, and $R^{17}$ is H or $C_1$-$C_4$ alkyl; p is 0, 1 or 2; $R^1$ and $R^2$ are independently H or $C_1$-$C_4$ alkyl or $R^1$ and $R^2$ together with the carbon to which they are attached form a 3-5 membered carbocyclic ring; k is 0 or k is 1 and $R^3$ is halo, $C_1$-$C_4$ alkyl or $C_1$-$C_4$ alkoxy; n is 3 and each $R^4$ and $R^5$ are independently selected from H and $C_1$-$C_3$ alkyl; Z is CH or N; Y is —O— or —C($R^4$)($R^5$)—; q is 1; $R^8$ and $R^9$ are each H; Q is a substituted or unsubstituted phenyl or furanyl group or a benzo[1,3]dioxyl or benzo[1,4]dioxyl group, where the substituted phenyl or furanyl group contains one, two or three substituents selected from halo, $C_1$-$C_4$ alkyl; $C_1$-$C_4$ alkylthio; or —NR$^{Q1}$R$^{Q2}$, where R$^{Q1}$ and R$^{Q2}$ taken together with the nitrogen to which they are attached form a 4-7 membered heterocyclic ring, which may optionally contain one or more additional heteroatoms selected form N, O and S; t is 0 or 1; m is 0 or 1; $R^6$ and $R^7$ are independently selected from H and $C_1$-$C_4$ alkyl; $W^1$ is unsubstituted phenyl, naphthyl, pyridyl, thienyl or pyrrolyl or substituted phenyl or pyridyl containing one or two substituents independently selected from halo, alkyl and alkoxy, specifically, chloro, methyl and methoxy; $W^2$ is $C_1$-$C_4$ alkyl, $C_2$-$C_4$ alkynyl, $C_3$-$C_6$ cycloalkyl, aryl, Het hydroxy, aryloxy-, $C_1$-$C_4$ alkoxy-, —OCOC$_1$-$C_4$ alkyl, —OCOaryl, or —NR$^{W1}$R$^{W2}$, where R$^{W1}$ and R$^{W2}$ are independently H or $C_1$-$C_4$ alkyl or taken together with the nitrogen to which they are attached form a 4-7 membered heterocyclic ring, which may optionally contain one or more additional heteroatoms selected form N, O and S; $W^3$ is H or $C_1$-$C_4$ alkyl; or a pharmaceutically acceptable salt or hydrate thereof.

18. The compound according to claim 1, wherein X is chloro, bromo, cyano, carboxy-, methylcarboxy-, hydroxy, methoxy, methyl, trifluoromethyl, 1,3-dihydroxy-prop-2-yl (—CH(CH$_2$OH)$_2$, isopropyl, n-butyl, isobutyl, 2,2-dimethylpropyl, phenylcarbonyl, triazolyl, tetrazolyl, —NH$_2$, —NHCH$_3$, —NHCH$_2$CH$_3$, —NHCH$_2$CH$_2$CH$_3$, —NHCH$_2$CH$_2$CH$_2$CH$_3$, —NHCH$_2$CH$_2$CH$_2$CH$_2$CH$_3$, —NHCH$_2$C(CH$_3$)$_3$, —NHCH$_2$CH(CH$_3$)$_2$, —NHCH$_2$CH$_2$CH(CH$_3$)$_2$, —NH-cyclopentyl, —NH-phenyl, —NHCH2-cyclopropyl, —NHCH(CH$_3$)$_2$, —NHCH$_2$CF$_3$, —N(CH$_3$)$_2$, —N(CH$_2$CH$_3$)$_2$, —NHCH(CH$_2$CH$_3$)$_2$, —NHCH$_2$CH(CH$_2$CH$_3$)$_2$, —NHCH$_2$CH$_2$OH, —NHCH$_2$CO$_2$H, —N(CH$_3$)CH$_2$CO$_2$H, —NHC(CH$_3$)$_2$CO$_2$H, —NHCH(CH$_3$)CO$_2$H, —(R)—NHCH(CH$_3$)CO$_2$H, —(S)—NHCH(CH$_3$)CO$_2$H, —NHCH$_2$-1H-imidazol-2-yl, —NHCH$_2$-(1-CH$_3$-iimidazol-2-yl, —NH-(pyrimidin-2-yl), -morpholin-4-yl, -thiomorpholin-4-yl, -piperidin-1-yl, -piperidin-1-yl-(4-carboxylic acid), -piperidin-1-yl-(4-acetic acid), -piperidin-4-yl-(1-acetic acid), -2,5-dimethyl-pyrrol-1-yl, -pyrrolidin-1-yl, —((R)-2-CO$_2$H-pyrrolidin-1-yl), —((S)-2-CO$_2$H-pyrrolidin-1-yl), -piperazin-1-yl, -(4-methyl-piperazin-1-yl), -piperazin-1-yl-(4-acetic acid), —NHCH$_2$-(5-bromo-thien-2-yl), —NHCH$_2$-1H-imidazol-2-yl, —NHCH$_2$-(1-methyl-imidazol-2-yl, —NHCOCH$_3$, —N(CH$_3$)COCH$_3$, —NHCO$_2$C(CH$_3$)$_3$, —NHCOCH$_2$CH$_3$, —NHCOC(CH$_3$)$_2$, —NHCO-furan-2-yl, —N(CH$_3$)CO-furan-2-yl, —NHCO-thien-2-yl, —NHCO-cyclopropyl, —NHCO-(5-bromo-thien-2-yl), —NHCO-(2,5-dimethyl-pyrrol-3-yl), —NHSO$_2$CH$_3$, —N(CH$_3$)SO$_2$CH$_3$, —NHSO$_2$CF$_3$, —NHSO$_2$phenyl, —N(CH$_3$)SO$_2$phenyl, —NHSO$_2$CH$_2$CH$_3$, —NHSO$_2$CH$_2$CF$_3$, —NHSO$_2$CH$_2$CH$_2$CH$_3$, —NHSO$_2$CH(CH$_3$)$_2$,—NHCONH(2-chlorophenyl), —N(CH$_3$)CONH(3,5-dimethoxyphenyl), —N(CH$_3$)CONH(2-chlorophenyl), —N(CH$_3$)CO-(benzo[1,3]diox-5-yl), —SO$_2$NHCH$_3$, and —SO$_2$N(CH$_3$)$_2$; p is 0, 1 or 2; $R^1$ and $R^2$ are H $C_1$-$C_4$ alkyl or $R^1$ and $R^2$ together with the carbon to which they are attached form a 3, 4 or 5 membered carbocyclic ring; Z is CH of N; k is 0 or k is 1 and $R^3$ is methyl, trifluoromethyl, chloro or methoxy; and $R^4$ and $R^5$ are independently selected from H and methyl; Y is —O— or —C($R^4$)($R^5$)—; q is 1; $R^8$ and $R^9$ are each H; Q is 2-chloro-3-(trifluoromethyl)phenyl, 3-methyl-4-fluoro-phenyl, 4-tert-butyl-phenyl, 4-(methylthio)phenyl, 2,4,5-trifluoro-phenyl, 4-isopropyl-phenyl, 5-(piperidin-1-yl)-furan-2-yl, benzo[1,3]diox-5-yl, or 2,3-dihydrobenzo[1,4]dioxin-6-yl; t is 0 or 1; m is 0 or 1; $R^6$ and $R^7$ are independently selected from H and methyl; $W^1$ is phenyl, naphth-1-yl, pyrid-2-yl, 4-methyl-pyrid-2-yl, thien-2-yl, thien-3-yl, pyrrol-2-yl, 2-chlorophenyl, 3-chlorophenyl, 4-chlorophenyl, 2-methoxyphenyl, or 4-methoxyphenyl; $W^2$ is methyl, ethyl, ethynyl, isopropyl, n-butyl, 2-methylpropyl, trifluorormethyl, cyclohexyl, unsubstituted phenyl, hydroxy, methoxy, phenoxy, dimethylamino, morpholin-4-yl, phenylcarbonyloxy, or methylcarbonyloxy; $W^3$ is H or methyl; or a pharmaceutically acceptable salt or hydrate thereof.

19. The compound according to claim 1, wherein $W^1$ and $W^2$ are not each independently $C_3$-$C_8$ cycloalkyl or aryl or $W^3$ is not H or any one of $R^6$ or $R^7$ is not H or $R^8$ and $R^9$ are each $C_1$-$C_4$ alkyl when:

X is COOR$^{10}$;

Z is CH or CR$^3$ and k is 0-4 or Z is N and k is 0-3;

p is 0-8;

n is 3;

q is 0 or 1;

Q is selected from optionally unsubstituted or substituted $C_3$-$C_8$ cycloalkyl, phenyl and monocyclic Het;

each $R^1$ and $R^2$ is independently selected from H, $C_1$-$C_6$ alkyl, —OH, —O—$C_1$-$C_6$ alkyl, —SH, and —S—$C_1$-$C_6$ alkyl; and each $R^3$ is the same or different and is independently selected from halo, cyano, nitro, —CONR$^{12}$R$^{13}$, —COR$^{14}$, —SR$^{11}$, —SO$_2$R$^{11}$, —SOR$^{14}$, —OCOR$^{14}$ and optionally unsubstituted or substituted $C_1$-$C_6$ alkyl, $C_3$-$C_6$ alkenyl, -5-6 membered-Het, —C$_0$-$C_6$ alkyl-CO$_2$R$^{11}$, or —C$_0$-$C_6$ alkyl-NR$^{12}$R$^{13}$.

20. A compound selected from:

2-(3-{3-[[2-Chloro-3-(trifluoromethyl)benzyl](2,2-dephenylethyl)amino]propoxy}phenyl)-ethanol; 2-(3-{3-[[2-Chloro-3-(trifluoromethyl)benzyl](2,2-diphenylethyl)amino]propoxy}-phenyl)acetic acid, N-oxide; (3-{3-[[2-Chloro-3-(trifluoromethyl)benzyl](2,2-diphenylethyl)amino]propoxy}-bromobenzene; (4-{3-[[2-Chloro-3-(trifluoromethyl)benzyl](2,2-diphenyl-ethyl)amino]propoxy}-bromobenzene; (2-Chloro-3-trifluoromethyl-benzyl)-(2,2-diphenylethyl)-{3-[3-(1,2,4-triazol-3-ylmethyl)-phenoxy]-propyl}-amine; (2-Chloro-3-trifluoromethyl-benzyl)-(2,2-diphenyl-ethyl)-{3-[3-(1,2,3,4-tetrazol-5-ylmethyl)-phenoxy]-propyl}-amine; (2-Chloro-3-trifluoromethyl-benzyl)-(2-cyclohexyl-2-phenyl-ethyl)-{3-[3-(1,2,3,4-tetrazol-5-ylmethyl)-phenoxy]-propyl}-amine; (S)-2-Chloro-3-trifluoromethyl-benzyl)-(2-phenyl-propyl)-{3-[3-(1,2,3,4-tetrazol-3-ylmethyl)-phenoxy]-propyl}-amine; (R)-(2-Chloro-3-trifluoromethyl-benzyl)-(2-phenyl-propyl)-{3-[3-(1,2,3,4-tetrazol-3-ylmethyl)-phenoxy]-propyl}-amine; (S)-2-(3-{3-[[2-Chloro-3-(trifluoromethyl)benzyl](2-phenyl-propyl)amino]propoxy}-phenyl)acetic acid; (R)-2-(3-{3-[[2-Chloro-3-(trifluoromethyl)benzyl](2-phenyl-propyl)amino]propoxy}-phenyl)acetic acid; Chloro-3-(trifluoromethyl)benzyl]naphthalen-1-ylmethyl-amino]propoxy}-phenyl)acetic acid; 2-(3-{3-[[2-Chloro-3-(trifluoromethyl)benzyl]-benzylamino]propoxy}-phenyl)acetic acid; 2-(3-{3-[[2-Chloro-3-(trifluoromethyl)-benzyl]phenethylamino]propoxy}-phenyl)acetic acid; 2-(3-{3-[[2-Chloro-3-(trifluoromethyl)benzyl](2-hydroxy-2-phenyl-ethyl)amino]propoxy}-phenyl)acetic acid; 2-(3-{3-[[2-

Chloro-3-(trifluoromethyl)benzyl](2-acetoxy-2-phenyl-ethyl)amino]propoxy}-phenyl)acetic acid; 2-(3-{3-[[2-chloro-3-(trifluoromethyl)benzyl](2-phenoxy-2-phenyl-ethyl)amino]propoxy}-phenyl)acetic acid; Benzoic acid 2-[3-(3-carboxymethyl-phenoxy)-{2-chloro-3-(trifluoromethyl)benzyl}propylamino]-1-phenyl ethyl ester; (3-{3-[(2-Acetoxy-2-phenyl-ethyl)-(2-chloro-3-trifluoromethyl-benzyl)-amino]-propoxy}-phenyl)-acetc acid methyl ester; Benzoic acid 2-[3-(3-methoxycarbonylmethyl-phenoxy){2-chloro-3-(trifluoromethyl)benzyl}propylamino]-1-phenyl ethyl ester; (3-{4-[(2-Chloro-3-(trifluoromethyl)benzyl)-(2,2-diphenylethyl)-amino]butyl}phenyl)-acetic acid; (3-{3-[(4-Fluoro-3-methyl-benzyl)-((R)-2-phenyl-propyl)-amino]-propoxy}-phenyl)-acetic acid; (3-{3-[Benzo[1,3]dioxol-5-ylmethyl-((R)-2-phenyl-propyl)-amino]-propoxy}phenyl)-acetic acid; (3-{3-[(4-tert-Butyl-benzyl)-((R)-2-phenyl-propyl)-amino]-propoxy}-phenyl)-acetic acid; (3-{3-[(2,3-Dihydro-benzo[1,4]dioxin-6-ylmethyl)-((R)-2-phenyl-propyl)-amino]-propoxy}-phenyl)-acetic acid; (3-{3-[(4-Methylsulfanyl-benzyl)-((R)-2-phenyl-propyl)-amino]-propoxy}-phenyl)-acetic acid; (3-{3-[((R)-2-Phenyl-propyl)-(2,4,5-trifluoro-benzyl)-amino]-propoxy}-phenyl)-acetic acid; (3-{3-[((R)-2-Phenyl-propyl)-(5-piperidin-1-yl-furan-2-ylmethyl)-amino]-propoxy}-phenyl)-acetic acid; (3-{3-[(4-Isopropyl-benzyl)-((R)-2-phenyl-propyl)-amino]-propoxy}-phenyl)-acetic acid; 2-(3-{3-[(2-Chloro-3-trifluoromethyl-benzyl)-diphenylethyl-amino]-propoxy}-phenyl)-propane-1,3-diol; N-(3-{3-[(2-Chloro-3-trifluoromethyl-benzyl)-2,2-diphenylethyl-amino]-propoxy}-phenyl)-carbamic acid tert-butyl ester; 3-{3-[(2-Chloro-3-trifluoromethyl-benzyl)-2,2-diphenylethylamino]-propoxy}-phenylamine; N-(3-{3-[(2-Chloro-3-trifluoromethyl-benzyl)-2,2-diphenyl-ethyl-amino]-propoxy}-phenyl)-acetamide; Furan-2-carboxylic acid N-(3-{3-[(2-Chloro-3-trifluoromethyl-benzyl)-2,2-diphenylethyl-amino]-propoxy}-phenyl)-amide; N-(3-{3-[(2-Chloro-3-trifluoromethyl-benzyl)-2,2-diphenylethyl-amino]-propoxy}-phenyl)-methanesulfonamide; N-(3-{3-[(2-Chloro-3-trifluoromethyl-benzyl)-2,2-diphenylethyl-amino]-propoxy}-phenyl)-benzenesulfonamide; 1-(2-Chloro-phenyl)-3-(3-{3-[(2-chloro-3-trifluoromethyl-benzyl)-2,2-diphenylethyl-amino]-propoxy}-phenyl)-urea; N-(3-{3-[(2-Chloro-3-trifluoromethyl-benzyl)-2,2-diphenylethyl-amino]-propoxy}-phenyl)-N-methyl-amine; N-(3-{3-[(2-Chloro-3-trifluoromethyl-benzyl)-2,2-diphenylethyl-amino]-propoxy}-phenyl)-N-methyl-acetamide; Furan-2-carboxylic acid N-(3-{3-[(2-Chloro-3-trifluoromethyl-benzyl)-2,2-diphenylethyl-amino]-propoxy}-phenyl)-N-methyl-amide; N-(3-{3-[(2-Chloro-3-trifluoromethyl-benzyl)-2,2-diphenylethyl-amino]-propoxy}-phenyl)-N-methyl-methanesulfonamide; (3-{3-[(2-Chloro-3-trifluoromethyl-benzyl)-2,2-diphenylethyl-amino]-propoxy}-phenyl)-N-methyl-benzenesulfonamide; 3-(2-Chloro-phenyl)-1-(3-{3-[(2-chloro-3-trifluoromethyl-benzyl)-2,2-diphenylethyl-amino]-propoxy}-phenyl)-1-methyl-urea; Benzo[1,3]dioxole-5-carboxylic acid N-(3-{3-[(2-Chloro-3-trifluoromethyl-benzyl)-2,2-diphenylethyl-amino]-propoxy}-phenyl)-N-methyl-amide; 1-(3-{3-[(2-Chloro-3-trifluoromethyl-benzyl)-2,2-diphenylethyl-amino]-propoxy}-phenyl)-3-(3,5-dimethoxy-phenyl)-1-methyl-urea; Propane-1-sulfonic acid (5-{3-[(2-chloro-3-trifluoromethyl-benzyl)-diphenylethyl-amino]-propoxy}-2-methyl-phenyl)-amide; 3-{3-[(2-Chloro-3-trifluoromethyl-benzyl)-diphenylethyl-amino]-propoxy}-2-methyl-phenylamine; 2-Chloro-5-{3-[(2-chloro-3-trifluoromethyl-benzyl)-diphenylethyl-amino]-propoxy}-phenylamine; 3-{3-[(2-Chloro-3-trifluoromethyl-benzyl)-(2,2-diphenyl-ethyl)-amino]-propoxy}-phenyl)-cyclopentyl-amine; (3-{3-[(2-Chloro-3-trifluoromethyl-benzyl)-(2,2-diphenyl-ethyl)-amino]-propoxy}-phenyl)-isopropyl-amine; Chloro-3-trifluoromethyl-benzyl)-(2,2-diphenyl-ethyl)-amino]-propoxy}-phenyl)-ethyl-amine; (3-{3-[(2-Chloro-3-trifluoromethyl-benzyl)-(2,2-diphenyl-ethyl)-amino]-propoxy}-phenyl)-(3-methyl-butyl)-amine; (3-{3-[(2-Chloro-3-trifluoromethyl-benzyl)-diphenylethyl-amino]-propoxy}-phenyl)-isobutyl-amine; (3-{3-[(2-Chloro-3-trifluoromethyl-benzyl)-(2,2-diphenyl-ethyl)-amino]-propoxy}-phenyl)-(2,2,2-trifluoroethyl)-amine; (3-{3-[(2-Chloro-3-trifluoromethyl-benzyl)-(2,2-diphenyl-ethyl)-amino]-propoxy}-phenyl)-cyclopropylmethy-1-amine; (3-{3-[(2-Chloro-3-trifluoromethyl-benzyl)-(2,2-diphenyl-ethyl)-amino]-propoxy}-phenyl)-(2-ethyl-butyl)-amine; (3-{3-[(2-Chloro-3-trifluoromethyl-benzyl)-(2,2-diphenyl-ethyl)-amino]-propoxy}-phenyl)-(2,2-dimethyl-propyl)-amine; (3-{3-[(2-Chloro-3-trifluoromethyl-benzyl)-(2,2-diphenyl-ethyl)-amino]-propoxy}-phenyl)-hexyl-amine; Butyl-(3-{3[(2-chloro-3-trifluoromethyl-benzyl)-(2,2-diphenyl-ethyl)-amino]-propoxy}-phenyl)-amine; [1-(3-{3-[(2-Chloro-3-(trifluoromethyl)-benzyl)-(2,2-diphenylethyl)-amino]-propoxy}-phenyl-piperidine-4-carboxylic acid; [1-(3-{3-[(2-Chloro-3-(trifluoromethyl)-benzyl)-(2,2-diphenylethyl)-amino]-propoxy}-phenyl-piperidine-4-yl-acetic acid; [4-(3-{3-[(2-Chloro-3-(trifluoromethyl)-benzyl)-(2,2-diphenylethyl-amino]-propoxy}-phenyl)-piperidin-1-yl]-acetic acid; rac-±-(3-{3-[(2-Chloro-3-trifluoromethyl-benzyl)-(trifluoro-phenyl-propyl)-amino]-propoxy}-phenyl)-acetic acid; rac-±-(3-{3-[(2-Chloro-3-trifluoromethyl-benzyl)-(2-dimethylamino-2-phenyl-ethyl)-amino]-propoxy}-phenyl)-acetic acid; rac-±-(3-{3-[(2-Chloro-3-trifluoromethyl-benzyl)-(2-morpholin-4-yl-2-phenyl-ethyl)-amino]-propoxy}-phenyl)-acetic acid; (2-Chloro-3-trifluoromethyl-benzyl)-(2,2-diphenyl-ethyl)-[3-(6-morpholin-4-yl-pyridin-2-yloxy)-propyl]-amine; [3-(6-Chloro-pyridin-2-yloxy)-propyl]-(2-Chloro-3-trifluoromethyl-benzyl)-(2,2-diphenyl-ethyl)-amine; (2-Chloro-3-trifluoromethyl-benzyl)-(2,2-diphenyl-ethyl)-{3-[6-(4-methyl-piperazin-1-yl)-pyridin-2-yloxy]-propyl}-amine; (2-Chloro-3-trifluoromethyl-benzyl)-(2,2-diphenyl-ethyl)-[3-(6-piperazin-1-yl-pyridin-2-yloxy)-propyl]-amine; [4-(6-{3-[(2-Chloro-3-trifluoromethyl-benzyl)-(2,2-diphenyl-ethyl)-amino]-propoxy}-pyridin-2-yl)-piperazin-1-yl]-acetic acid; 2-(3-{3-[[2-Chloro-3-(trifluoromethyl)benzyl]((S)-2-phenyl-propyl)amino]-(R)-1-methyl-propoxy}-phenyl)acetic acid; 2-(3-{3-[[2-Chloro-3-(trifluoromethyl)benzyl]((S)-2-phenyl-propyl)amino]-(R)-1-methyl-propoxy}-phenyl)ethanol; 2-(3-{3-[[2-Chloro-3-(trifluoromethyl)benzyl]((S)-2-phenyl-propyl)amino]-(R)-2-methyl-propoxy}-phenyl)acetic acid; 2-(3-{3-[[2-Chloro-3-(trifluoromethyl)benzyl]((S)-2-phenyl-propyl)amino]-(R)-2-methyl-propoxy}-phenyl)ethanol; 2-(3-{3-[[2-Chloro-3-(trifluoromethyl)benzyl]((R)-2-phenyl-propyl)amino]-(R)-2-methyl-propoxy}-phenyl)acetic acid; 2-(3-{3-[[2-Chloro-3-

(trifluoromethyl)benzyl]((R)-2-phenyl-propyl)amino]-(R)-2-methyl-propoxy}-phenyl)ethanol; (R)-2-(3-{3-[[2-Chloro-3-(trifluoromethyl)benzyl](2,2-diphenylethyl)amino]-2-methyl-propoxy}-phenyl) ethanol; 3-{3-[(3-Chloro-2-trifluoromethyl-benzyl)-diphenylethyl-amino]-propoxy-N,N-dimethyl-benzenesulfonamide; Cyclopropanecarboxylic acid 3-{3-[(2-chloro-3-trifluoromethyl-benzyl)-diphenyl-ethyl-amino]-propoxy}-benzylamide; N-(3-{3-[(2-Chloro-3-trifluoromethyl-benzyl)-diphenylethyl-amino]-propoxy}-benzyl)-isobutyramide; Acetic acid (3-{3-[(2-chloro-3-trifluoromethyl-benzyl)-diphenyl-ethyl-amino]-propoxy}-benzylcarbamoyl)-methyl ester; N-(3-{3-[(2-Chloro-3-trifluoromethyl-benzyl)-diphenylethyl-amino]-propoxy}-benzyl)-propionamide; 2,5-Dimethyl-2-H-pyrazole-3-carboxylic acid 3-{3-[(2-chloro-3-trifluoromethyl-benzyl)-diphenyl-ethyl-amino]-propoxy}-benzylamide; (2-Chloro-3-trifluoromethyl-benzyl)-(2,2-diphenyl-ethyl)-(3-o-tolyloxy-propyl)-amine; 2-{3-[(2-Chloro-3-trifluoromethyl-benzyl)-diphenylethyl-amino]-propoxy}-benzonitrile; [3-{3-[(2-Chloro-3-trifluoromethyl-benzyl)-diphenylethyl-amino]-propoxy}benzonitrile; [3-(3-Chloro-phenoxy)-propyl]-(2-chloro-3-trifluoromethyl-benzyl)-(2,2-diphenyl-ethyl)-amine; (2-Chloro-3-trifluoromethyl-benzyl)-(2,2-diphenyl-ethyl)-[3-(2-methoxy-phenoxy)-propyl]-amine; [3-(2-Chloro-phenoxy)-propyl]-(2-chloro-3-trifluoromethyl-benzyl)-(2,2-diphenyl-ethyl)-amine; (2-Chloro-3-trifluoromethyl-benzyl)-(2,2-diphenyl-ethyl)-(3-phenoxy-propyl)-amine; (2-Chloro-3-trifluoromethyl-benzyl)-(2,2-diphenyl-ethyl)-[3-(3-isopropyl-phenoxy)-propyl]-amine; (2-Chloro-3-trifluoromethyl-benzyl)-(2,2-diphenyl-ethyl)-[3-(4-methoxy-phenoxy)-propyl]-amine; 3-{3-[(Chloro-trifluoromethyl-benzyl)-diphenylethyl-amino]-propoxy}-phenol; 2-{3-[(Chloro-trifluoromethyl-benzyl)-diphenylethyl-amino-propoxy}-phenol; 3-{3-[(Chloro-trifluoromethyl-benzyl)-diphenylethyl-amino]-propoxy}-phenylamine; (2-Chloro-3-trifluoromethyl-benzyl)-(2,2-diphenyl-ethyl)-[3-(3-trifluoromethyl-phenoxy)-propyl]-amine; 1-(3-{3-[(Chloro-trifluoromethyl-benzyl)-diphenylethyl-amino]-propoxy}-phenyl)-ethanone; (3-{3-[(2-Chloro-3-trifluoromethyl-benzyl)-diphenylethyl-amino]-propoxy}-phenyl)-phenyl-amine; [3-(Benzo[1,3] dioxol-5-yloxy)-propyl]-(2-chloro-3-trifluoromethyl-benzyl)-(2,2-diphenyl-ethyl)-amine; (2-Chloro-3-trifluoromethyl-benzyl)-(2,2-diphenyl-ethyl)-(3-m-tolyloxy-propyl)-amine; (2-Chloro-3-trifluoromethyl-benzyl)-(2,2-diphenyl-ethyl)-[3-(3-methoxy-phenoxy)-propyl]-amine; (2-Chloro-3-trifluoromethyl-benzyl)-(2,2-diphenyl-ethyl)-[3-(3-isobutyl-phenoxy)-propyl]-amine; [3-(3-Butyl-phenoxy)-propyl]-(2-chloro-3-trifluoromethyl-benzyl)-(2,2-diphenyl-ethyl)-amine; (2-Chloro-3-trifluoromethyl-benzyl)-{3-[3-(2,2-dimethyl-propyl)-phenoxy]-propyl}-(2,2-diphenyl-ethyl)-amine; (4-{3-[(2-Chloro-3-trifluoromethyl-benzyl)-diphenylethyl-amino]-propoxy}-benzyl)-methyl-amine; (2-Chloro-3-trifluoromethyl-benzyl)-[3-(4-dimethylaminomethyl-phenoxy)-propyl]-(2,2-diphenyl-ethyl)-amine; (2-Chloro-3-trifluoromethyl-benzyl)-(2,2-diphenyl-ethyl)-[3-(4-morpholin-4-ylmethyl-phenoxy)-propyl]-amine; (2-Chloro-3-trifluoromethyl-benzyl)-(2,2-diphenyl-ethyl)-{3-[4-(4-methyl-piperazin-1-ylmethyl)-phenoxy]-propyl}-amine; (3-{3-[(Chloro-trifluoromethyl-benzyl)-diphenylethyl-amino]-propoxy}-benzyl)-methyl-amine; (2-Chloro-3-trifluoromethyl-benzyl)-[3-(3-dimethylaminomethyl-phenoxy)-propyl]-(2,2-diphenyl-ethyl)-amine; (2-Chloro-3-trifluoromethyl-benzyl)-(2,2-diphenyl-ethyl)-[3-(3-morpholin-4-ylmethyl-phenoxy)-propyl]-amine; (2-Chloro-3-trifluoromethyl-benzyl)-(2,2-diphenyl-ethyl)-{3-[3-(4-methyl-piperazin-1-ylmethyl)-phenoxy]-propyl}-amine; (3-{3-[(2-Chloro-3-trifluoromethyl-benzyl)-diphenylethyl-amino]-propoxy}-benzyl)-isopropyl-amine; {3-[(2-Chloro-3-trifluoromethyl-benzyl)-(2,2-diphenyl-ethyl-amino)]-propoxy}-4-trifluoromethyl-phenylamine; {3-[(2-Chloro-3-trifluoromethyl-benzyl)-(2,2-diphenyl-ethyl-amino)]-propoxy}-4-methyl-phenylamine; Ethanesulfonic acid (3-{3-[(2-chloro-3-trifluoromethyl-benzyl)-(2,2-diphenyl-ethyl-amino)]-propoxy}-4-methyl-phenyl)-amide; Propane-2-sulfonic acid (3-{3-[(2-chloro-3-trifluoromethyl-benzyl)-(2,2-diphenyl-ethyl-amino)]-propoxy}-4-methyl-phenyl)-amide; Methanesulfonic acid (3-{3-[(2-Chloro-3-trifluoromethyl-benzyl)-(2,2-diphenyl-ethyl-amino)]-propoxy}-4-methyl-phenyl)-amide; 2,2,2-Trifluoro-ethanesulfonic acid (3-{3-[(2-Chloro-3-trifluoromethyl-benzyl)-(2,2-diphenyl-ethyl-amino)]-propoxy}-4-methyl-phenyl)-amide; Ethanesulfonic acid (3-{3-[(2-Chloro-3-trifluoromethyl-benzyl)-(2,2-diphenyl-ethyl-amino)]-propoxy}-phenyl)-amide; 2,2,2-Trifluoro-ethanesulfonic acid (3-{3-[(2-Chloro-3-trifluoromethyl-benzyl)-(2,2-diphenyl-ethyl-amino)]-propoxy}-phenyl)-amide; N-(3-{3-[(2-Chloro-3-trifluoromethyl-benzyl)-(2,2-diphenyl-ethyl-amino)]-propoxy}-phenyl)-1,1,1-trifluoro-methanesulfonamide; Propane-2-sulfonic acid (3-{3-[(2-Chloro-3-trifluoromethyl-benzyl)-(2,2-diphenyl-ethyl-amino)]-propoxy}-phenyl)-amide; {3-[(2-Chloro-3-trifluoromethyl-benzyl)-(2,2-diphenyl-ethyl-amino)]-propoxy}-4-methoxy-phenylamine; Ethanesulfonic acid (3-{3-[(2-chloro-3-trifluoromethyl-benzyl)-(2,2-diphenyl-ethyl-amino)]-propoxy}-4-methoxy-phenyl)-amide; (2-Chloro-3-trifluoromethyl-benzyl)-{3-[3-(2-morpholin-4-yl-ethyl)-phenoxy]-propyl}-((S)-2-phenyl-propyl amine; (2-Chloro-3-trifluoromethyl-benzyl)-{3-[3-(2-ethylamino-ethyl)-phenoxy]-propyl}-((S)-2-phenyl-propyl)-amine; (3-{(R)-3-[(2-Chloro-3-trifluoromethyl-benzyl)-((S)-2-phenyl-propyl)-amino]-butoxy}-phenyl)-acetic acid; (3-{(S)-3-[(2-Chloro-3-trifluoromethyl-benzyl)-((S)-2-phenyl-propyl)-amino]-butoxy}-phenyl)-acetic acid; 2-(3-{3-[(2-Chloro-3-trifluoromethyl-benzyl)-((S)-2-phenyl-propyl)-amino]-propoxy}-phenyl)-ethanol; 2-(3-{3-[(2-Chloro-3-trifluoromethyl-benzyl)-((S)-2-phenyl-propyl)-amino]-propoxy}-phenyl)-2-methyl-propionic acid; 2-(3-{3-[(2-Chloro-3-trifluoromethyl-benzyl)-((R)-2-phenyl-propyl)-amino]-propoxy}-phenyl)-2-methyl-propionic acid; (3-{3-[(2-Chloro-3-trifluoromethyl-benzyl)-(2-thiophen-3-yl-propyl)-amino]-propoxy}-phenyl)-acetic acid; 2-(3-{3-[(2-Chloro-3-trifluoromethyl-benzyl)-(2-thiophen-3-yl-propyl)-amino]-propoxy}-phenyl)-ethanol; (3-{3-[(2-Chloro-3-trifluoromethyl-benzyl)-(2-thiophen-2-yl-propyl)-amino]-propoxy}-phenyl)-acetic acid; (3-{3-[(2-Chloro-3-trifluoromethyl-benzyl)-(2-pyridin-2-yl-propyl)-amino]-propoxy}-phenyl)-acetic acid; [3-(3-{(2-Chloro-3-trifluoromethyl-benzyl)-[2-(4-methyl-pyridin-2-yl)-propyl]-amino}-propoxy)-phenyl]-acetic acid; [3-(3-{(2-Chloro-3-trifluoromethyl-benzyl)-[3,3,3-trifluoro- 2-(1H-pyrrol-2-yl)-propyl]-amino}-propoxy)-phenyl]-acetic acid; (2-Chloro-3-trifluoromethyl-benzyl)-(2,2-diphenyl-ethyl)-(3-{3-[2-(4-methyl-piperazin-1-yl)-ethyl]-phenoxy}-propyl)-amine; (2-Chloro-3-trifluoromethyl-benzyl)-(2,2-diphenyl-ethyl)-{3-[3-(2-methylamino-ethyl)-phenoxy]-propyl}-amine; (2-Chloro-3-trifluoromethyl-benzyl)-(2,2-diphenyl-ethyl)-[3-(3-{2-[(1H-imidazol-2-ylmethyl)-amino]-ethyl}-phenoxy)-propyl]-amine; (2-Chloro-3-trifluoromethyl-benzyl)-(2,2-diphenyl-ethyl)-{3-[3-(2-ethylamino-ethyl)-phenoxy]-propyl}-amine; [3-(3-{2-[(5-Bromo-thiophen-2-ylmethyl)-amino]-ethyl}-phenoxy)-propyl]-(2-chloro-3-trifluoromethyl-benzyl)-(2,2-diphenyl-ethyl)-amine; (2-Chloro-3-trifluoromethyl-benzyl)-(2,2-diphenyl-ethyl)-[3-(3-{2-[(thiophen-2-ylmethyl)-amino]-ethyl}-phenoxy)-propyl]-amine; (2-Chloro-3-trifluoromethyl-benzyl)-{3-[3-(2-dimethylamino-ethyl)-phenoxy]-propyl}-(2,2-diphenyl-ethyl)-amine; (2-Chloro-3-trifluoromethyl-benzyl)-(2,2-diphenyl-ethyl)-{3-[3-(2-pyrrolidin-1-yl-ethyl)-phenoxy]-propyl}-amine; (2-Chloro-3-trifluoromethyl-benzyl)-(2,2-diphenyl-ethyl)-{3-[3-(2-morpholin-4-yl-ethyl)-phenoxy]-propyl}-amine; (2-Chloro-3-trifluoromethyl-benzyl)-(2,2-diphenyl-ethyl)-{(R)-1-methyl-3-[3-(2-morpholin-4-yl-ethyl)-phenoxy]-propyl}-amine; (2-Chloro-3-trifluoromethyl-benzyl)-(2,2-diphenyl-ethyl)-{(R)-2-methyl-3-[3-(2-morpholin-4-yl-ethyl)-phenoxy]-propyl}-amine; {3-[3-(2-Amino-ethyl)-phenoxy]-propyl}-(2-chloro-3-trifluoromethyl-benzyl)-(2,2-diphenyl-ethyl)-amine; [2-(3-{3-[(2-chloro-3-trifluoromethyl-benzyl)-diphenylethyl-amino]-propoxy}-phenyl)-ethyl]-isopropyl-amine; [2-(3-{3-[(2-chloro-3-trifluoromethyl-benzyl)-diphenylethyl-amino]-propoxy}-phenyl)-ethyl]-propyl-amine; 2-[2-(3-{3-[(2-chloro-3-trifluoromethyl-benzyl)-diphenylethyl-amino]-propoxy}-phenyl)-ethylamino]-ethanol; (2-Chloro-3-trifluoromethyl-benzyl)-(2,2-diphenyl-ethyl)-[3-(3-{2-[(1-methyl-1H-imidazol-2-ylmethyl)-amino]-ethyl}-phenoxy)-propyl]-amine; (2-Chloro-3-trifluoromethyl-benzyl)-(2,2-diphenyl-ethyl)-{3-[3-(2-thiomorpholin-4-yl-ethyl)-phenoxy]-propyl}-amine; [2-(3-{3-[(2-chloro-3-trifluoromethyl-benzyl)-diphenylethyl-amino]-propoxy}-phenyl)-ethylamino]-acetic acid; [2-(3-{(R)-3-[(2-chloro-3-trifluoromethyl-benzyl)-diphenylethyl-amino]-butoxy}-phenyl)-ethylamino]-acetic acid; {[2-(3-{3-[(2-chloro-3-trifluoromethyl-benzyl)-diphenylethyl-amino]-propoxy}-phenyl)-ethyl]-methyl-amino}-acetic acid; 2-[2-(3-{3-[(2-chloro-3-trifluoromethyl-benzyl)-diphenylethyl-amino]-propoxy}-phenyl)-ethylamino]-2-methyl-propionic acid; (S)-2-[2-(3-{3-[(2-chloro-3-trifluoromethyl-benzyl)-diphenylethyl-amino]-propoxy}-phenyl)-ethylamino]-propionic acid; (R)-1-[2-(3-{3-[(2-chloro-3-trifluoromethyl-benzyl)-diphenylethyl-amino]-propoxy}-phenyl)-ethyl]-pyrrolidine-2-carboxylic acid; (S)-1-[2-(3-{3-[(2-chloro-3-trifluoromethyl-benzyl)-diphenylethyl-amino]-propoxy}-phenyl)-ethyl]-pyrrolidine-2-carboxylic acid; [2-(3-{3-[(2-chloro-3-trifluoromethyl-benzyl)-diphenylethyl-amino]-propoxy}-phenyl)-ethyl]-pyrimidin-2-yl-amine; (2-Chloro-3-trifluoromethyl-benzyl)-(2,2-diphenyl-ethyl)-[3-(3-morpholin-4-yl-phenoxy)-propyl]-amine; (2-Chloro-3-trifluoromethyl-benzyl)-(2,2-diphenyl-ethyl)-[3-(3-piperidin-1-yl-phenoxy)-propyl]-amine; (3-{3-[(2-chloro-3-trifluoromethyl-benzyl)-diphenyl-ethyl-amino]-propoxy}-phenyl)-diethyl-amine; (2-Chloro-3-trifluoromethyl-benzyl)-{3-[3-(2,5-dimethyl-pyrrol-1-yl)-phenoxy]-propyl}-(2,2-diphenyl-ethyl)-amine; (2-Chloro-3-trifluoromethyl-benzyl)-(2,2-diphenyl-ethyl)-[3-(3-piperazin-1-yl-phenoxy)-propyl]-amine; (2-Chloro-3-trifluoromethyl-benzyl)-((S)-2-phenyl-propyl)-[3-(3-piperazin-1-yl-phenoxy)-propyl]-amine; (2-Chloro-3-trifluoromethyl-benzyl)-(2,2-diphenyl-ethyl)-[(R)-2-methyl-3-(3-piperazin-1-yl-phenoxy)-propyl]-amine; [4-(3-{3-[(2-chloro-3-trifluoromethyl-benzyl)-diphenylethyl-amino]-propoxy}-phenyl)-piperazin-1-yl]-acetic acid; [4-(3-{3-[(2-chloro-3-trifluoromethyl-benzyl)-((S)-2-phenyl-propyl)-amino]-propoxy}-phenyl)-piperazin-1-yl]-acetic acid; [4-(3-((R)-[(2-chloro-3-trifluoromethyl-benzyl)-diphenylethyl-amino]-methyl-propoxy}-phenyl)-piperazin-1-yl]-acetic acid; (2-Chloro-3-trifluoromethyl-benzyl)-(2,2-diphenyl-ethyl)-{3-[3-(4-methyl-piperazin-1-yl)-phenoxy]-propyl}-amine; (2-Chloro-3-trifluoromethyl-benzyl)-(2,2-diphenyl-ethyl)-[3-(3-pyrrolidin-1-yl-phenoxy)-propyl]-amine; (3-{3-[(2-chloro-3-trifluoromethyl-benzyl)-diphenylethyl-amino]-propoxy}-phenylamino)-acetic acid; [(3-{3-[(2-chloro-3-trifluoromethyl-benzyl)-diphenylethyl-amino]-propoxy}-phenyl)-N-methyl-amino]-acetic acid; N-(2,2-Diphenylethyl)-N-(2-chloro-3-trifluoromethylbenzyl)-3-[3-(2-methyl-2-aminopropyl)phenoxy]propylamine; N-(2,2-Diphenylethyl)-N-(2-chloro-3-trifluoromethylbenzyl)-3-(3-[2-hydroxymethyl]phenoxy)propylamine, N-(2,2-Diphenylethyl)-N-(2-chloro-3-trifluoromethylbenzyl)-3-(3-[2-hydroxy-2-methylpropyl]phenoxy)propylamine; N-(2,2-Diphenylethyl)-N-(2-chloro-3-trifluoromethylbenzyl)-3-(3-N-methylsulfonamidophenoxy)propylamine; N-(2-[2-Chlorophenyl]-propyl)-N-(2-chloro-3-trifluoromethylbenzyl)-3-(3-carboxymethylenephenoxy)propylamine; N-(2-[3-Chlorophenyl]-propyl)-N-(2-chloro-3-trifluoromethylbenzyl)-3-(3-carboxymethylenephenoxy)propylamine; N-(2-[4-Chlorophenyl]-propyl)-N-(2-chloro-3-trifluoromethylbenzyl)-3-(3-carboxymethylenephenoxy)propylamine; N-(2-[2-Methoxyphenyl]-propyl)-N-(2-chloro-3-trifluoromethylbenzyl)-3-(3-carboxymethylenephenoxy)propylamine; N-(2-[4-Methoxyphenyl]-propyl)-N-(2-chloro-3-trifluoromethylbenzyl)-3-(3-carboxymethylenephenoxy)propylamine; N-(2-Phenyl-4-methylpentyl)-N-(2-chloro-3-trifluoromethylbenzyl)-3-(3-carboxymethylenephenoxy)propylamine; N-(2-Phenylbutyl)-N-(2-chloro-3-trifluoromethylbenzyl)-3-(3-carboxymethylenephenoxy)propylamine; N-(2-[2-Methyl-2-phenyl]propyl)-N-(2-chloro-3-trifluoromethylbenzyl)-3-(3-carboxymethylenephenoxy)propylamine; N-(2-Phenyl-3-methylbutyl)-N-(2-chloro-3-trifluoromethylbenzyl)-3-(3-carboxymethylenephenoxy)propylamine; N-(2-Phenylhexyl)-N-(2-chloro-3-trifluoromethylbenzyl)-3-(3-carboxymethylenephenoxy)propylamine; N-(2-Phenyl-3-butynyl)-N-(2-chloro-3-trifluoromethylbenzyl)-3-(3-carboxymethylenephenoxy)propylamine; (S)-N-(2-Phenyl-2-methoxyethyl)-N-(2-chloro-3- trifluoromethylbenzyl)-3-(3-carboxymethylenephenoxy)propylamine; (R)-N-(2-Phenyl-2-methoxyethyl)-N-(2-chloro-3-trifluoromethylbenzyl)-3-(3-carboxymethylenephenoxy)propylamine; (R)-N-(2-Phenyl-2-methoxyethyl)-N-2-chloro-3-trifluoromethylbenzyl)-3-(3-[2-hydroxy-2-methylpropyl]phenoxy)propylamine; 1-(3-{3-[(2-Chloro-3-trifluoromethyl-benzyl)-diphenylethyl-amino]-propoxy}-phenyl)-cyclobutanecarboxylic acid; 1-(3-{3-[(2-Chloro-3-trifluoromethyl-benzyl)-diphenylethyl-amino]-propoxy}-phenyl)-cyclopentanecarboxylic acid; 1-(3-{3-[(2-Chloro-3-trifluoromethyl-benzyl)-(2,2-diphenyl-ethyl)-amino]-propoxy}-phenyl)-cyclopropanecarboxylic acid;
and a pharmaceutically acceptable salt or hydrate thereof.

21. The compound according to claim 1, selected from:
2-(3-{3-[[2-chloro-3-(trifluoromethyl)benzyl](2,2-dephenylethyl)amino]propoxy}phenyl)-ethanol,
(2-chloro-3-trifluoromethyl-benzyl)-(2,2-diphenylethyl)-{3-[3-(1,2,4-triazol-3-ylmethyl)-phenoxy]-propyl}-amine,
(2-chloro-3-trifluoromethyl-benzyl)-(2,2-diphenylethyl)-{3-[3-(1,2,3,4-tetrazol-5-ylmethyl)-phenoxy]-propyl}-amine,
(2-chloro-3-trifluoromethyl-benzyl)-(2-cyclohexyl-2-phenyl-ethyl)-{3-[3-(1,2,3,4-tetrazol-5-ylmethyl)-phenoxy]-propyl}-amine,
2-(3-{3-[[2-chloro-3-(trifluoromethyl)benzyl]-benzylamino]propoxy}-phenyl)acetic acid,
2-(3-{3-[[2-chloro-3-(trifluoromethyl)-benzyl]phenethylamino]propoxy}-phenyl)acetic acid,
2-(3-{3-[[2-chloro-3-(trifluoromethyl)benzyl](2-hydroxy-2-phenyl-ethyl)amino]propoxy}-phenyl)acetic acid,
2-(3-{3-[[2-chloro-3-(trifluoromethyl)benzyl](2-acetoxy-2-phenyl-ethyl)amino]propoxy}-phenyl)acetic acid,
2-(3-{3-[[2-chloro-3-(trifluoromethyl)benzyl](2-phenoxy-2-phenyl-ethyl)amino]propoxy}-phenyl)acetic acid,
(3-{3-[(2-acetoxy-2-phenylethyl)(2-chloro-3-trifluoromethyl-benzyl)-amino]-propoxy}-phenyl)-acetic acid methyl ester,
benzoic acid 2-[3-(3-methoxycarbonylmethyl-phenoxy){2-chloro-3-(trifluoromethyl)benzyl}propylamino]-1-phenyl ethyl ester,
(3-{4-(2-chloro-3-trifluoromethyl)benzyl)-(2,2-diphenylethyl)-amino]butyl}phenyl)-acetic acid,
furan-2-carboxylic acid N-(3-{3-[(2-Chloro-3-trifluoromethyl-benzyl)-2,2-diphenylethyl-amino]-propoxy}-phenyl)-amide,
1-(3-{3-[(2-chloro-3-trifluoromethyl-benzyl)-diphenyl-ethyl-amino]-propoxy}-phenyl)-cyclobutanecarboxylic acid,
N-(2,2-diphenylethyl)-N-(2-chloro-3-trifluoromethylbenzyl)-3-(3-[2-hydroxy-2-methylpropyl]phenoxy)propylamine,
(2-chloro-3-trifluoromethyl-benzyl)-(2,2-diphenylethyl)-[3-(3-{2-[(1H-imidazol-2-ylmethyl)-amino]-ethyl}-phenoxy)-propyl]-amine,
N-(3-{3-[(2-chloro-3-trifluoromethyl-benzyl)-2,2-diphenylethyl-amino]-propoxy}-phenyl)-methanesulfonamide,
N-(3-{3-[(2-chloro-3-trifluoromethyl-benzyl)-2,2-diphenylethyl-amino]-propoxy}-phenyl)-N-methyl-amine,
[2-(3-{3-[(2-chloro-3-trifluoromethyl-benzyl)-diphenylethyl-amino]-propoxy}-phenyl)-ethylamino]-acetic acid,
N-(2-[3-chlorophenyl]-propyl)-N-(2-chloro-3-trifluoromethylbenzyl)-3-(3-carboxymethylenephenoxy)propylamine,
[4-(3-{3-[(2-chloro-3-trifluoromethyl-benzyl)-diphenylethyl-amino]-propoxy}-phenyl)-piperazin-1-yl]-acetic acid,
(2-chloro-3-trifluoromethyl-benzyl)-(2,2-diphenylethyl)-{3-[3-(4-methyl-piperazin-1-yl)-phenoxy]-propyl}-amine,
[1-(3-{3-[(2-chloro-3-(trifluoromethyl)-benzyl)-(2,2-diphenylethyl)-amino]-propoxy}-phenyl-piperidine-4-carboxylic acid,
and a pharmaceutically acceptable salt or hydrate thereof.

22. The compound according to claim 1, selected from:
(S)-(2-chloro-3-trifluoromethyl-benzyl)-(2-phenyl-propyl)-{3-[3-(1,2,3,4-tetrazol-3-ylmethyl)-phenoxy]-propyl}-amine,
(R)-(2-chloro-3-trifluoromethyl-benzyl)-(2-phenyl-propyl)-{3-[3-(1,2,3,4-tetrazol-3-ylmethyl)-phenoxy]-propyl}-amine,
(S)-2-(3-{3-[[2-chloro-3-(trifluoromethyl)benzyl](2-phenyl-propyl)amino]propoxy}-phenyl)acetic acid,
(R)-2-(3-{3-[[2-chloro-3-(trifluoromethyl)benzyl](2-phenyl-propyl)amino]propoxy}-phenyl)acetic acid,
(R)-1-[2-(3-{3-[(2-chloro-3-trifluoromethyl-benzyl)-diphenylethyl-amino]-propoxy}-phenyl)-ethyl]-pyrrolidine-2-carboxylic acid,
(2-chloro-3-trifluoromethyl-benzyl)-{3-[3-(2-morpholin-4-yl-ethyl)-phenoxy]-propyl}-((S)-2-phenyl-propyl amine,
2-(3-{3-[(2-chloro-3-trifluoromethyl-benzyl)-((S)-2-phenyl-propyl)-amino]-propoxy}-phenyl)-2-methyl-propionic acid,
(3-{(R)-3-[(2-chloro-3-trifluoromethyl-benzyl)-((S)-2-phenyl-propyl)-amino]-butoxy}-phenyl)-acetic acid,
[4-(3-{3-[(2-chloro-3-trifluoromethyl-benzyl)-((S)-2-phenyl-propyl)-amino]-propoxy}-phenyl)-piperazin-1-yl]-acetic acid,
[4-(3-{(R)-[(2-chloro-3-trifluoromethyl-benzyl)-diphenylethyl-amino]-methyl-propoxy}-phenyl)-piperazin-1-yl]-acetic acid,
and a pharmaceutically acceptable salt or hydrate thereof.

23. A pharmaceutical composition comprising a compound according to claim 1 and a pharmaceutically acceptable carrier or diluent.

24. A method for the prevention or treatment of an LXR mediated disease or condition, wherein said disease or condition is selected from atherosclerosis and inflammation, comprising administering a therapeutically effective amount of the compound according to claim 1.

25. The method according to claim 24, comprising administering a therapeutically effective amount of the compound according to claim 3.

26. The method according to claim 24, comprising administering a therapeutically effective amount of the compound according to claim 7.

27. The method according to claim 24, comprising administering a therapeutically effective amount of the compound according to claim 8.

28. The method according to claim 24, comprising administering a therapeutically effective amount of the compound according to claim 9.

29. The method according to claim 24, comprising administering a therapeutically effective amount of the compound according to claim 11.

30. The method according to claim 24, comprising administering a therapeutically effective amount of the compound according to claim 14.

31. The method according to claim 24, comprising administering a therapeutically effective amount of the compound according to claim 15.

32. The method according to claim 24, comprising administering a therapeutically effective amount of the compound according to claim 17.

33. The method according to claim 24, comprising administering a therapeutically effective amount of the compound according to claim 18.

34. The method according to claim 27, comprising administering a compound selected from:

2-(3-{3-[[2-chloro-3-(trifluoromethyl)benzyl](2,2-dephenylethyl)amino]propoxy}phenyl)-ethanol,
(2-chloro-3-trifluoromethyl-benzyl)-(2,2-diphenylethyl){3-[3-(1,2,4-triazol-3-ylmethyl)-phenoxy]-propyl}-amine,
(2-chloro-3-trifluoromethyl-benzyl)-(2,2-diphenyl-ethyl)-{3-[3-(1,2,3,4-tetrazol-5-ylmethyl)-phenoxy]-propyl}-amine,
(S)-(2-chloro-3-trifluoromethyl-benzyl)-(2-phenyl-propyl)-{3-[3-(1,2,3,4-tetrazol-3-ylmethyl)-phenoxy]-propyl}-amine,
(R)-(2-chloro-3-trifluoromethyl-benzyl)-(2-phenyl-propyl)-{3-[3-(1,2,3,4-tetrazol-3-ylmethyl)-phenoxy]-propyl}-amine,
(S-)-2-(3-{3-[[2-chloro-3-(trifluoromethyl)benzyl](2-phenyl-propyl)amino]-propoxy}-phenyl)acetic acid,
(R-)-2-(3-{3-[[2-chloro-3-(trifluoromethyl)benzyl](2-phenyl-propyl)amino]-propoxy}-phenyl)acetic acid,
2-(3-{3-[[2-chloro-3-(trifluoromethyl)benzyl](2-acetoxy-2-phenyl-ethyl)amino]propoxy}-phenyl)acetic acid,
(3-{3-[(2-acetoxy-2-phenyl-ethyl)-(2-chloro-3-trifluoromethyl-benzyl)-amino]-propoxy}-phenyl)-acetic acid methyl ester,
(3-{4-[(2-chloro-3-(trifluoromethyl)benzyl)-(2,2-diphenylethyl)-amino]butyl}phenyl)-acetic acid,
1-(3-{3-[(2-chloro-3-trifluoromethyl-benzyl)-diphenylethyl-amino]-propoxy}-phenyl)-cyclobutanecarboxylic acid,
N-(2,2-diphenylethyl)-N-(2-chloro-3-trifluoromethylbenzyl)-3-(3-[2-hydroxy-2-methylpropyl]phenoxy)propylamine,
(2-chloro-3-trifluoromethyl-benzyl)-(2,2-diphenyl-ethyl)-[3-(3-{2-[(1H-imidazol-2-ylmethyl)-amino]-ethyl}-phenoxy)-propyl]-amine,
N-(3-{3-[(2-chloro-3-trifluoromethyl-benzyl)-2,2-diphenylethyl-amino]-propoxy}-phenyl)-methanesulfonamide,
N-(3-{3-[(2-chloro-3-trifluoromethyl-benzyl)-2,2-diphenylethyl-amino]-propoxy}-phenyl)-N-methyl-amine,
[2-(3-{3-[(2-chloro-3-trifluoromethyl-benzyl)-diphenylethyl-amino]-propoxy}-phenyl)-ethylamino]-acetic acid,
(R)-1-[2-(3-{3-[(2-chloro-3-trifluoromethyl-benzyl)-diphenylethyl-amino]-propoxy}-phenyl)-ethyl]-pyrrolidine-2-carboxylic acid,
furan-2-carboxylic acid N-(3-{3-[(2-chloro-3-trifluoromethyl-benzyl)-2,2-diphenylethyl-amino]-propoxy}-phenyl)-amide,
N-(2-[3-chlorophenyl]-propyl)-N-(2-chloro-3-trifluoromethylbenzyl)-3-(3-carboxymethylenephenoxy)propylamine,
(2-chloro-3-trifluoromethyl-benzyl)-{3-[3-(2-morpholin-4-yl-ethyl)-phenoxy]-propyl}-((S)-2-phenyl-propyl amine,
[4-(3-{3-[(2-chloro-3-trifluoromethyl-benzyl)-diphenylethyl-amino]-propoxy}phenyl)-piperazin-1-yl]-acetic acid,
2-(3-{3-[(2-chloro-3-trifluoromethyl-benzyl)-((S)-2-phenyl-propyl)-amino]-propoxy}-phenyl)-2-methyl-propionic acid,
(2-chloro-3-trifluoromethyl-benzyl)-(2,2-diphenyl-ethyl){3-[3-(4-methyl-piperazin-1-yl)-phenoxy]-propyl}-amine,
(3-{(R)-3-[(2-chloro-3-trifluoromethyl-benzyl)-((S)-2-phenyl-propyl)-amino]-butoxy}-phenyl)-acetic acid,
[1-(3-{3-[(2-chloro-3-(trifluoromethyl)-benzyl)-(2,2-diphenylethyl)-amino]-propoxy}-phenyl-piperidine-4-carboxylic acid,
[4-(3-{3-[(2-chloro-3-trifluoromethyl-benzyl)-((S)-2-phenyl-propyl)-amino]-propoxy}-phenyl)-piperazin-1-yl]-acetic acid,
[4-(3-{(R)-[(2-chloro-3-trifluoromethyl-benzyl)-diphenylethyl-amino]-methyl-propoxy}-phenyl)-piperazin-1-yl]-acetic acid, and a pharmaceutically acceptable salt or hydrate thereof.

35. A method for increasing reverse cholesterol transport, said method comprising administering a therapeutically effective amount of the compound according to claim 1.

36. A method for inhibiting cholesterol absorption, said method comprising administering a therapeutically effective amount of the compound according to claim 1.

* * * * *